(12) United States Patent
Li et al.

(10) Patent No.: US 9,120,779 B2
(45) Date of Patent: Sep. 1, 2015

(54) INHIBITORS OF HCV NS5A

(75) Inventors: Leping Li, San Francisco, CA (US); Min Zhong, San Francisco, CA (US)

(73) Assignee: PRESIDIO PHARMACEUTICALS, INC., San Francisco, CA (US)

( * ) Notice: Subject to any disclaimer, the term of this patent is extended or adjusted under 35 U.S.C. 154(b) by 547 days.

(21) Appl. No.: 13/132,606

(22) PCT Filed: Dec. 2, 2009

(86) PCT No.: PCT/US2009/066467
§ 371 (c)(1),
(2), (4) Date: Jun. 2, 2011

(87) PCT Pub. No.: WO2010/065681
PCT Pub. Date: Jun. 10, 2010

(65) Prior Publication Data
US 2011/0237579 A1    Sep. 29, 2011

Related U.S. Application Data

(60) Provisional application No. 61/119,723, filed on Dec. 3, 2008, provisional application No. 61/173,590, filed on Apr. 28, 2009, provisional application No. 61/182,952, filed on Jun. 1, 2009.

(51) Int. Cl.
*A61K 31/4178* (2006.01)
*A61K 31/4184* (2006.01)
*C07D 403/14* (2006.01)
*C07D 235/02* (2006.01)
*C07D 235/04* (2006.01)
*C07D 233/54* (2006.01)
*C07D 401/14* (2006.01)
*C07D 233/64* (2006.01)
*C07D 405/14* (2006.01)
*C07D 413/14* (2006.01)
*C07D 417/14* (2006.01)

(52) U.S. Cl.
CPC ............ *C07D 403/14* (2013.01); *C07D 233/64* (2013.01); *C07D 401/14* (2013.01); *C07D 405/14* (2013.01); *C07D 413/14* (2013.01); *C07D 417/14* (2013.01)

(58) Field of Classification Search
CPC .. C07D 235/02; C07D 235/04; C07D 233/54; C07D 403/14; A61K 31/4178; A61K 31/4184

USPC ............... 548/311.1, 302.1, 306.1, 313.1; 514/397, 394
See application file for complete search history.

(56) References Cited

U.S. PATENT DOCUMENTS

| | | | |
|---|---|---|---|
| 5,442,064 A | 8/1995 | Pieper et al. | |
| 7,659,270 B2 * | 2/2010 | Bachand et al. | ........... 514/235.8 |
| 2001/0039277 A1 | 11/2001 | Elliott et al. | |

FOREIGN PATENT DOCUMENTS

| | | |
|---|---|---|
| WO | 03007959 A1 | 1/2003 |
| WO | 2004035549 A1 | 4/2004 |
| WO | 2004047745 A2 | 6/2004 |
| WO | 2005007648 A2 | 1/2005 |
| WO | 2006133326 A1 | 12/2006 |
| WO | WO 2007/014922 A1 * | 2/2007 |
| WO | 2007119463 A1 | 10/2007 |
| WO | 2008021928 A2 | 2/2008 |
| WO | 2008021936 A2 | 2/2008 |
| WO | 2008073461 A2 | 6/2008 |
| WO | 2010017401 A1 | 2/2010 |
| WO | 2010091413 A1 | 8/2010 |
| WO | 2010099527 A1 | 9/2010 |

OTHER PUBLICATIONS

U.S. Appl. No. 13/260,378, commonly assigned.*
Extended European Search Report dated Jun. 29, 2012 issued in PCT/US2009/066467.
Stoicescu-Crivat et al., Poly -1,3,4-Oxadiazoles. II. La Polycondensation De L'Aminomethyl- et p-Aminophenyl-5-Tetrazole Avec Les Dichlorures Acides. Revue Roumaine De Chimie Jan. 1966;11:1135-1140.
International Search Report and Written Opinion issued in EP 13189259.8 dated Aug. 8, 2014.
Office Action issued by the Israeli Patent Office in Israel Patent Application No. 213279 dated Nov. 30, 2014—includes Engl lang transl.

* cited by examiner

*Primary Examiner* — Kamal Saeed
*Assistant Examiner* — Janet L Coppins
(74) *Attorney, Agent, or Firm* — Sam K. Tahmassebi; TechLaw LLP

(57) ABSTRACT

The invention relates to non-macrocyclic, non-peptidic, substituted heterocyclic compounds useful for inhibiting hepatitis C virus ("HCV") replication, particularly functions of the non-structural 5A ("NS5A") protein of HCV.

18 Claims, No Drawings

INHIBITORS OF HCV NS5A

STATEMENT OF RELATED APPLICATIONS

This application is filed under 35 U.S.C. §371 as the U.S. national phase of International Application PCT/US2009/066467, filed Dec. 2, 2009, which designated the U.S. and claims the benefit of U.S. provisional applications 61/119,723 filed Dec. 3, 2008; 61/173,590 filed Apr. 28, 2009; and 61/182,952 filed Jun. 1, 2009.

FIELD OF THE INVENTION

The invention relates to compounds useful for inhibiting hepatitis C virus ("HCV") replication, particularly functions of the non-structural 5A ("NS5A") protein of HCV.

BACKGROUND OF THE INVENTION

HCV is a single-stranded RNA virus that is a member of the Flaviviridae family. The virus shows extensive genetic heterogeneity as there are currently seven identified genotypes and more than 50 identified subtypes. In HCV infected cells, viral RNA is translated into a polyprotein that is cleaved into ten individual proteins. At the amino terminus are structural proteins: the core (C) protein and the envelope glycoproteins, E1 and E2. p7, an integral membrane protein, follows E1 and E2. Additionally, there are six non-structural proteins, NS2, NS3, NS4A, NS4B, NS5A and NS5B, which play a functional role in the HCV lifecycle. (see, for example, Lindenbach, B. D. and C. M. Rice, *Nature.* 436:933-938, 2005).

Infection by HCV is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves interferon-alpha, alone, or in combination with ribavirin. The treatment is cumbersome and sometimes has debilitating and severe side effects and many patients do not durably respond to treatment. New and effective methods of treating HCV infection are urgently needed.

SUMMARY OF THE INVENTION

Essential features of the NS5A protein of HCV make it an ideal target for inhibitors. The present disclosure describes a class of compounds targeting the NS5A protein and methods of their use to treat HCV infection in humans.

In a first aspect, compounds of formula I are provided:

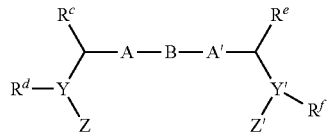

wherein,
A and A' are independently selected from the group consisting of a single bond, $-(CR_2)_n-C(O)-(CR_2)_p-$, $-(CR_2)_n-O-(CR_2)_p-$, $-(CR_2)_n-N(R^N)$ $-(CR_2)_p-$, $-(CR_2)_n-S(O)_k-N(R^N)-(CR_2)_p-$, $-(CR_2)_n-C(O)-N(R^N)-(CR_2)_p-$, $-(CR_2)_n-N(R^N)-C(O)-N(R^N)-(CR_2)_p-$, $-(CR_2)_n-C(O)-O-(CR_2)_p-$, $-(CR_2)_n-N(R^N)-S(O)_k-N(R^N)-(CR_2)_p-$ and $-(CR_2)_n-N(R^N)-C(O)-O-(CR_2)_p-$ and a heteroaryl group selected from the group consisting of

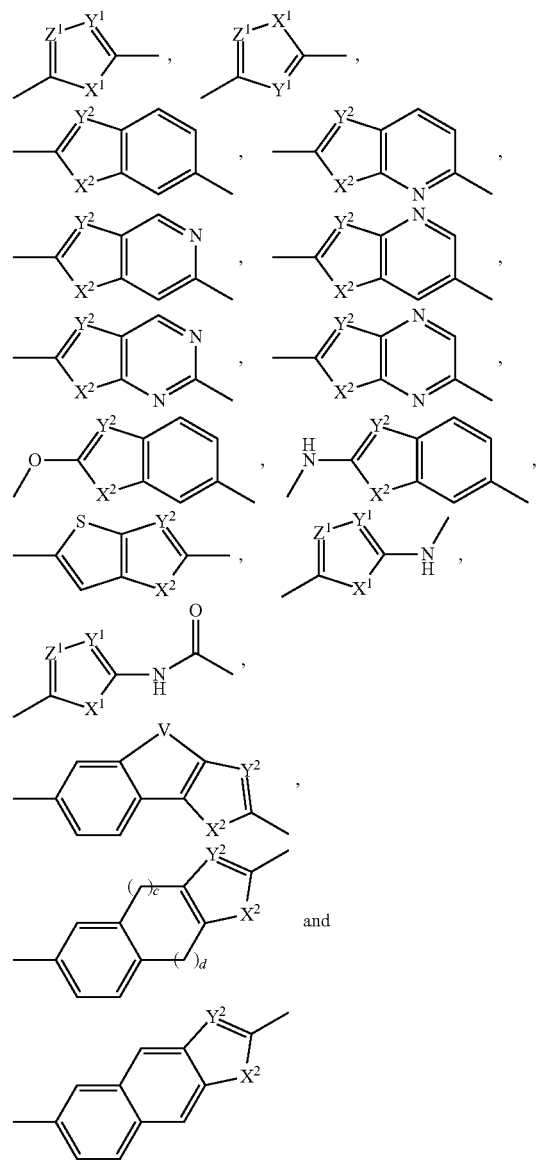

wherein:
$X^1$ is $CH_2$, NH, O or S,
$Y^1$, $Y^2$ and $Z^1$ are each independently CH or N,
$X^2$ is NH, O or S,
V is $-CH_2-CH_2-$, $-CH=CH-$, $-N=CH-$, $(CH_2)_a-N(R^N)-(CH_2)_b-$ or $-(CH_2)_a-O-(CH_2)_b-$, wherein a and b are independently 0, 1, 2, or 3 with the proviso that a and b are not both 0,

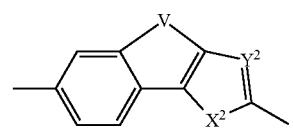

optionally includes 1 or 2 nitrogens as heteroatoms on the phenyl residue, the carbons of the heteroaryl group are each independently optionally substituted with a substituent selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, a and b are independently 1, 2, or 3.

c and d are independently 1 or 2, n and p are independently 0, 1, 2 or 3, k is 0, 1, or 2, each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and wherein for each A and A', B may be attached to either side of A and A' so that in the example of A or A' being

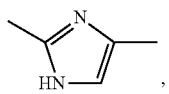

the A-B-A' can be any of:

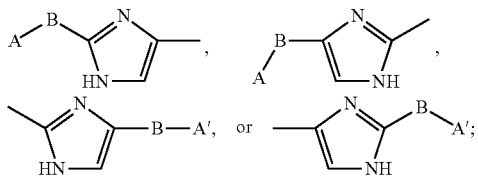

B is Q or Q-Q, wherein each Q is independently selected from the group consisting of a cycloalkyl group, cycloalkenyl group, heterocycle, aryl group or heteroaryl group, with the proviso that only one Q is a six member aromatic ring when B is Q-Q and with the proviso that if B is Q-Q, any Q is that is polycyclic is connected to the remainder of the molecule through only one cycle of the polycycle;

R$^c$, R$^d$, R$^e$ and R$^f$ are each independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein, each hetero atom, if present, is independently N, O or S, each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S, R$^c$ and R$^d$ are optionally joined to form a 4- to 8-membered heterocycle which is optionally fused to another 3- to 6-membered heterocycle or heteroaryl ring, and R$^e$ and R$^f$ are optionally joined to form a 4- to 8-membered heterocycle which is optionally fused to another 3- to 6-membered heterocycle or heteroaryl ring;

Y and Y' are each independently carbon or nitrogen; and

Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

In a first embodiment of the first aspect, each Q is independently optionally substituted with one or more substituents each independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and if Q is not aromatic, it is optionally substituted with oxo.

In a second embodiment of the first aspect, each Q is independently optionally substituted with —CN, —OCF$_3$, —OCHF$_2$, —CF$_3$ or —F.

In a third embodiment of the first aspect, B is selected from the group consisting of

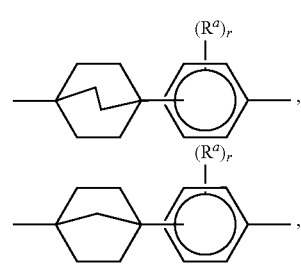

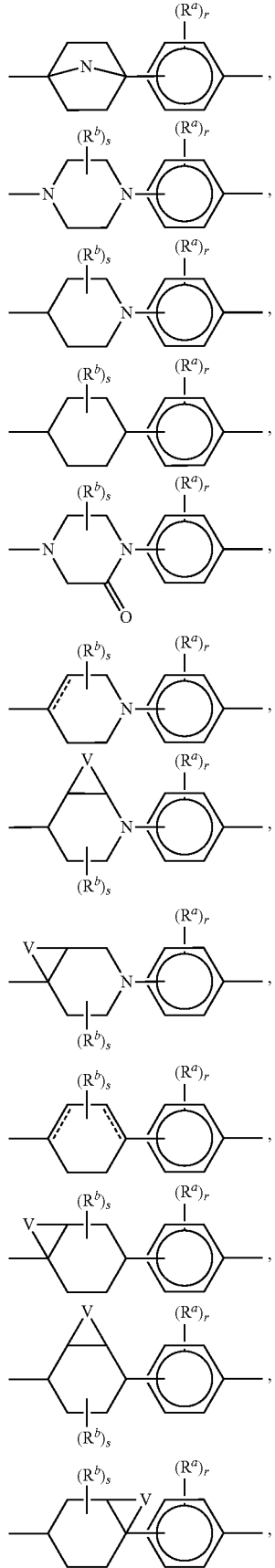

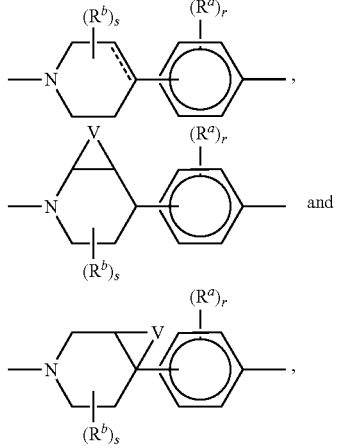

wherein:

is a divalent aryl or heteroaryl group which may be polycyclic with varying connective patterns;

V is —$CH_2$—, —$CH_2$—$CH_2$—, —CH=CH—, —N=CH—, $(CH_2)_a$—$N(R^N)$—$(CH_2)_b$— or —$(CH_2)_a$—O—$(CH_2)_b$—, wherein a and b are independently 0, 1, 2, or 3 with the proviso that a and b are not both 0;

each r and s is independently 0, 1, 2, 3, or 4;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each $R^b$ is independently $C_1$-$C_{12}$ alkyl, hydroxyl, halogen, or oxo.

In a fourth embodiment of the first aspect,

if present, is selected from the group consisting of

-continued

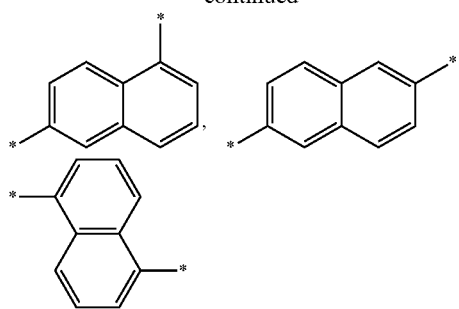

wherein * indicates attachment points to the remainder of the compound, and each phenyl residue optionally includes 1 or 2 nitrogens as heteroatoms.

In a fifth embodiment of the first aspect, each $R^a$, if present, —CN, —OCF$_3$, —OCHF$_2$, —CF$_3$, or —F.

In a sixth embodiment of the first aspect, A and A' are independently selected from the group consisting of a single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$— and —(CR$_2$)$_n$—N(R$^N$)—C(O)—O—(CR$_2$)$_p$— and a heteroaryl group selected from the group consisting oF

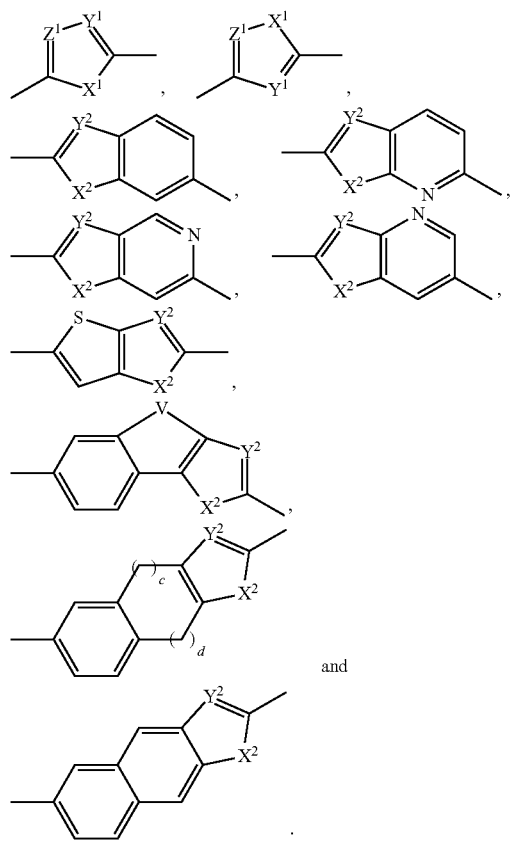

In a seventh embodiment of the first aspect, A and A' are independently selected from the group consisting of a single bond,

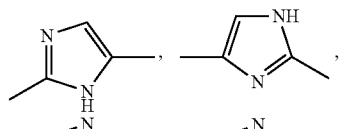

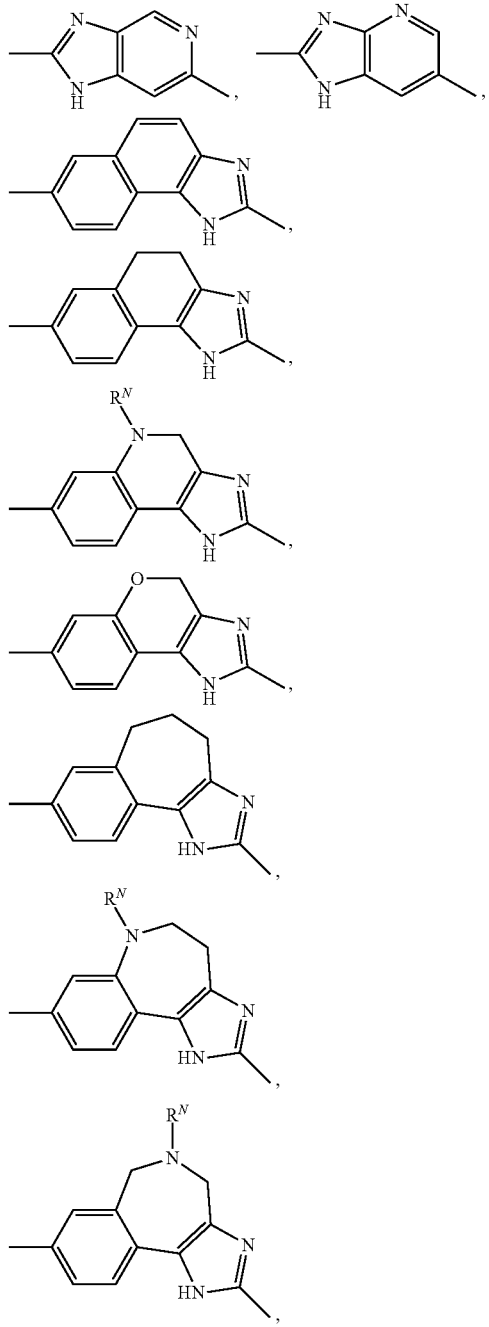

-continued

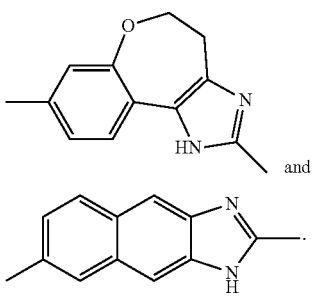
and

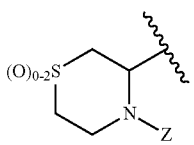

In an eighth embodiment of the first aspect, $R^c$, $R^d$, $R^e$ and $R^f$ are each independently selected from the group consisting of: hydrogen, $C_1$ to $C_8$ alkyl and $C_1$ to $C_8$ heteroalkyl, wherein, each hetero atom, if present, is independently N, O or S, $R^c$ and $R^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In a ninth embodiment of the first aspect, one or both of $R^c$ and $R^d$ or $R^e$ and $R^f$ are optionally joined to form a 4- to 8-membered heterocycle which is optionally fused to another 3- to 6-membered heterocycle.

In a tenth embodiment of the first aspect, $R^c$ and $R^d$ are joined and form a heterocyclic fused ring system selected from the group consisting of:

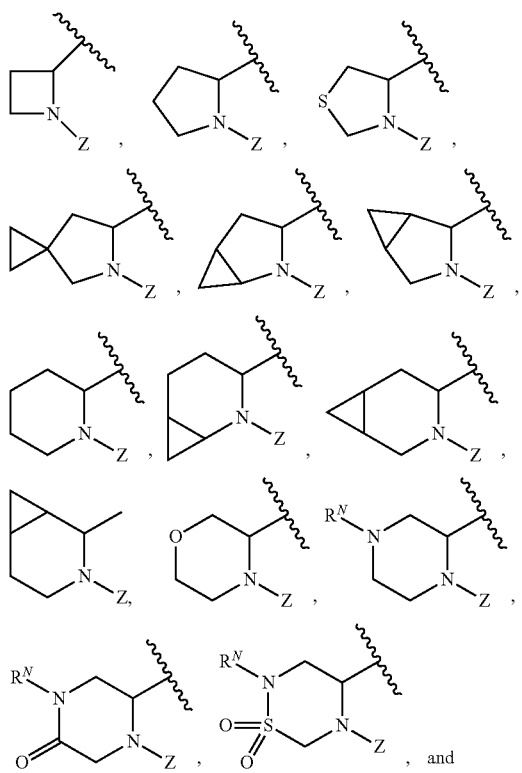

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In an eleventh embodiment of the first aspect, $R^e$ and $R^f$ are joined and form a heterocyclic fused ring system selected from the group consisting of:

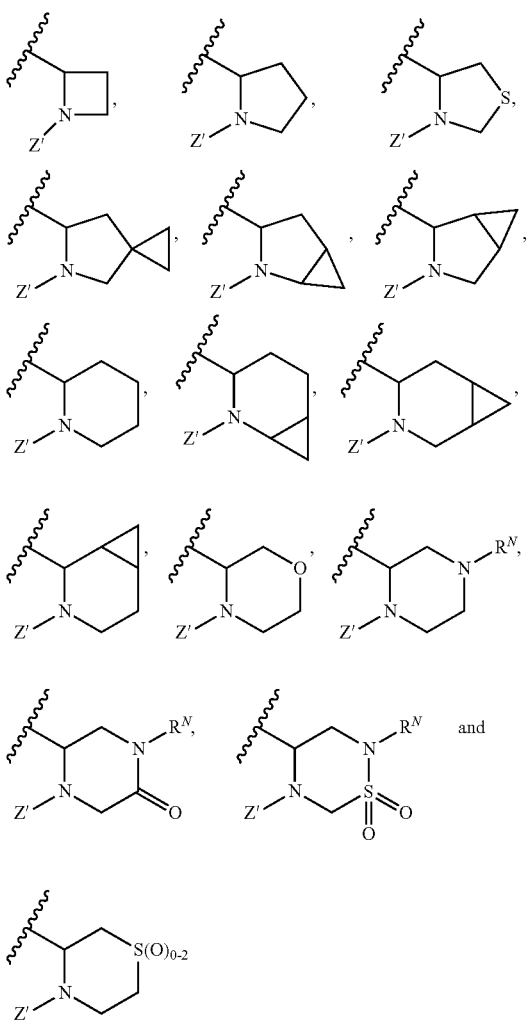

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula III:

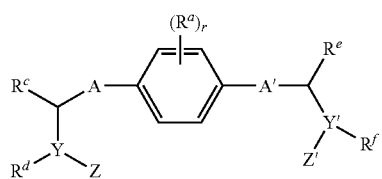
wherein
A is selected from the group consisting of
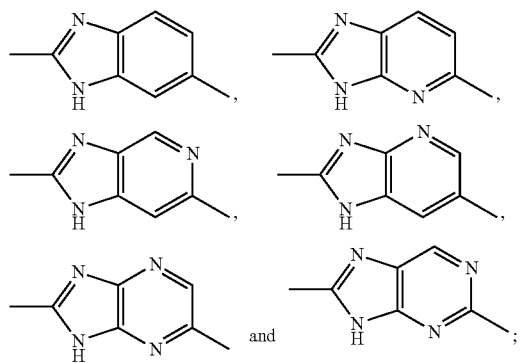
and
A' is selected from the group consisting of single bond,
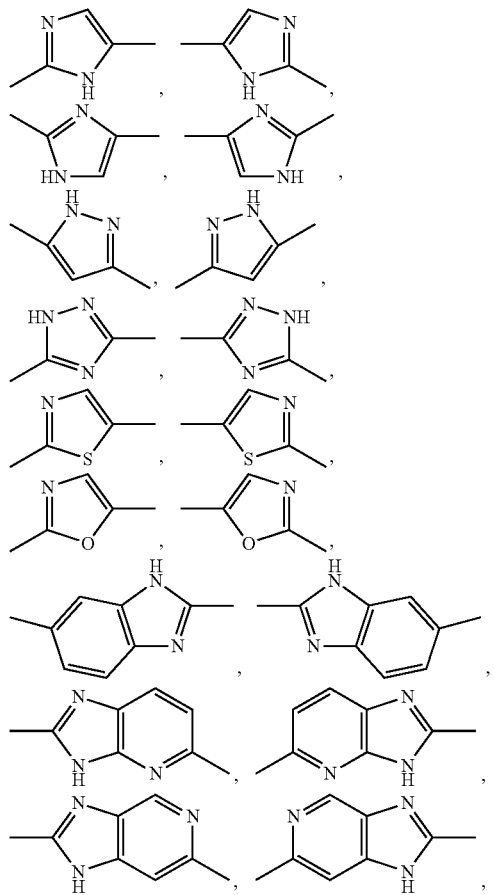
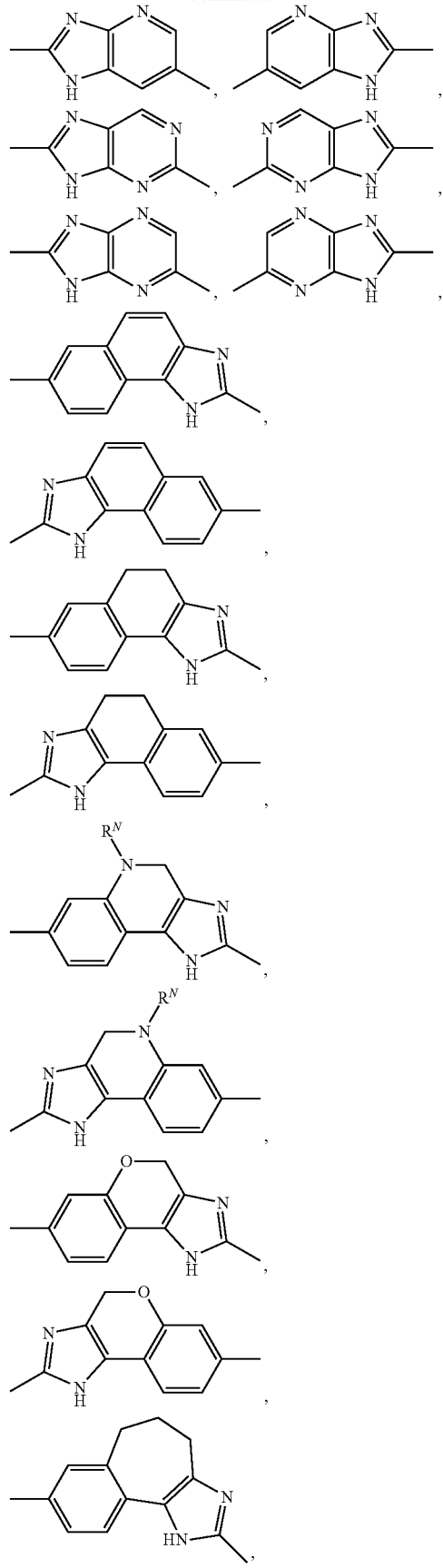

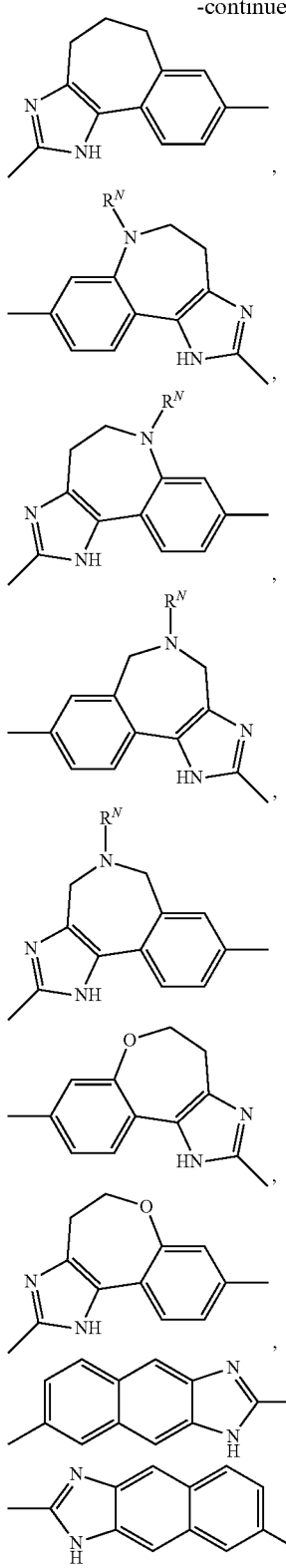

—(CR$_2$)$_n$—O—(CR$_2$)$_p$—,     —(CR$_2$)$_n$—C(O)N(R$^N$)—(CR$_2$)$_p$—, —(CR$_2$)$_n$—C(O)—(CR$_2$)$_p$— and —(CR$_2$)$_n$—N(R$^N$)C(O)—(CR$_2$)$_p$— wherein R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is selected from the group consisting of 0, 1, 2, 3, or 4.

In a first embodiment of the second aspect, A' is

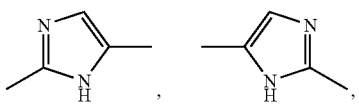

—(CR$_2$)$_n$—C(O)—(CR$_2$)$_p$—,     —(CR$_2$)$_n$—C(O)N(R$^N$)—(CR$_2$)$_p$—, or —(CR$_2$)$_n$—N(R$^N$)C(O)—(CR$_2$)$_p$—.

In a second embodiment of the second aspect, A' is

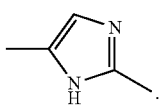

In a third embodiment of the second aspect, compounds have formula IIIa:

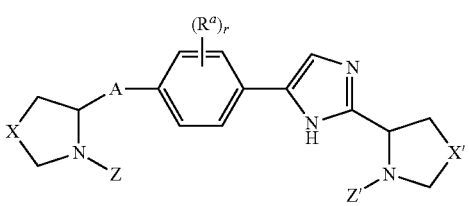

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth embodiment of the second aspect, compounds have formula III wherein A' is selected from the group consisting of

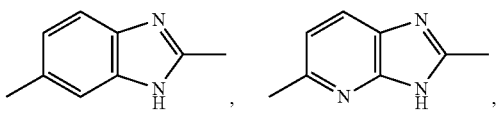

-continued

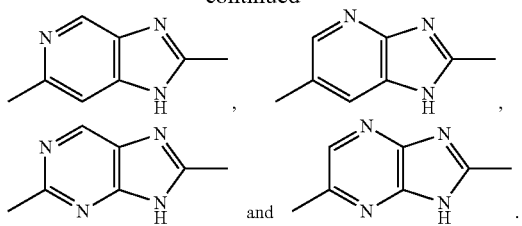

In a fifth embodiment of the second aspect, compounds have formula IIIb:

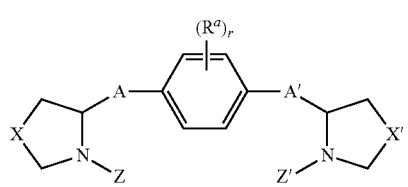

wherein:
A is selected from the group consisting of

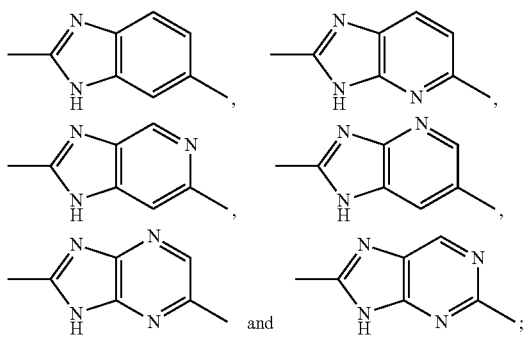

A' is selected from the group consisting of

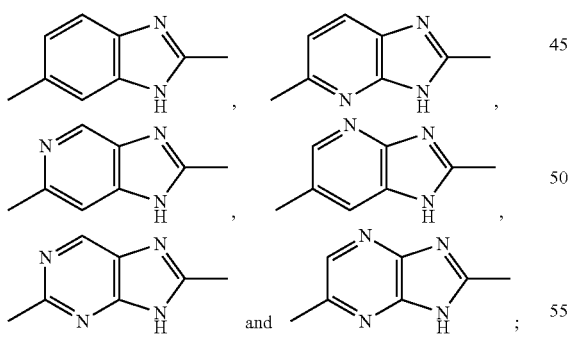

and
X and X' are each independently selected from the group consisting of a bond, —CH$_2$—, —CH$_2$—CH$_2$, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a third aspect of the invention, compounds have formula IV:

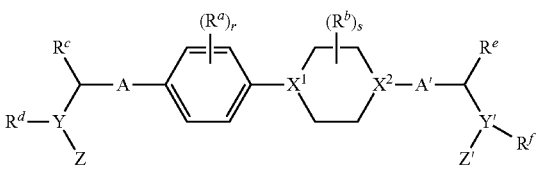

wherein
A and A' are independently selected from the group consisting of single bond,

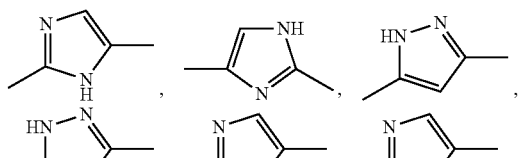

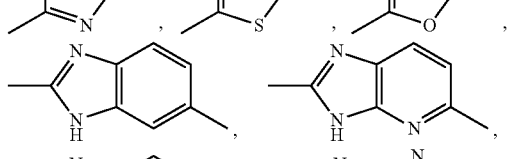

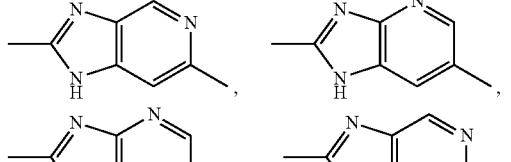

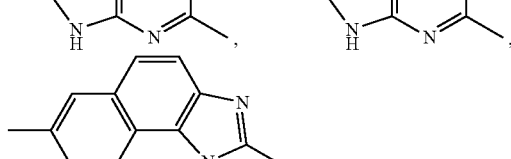

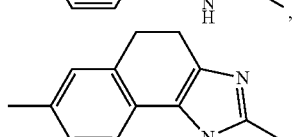

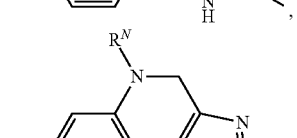

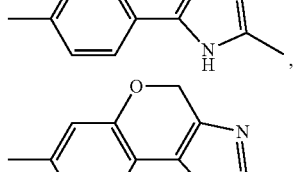

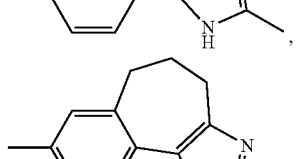

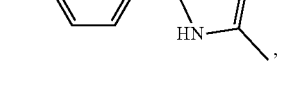

-continued

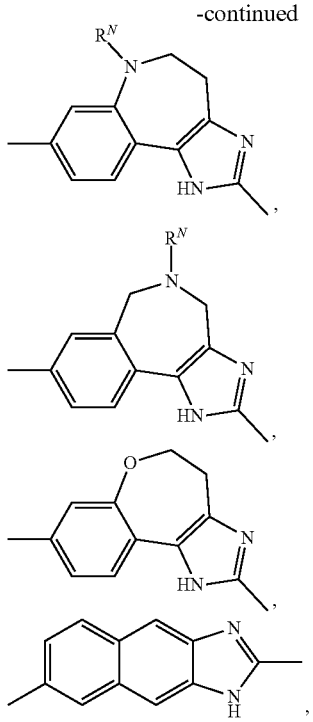

—(CR$_2$)$_n$—C(O)—(CR$_2$)$_p$—, —(CR$_2$)$_n$—O—(CR$_2$)$_p$— and —(CR$_2$)$_n$—C(O)N(R$^N$)—(CR$_2$)$_p$—, wherein: R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

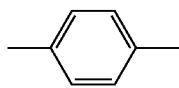

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

each R$^b$ is independently C$_1$-C$_5$ alkyl, hydroxyl, halogen, or oxo;

s is 0, 1, 2, 3, 4, 5, or 6; and each of X$^1$ and X$^2$ are independently C or N.

In a first embodiment of the third aspect, A and A' are each independently

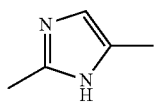

or —(CR$_2$)$_n$—C(O)N(R$^N$)—(CR$_2$)$_p$—.

In a second embodiment of the third aspect, compounds have formula IVa:

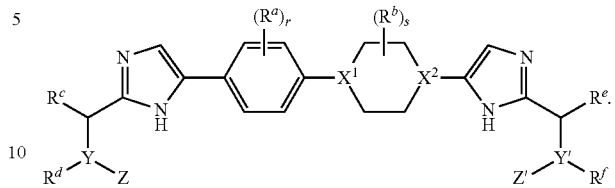

In a third embodiment of the third aspect, compounds have formula IVb:

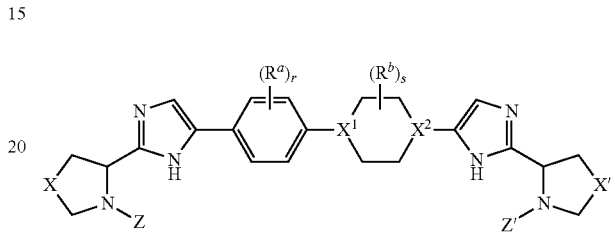

wherein X and X' are each independently selected from the group consisting of a bond, —CH$_2$—, —CH$_2$—CH$_2$, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth aspect of the invention, compounds have formula V: wherein

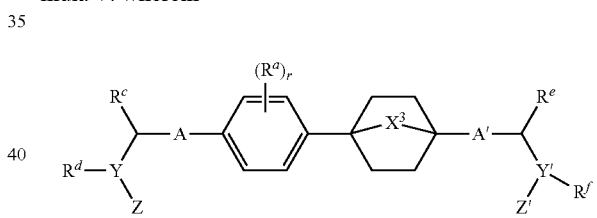

A and A' are independently selected from the group consisting of single bond,

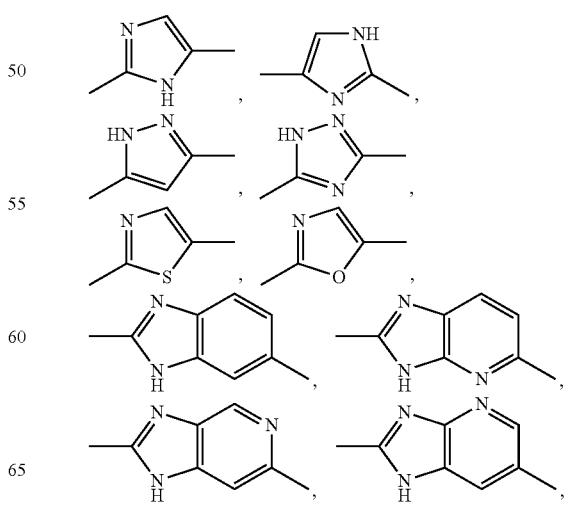

-continued

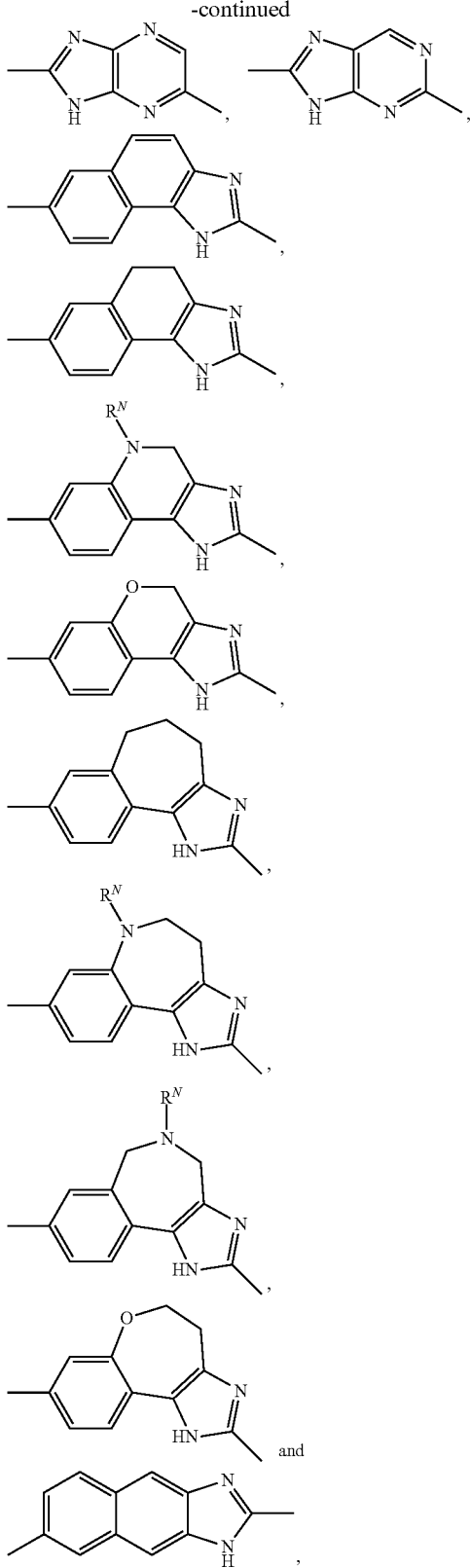

—(CR$_2$)$_n$—C(O)—(CR$_2$)$_p$—, —(CR$_2$)$_n$—O—(CR$_2$)$_p$— and —(CR$_2$)$_n$—C(O)—N(R$^N$)—(CR$_2$)$_p$—, wherein R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

X$^3$ is chosen from the group consisting of —CH$_2$—, —CH$_2$—CH$_2$, —CH═CH—, —O—, —S—, —S(O)$_{1-2}$—, —CH$_2$—O—, —NR$^1$— and —CH$_2$—NR$^1$— wherein R$^1$ is chosen from the group consisting of hydrogen, C$_1$ to C$_8$ alkyl, and C$_1$ to C$_8$ heteroalkyl;

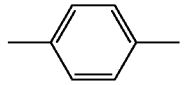

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is 0, 1, 2, 3 or 4.

In a first embodiment of the fourth aspect, A and A' are each independently

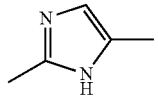

or —(CR$_2$)$_n$—C(O)N(R$^N$)—(CR$_2$)$_p$—.

In a second embodiment of the fourth aspect, compounds have formula Va:

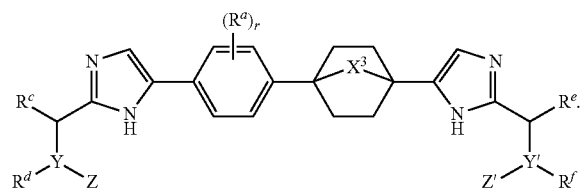

In a third embodiment of the fourth aspect, compounds have formula Vb:

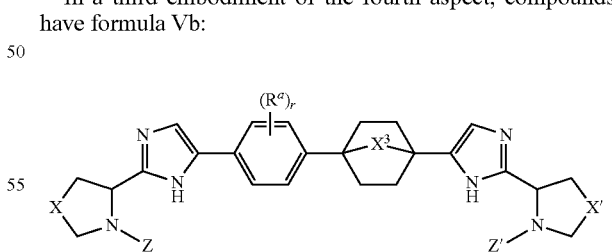

wherein X and X' are each independently selected from the group consisting of a bond, —CH$_2$, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifth aspect of the invention, compounds have formula VI:

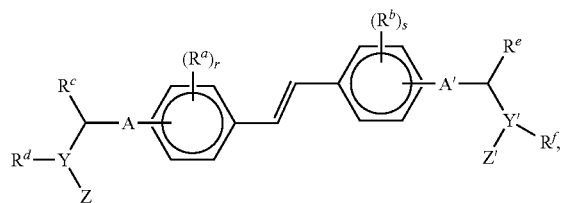

wherein
each

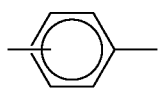

is independently a divalent aryl or heteroaryl group which may be polycyclic with varying connective patterns;
each r is independently 0, 1, 2, 3, or 4;
each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
A and A' are independently selected from the group consisting of a single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—S(O)$_k$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$—, —(CR$_2$)$_n$—C(O)—O—(CR$_2$)$_p$—, —(CR$_2$)$_n$—N(R$^N$)—S(O)$_k$—N(R$^N$)—(CR$_2$)$_p$—, and —(CR$_2$)$_n$—N(R$^N$)—C(O)—O—(CR$_2$)$_p$— and a heteroaryl group selected from the group consisting of

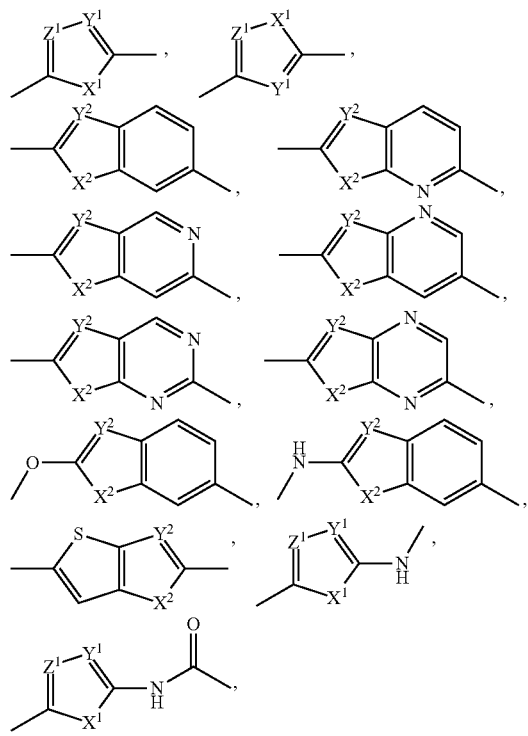

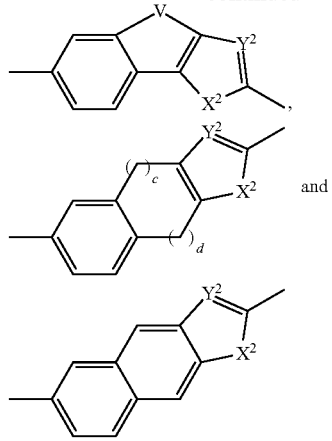

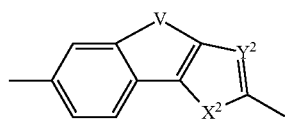

wherein:
X$^1$ is CH$_2$, NH, O or S,
Y$^1$, Y$^2$ and Z$^1$ are each independently CH or N, X$^2$ is NH, O or S,
V is —CH$_2$—CH$_2$—, —CH=CH—, —N=CH—, (CH$_2$)$_a$—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0, optionally includes 1 or 2 nitrogens as heteroatoms on the phenyl residue,
the carbons of the heteroaryl group are each independently optionally substituted with a substituent selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
a and b are independently 1, 2, or 3.
c and d are independently 1 or 2,
n and p are independently 0, 1, 2 or 3,
k is 0, 1, or 2,
each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and wherein for each A and A', B may be attached to either side of A and A' so that in the example of A or A' being

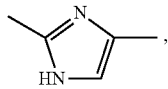, the A-B-A' can be any of:

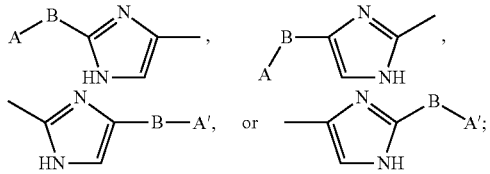

$R^c$, $R^d$, $R^e$ and $R^f$ are each independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
  each hetero atom, if present, is independently N, O or S,
  each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
  $R^c$ and $R^d$ are optionally joined to form a 4- to 8-membered heterocycle which is optionally fused to another 3- to 6-membered heterocycle or heteroaryl ring, and
  $R^e$ and $R^f$ are optionally joined to form a 4- to 8-membered heterocycle which is optionally fused to another 3- to 6-membered heterocycle or heteroaryl ring;
Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, $-[U-(CR^4{}_2)_t-NR^5-(CR^4{}_2)_t]_u-U-(CR^4{}_2)_t-NR^7-(CR^4{}_2)_t-R^8$, $-U-(CR^4{}_2)_t-R^8$ and $-[U-(CR^4{}_2)_t-NR^5-(CR^4{}_2)_t]_u-U-(CR^4{}_2)_t-O-(CR^4{}_2)_t-R^8$, wherein,
  U is selected from the group consisting of $-C(O)-$, $-C(S)-$ and $-S(O)_2-$,
  each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl,
  $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, $-C(O)-R^{81}$, $-C(S)-R^{81}$, $-C(O)-O-R^{81}$, $-C(O)-N-R^{81}{}_2$, $-S(O)_2-R^{81}$ and $-S(O)_2-N-R^{81}{}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl,
  optionally, $R^7$ and $R^8$ together form a 4-7 membered ring,
  each t is independently 0, 1, 2, 3, or 4, and
  u is 0, 1, or 2.

In a first embodiment of the fifth aspect, each

is independently selected from the group consisting of

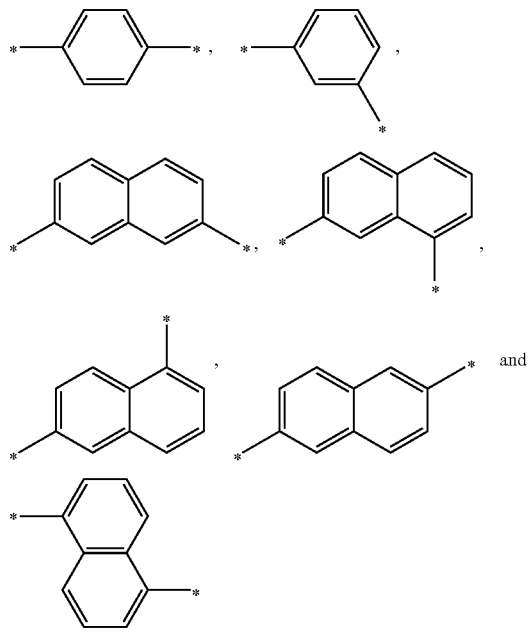

wherein * indicates attachment points to the remainder of the compound, and each phenyl residue optionally includes 1 or 2 nitrogens as heteroatoms.

In a second embodiment of the fifth aspect, A and A' are independently selected from the group consisting of a single bond, $-(CR_2)_n-C(O)-(CR_2)_p-$, $-(CR_2)_n-O-(CR_2)_p-$, $-(CR_2)_n-N(R^N)-(CR_2)_p-$, $-(CR_2)_n-C(O)-N(R^N)-(CR_2)_p-$, $-(CR_2)_n-N(R^N)-C(O)-N(R^N)-(CR_2)_p-$ and $-(CR_2)_n-N(R^N)-C(O)-O-(CR_2)_p-$ and a heteroaryl group selected from the group consisting of

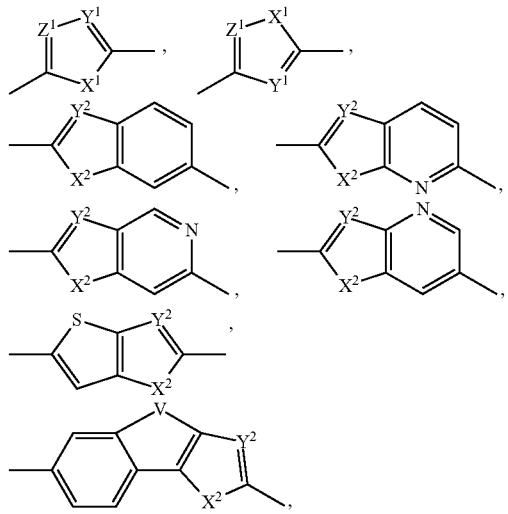

-continued

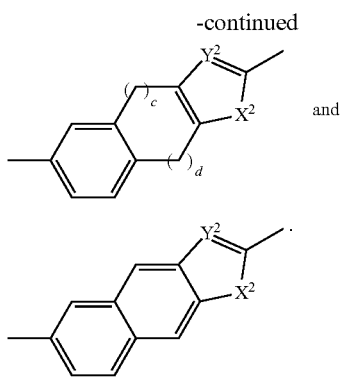

In a third embodiment of the fifth aspect, A and A' are independently selected from the group consisting of a single bond

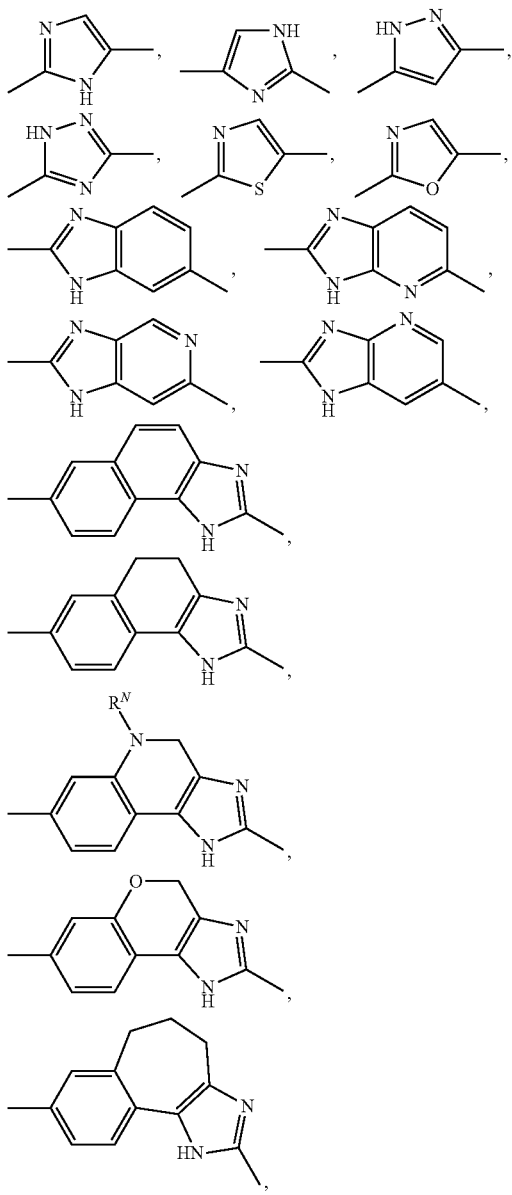

-continued

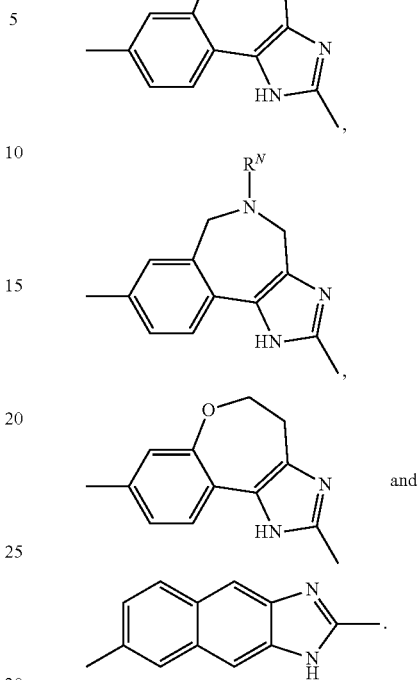

In a fourth embodiment of the fifth aspect, A and A' are each independently

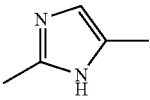

or —$(CR_2)_n$—$C(O)N(R^N)$—$(CR_2)_p$—.

In a sixth aspect of the invention, in any compound of the second through fifth aspects, $R^c$, $R^d$, $R^e$ and $R^f$ are each independently selected from the group consisting of: hydrogen, $C_1$ to $C_8$ alkyl and $C_1$ to $C_8$ heteroalkyl, wherein, each hetero atom, if present, is independently N, O or S, $R^c$ and $R^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In a first embodiment of the sixth aspect, one of $R^c$ and $R^d$ or $R^e$ and $R^f$ are joined to form a 4- to 8-membered heterocycle which is optionally fused to another 3- to 6-membered heterocycle.

In a second embodiment of the sixth aspect, both of $R^c$ and $R^d$ and $R^e$ and $R^f$ are joined to form a 4- to 8-membered heterocycle which is optionally fused to another 3- to 6-membered heterocycle.

In a third embodiment of the sixth aspect, $R^c$ and $R^d$ are joined and form a heterocyclic fused ring system selected from the group consisting of:

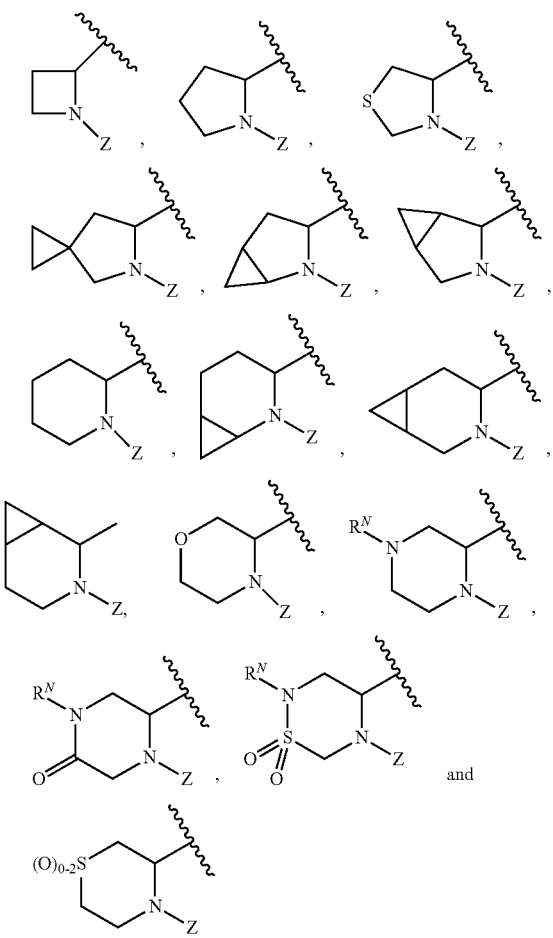

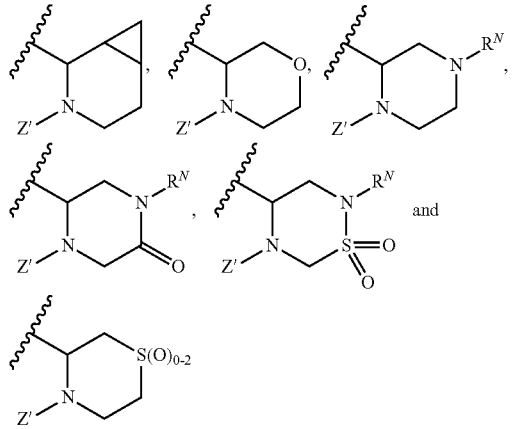

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a fourth embodiment of the sixth aspect, $R^e$ and $R^f$ are joined and form a heterocyclic fused ring system selected from the group consisting of:

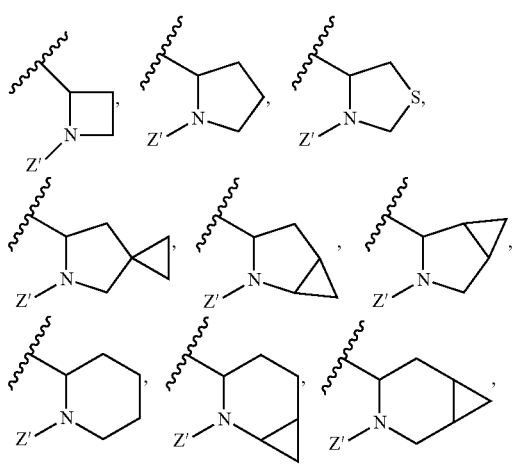

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a seventh aspect of the invention, each $R^a$, if present in a compound of any of the second through sixth aspects, is independently —CN, —OCF$_3$, —OCHF$_2$, —CF$_3$, or —F.

In an eighth aspect of the invention, if present in any compound of any of the previous aspects, one of Y and Y' is N.

In a first embodiment of the eighth aspect, both Y and Y' are N.

In a ninth aspect of the invention, Z and Z' in any of the previous aspects are each 1-3 amino acids.

In a first embodiment of the ninth aspect, the amino acids are in the D configuration.

In a tenth aspect of the invention, Z and Z' in any of the previous aspects are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$.

In a first embodiment of the tenth aspect, one or both of Z and Z' are —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a second embodiment of the tenth aspect, one or both of Z and Z' are —U—(CR$^4_2$)$_t$—NR$^5$—(CR$^4_2$)$_t$—U—(CR$^4_2$)$_t$—NR$^7$—(CR$^4_2$)$_t$—R$^8$.

In a third embodiment of the tenth aspect, one or both of Z and Z' are —U—(CR$^4_2$)$_t$—NR$^7$—(CR$^4_2$)$_t$—R$^8$.

In a fourth embodiment of the tenth aspect, one or both of Z and Z' are —[C(O)—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a fifth embodiment of the tenth aspect, one or both of Z and Z' are —C(O)—(CR$^4_2$)$_t$—NR$^5$—(CR$^4_2$)$_t$—U—(CR$^4_2$)$_t$—NR$^7$—(CR$^4_2$)$_t$—R$^8$.

In a sixth embodiment of the tenth aspect, one or both of Z and Z' are —[C(O)—(CR$^4_2$)$_t$—NR$^5$—(CR$^4_2$)$_t$]$_u$—C(O)—(CR$^4_2$)$_t$—NR$^7$—(CR$^4_2$)$_t$—R$^8$.

In a seventh embodiment of the tenth aspect, one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

In an eighth embodiment of the tenth aspect, one or both of Z and Z' are —C(O)—(CR$^4_2$)$_t$—NR$^7$—(CR$^4_2$)$_t$—R$^8$.

In a ninth embodiment of the tenth aspect, one or both of Z and Z' are —C(O)—(CR$^4_2$)$_n$—NR$^7$—(CR$^4_2$)$_n$—C(O)—R$^{81}$.

In a tenth embodiment of the tenth aspect, one or both of Z and Z' are —C(O)—(CR$^4_2$)$_n$—NR$^7$—C(O)—R$^{81}$.

In an eleventh embodiment of the tenth aspect, one or both of Z and Z' are —C(O)—(CR$^4_2$)$_n$—NR$^7$—(CR$^4_2$)$_n$—C(O)—O—R$^{81}$.

In a twelfth embodiment of the tenth aspect, one or both of Z and Z' are —C(O)—(CR$^4_2$)$_n$—NR$^7$—C(O)—O—R$^{81}$.

In a thirteenth embodiment of the tenth aspect, one or both of Z and Z' are —U—(CR$^4_2$)$_t$—R$^8$.

In a fourteenth embodiment of the tenth aspect, one or both of Z and Z' are —C(O)—(CR$^4_2$)$_t$—R$^8$.

In a fifteenth embodiment of the tenth aspect, one or both of Z and Z' are —[U—(CR$^4_2$)$_t$—NR$^5$—(CR$^4_2$)$_t$]$_u$—U—(CR$^4_2$)$_t$—O—(CR$^4_2$)$_t$—R$^8$.

In a sixteenth embodiment of the tenth aspect, one or both of Z and Z' are —U—(CR$^4_2$)$_t$—NR$^5$—(CR$^4_2$)$_t$—U—(CR$^4_2$)$_t$—O—(CR$^4_2$)$_t$—R$^8$.

In a seventeenth embodiment of the tenth aspect, one or both of Z and Z' are —C(O)—(CR$^4_2$)$_t$—NR$^5$—(CR$^4_2$)$_t$—C(O)—(CR$^4_2$)$_t$—O—(CR$^4_2$)$_t$—R$^8$.

In an eighteenth embodiment of the tenth aspect, one or both of Z and Z' are —U—(CR$^4_2$)$_t$—O—(CR$^4_2$)$_t$—R$^8$.

In a nineteenth embodiment of the tenth aspect, one or both of Z and Z' are —C(O)—(CR$^4_2$)$_t$—O—(CR$^4_2$)$_t$—R$^8$.

In a twentieth embodiment of the tenth aspect, one or both of Z and Z' are —C(O)—(CR$^4_2$)$_n$—NR$^7$—R$^8$ wherein R$^7$ and R$^8$ together form a 4-7 membered ring.

In an eleventh aspect of the invention, compounds have formula VII:

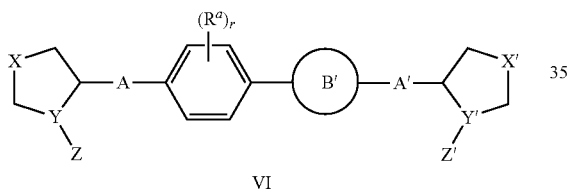

VI wherein,

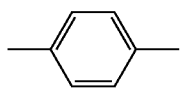

may include 1 or 2 nitrogens as heteroatoms, r is from 0 to 4, each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

A and A' are independently selected from the group consisting of

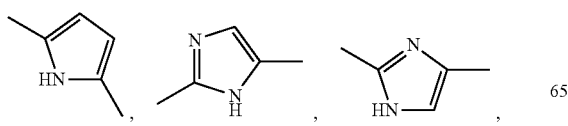

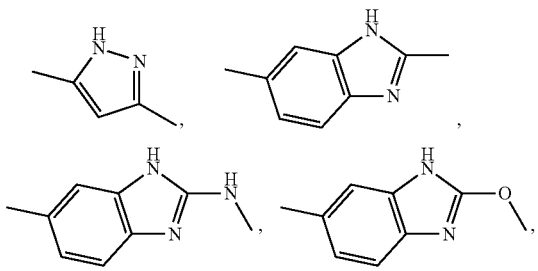

—(CR$_2$)$_n$—C(O)—(CR$_2$)$_p$—, —(CR$_2$)$_n$—O—(CR$_2$)$_p$— and —(CR$_2$)$_n$—C(O)N(R$^N$)—(CR$_2$)$_p$—, wherein, if A or A' is a heteroaryl group, it is optionally substituted with one or more of the substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and n and p are independently 0, 1, or 2, each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and for each A and A',

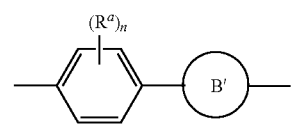

may be attached to either side of A and A' so that in the example of A or A' being

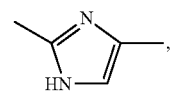

the

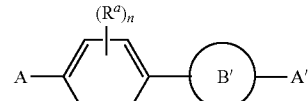

can be any of:

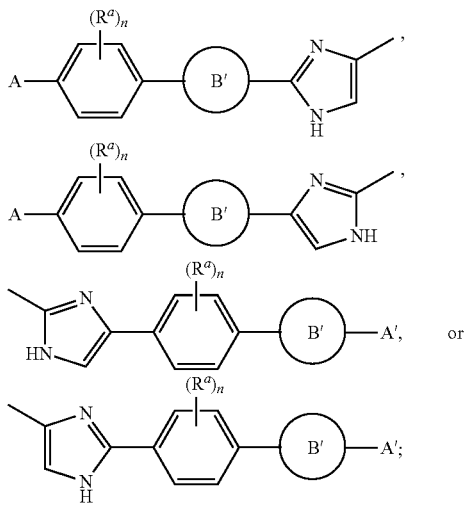

B' is

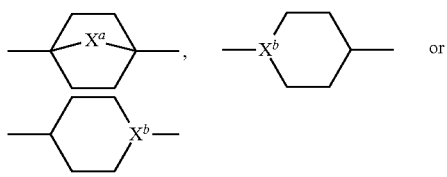

wherein,

B' is optionally substituted with between 1 and 4 substituents, each independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino and oxo, X$^a$ is chosen from the group consisting of —CH$_2$—, —CH$_2$—CH$_2$—, —CH=CH—, —O—, —S—, —S(=O)$_2$—, —CH$_2$—O—, —NR$^1$— and —CH$_2$—NR$^1$— wherein R$^1$ is chosen from the group consisting of hydrogen, C$_1$ to C$_8$ alkyl, and C$_1$ to C$_8$ heteroalkyl, and X$^b$ is either C or N;

X and X' are each either present or absent and if present, independently selected from the group consisting of a bond, —CH$_2$—, —CH$_2$—CH$_2$—, —CH=CH—, —O—, —S—, —S(O)$_2$—, —CH$_2$O—, —CH$_2$S—, —CH$_2$S(O)$_2$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl and aralkyl Y and Y' are each independently carbon or nitrogen; and Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4$$_2$)$_t$—NR$^5$—(CR$^4$$_2$)$_t$]$_u$—U—(CR$^4$$_2$)$_t$—NR$^7$—(CR$^4$$_2$)$_t$—R$^8$, —U—(CR$^4$$_2$)$_t$—R$^8$ and —[U—(CR$^4$$_2$)$_t$—NR$^5$—(CR$^4$$_2$)$_t$]$_u$—U—(CR$^4$$_2$)$_t$—O—(CR$^4$$_2$)$_t$—R$^8$, wherein, U is selected from the group consisting of —C(O)—, —C(S)— and —S(O)$_2$—, each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}$$_2$, —S(O)$_2$—R$^{81}$ and —S(O)$_2$—N—R$^{81}$$_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

In a twelfth aspect of the invention, compounds have formula VIII:

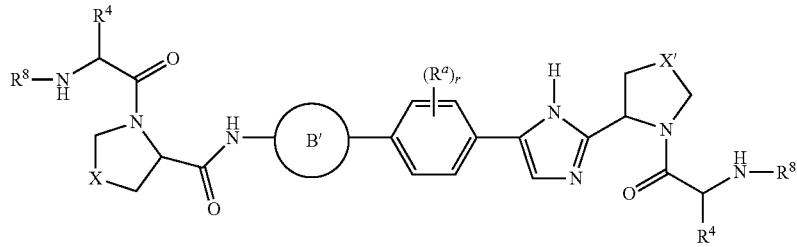

wherein:

B' is selected from the group consisting of

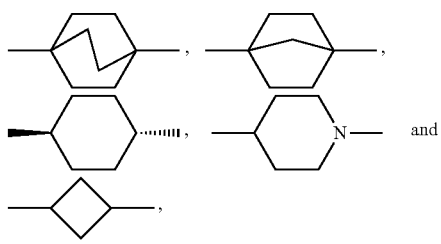

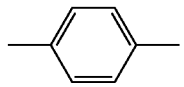

optionally includes 1 or 2 nitrogens as heteroatoms;

each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;

each $R^8$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, —C(O)—R$^{81}$, —C(S)—R$^{81}$, —C(O)—O—R$^{81}$, —C(O)—N—R$^{81}{}_2$, —S(O)$_2$—R$^{81}$, —S(O)$_2$—N—R$^{81}{}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl; and each $R^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

In a thirteenth aspect of the invention, compounds have formula IX:

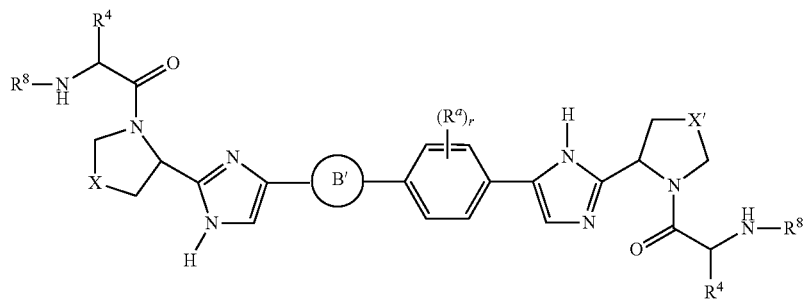

wherein:

B' is selected from the group consisting of

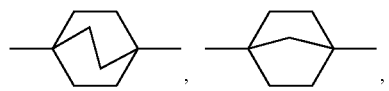

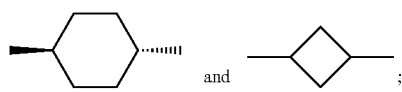

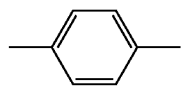

optionally includes 1, 2, 3, or 4 nitrogens as heteroatoms;

each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;

each $R^8$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, —C(O)—R$^{81}$, —C(S)—R$^{81}$, —C(O)—O—R$^{81}$, —C(O)—N—R$^{81}{}_2$, —S(O)$_2$—R$^{81}$, —S(O)$_2$—N—R$^{81}{}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl; and each $R^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

In a fourteenth aspect of the invention, compounds have formula X:

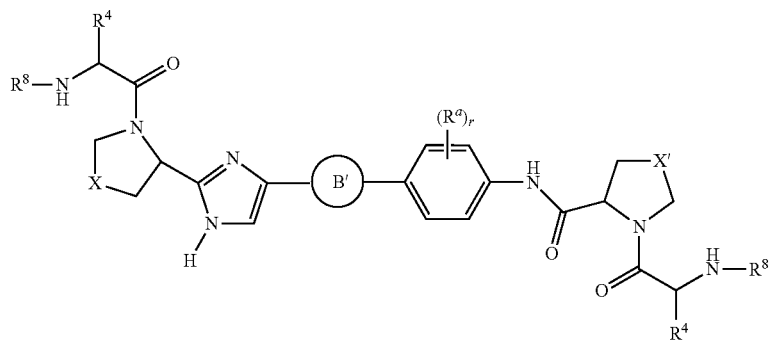

wherein:

B' is selected from the group consisting of

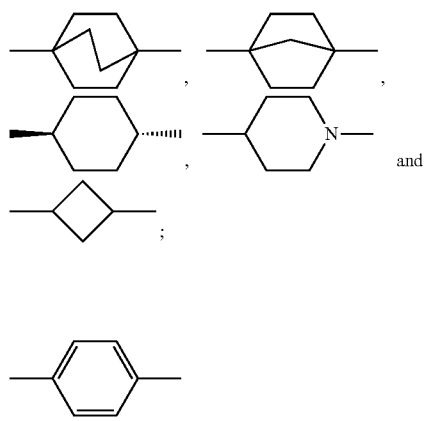

optionally includes 1 or 2 nitrogens as heteroatoms;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —$CH_2$—, —$CH_2$—$CH_2$—, —CH=CH—, —O—, —S—, —S(O)$_{1-2}$—, —$CH_2$O—, —$CH_2$S—, —$CH_2$S(O)$_{1-2}$— and —$CH_2$N($R^1$)—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl;

each $R^8$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, —C(O)—$R^{81}$, —C(S)—$R^{81}$, —C(O)—O—$R^{81}$, —C(O)—N—$R^{81}{}_2$, —S(O)$_2$—$R^{81}$, —S(O)$_2$—N—$R^{81}{}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl; and each $R^4$ is independently selected from the group consisting of hydrogen, $C_1$ to $C_8$ alkyl, $C_1$ to $C_8$ heteroalkyl, cycloalkyl, heterocycle, aryl, heteroaryl and aralkyl.

In a fifteenth aspect of the invention, compounds have formula XI:

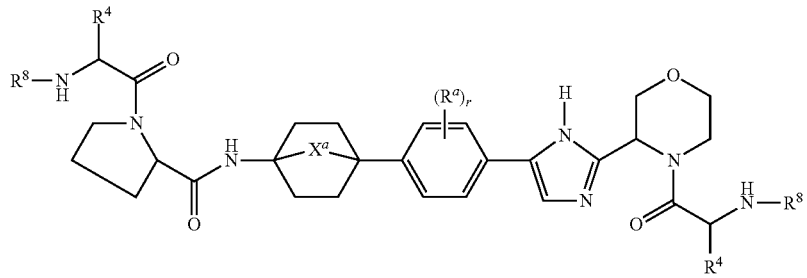

wherein:

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

$X^a$ is chosen from the group consisting of —$CH_2$—, —$CH_2$—$CH_2$—, —CH=CH—, —O—, —S—, —S(=O)$_2$—, —$CH_2$—O—, —$NR^1$— and —$CH_2$—$NR^1$— wherein $R^1$ is chosen from the group consisting of hydrogen, $C_1$ to $C_8$ alkyl, and $C_1$ to $C_8$ heteroalkyl, each $R^8$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, —C(O)—$R^{81}$, —C(S)—$R^{81}$, —C(O)—O—$R^{81}$, —C(O)—N—$R^{81}_2$, —S(O)$_2$—$R^{81}$, —S(O)$_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl; and each $R^4$ is independently selected from the group consisting of hydrogen, $C_1$ to $C_8$ alkyl, $C_1$ to $C_8$ heteroalkyl, cycloalkyl, heterocycle, aryl, heteroaryl and aralkyl.

The sixteenth aspect of the invention provides a pharmaceutical composition comprising the compounds of the invention.

The seventeenth aspect of the invention provides the use of the compounds of the invention in the manufacture of a medicament.

In a first embodiment of the seventeenth aspect, the medicament is for the treatment of hepatitis C.

The eighteenth aspect of the invention provides a method of treating hepatitis C comprising administering to a subject in need thereof, a therapeutically effective amount of a compound of the invention.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5$^{th}$ Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

The term "alkanoyl" as used herein contemplates a carbonyl group with a lower alkyl group as a substituent.

The term "alkenyl" as used herein contemplates substituted or unsubstituted, straight and branched chain alkene radicals, including both the E- and Z-forms, containing from two to eight carbon atoms. The alkenyl group may be optionally substituted with one or more substituents selected from the group consisting of halogen, —CN, —NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, S(O)R, SO$_2$R, —SO$_3$R, —S(O)$_2$N(R$^N$)$_2$, phosphate, phosphonate, cycloalkyl, cycloalkenyl, aryl and heteroaryl.

The term "alkoxy" as used herein contemplates an oxygen with a lower alkyl group as a substituent and includes methoxy, ethoxy, butoxy, trifluoromethoxy and the like. It also includes divalent substituents linked to two separated oxygen atoms such as, without limitation, —O—(CH$_2$)$_{1-4}$—O—, —O—CF$_2$—O—, —O—(CH$_2$)$_{1-4}$—O—(CH$_2$CH$_2$—O)$_{1-4}$— and —(O—CH$_2$CH$_2$—O)$_{1-4}$—.

The term "alkoxycarbonyl" as used herein contemplates a carbonyl group with an alkoxy group as a substituent.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "alkylene," "alkenylene" and "alkynylene" as used herein refers to the groups "alkyl," "alkenyl" and "alkynyl" respectively, when they are divalent, ie, attached to two atoms.

The term "alkylsulfonyl" as used herein contemplates a sulfonyl group which has a lower alkyl group as a substituent.

The term "alkynyl" as used herein contemplates substituted or unsubstituted, straight and branched carbon chain containing from two to eight carbon atoms and having at least one carbon-carbon triple bond. The term alkynyl includes, for example ethynyl, 1-propynyl, 2-propynyl, 1-butynyl, 3-methyl-1-butynyl and the like. The alkynyl group may be optionally substituted with one or more substituents selected from halo, —CN, NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "amino" as used herein contemplates a group of the structure —NR$^N_2$.

The term "amino acid" as used herein contemplates a group of the structure

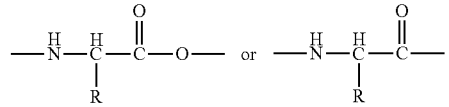

in either the D or the L configuration and includes but is not limited to the twenty "standard" amino acids: isoleucine, leucine, lysine, methionine, phenylalanine, threonine, tryptophan, valine, alanine, asparagine, aspartate, cysteine, glutamate, glutamine, glycine, proline, serine, tyrosine, arginine and histidine. The present invention also includes, without limitation, D-configuration amino acids, beta-amino acids, amino acids having side chains as well as all non-natural amino acids known to one skilled in the art.

The term "aralkyl" as used herein contemplates a lower alkyl group which has as a substituent an aromatic group, which aromatic group may be substituted or unsubstituted. The aralkyl group may be optionally substituted with one or more substituents selected from halogen, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —$CO_2R$, —$C(O)R$, —O—R, —$N(R^N)_2$, —$N(R^N)C(O)R$, —$N(R^N)S(O)_2R$, —SR, —$C(O)N(R^N)_2$, —$OC(O)R$, —$OC(O)N(R^N)_2$, —SOR, —$SO_2R$, —$SO_3R$, —$S(O)_2N(R^N)_2$, —$SiR_3$, —$P(O)R$, phosphate, phosphonate, cycloalkyl, cycloalkenyl, aryl and heteroaryl.

The term "arylsulfonyl" as used herein contemplates a sulfonyl group which has as a substituent an aryl group. The term is meant to include, without limitation, monovalent as well as multiply valent aryls (eg, divalent aryls).

The term "carbamoyl" as used herein contemplates a group of the structure

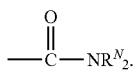

The term "carbonyl" as used herein contemplates a group of the structure

The term "carboxyl" as used herein contemplates a group of the structure

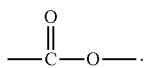

The term "cycloalkyl" as used herein contemplates substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from halo, —CN, —$NO_2$, —$CO_2R$, —C(O)R, —O—R, —$N(R^N)_2$, —$N(R^N)C(O)R$, —$N(R^N)S(O)_2R$, —SR, —$C(O)N(R^N)_2$, —$OC(O)R$, —$OC(O)N(R^N)_2$, —SOR, —$SO_2R$, —$S(O)_2N(R^N)_2$, phosphate, phosphonate, alkyl, cycloalkenyl, aryl and heteroaryl.

The term "cycloalkenyl" as used herein contemplates substituted or unsubstituted cyclic alkenyl radicals containing from four to twelve carbon atoms in which there is at least one double bond between two of the ring carbons and includes cyclopentenyl, cyclohexenyl and the like. The term "cycloalkenyl" also includes polycyclic systems having two rings in which two or more atoms are common to two adjoining rings (the rings are "fused"). The cycloalkenyl group may be optionally substituted with one or more substituents selected from halo, —CN, —$NO_2$, —$CO_2R$, —C(O)R, —O—R, —$N(R^N)_2$, —$N(R^N)C(O)R$, —$N(R^N)S(O)_2R$, —SR, —$C(O)N(R^N)_2$, —$OC(O)R$, —$OC(O)N(R^N)_2$, —SOR, —$SO_2R$, —$S(O)_2N(R^N)_2$, phosphate, phosphonate, alkyl, cycloalkenyl, aryl and heteroaryl.

The term "halo" or "halogen" as used herein includes fluorine, chlorine, bromine and iodine.

The term "heteroalkyl" as used herein contemplates an alkyl with one or more heteroatoms.

The term "heteroatom", particularly within a ring system, refers to N, O and S.

The term "heterocyclic group," "heterocycle" or "heterocyclic ring" as used herein contemplates substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidino and the like and cyclic ethers, such as tetrahydrofuran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —CN, —$NO_2$, —$CO_2R$, —C(O)R, —O—R, —$N(R^N)_2$, —$N(R^N)C(O)R$, —$N(R^N)S(O)_2R$, —SR, —$C(O)N(R^N)_2$, —$OC(O)R$, —$OC(O)N(R^N)_2$, —SOR, —$SO_2R$, —$SO_3R$, —$S(O)_2N(R^N)_2$, —$SiR_3$, —$P(O)R$, phosphate, phosphonate, cycloalkyl, cycloalkenyl, aryl and heteroaryl.

The term "oxo" as used herein contemplates an oxygen atom attached with a double bond.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

The terms "phosphate" and "phosphonate" as used herein refer to the moieties having the following structures, respectively:

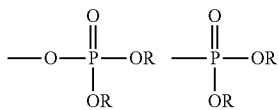

The terms "salts" and "hydrates" refers to the hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity, flowability and manufacturability of the resulting bulk drug.

The term sulfonamide as used herein contemplates a group having the structure

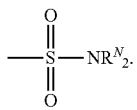

The term "sulfonate" as used herein contemplates a group having the structure

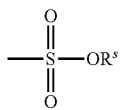

wherein $R^s$ is selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkanoyl, or $C_1$-$C_{10}$ alkoxycarbonyl.

The term "sulfonyl" as used herein contemplates a group having the structure

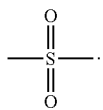

"Substituted sulfonyl" as used herein contemplates a group having the structure

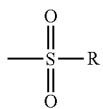

including, but not limited to alkylsulfonyl and arylsulfonyl.

The term "thiocarbonyl," as used herein, means a carbonyl wherein an oxygen atom has been replaced with a sulfur.

Each R is independently selected from hydrogen, —OH, —CN, —NO$_2$, halogen, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino, and oxo.

Each $R^N$ is independently selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide. Two $R^N$ may be taken together with C, O, N or S to which they are attached to form a five to seven membered ring which may optionally contain a further heteroatom.

The compounds of the present invention may be used to inhibit or reduce the activity of HCV, particularly HCV's NS5A protein. In these contexts, inhibition and reduction of activity of the NS5A protein refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100%, or any number in between, may be preferred for particular applications.

In a first aspect, compounds of formula I are provided:

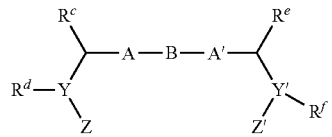

wherein,

A and A' are independently selected from the group consisting of a single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—S(O)$_k$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$—, —(CR$_2$)$_n$—C(O)—O—(CR$_2$)$_p$—, —(CR$_2$)$_n$—N(R$^N$)—S(O)$_k$—N(R$^N$)—(CR$_2$)$_p$— and —(CR$_2$)$_n$—N(R$^N$)—C(O)—O—(CR$_2$)$_p$— and a heteroaryl group selected from the group consisting of

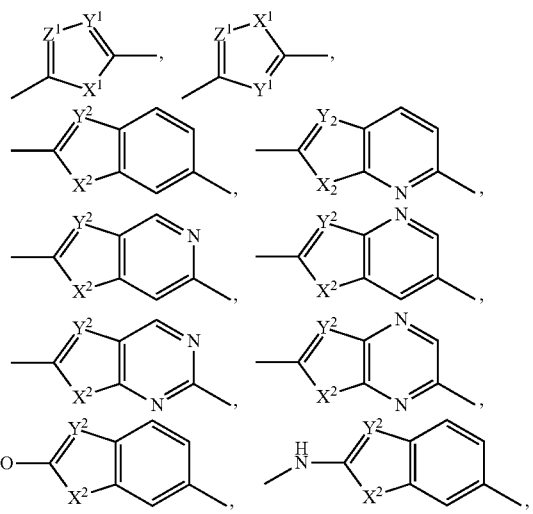

-continued

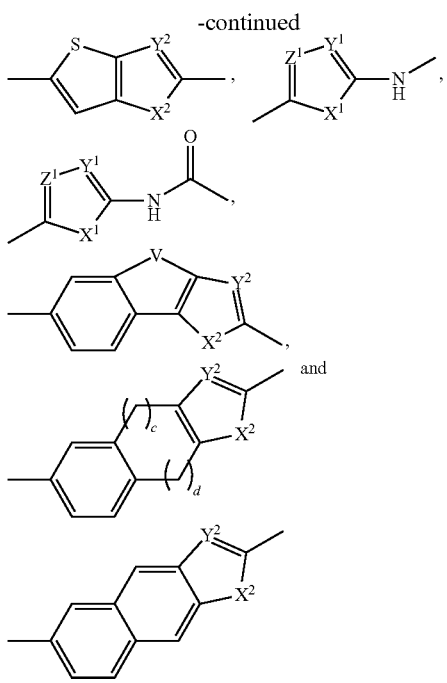

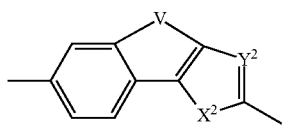

wherein:
$X^1$ is $CH_2$, NH, O or S,
$Y^1$, $Y^2$ and $Z^1$ are each independently CH or N,
$X^2$ is NH, O or S,
V is —$CH_2$—$CH_2$—, —CH=CH—, —N=CH—, —$(CH_2)_a$—$N(R^N)$—$(CH_2)_b$— or —$(CH_2)_a$—O—$(CH_2)_b$—, wherein a and b are independently 0, 1, 2, or 3 with the proviso that a and b are not both 0,

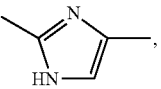

optionally includes 1 or 2 nitrogens as heteroatoms on the phenyl residue,
the carbons of the heteroaryl group are each independently optionally substituted with a substituent selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
a and b are independently 1, 2, or 3.
c and d are independently 1 or 2,
n and p are independently 0, 1, 2 or 3,
k is 0, 1, or 2,
each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, each $R^N$ is independently selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and wherein for each A and A', B may be attached to either side of A and A' so that in the example of A or A' being

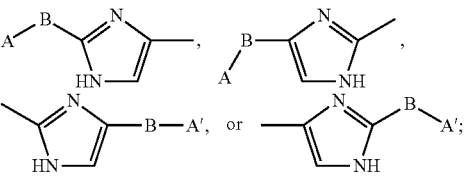

the A-B-A' can be any of:

B is Q or Q-Q, wherein each Q is independently selected from the group consisting of a cycloalkyl group, cycloalkenyl group, heterocycle, aryl group or heteroaryl group, with the proviso that only one Q is a six member aromatic ring when B is Q-Q and with the proviso that if B is Q-Q, any Q is that is polycyclic is connected to the remainder of the molecule through only one cycle of the polycycle;

$R^c$, $R^d$, $R^e$ and $R^f$ are each independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
each hetero atom, if present, is independently N, O or S,
each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
$R^c$ and $R^d$ are optionally joined to form a 4- to 8-membered heterocycle which is optionally fused to another 3- to 6-membered heterocycle or heteroaryl ring, and
$R^e$ and $R^f$ are optionally joined to form a 4- to 8-membered heterocycle which is optionally fused to another 3- to 6-membered heterocycle or heteroaryl ring;

Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—$(CR^4_2)_t$—$NR^5$—$(CR^4_2)_t]_u$—U—$(CR^4_2)_t$—$NR^7$—$(CR^4_2)_t$—$R^8$, —U—$(CR^4_2)_t$—$R^8$ and —[U—$(CR^4_2)_t$—$NR^5$—$(CR^4_2)_t]_u$—U—$(CR^4_2)_t$—O—$(CR^4_2)_t$—$R^8$, wherein,
U is selected from the group consisting of —C(O)—, —C(S)— and —S(O)$_2$—,
each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, R[8] is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R[81], —C(S)—R[81], —C(O)—O—R[81], —C(O)—N—R[81]$_2$, —S(O)$_2$—R[81] and —S(O)$_2$—N—R[81]$_2$, wherein each R[81] is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, R[7] and R[8] together form a 4-7 membered ring, each t is independently 0, 1, 2, 3, or 4, and u is 0, 1, or 2.

The compounds of the present invention include pharmaceutically acceptable salts of I as well as an optically pure enantiomer, racemate or diastereomeric mixtures thereof.

In a first embodiment of the first aspect, each Q is independently optionally substituted with one or more substituents each independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and if Q is not aromatic, it is optionally substituted with oxo.

In a second embodiment of the first aspect, each Q is independently optionally substituted with —CN, —OCF$_3$, —OCHF$_2$, —CF$_3$, or —F.

In a third embodiment of the first aspect, B is selected from the group consisting of

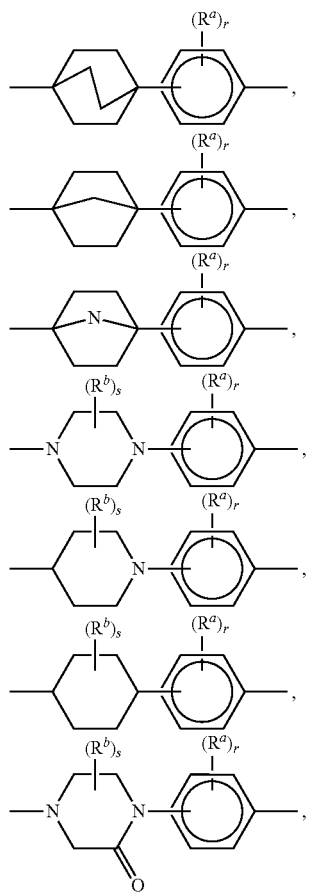

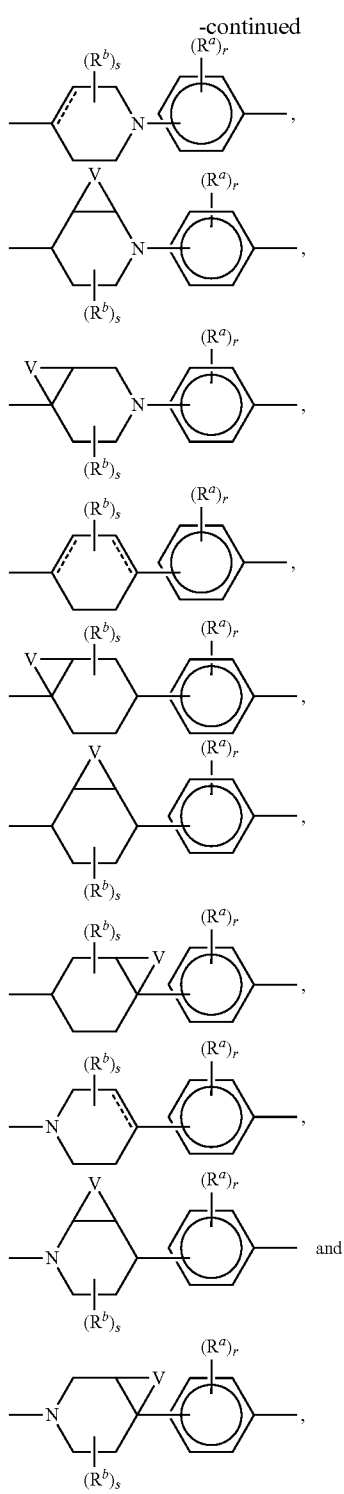

wherein:

is a divalent aryl or heteroaryl group which may be polycyclic with varying connective patterns;

V is —CH$_2$—, —CH$_2$—CH$_2$—, —CH=CH—, —N=CH—, (CH$_2$)$_a$—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0;

each r and s is independently 0, 1, 2, 3, or 4;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each R$^b$ is independently C$_1$-C$_{12}$ alkyl, hydroxyl, halogen or oxo.

In a fourth embodiment of the first aspect,

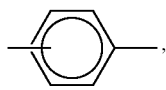

if present, is selected from the group consisting of

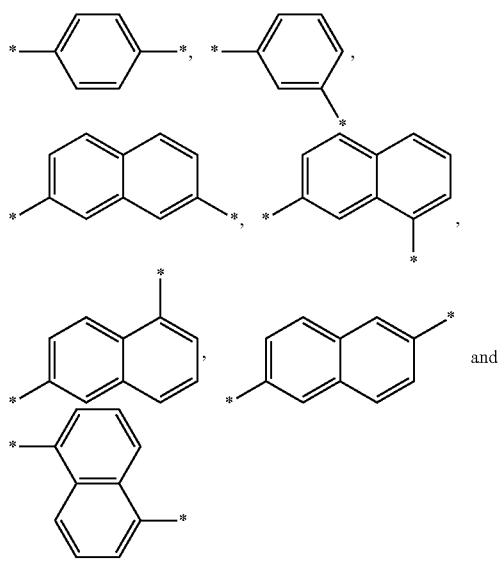

wherein * indicates attachment points to the remainder of the compound, and each phenyl residue optionally includes 1 or 2 nitrogens as heteroatoms.

In a fifth embodiment of the first aspect, each R$^a$, if present, is independently —CN, —OCF$_3$, —OCHF$_2$, —CF$_3$, or —F.

In a sixth embodiment of the first aspect, A and A' are independently selected from the group consisting of a single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$— and —(CR$_2$)$_n$—N(R$^N$)—C(O)—O—(CR$_2$)$_p$— and a heteroaryl group selected from the group consisting of

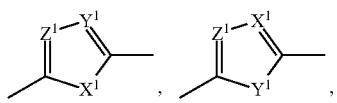

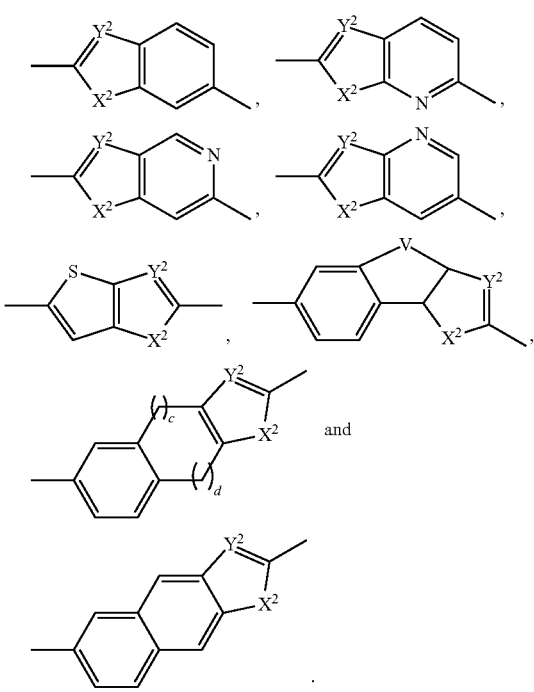

In a seventh embodiment of the first aspect, A and A' are independently selected from the group consisting of a single bond,

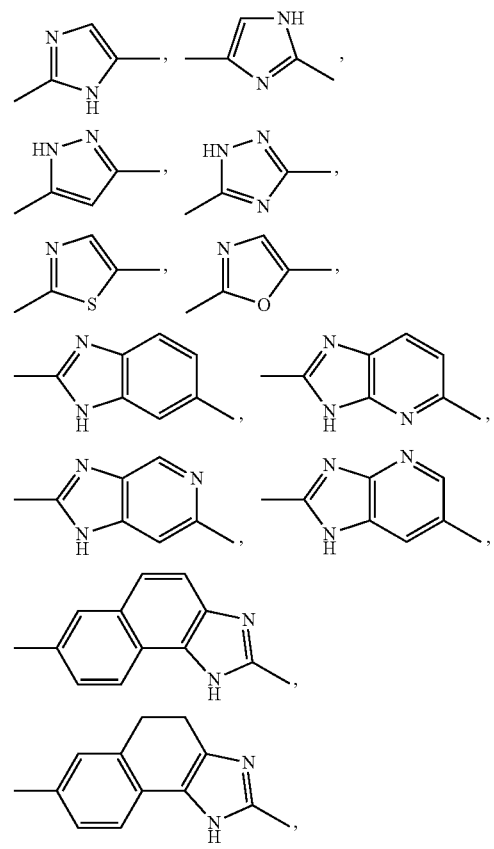

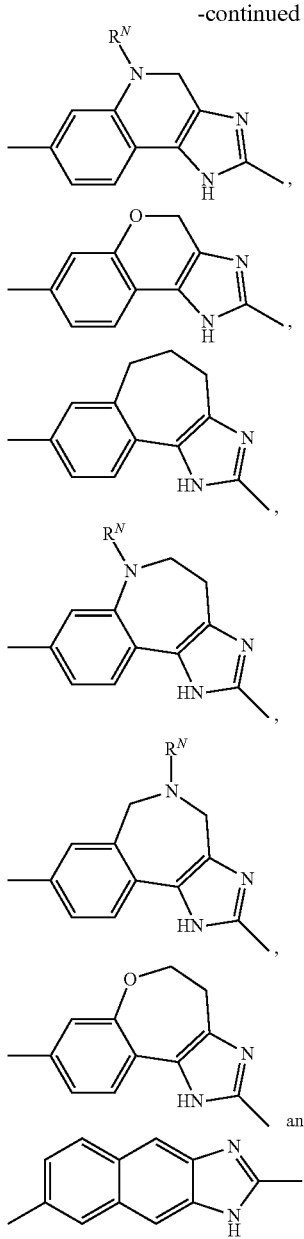

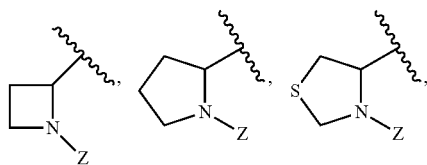

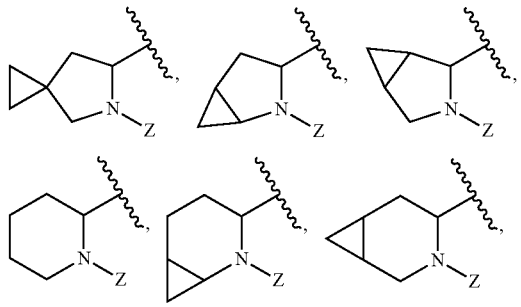

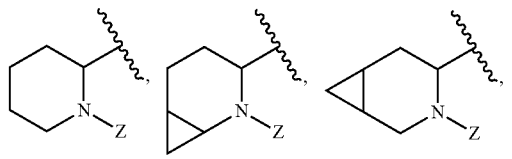

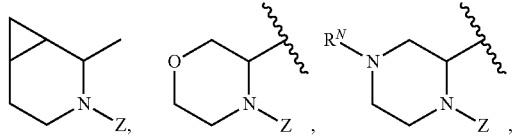

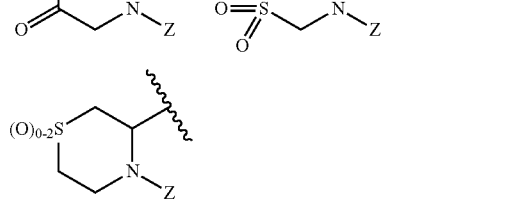

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In an eleventh embodiment of the first aspect, $R^e$ and $R^f$ are joined and form a heterocyclic fused ring system selected from the group consisting of:

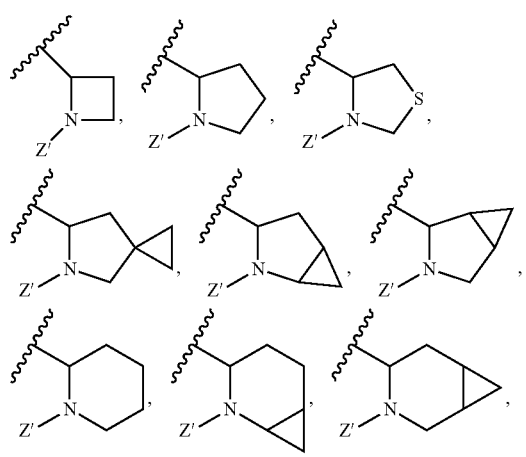

In an eighth embodiment of the first aspect, $R^c$, $R^d$, $R^e$ and $R^f$ are each independently selected from the group consisting of: hydrogen, $C_1$ to $C_8$ alkyl and $C_1$ to $C_8$ heteroalkyl, wherein,
  each hetero atom, if present, is independently N, O or S,
  $R^c$ and $R^d$ are optionally joined to form a 4- to 8-membered heterocycle which is optionally fused to another 3- to 6-membered heterocycle, and
  $R^e$ and $R^f$ are optionally joined to form a 4- to 8-membered heterocycle which is optionally fused to another 3- to 6-membered heterocycle.

In a ninth embodiment of the first aspect, one or both of $R^c$ and $R^d$ or $R^e$ and $R^f$ are optionally joined to form a 4- to 8-membered heterocycle which is optionally fused to another 3- to 6-membered heterocycle.

In a tenth embodiment of the first aspect, $R^c$ and $R^d$ are joined and form a heterocyclic fused ring system selected from the group consisting of:

-continued

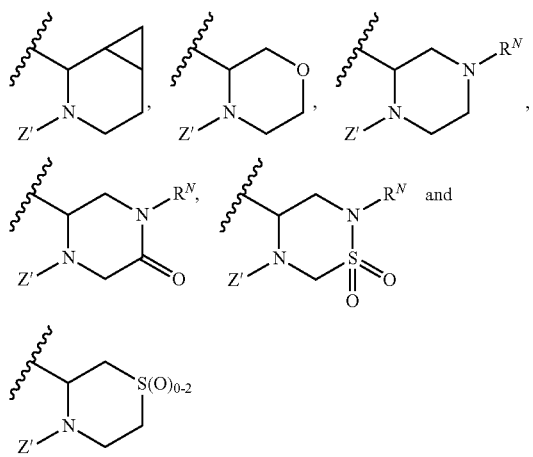

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula III:

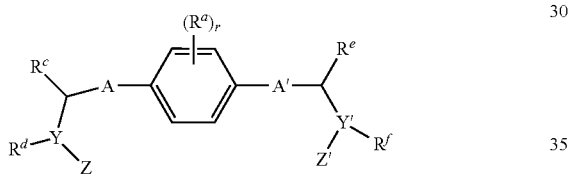

wherein

A is selected from the group consisting of

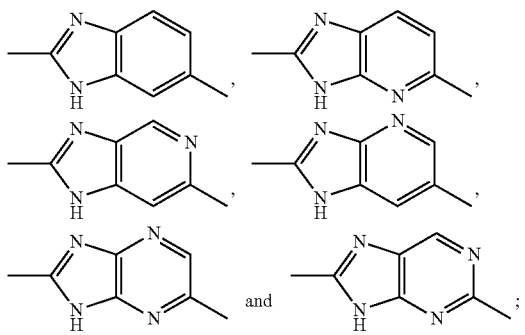

and ;

A' is selected from the group consisting of single bond,

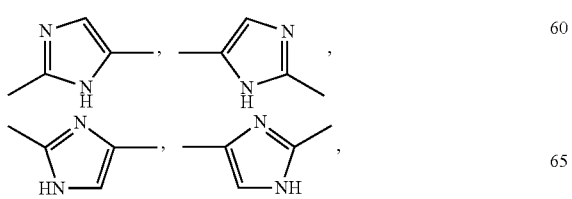

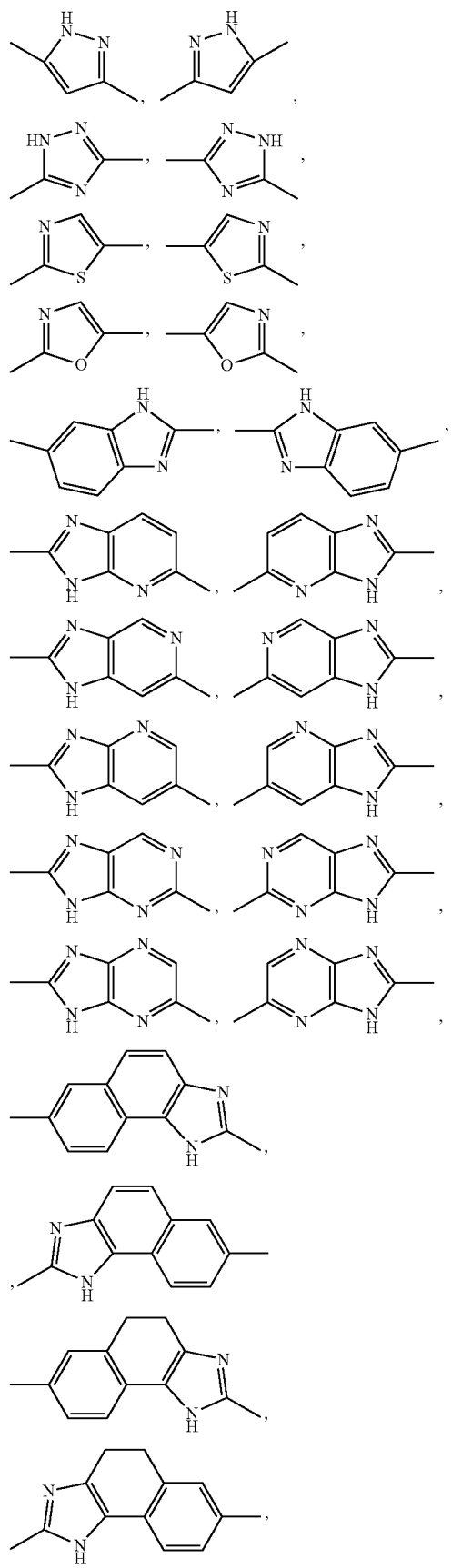

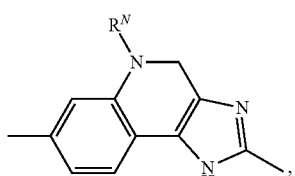,

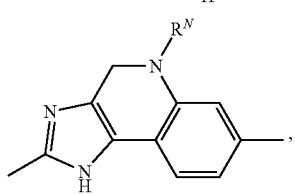,

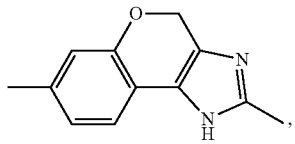,

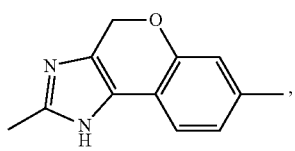,

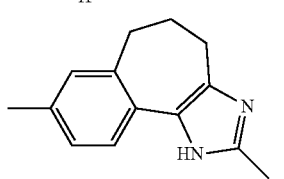,

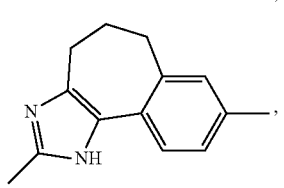,

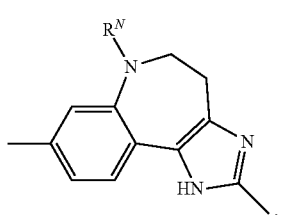,

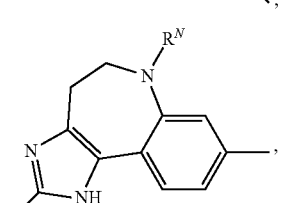,

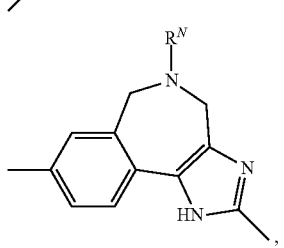,

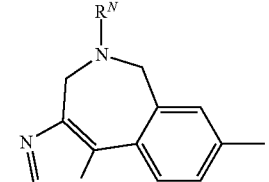,

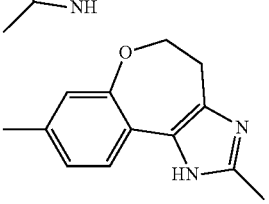,

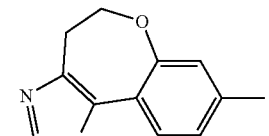,

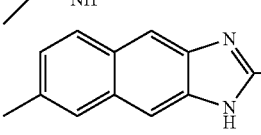,

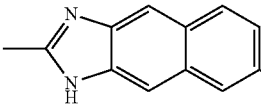,

—(CR$_2$)$_n$—C(O)—(CR$_2$)$_p$—, —(CR$_2$)$_n$—O—(CR$_2$)$_p$—, —(CR$_2$)$_n$—C(O)N(R$^N$)—(CR$_2$)$_p$— and —(CR$_2$)$_n$—N(R$^N$)C(O)—(CR$_2$)$_p$— wherein R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

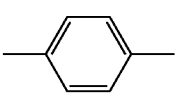

optionally includes 1 or 2 nitrogens as heteroatoms;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
r is selected from the group consisting of 0, 1, 2, 3, or 4.

The compounds of the present invention include pharmaceutically acceptable salts of III as well as an optically pure enantiomer, racemate or diastereomeric mixtures thereof.

In a first embodiment of the second aspect, A' is

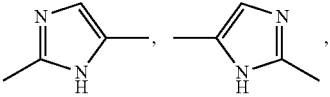

—(CR$_2$)$_n$—C(O)—(CR$_2$)$_p$—, —(CR$_2$)$_n$—C(O)N(R$^N$)—(CR$_2$)$_p$—, or —(CR$_2$)$_n$—N(R$^N$)C(O)—(CR$_2$)$_p$—.

In a second embodiment of the second aspect, A' is

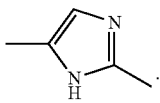

In a third embodiment of the second aspect, compounds have formula IIIa:

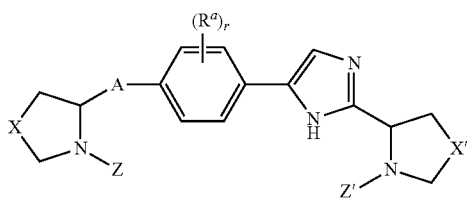

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIa as well as an optically pure enantiomer, racemate or diastereomeric mixtures thereof.

In a fourth embodiment of the second aspect, compounds have formula III wherein A' is selected from the group consisting of

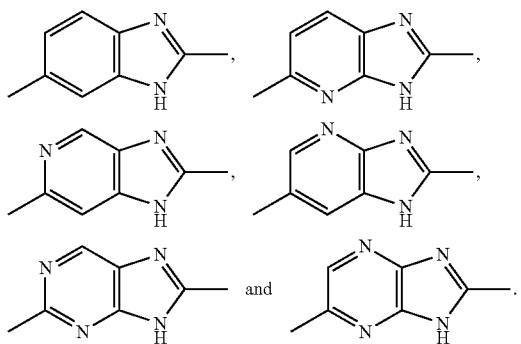

In a fifth embodiment of the second aspect, compounds have formula IIIb:

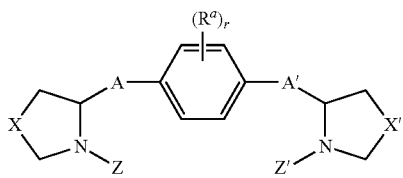

wherein:
A is selected from the group consisting of

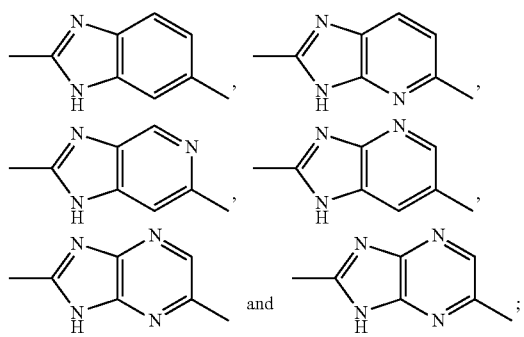

A' is selected from the group consisting of

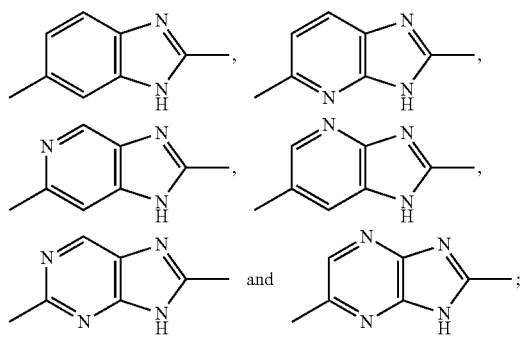

and
X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IIIb as well as an optically pure enantiomer, racemate or diastereomeric mixtures thereof.

In a third aspect of the invention, compounds have formula IV:

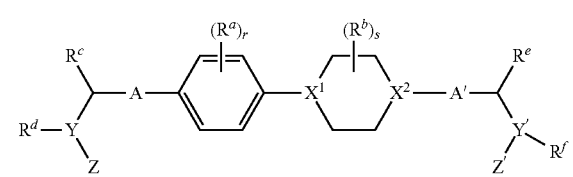

wherein
A and A' are independently selected from the group consisting of single bond,

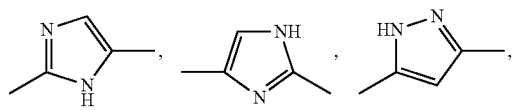

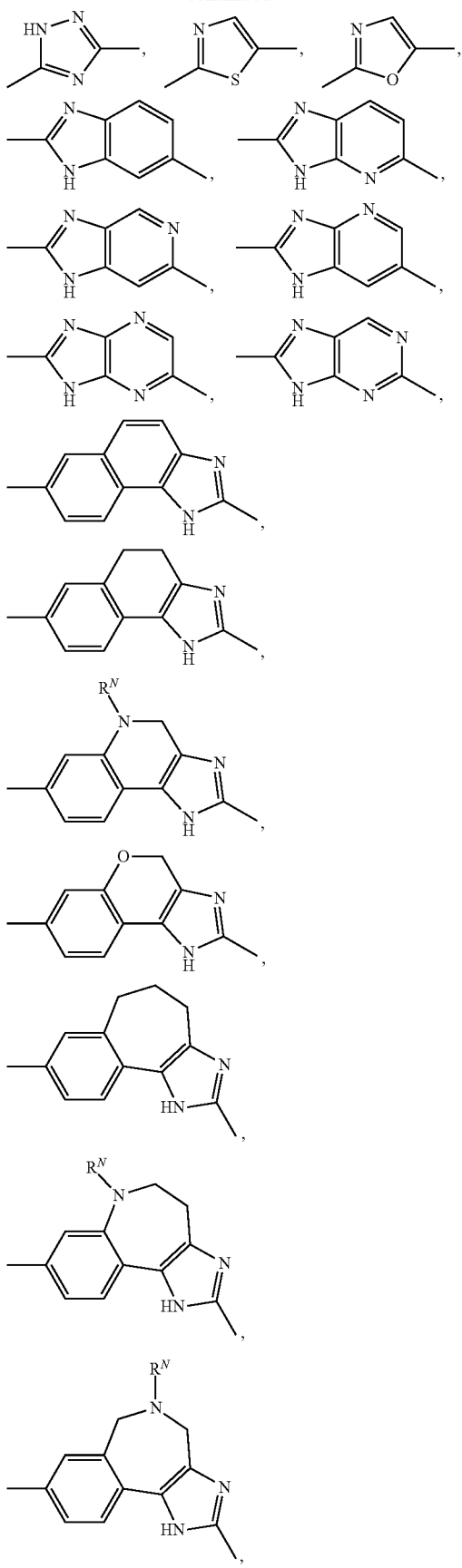

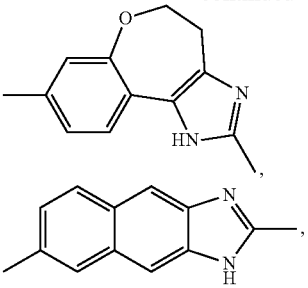

—(CR$_2$)$_n$—C(O)—(CR$_2$)$_p$—, —(CR$_2$)$_n$—O—(CR$_2$)$_p$— and —(CR$_2$)$_n$—C(O)N(R$^N$)—(CR$_2$)$_p$—, wherein: R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

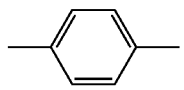

optionally includes 1 or 2 nitrogens as heteroatoms;
  each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  r is 0, 1, 2, 3 or 4;
  each R$^b$ is independently C$_1$-C$_5$ alkyl, hydroxyl, halogen, or oxo;
  s is 0, 1, 2, 3, 4, 5, or 6; and
  each of X$^1$ and X$^2$ are independently C or N.

The compounds of the present invention include pharmaceutically acceptable salts of IV as well as an optically pure enantiomer, racemate or diastereomeric mixtures thereof.

In a first embodiment of the third aspect, A and A' are each independently

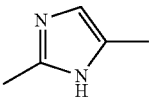

or —(CR$_2$)$_n$—C(O)N(R$^N$)—(CR$_2$)$_p$—.

In a second embodiment of the third aspect, compounds have formula IVa:

![Formula IVa structure]

The compounds of the present invention include pharmaceutically acceptable salts of IVa as well as an optically pure enantiomer, racemate or diastereomeric mixtures thereof.

In a third embodiment of the third aspect, compounds have formula IVb:

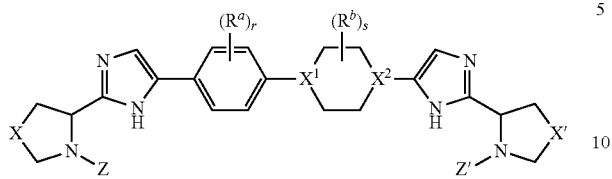

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of IVb as well as an optically pure enantiomer, racemate or diastereomeric mixtures thereof.

In a fourth aspect of the invention, compounds have formula V:

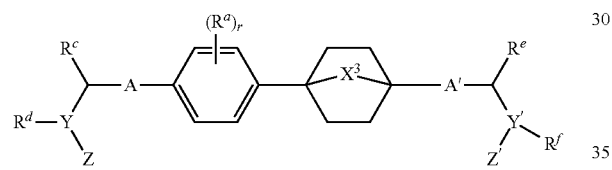

wherein

A and A' are independently selected from the group consisting of single bond,

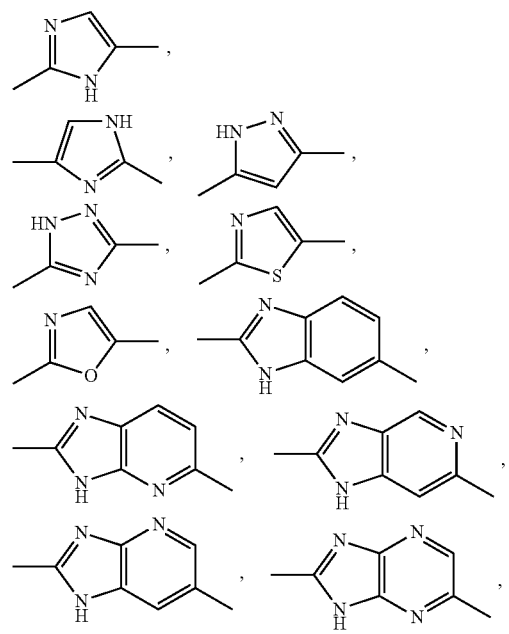

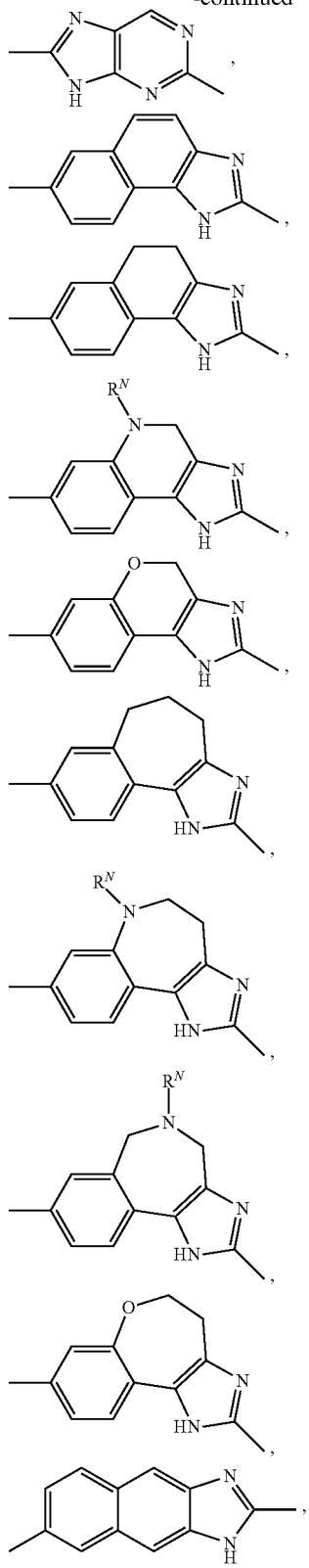

—(CR$_2$)$_n$—C(O)—(CR$_2$)$_p$—, —(CR$_2$)$_n$—O—(CR$_2$)$_p$— and —(CR$_2$)$_n$—C(O)—N(R$^N$)—(CR$_2$)$_p$—, wherein R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

$X^3$ is chosen from the group consisting of —$CH_2$—, —$CH_2$—$CH_2$—, —CH=CH—, —O—, —S—, —S(O)$_{1-2}$—, —$CH_2$—O—, —$NR^1$— and —$CH_2$—$NR^1$— wherein $R^1$ is chosen from the group consisting of hydrogen, $C_1$ to $C_8$ alkyl, and $C_1$ to $C_8$ heteroalkyl;

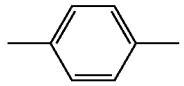

optionally includes 1 or 2 nitrogens as heteroatoms;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is 0, 1, 2, 3 or 4.

The compounds of the present invention include pharmaceutically acceptable salts of V as well as an optically pure enantiomer, racemate or diastereomeric mixtures thereof.

In a first embodiment of the fourth aspect, A and A' are each independently

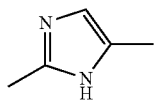

or —$(CR_2)_n$—C(O)N($R^N$)—$(CR_2)_p$—.

In a second embodiment of the fourth aspect, compounds have formula Va:

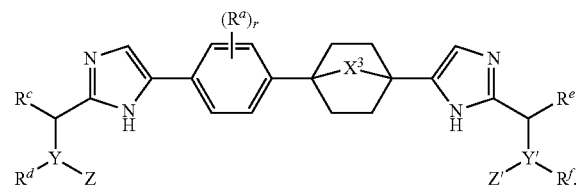

The compounds of the present invention include pharmaceutically acceptable salts of Va as well as an optically pure enantiomer, racemate or diastereomeric mixtures thereof.

In a third embodiment of the fourth aspect, compounds have formula Vb:

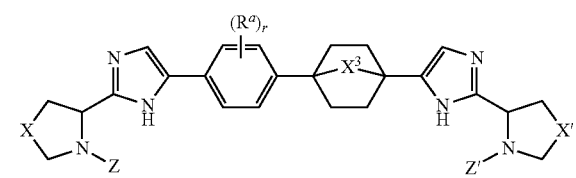

wherein X and X' are each independently selected from the group consisting of a bond, —$CH_2$—, —$CH_2$—$CH_2$—, —CH=CH—, —O—, —S—, —S(O)$_{1-2}$—, —$CH_2$O—, —$CH_2$S—, —$CH_2$S(O)$_{1-2}$— and —$CH_2$N($R^1$)—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

The compounds of the present invention include pharmaceutically acceptable salts of Vb as well as an optically pure enantiomer, racemate or diastereomeric mixtures thereof.

In a fifth aspect of the invention, compounds have formula VI:

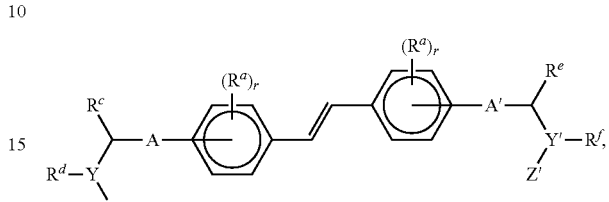

wherein each

is independently a divalent aryl or heteroaryl group which may be polycyclic with varying connective patterns;

each r is independently 0, 1, 2, 3, or 4;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

A and A' are independently selected from the group consisting of a single bond, —$(CR_2)_n$—C(O)—$(CR_2)_p$—, —$(CR_2)_n$—O—$(CR_2)_p$—, —$(CR_2)_n$—N($R^N$)—$(CR_2)_p$—, —$(CR_2)_n$—S(O)$_k$—N($R^N$)—$(CR_2)_p$—, —$(CR_2)_n$—C(O)—N($R^N$)—$(CR_2)_p$—, —$(CR_2)_n$—N($R^N$)—C(O)—N($R^N$)—$(CR_2)_p$—, —$(CR_2)_n$—C(O)—O—$(CR_2)_p$—, —$(CR_2)_n$—N($R^N$)—S(O)$_k$—N($R^N$)—$(CR_2)_p$— and —$(CR_2)_n$—N($R^N$)—C(O)—O—$(CR_2)_p$— and a heteroaryl group selected from the group consisting of

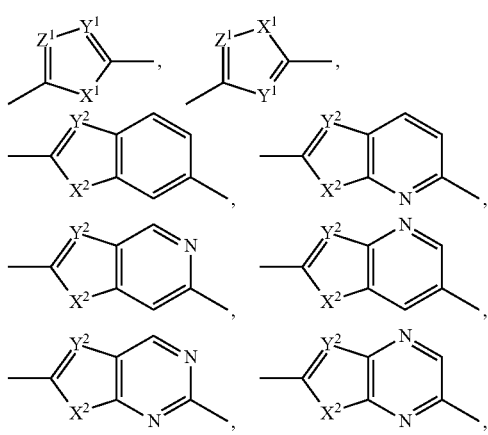

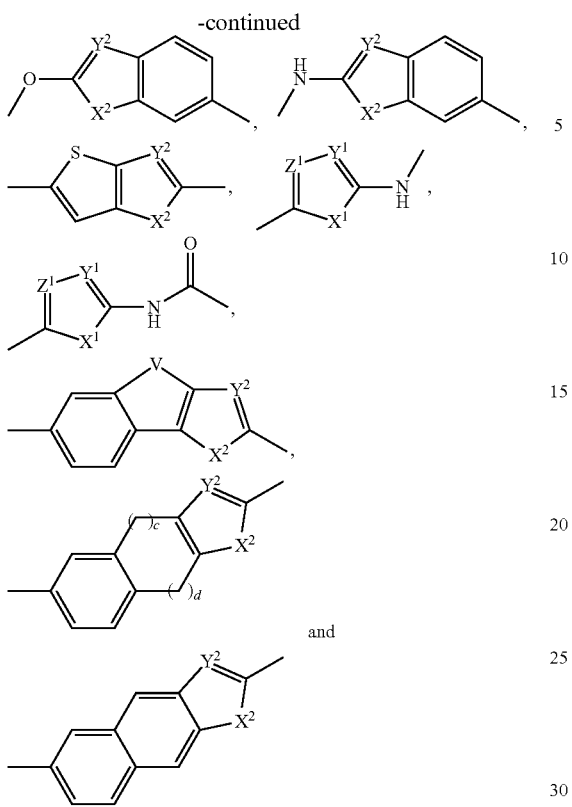

and wherein:
X$^1$ is CH$_2$, NH, O or S,
Y$^1$, Y$^2$ and Z$^1$ are each independently CH or N,
X$^2$ is NH, O or S,
V is —CH$_2$—CH$_2$—, —CH=CH—, —N=CH—, (CH$_2$)$_a$—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0,

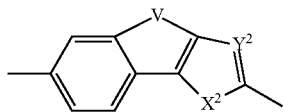

optionally includes 1 or 2 nitrogens as heteroatoms on the phenyl residue,
the carbons of the heteroaryl group are each independently optionally substituted with a substituent selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
a and b are independently 1, 2, or 3.
c and d are independently 1 or 2, n and p are independently 0, 1, 2 or 3,
k is 0, 1, or 2,
each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and
wherein for each A and A', B may be attached to either side of A and A' so that in the example of A or A' being

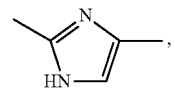

the A-B-A' can be any of:

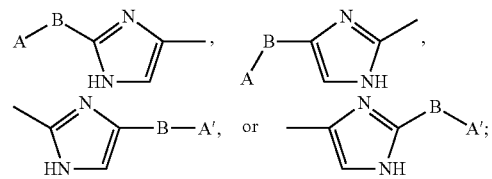

R$^c$, R$^d$, R$^e$ and R$^f$ are each independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein,
each hetero atom, if present, is independently N, O or S,
each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S,
R$^c$ and R$^d$ are optionally joined to form a 4- to 8-membered heterocycle which is optionally fused to another 3- to 6-membered heterocycle or heteroaryl ring, and
R$^e$ and R$^f$ are optionally joined to form a 4- to 8-membered heterocycle which is optionally fused to another 3- to 6-membered heterocycle or heteroaryl ring;
Y and Y' are each independently carbon or nitrogen; and
Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein,
U is selected from the group consisting of —C(O)—, —C(S)— and —S(O)$_2$—,
each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl,
R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}{}_2$, —S(O)$_2$—R$^{81}$ and —S(O)$_2$—N—R$^{81}{}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

The compounds of the present invention include pharmaceutically acceptable salts of VI as well as an optically pure enantiomer, racemate or diastereomeric mixtures thereof.

In a first embodiment of the fifth aspect, each

is independently selected from the group consisting of

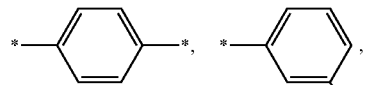

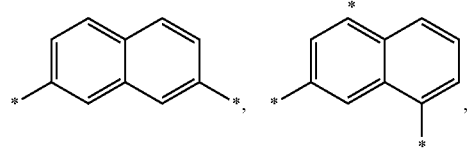

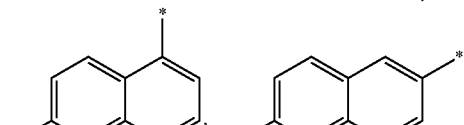

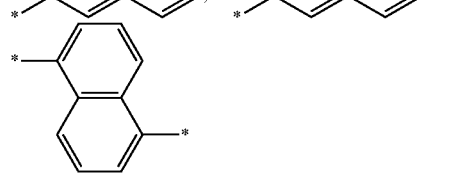

wherein * indicates attachment points to the remainder of the compound and each phenyl residue optionally includes 1 or 2 nitrogens as heteroatoms.

In a second embodiment of the fifth aspect, A and A' are independently selected from the group consisting of a single bond, —(CR$_2$)$_n$—O—(CR$_2$)$_p$—, —(CR$_2$)$_n$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$— and —(CR$_2$)$_n$—N(R$^N$)—C(O)—O—(CR$_2$)$_p$— and a heteroaryl group selected from the group consisting of

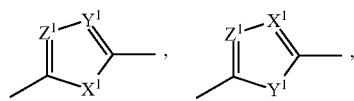

-continued

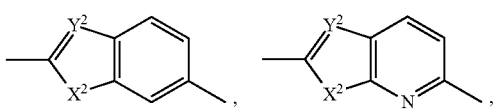

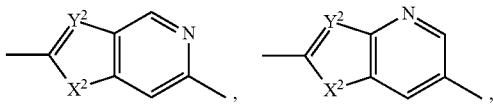

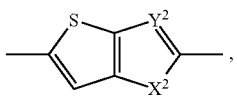

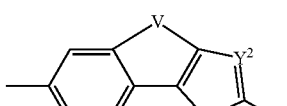

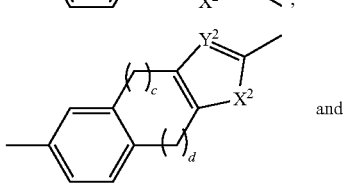

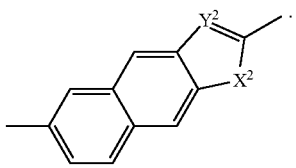

In a third embodiment of the fifth aspect, A and A' are independently selected from the group consisting of a single bond,

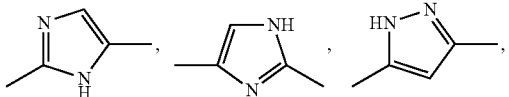

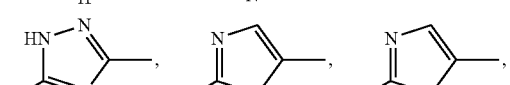

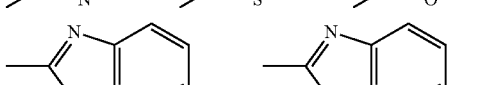

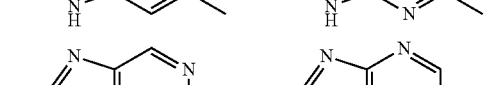

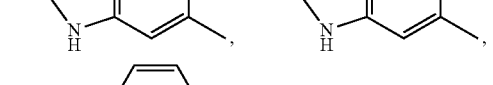

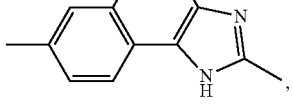

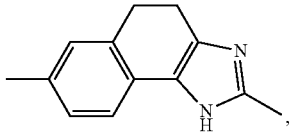

-continued

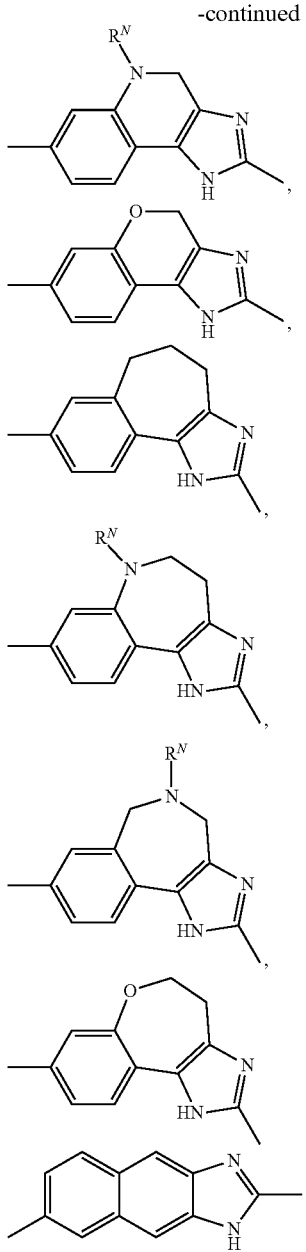

In a fourth embodiment of the fifth aspect, A and A' are each independently

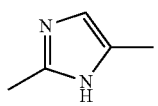

or —(CR$_2$)$_n$—C(O)N(R$^N$)—(CR$_2$)$_p$—.

In a sixth aspect of the invention, in any compound of the second through fifth aspects, R$^c$, R$^d$, R$^e$ and R$^f$ are each independently selected from the group consisting of: hydrogen, C$_1$ to C$_8$ alkyl and C$_1$ to C$_8$ heteroalkyl, wherein,
each hetero atom, if present, is independently N, O or S,
R$^c$ and R$^d$ are optionally joined to form a 4- to 8-membered heterocycle which is optionally fused to another 3- to 6-membered heterocycle, and R$^e$ and R$^f$ are optionally joined to form a 4- to 8-membered heterocycle which is optionally fused to another 3- to 6-membered heterocycle.

In a first embodiment of the sixth aspect, one of R$^c$ and R$^d$ or R$^e$ and R$^f$ are joined to form a 4- to 8-membered heterocycle which is optionally fused to another 3- to 6-membered heterocycle.

In a second embodiment of the sixth aspect, both of R$^c$ and R$^d$ and R$^e$ and R$^f$ are joined to form a 4- to 8-membered heterocycle which is optionally fused to another 3- to 6-membered heterocycle.

In a third embodiment of the sixth aspect, R$^c$ and R$^d$ are joined and form a heterocyclic fused ring system selected from the group consisting of:

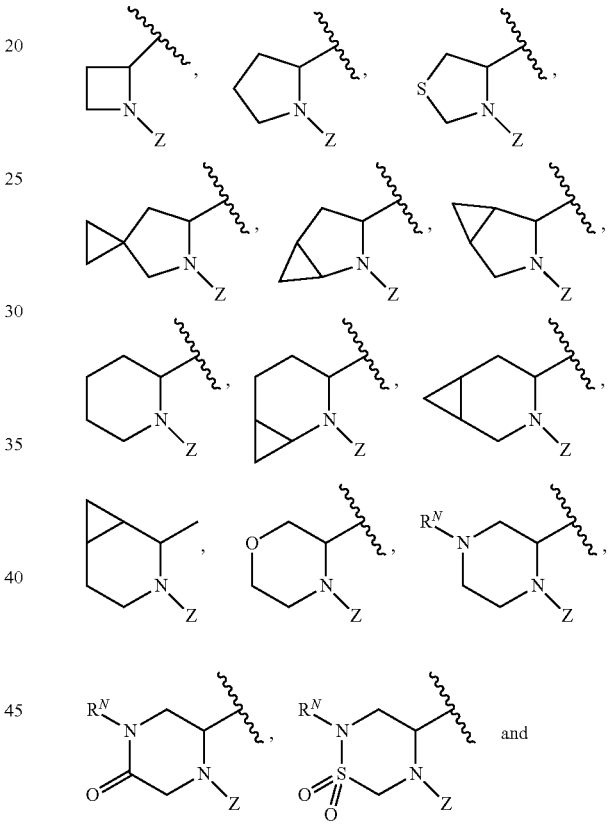

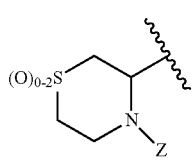

wherein R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a fourth embodiment of the sixth aspect, R$^e$ and R$^f$ are joined and form a heterocyclic fused ring system selected from the group consisting of:

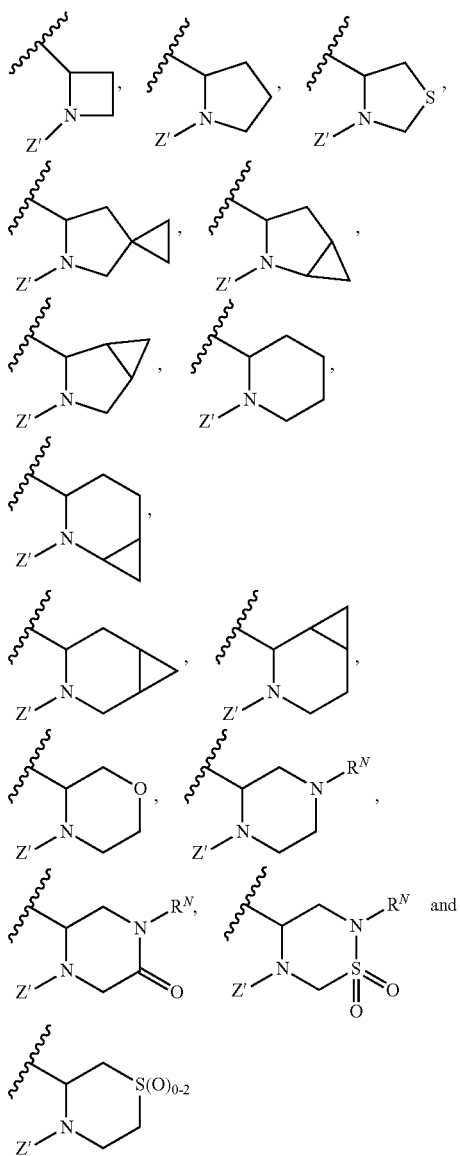

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a seventh aspect of the invention, each $R^a$, if present in a compound of any of the second through sixth aspects, is independently —CN, —OCF$_3$, —OCHF$_2$, —CF$_3$, or —F.

In an eighth aspect of the invention, if present in any compound of any of the previous aspects, one of Y and Y' is N.

In a first embodiment of the eighth aspect, both Y and Y' are N.

In a ninth aspect of the invention, Z and Z' in any of the previous aspects are each 1-3 amino acids.

In a first embodiment of the ninth aspect, the amino acids are in the D configuration.

In a tenth aspect of the invention, Z and Z' in any of the previous aspects are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$.

In a first embodiment of the tenth aspect, one or both of Z and Z' are —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a second embodiment of the tenth aspect, one or both of Z and Z' are —U—(CR$^4_2$)$_t$—NR$^5$—(CR$^4_2$)$_t$—U—(CR$^4_2$)$_t$—NR$^7$—(CR$^4_2$)$_t$—R$^8$.

In a third embodiment of the tenth aspect, one or both of Z and Z' are —U—(CR$^4_2$)$_t$—NR$^7$—(CR$^4_2$)$_t$—R$^8$.

In a fourth embodiment of the tenth aspect, one or both of Z and Z' are —[C(O)—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a fifth embodiment of the tenth aspect, one or both of Z and Z' are —C(O)—(CR$^4_2$)$_t$—NR$^5$—(CR$^4_2$)$_t$—U—(CR$^4_2$)$_t$—NR$^7$—(CR$^4_2$)$_t$—R$^8$.

In a sixth embodiment of the tenth aspect, one or both of Z and Z' are —[C(O)—(CR$^4_2$)$_t$—NR$^5$—(CR$^4_2$)$_t$]$_u$—C(O)—(CR$^4_2$)$_t$—NR$^7$—(CR$^4_2$)$_t$—R$^8$.

In a seventh embodiment of the tenth aspect, one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

In an eighth embodiment of the tenth aspect, one or both of Z and Z' are —C(O)—(CR$^4_2$)$_t$—NR$^7$—(CR$^4_2$)$_t$—R$^8$.

In a ninth embodiment of the tenth aspect, one or both of Z and Z' are —C(O)—(CR$^4_2$)$_n$—NR$^7$—(CR$^4_2$)$_n$—C(O)—R$^{81}$.

In a tenth embodiment of the tenth aspect, one or both of Z and Z' are —C(O)—(CR$^4_2$)$_n$—NR$^7$—C(O)—R$^{81}$.

In an eleventh embodiment of the tenth aspect, one or both of Z and Z' are —C(O)—(CR$^4_2$)$_n$—NR$^7$—(CR$^4_2$)$_n$—C(O)—O—R$^{81}$.

In a twelfth embodiment of the tenth aspect, one or both of Z and Z' are —C(O)—(CR$^4_2$)$_n$—NR$^7$—C(O)—O—R$^{81}$.

In a thirteenth embodiment of the tenth aspect, one or both of Z and Z' are —U—(CR$^4_2$)$_t$—R$^8$.

In a fourteenth embodiment of the tenth aspect, one or both of Z and Z' are —C(O)—(CR$^4_2$)$_t$—R$^8$.

In a fifteenth embodiment of the tenth aspect, one or both of Z and Z' are —[U—(CR$^4_2$)$_t$—NR$^5$—(CR$^4_2$)$_t$]$_u$—U—(CR$^4_2$)$_t$—O—(CR$^4_2$)$_t$—R$^8$.

In a sixteenth embodiment of the tenth aspect, one or both of Z and Z' are —U—(CR$^4_2$)$_t$—NR$^5$—(CR$^4_2$)$_t$—U—(CR$^4_2$)$_t$—O—(CR$^4_2$)$_t$—R$^8$.

In a seventeenth embodiment of the tenth aspect, one or both of Z and Z' are —C(O)—(CR$^4_2$)$_t$—NR$^5$—(CR$^4_2$)$_t$—C(O)—(CR$^4_2$)$_t$—O—(CR$^4_2$)$_t$—R$^8$.

In an eighteenth embodiment of the tenth aspect, one or both of Z and Z' are —U—(CR$^4_2$)$_t$—O—(CR$^4_2$)$_t$—R$^8$.

In a nineteenth embodiment of the tenth aspect, one or both of Z and Z' are —C(O)—(CR$^4_2$)$_t$—O—(CR$^4_2$)$_t$—R$^8$.

In a twentieth embodiment of the tenth aspect, one or both of Z and Z' are —C(O)—(CR$^4_2$)$_n$—NR$^7$—R$^8$ wherein R$^7$ and R$^8$ together form a 4-7 membered ring.

In an eleventh aspect of the invention, compounds have formula VII:

VI wherein,

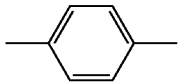

may include 1 or 2 nitrogens as heteroatoms,
r is from 0 to 4,
each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
A and A' are independently selected from the group consisting of

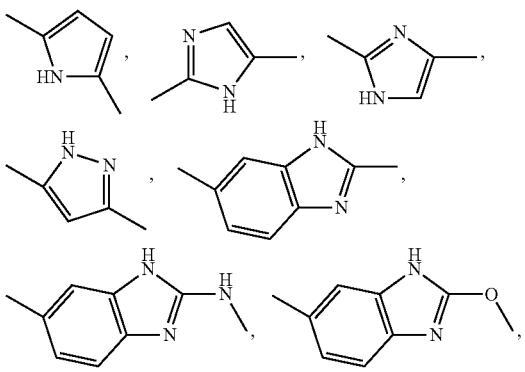

—(CR$_2$)$_n$—O—(CR$_2$)$_p$— and —(CR$_2$)$_n$—C(O)N(R$^N$)—(CR$_2$)$_p$—, wherein,
if A or A' is a heteroaryl group, it is optionally substituted with one or more of the substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
n and p are independently 0, 1, or 2,
each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
$R^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and
for each A and A',

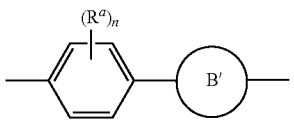

may be attached to either side of A and A' so that in the example of A or A' being

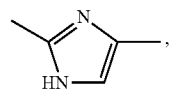

the

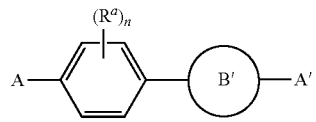

can be any of:

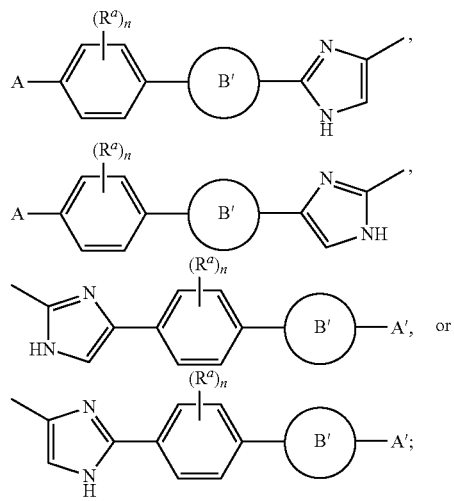

B' is

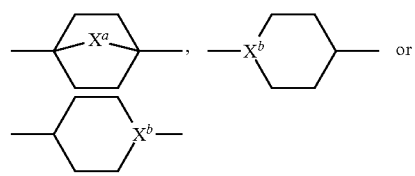

wherein,
B' is optionally substituted with between 1 and 4 substituents, each independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino and oxo,
$X^a$ is chosen from the group consisting of —CH$_2$—, —CH$_2$—CH$_2$—, —CH=CH—, —O—, —S—, —S(=O)$_2$—, —CH$_2$—O—, —NR$^1$— and —CH$_2$—NR$^1$— wherein R$^1$ is chosen from the group consisting of hydrogen, C$_1$ to C$_8$ alkyl, and C$_1$ to C$_8$ heteroalkyl, and
$X^b$ is either C or N;
X and X' are each either present or absent and if present, independently selected from the group consisting of a bond, —CH$_2$—, —CH$_2$—CH$_2$—, —CH=CH—, —O—, —S—, —S(O)$_2$—, —CH$_2$O—, —CH$_2$S—, —CH$_2$S(O)$_2$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl and aralkyl Y and Y' are each independently carbon or nitrogen; and Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

The compounds of the present invention include pharmaceutically acceptable salts of VII as well as an optically pure enantiomer, racemate or diastereomeric mixtures thereof.

In a twelfth aspect of the invention, compounds have formula VIII:

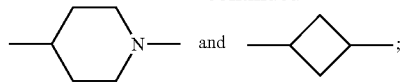

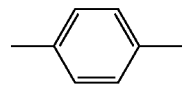

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;

each R$^8$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, —C(O)—R$^{81}$, —C(S)—R$^{81}$, —C(O)—O—R$^{81}$, —C(O)—N—R$^{81}_2$, —S(O)$_2$—R$^{81}$, —S(O)$_2$—N—R$^{81}_2$, wherein each R$^{81}$ is independently chosen from the group consisting of hydrogen, C$_1$ to C$_8$ alkyl, C$_1$ to

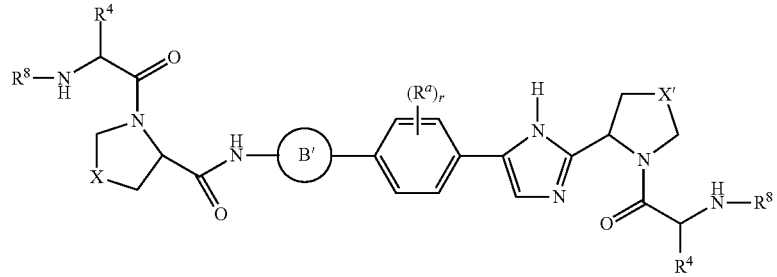

wherein:

B' is selected from the group consisting of

C$_8$ heteroalkyl, cycloalkyl, heterocycle, aryl, heteroaryl and aralkyl; and each R$^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

The compounds of the present invention include pharmaceutically acceptable salts of IX as well as an optically pure enantiomer, racemate or diastereomeric mixtures thereof.

In a thirteenth aspect of the invention, compounds have formula IX:

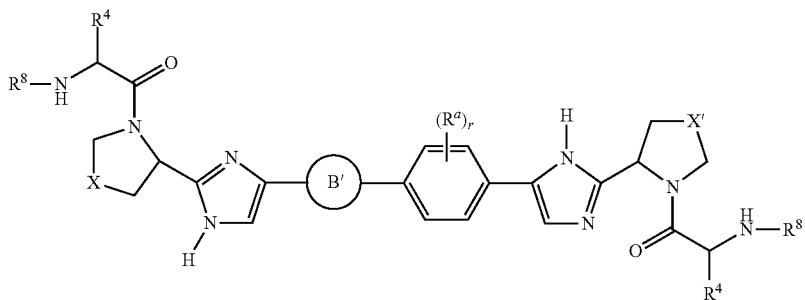

wherein:

B' is selected from the group consisting of

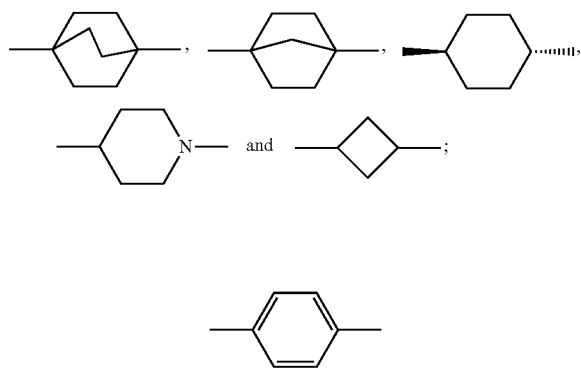

optionally includes 1 or 2 nitrogens as heteroatoms;

each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;

each R$^8$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, —C(O)—R$^{81}$, —C(S)—R$^{81}$, —C(O)—O—R$^{81}$, —C(O)—N—R$^{81}$$_2$, —S(O)$_2$—R$^{81}$, —S(O)$_2$—N—R$^{81}$$_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl; and each R$^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

The compounds of the present invention include pharmaceutically acceptable salts of IX as well as an optically pure enantiomer, racemate or diastereomeric mixtures thereof.

In a fourteenth aspect of the invention, compounds have formula X:

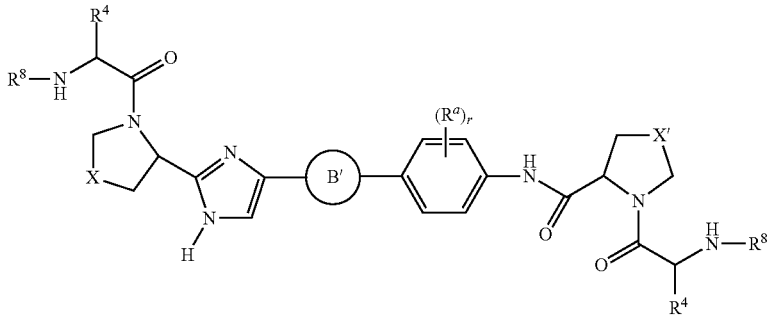

wherein:

B' is selected from the group consisting of

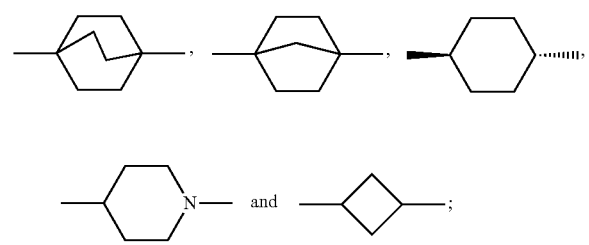

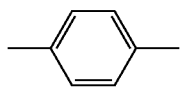

optionally includes 1 or 2 nitrogens as heteroatoms;

each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;

each $R^8$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, —C(O)—R$^{81}$, —C(S)—R$^{81}$, —C(O)—O—R$^{81}$, —C(O)—N—R$^{81}$$_2$, —S(O)$_2$—R$^{81}$, —S(O)$_2$—N—R$^{81}$$_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl; and each $R^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

The compounds of the present invention include pharmaceutically acceptable salts of X as well as an optically pure enantiomer, racemate or diastereomeric mixtures thereof.

In a fifteenth aspect of the invention, compounds have formula XI:

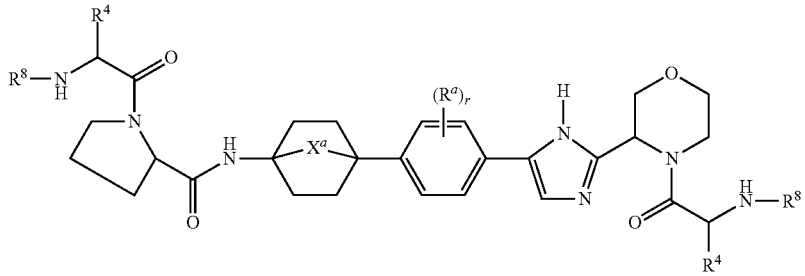

wherein:

each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

$X^a$ is chosen from the group consisting of —CH$_2$—, —CH$_2$—CH$_2$—, —CH═CH—, —O—, —S—, —S(═O)$_2$—, —CH$_2$—O—, —NR$^1$— and —CH$_2$—NR$^1$— wherein R$^1$ is chosen from the group consisting of hydrogen, C$_1$ to C$_8$ alkyl, and C$_1$ to C$_8$ heteroalkyl, each $R^8$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, —C(O)—R$^{81}$, —C(S)—R$^{81}$, —C(O)—O—R$^{81}$, —C(O)—N—R$^{81}$$_2$, —S(O)$_2$—R$^{81}$, —S(O)$_2$—N—R$^{81}$$_2$, wherein each R$_{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl; and each $R^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

The compounds of the present invention include pharmaceutically acceptable salts of XI as well as an optically pure enantiomer, racemate or diastereomeric mixtures thereof.

In an additional aspect of the invention, compounds of formula XII are provided:

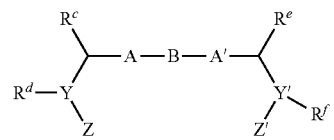

wherein,

A and A' are independently selected from the group consisting of a single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—S(O)$_k$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$—, —(CR$_2$)$_n$—C(O)—O—(CR$_2$)$_p$—, —(CR$_2$)$_n$—N(R$^N$)—S(O)$_k$—N(R$^N$)—(CR$_2$)$_p$— and —(CR$_2$)$_n$—N(R$^N$)—C(O)—O—(CR$_2$)$_p$— and a heteroaryl group selected from the group consisting of

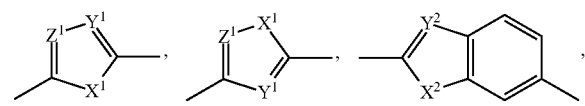

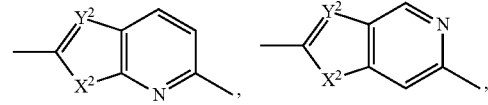

-continued

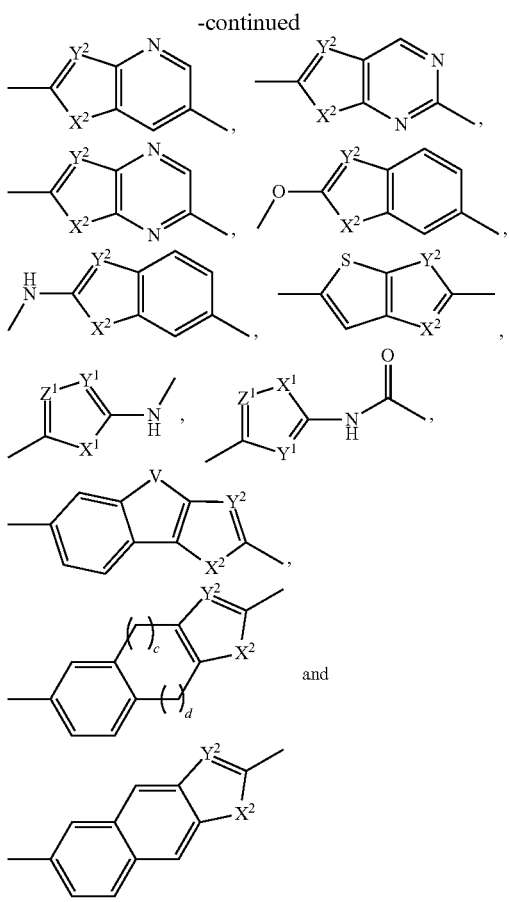

and

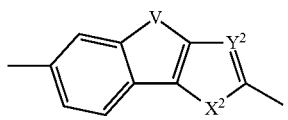

wherein:
X$^1$ is CH$_2$, NH, O or S,
Y$^1$, Y$^2$ and Z$^1$ are each independently CH or N,
X$^2$ is NH, O or S,
V is —CH$_2$—CH$_2$—, —CH═CH—, —N═CH—, (CH$_2$)$_a$—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0,

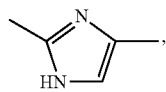

optionally includes 1 or 2 nitrogens as heteroatoms on the phenyl residue,
the carbons of the heteroaryl group are each independently optionally substituted with a substituent selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, a and b are independently 1, 2, or 3,
c and d are independently 1 or 2,
n and p are independently 0, 1, 2 or 3,
k is 0, 1, or 2,
each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and
wherein for each A and A', B may be attached to either side of A and A' so that in the example of A or A' being

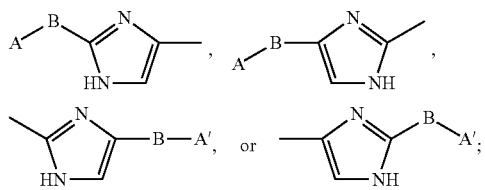

the A-B-A' can be any of:

B is selected from the group consisting of

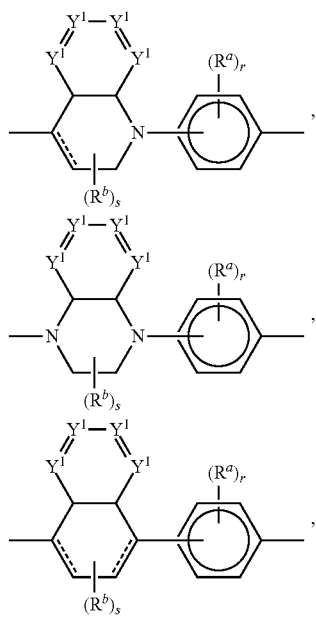

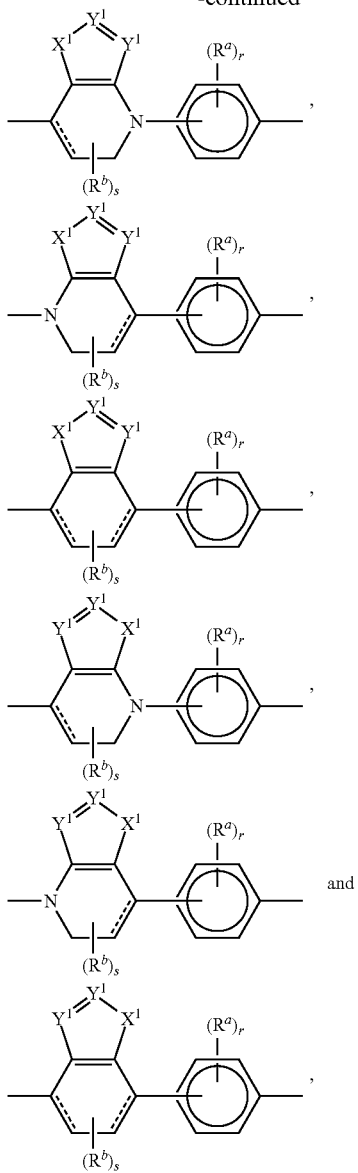

wherein:

is a divalent aryl or heteroaryl group which may be polycyclic with varying connective patterns;

V is —$CH_2$—, —$CH_2$—$CH_2$—, —CH=CH—, —N=CH—, $(CH_2)_a$—$N(R^N)$—$(CH_2)_b$— or —$(CH_2)_a$—O—$(CH_2)_b$—, wherein a and b are independently 0, 1, 2, or 3 with the proviso that a and b are not both 0;

$X^1$ is $CH_2$, NH, O or S, each $Y^1$ is independently CH or N, each r and s is independently 0, 1, 2, 3 or 4;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each $R^b$ is independently selected from the group consisting of $C_1$-$C_{12}$ alkyl, hydroxyl, halogen and oxo;

$R^c$, $R^d$, $R^e$, and $R^f$ are each independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$, and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 6-membered heterocycle or heteroaryl ring, and $R^e$ and $R^f$ are optionally joined to form a 4- to 8-membered heterocycle which is optionally fused to another 3- to 6-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—$(CR^4_2)_t$—$NR^5$—$(CR^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$(CR^4_2)_t$—$R^8$, wherein, U is selected from the group consisting of —C(O)—, —C(S)—, and —$S(O)_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —$S(O)_2$—$R^{81}$, and —$S(O)_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

The compounds of the present invention include pharmaceutically acceptable salts of XII as well as an optically pure enantiomer, racemate or diastereomeric mixtures thereof.

The compounds of the invention are prepared by synthetic routes and procedures that are illustrated in the various synthetic schemes below. The synthetic routes shown in schemes below are disclosed for the purpose of illustration and are not meant to be interpreted as limiting the processes to make the embodied compounds by any other methods. It will be appreciated by those skilled in the art that a number of methods are available for the preparation of the compounds of the present invention. These compounds may be prepared by processes which include processes known in the chemical art for the production of structurally analogous compounds or by a novel process described herein. One of the general strategies includes building the central scaffold followed by gradual functional group transformations of the two ends either simultaneously. In order to differentially functionalize the two ends, some orthogonal functional group protection and deprotection strategies are used (T. W. Greene & P. G. M. Wutts, *Protective Groups in Organic Synthesis*, John Wiley & Sons, 3rd edition, 1999). Another synthetic strategy entails the construction of the two halves of the molecule separately and coupling them toward the end of the synthesis. The cross coupling techniques employ conditions such as the Sonogashira, Suzuki-Miayura, or Stille reaction for connecting carbon-carbon bonds. For scaffold cores linked via a carbon-nitrogen bond, their syntheses typically utilize a nucleophilic aromatic substitution reaction, a Buchwald or a Ma cross coupling reaction. The functional groups, typically amines and carboxyl groups on either ends of the cores are generally orthogonally protected to allow for selective further manipulations as needed.

The following abbreviations are used throughout this application:
ACN Acetonitrile
aq Aqueous
Bn Benzyl
BnOH Benzyl alcohol
Boc t-butoxycarbonyl
DCE Dichloroethane
DCM Dichloromethane
DIEA(DIPEA) Diisopropylethylamine
DMA N,N-Dimethylacetamide
DME 1,2-Dimethoxyethane
DMF N,N-Dimethylformamide
DMSO Dimethylsulfoxide
DMTMM 4-(4,6-Dimethoxy-1,3,5-triazin-2-yl)-4-methyl-morpholinium chloride
DPPA Diphenylphosphoryl azide
DTT Dithiothreitol
EDC Ethylcarbodiimide hydrochloride
EDCl 1-Ethyl-3-[3-(dimethylamino) propyl]carbodiimide hydrochloride
EDTA Ethylene diamine tetraacetic acid
ESI Electrospray Ionization
Et₃N, TEA Triethylamine
EtOAc, EtAc Ethyl acetate
EtOH Ethanol
g Gram(s)
h Hour(s)
HBTU O-Benzotriazol-1-yl-N,N,N',N'-tetramethyluronium hexafluorophosphate
HOBt 1-Hydroxybenzotriazole
IC₅₀ The concentration of an inhibitor that causes a 50% reduction in a measured activity
LAH Lithium aluminum hydride
LDA Lithium diisopropylamide
LCMS Liquid Chramatography Mass Spectrometry
MeI Methyl Iodide
MeOH Methanol
min Minute(s)
mmol Millimole(s)
NMM 4-Methylmorpholine
NMP N-methylpyrrolidinone
PG Protective Group
PTT Phenyl trimethyl tribromide
Py Pyridine
rt Room temperature
TEA Triethylamine
Tf Trifluoromethanesulfonate
TFA Trifluoroacetic acid
TFAA Trifluoroacetic anhydride
THF Tetrahydrofuran
TLC Thin Layer Chromatography

EXAMPLE 1

General Synthesis

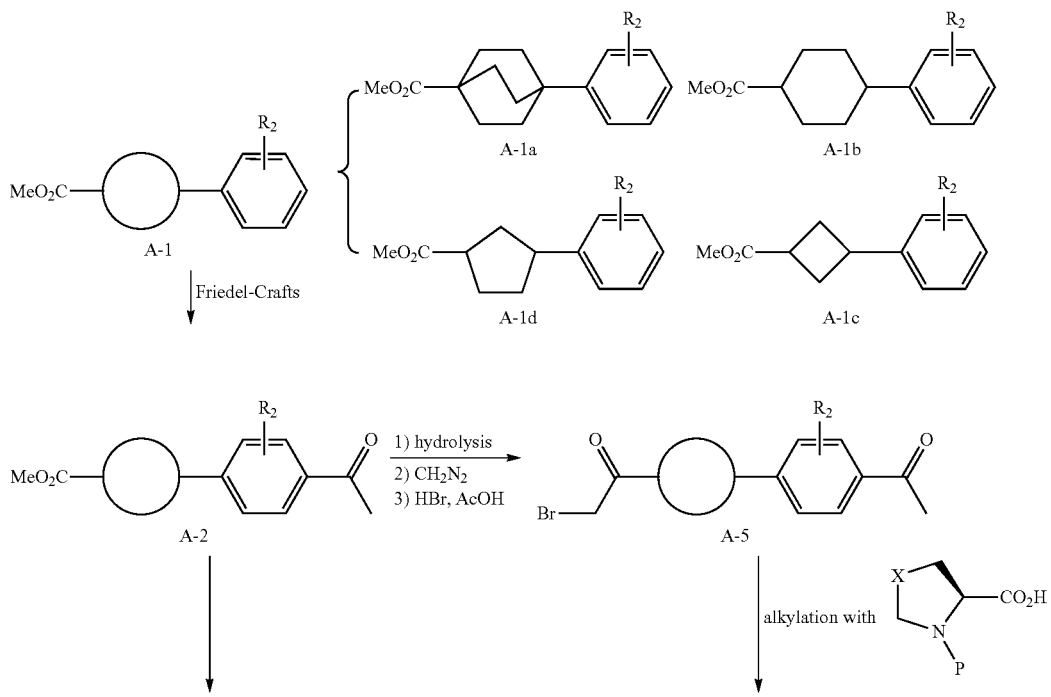

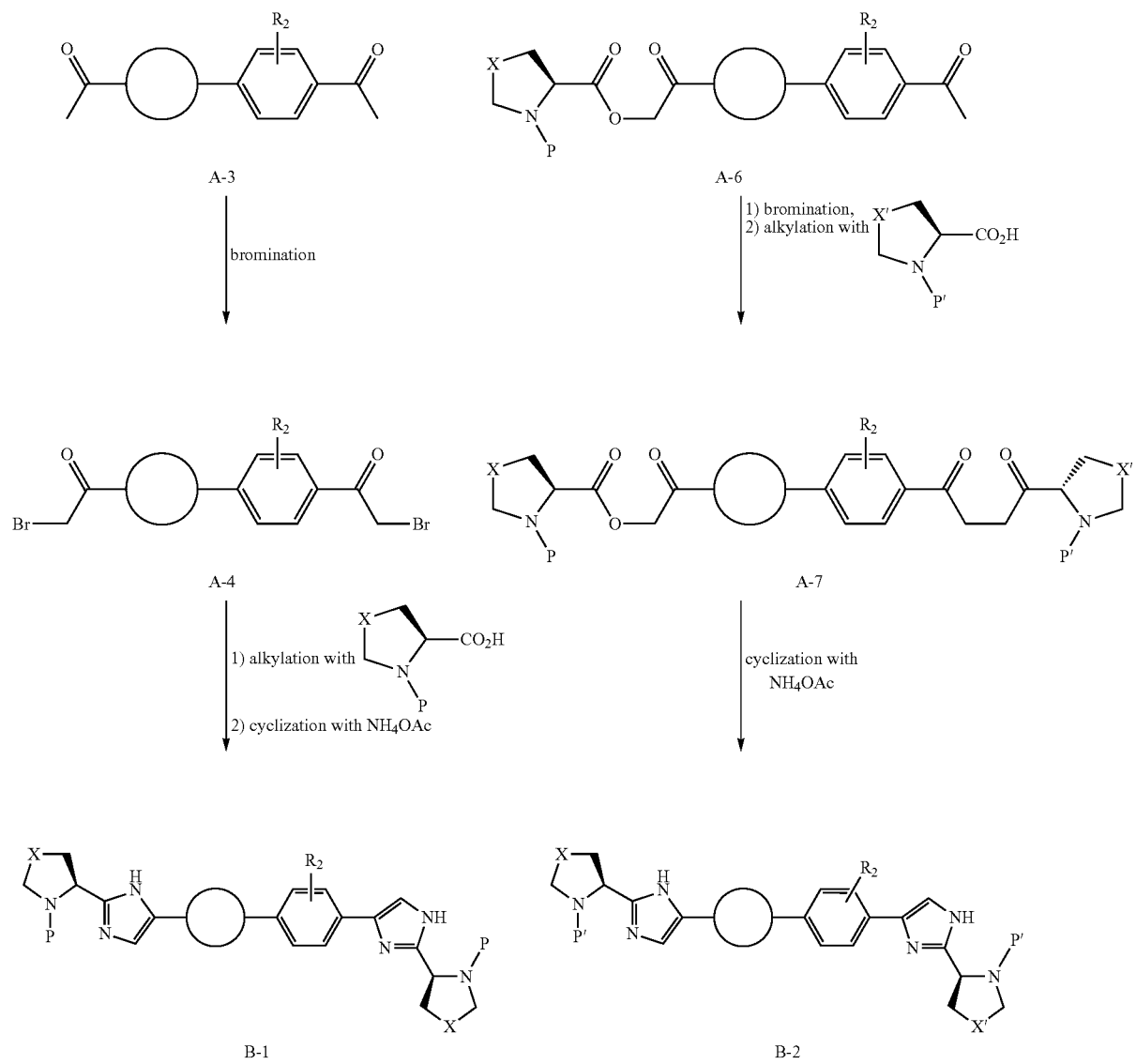
Schemes 1-1 and 1-2 illustrate the various methods of preparing aryl-carbocyclic central scaffolds (Bs) and how the two ends of the molecule can be differentially constructed in order to allow for selective functionalization of either end of the molecule.
Scheme 1-2
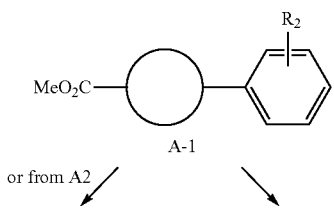

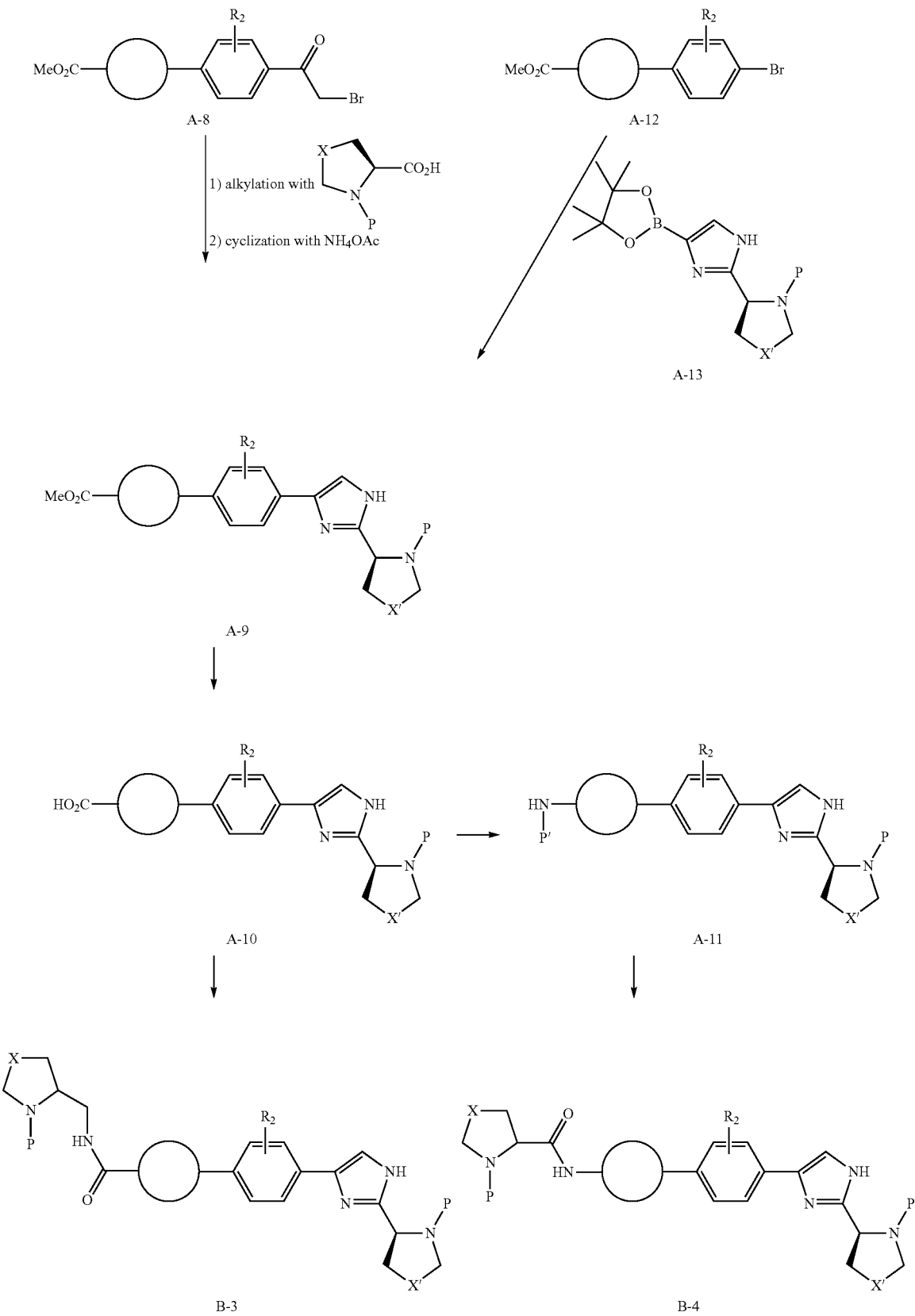

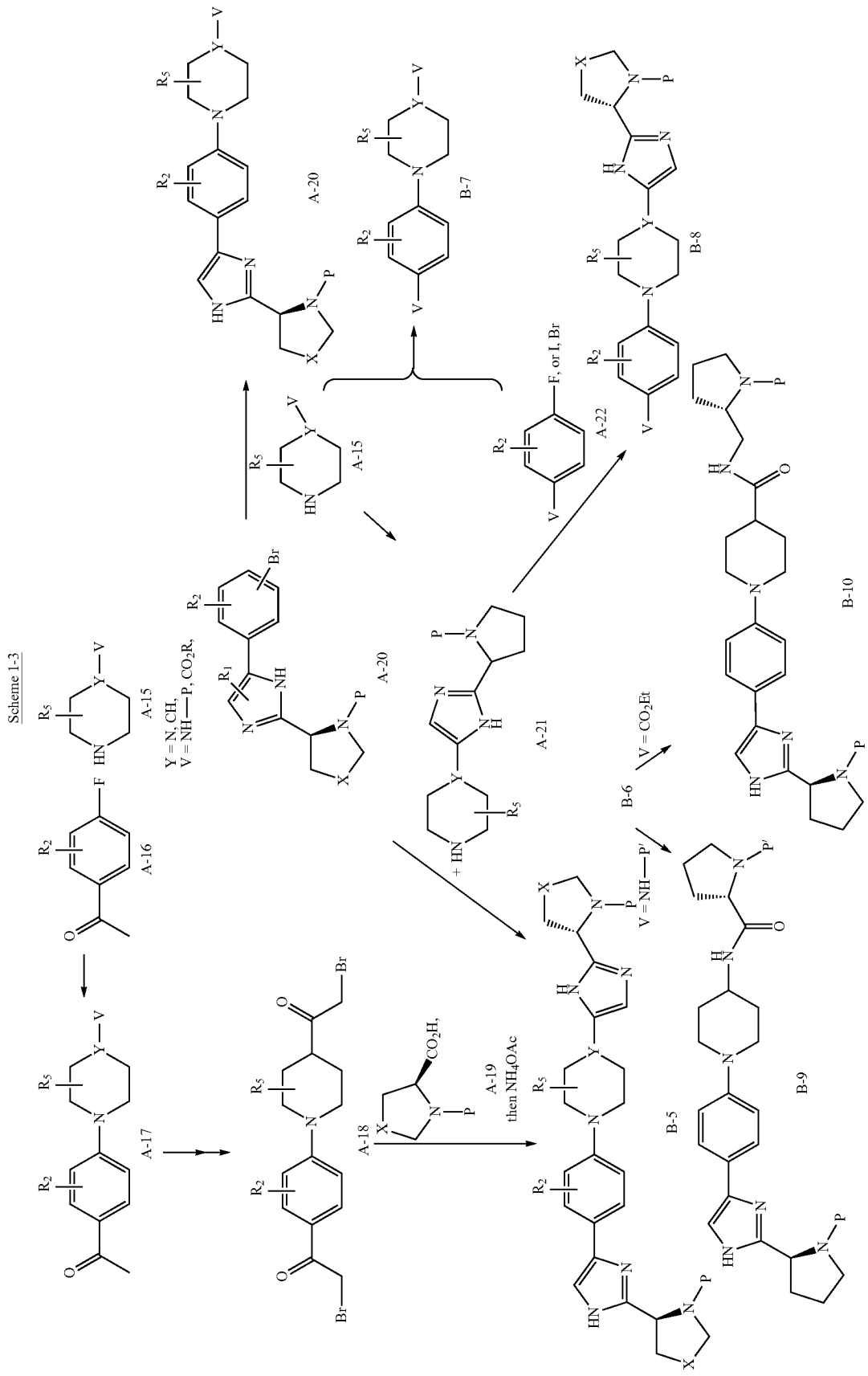

Scheme 1-3 outlines the preparation of core structures connected through a carbon-nitrogen bond. The nitrogen arylation is achieved using one of the several methods. In one embodiment, the acetophenone moiety and the V group in A-17 can be sequentially converted to a bromoketone as in A-18 for further introduction of the A-19 moiety. The coupling between A-15 and A-16 to A-17 represents a nucleophilic aromatic substitution method. Other methodologies employed include Buchwald or Ma couplings (*J. Org. Chem.* 2005, 70, 164), such as the coupling of A-15 with A-20 to B-6, A-15 with A-22 to B-7, A-21 with A-22 to B-8. When V is a carboxylate, it can be extended via an amide linkage. Taking B-6 as an example, the carboxylate can undergo a Curtis rearrangement to an amine, which in turn can be transformed to an amide (B-6 to B-9). Alternatively, the carboxylate can be hydrolyzed and converted to B-10 when reacts with a protected form of pyrrolidin-2-ylmethanamine. The methodologies outlined in this scheme are further depicted in other schemes described herein.

Scheme 1-4

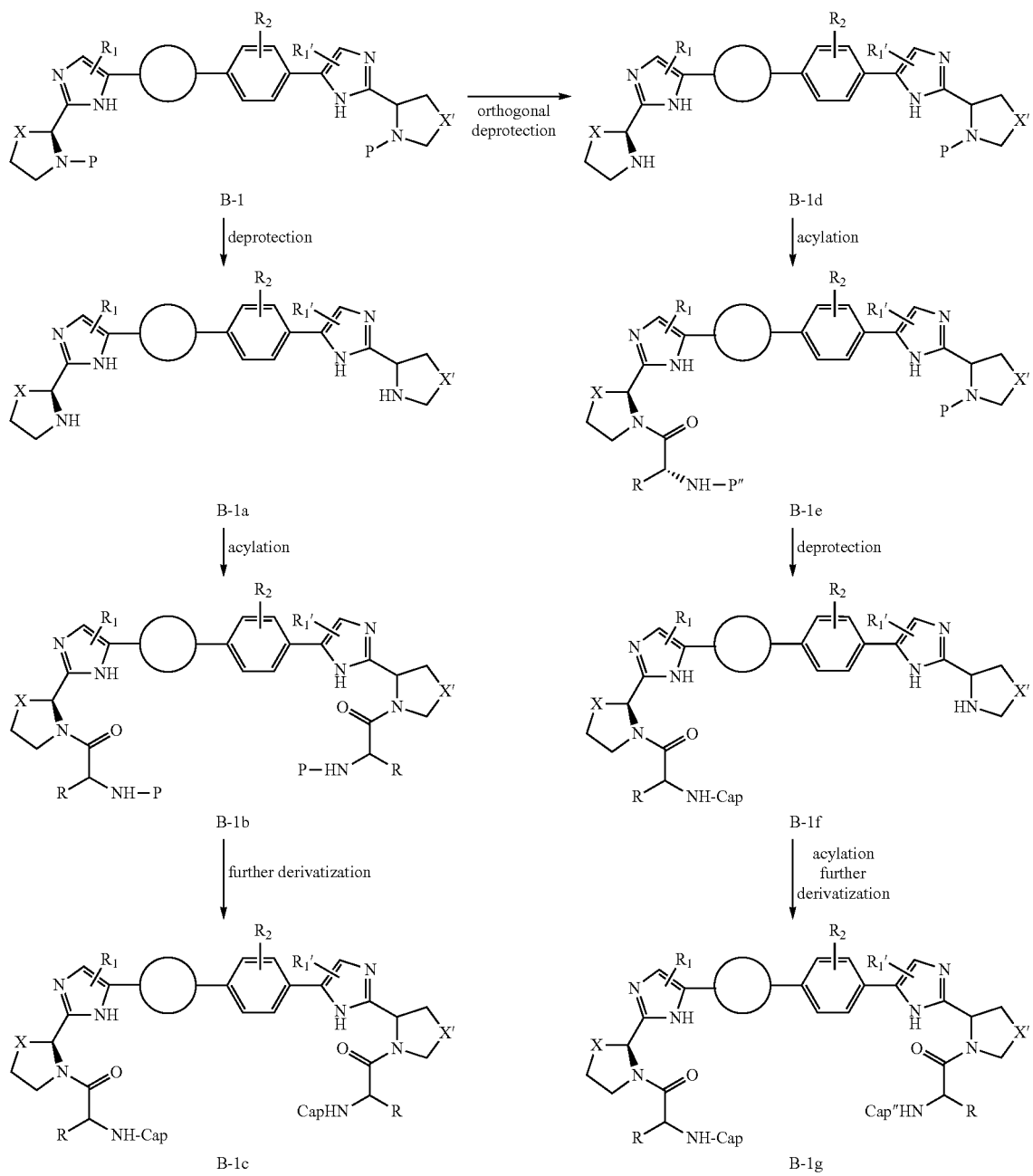

Scheme 1-4 illustrates some of the ways for further functional group transformations using scaffold B-1 as an example. Starting from a properly protected B-1, the nitrogen protecting groups P and P' can be removed simultaneously to give B-1a. When B-1a is treated together a suitably protected amino acid under standard peptide coupling conditions, such as HATU and a tertiary amine base, e.g. Hünig's base, the doubly coupled product B-1b is obtained. Typically, P refers to a protecting group such as Boc-, Cbz-, Troc-, etc. P can also be other alkyl, acyl, alkoxylcarbonyl, alkylaminocarbonyl groups that are intended for this position. When P is one of the removable groups, upon its removal, the free the amino group can be further derivatized to B-1c. The definition of Cap group is P and P'. The protecting groups P and P' can be removed selectively to free one of the two amino groups in B-1 as in the case of B-1 to B-1d. These skilled in the art will understand that the P' group can be deprotected while the P group is preserved to give an alternative structure such as B-1d. The free amino group of B-1d is coupled with another properly functionalized amino acid to give B-1e. When this process of selective deprotection and functionalization is repeated, compound B-1f is obtained. The newly introduced amino acid in B-1f can be the same as the residue on the left-hand side of the molecule or can be a different one. From B-1f, a variety of compounds (with a general formula of B-1g) are prepared with differentially functionalized end pieces.

In another embodiment, several key intermediates used in the construction of claimed scaffolds are depicted in the following schemes.

reactivity of the intermediates toward further reaction and will become one compound upon the removal of the protecting group. The iodo- or bromo-imidazole intermediate A-27 is used converted to is the corresponding borate A-28 under the conditions shown, or using conditions that are known to promote similar transformations. When the same intermediate A-27 is subjected to Sonogoshira coupling conditions, the acetylene compound A-28 is obtained after subsequent treatment with base. The use of intermediate as an alternative method of synthesizing arylimidazole intermediates such as A-1 and B-3 is illustrated in Scheme 1-1. These versatile building blocks are used in many other manners as will be shown in the schemes to follow.

Scheme 1-6

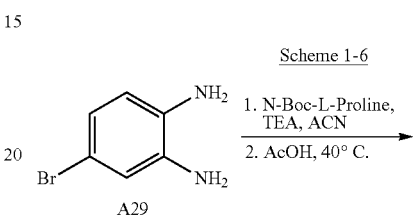

Scheme 1-5

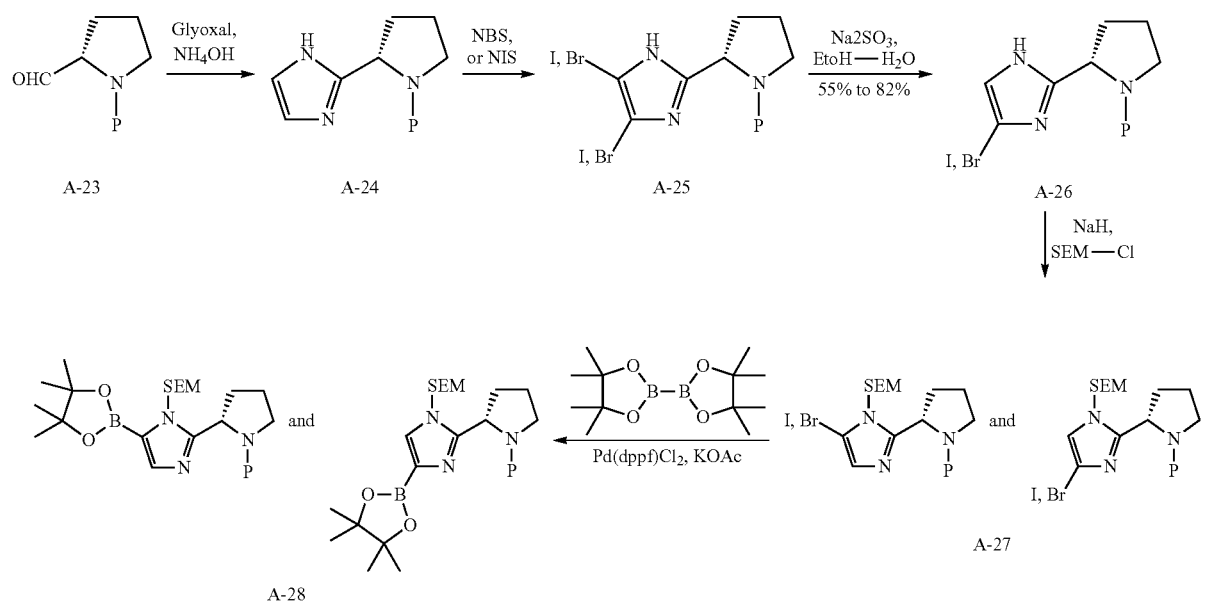

Scheme 1-5 using an L-proline-based structure as an example describes the synthesis of several key imidazole intermediates that are used for the construction of various more advanced intermediates in this invention. (References: a. *Polyhedron* 2005, 24, 2625, b. WO2008/021927). The readily available L-prolinaldehyde is converted to imidazole A-24 by reacting with glyoxal in the presence of ammonium hydroxide. The monohalogenation (bromination or iodination) is best achieved via a two-step sequence, i.e. non-selective dihalogenation followed by a selective removal of one of the two halogen atoms to A-26. To facilitate the further functionalization, the imidazole moiety is preferably protected with SEM or other protecting groups. The protection process does generate a mixture of regioisomers of the protecting group. However, such a mixture does not usually affect the -continued

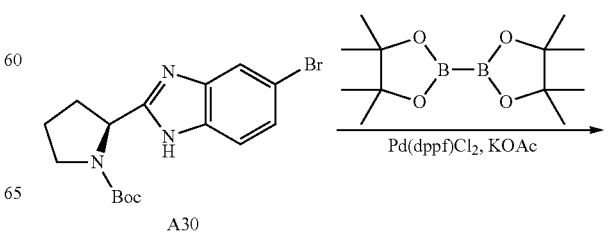

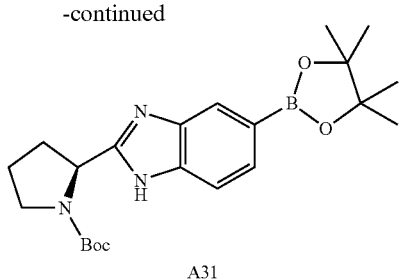

A31

Ref. *J. Med. Chem.* 2008, 51, 5109;
2006, 49, 3774; and 2002, 45, 5556

In another embodiment, the aryl-imidazole and benzoimidazole building blocks are synthesized using the route described in Scheme 1-6 (Ref. *J. Med. Chem.* 2008, 51, 5109; 2006, 49, 3774; and 2002, 45, 5556). Those in the art shall recognize that the phenyl, the proline and the protecting group on nitrogen may be replaced in order to achieve the desired functionality at a given position.

1970, 35, 917). Compound A-1b is prepared similarly. Another method to prepare the cyclohexyl-containing compounds such as A-1b and A-1b' is through a cross coupling reaction between vinyltrifolate and a phenylboronate (or a boronic acid). The letter V represents a carboxylate group, such as an ethoxylcarbonyl, or a protected amino group, or can be another functional group that can be further functionalized. Following the coupling step, the resulted styrenyl group can be preserved (A-1b') or can be saturated under hydrogenation condition to give A-1b. The cyclopentyl analog A-1c may be made by similar route. The four-carbon analog is made in sequence as shown.

Synthesis of Example Compounds

The examples below provide exemplary synthetic methods for the preparation of the compounds of the present invention. One of skill in the art will understand that additional methods are also useful. The compounds of the invention can be made using conventional organic synthesis using starting materials, reagents and reactions well known in the art.

Reagents and solvents used below can be obtained from commercial sources such as Aldrich Chemical Co. (Milwau-

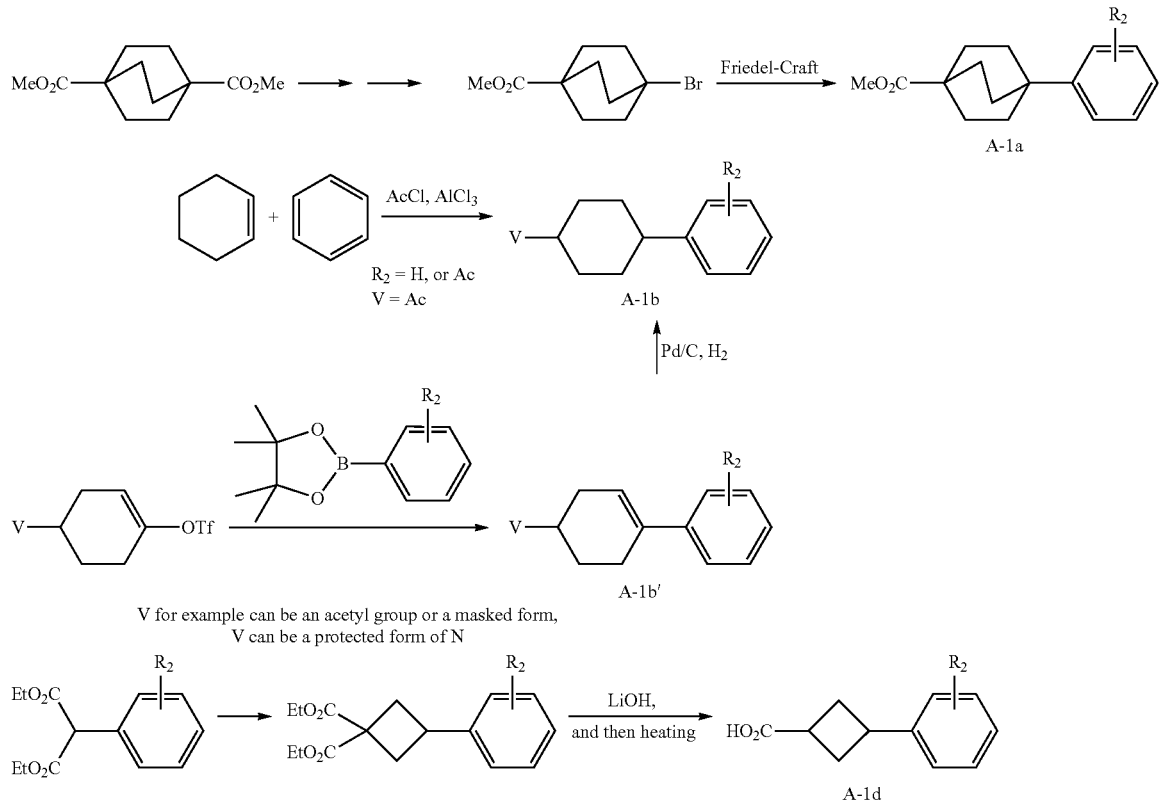

In another embodiment, the building blocks used in Scheme 1-1 for the synthesis of scaffolds such as B-1 to B-4 and others are synthesized using routes described in Scheme 1-7. The preparation of A-1a starts with the dimethyl bicyclo [2.2.2]octane-1,4-dicarboxylate, one of the methyl ester group is selectively hydrolyzed to the acid, which in turn is converted to a bromo group to give methyl 4-bromobicyclo [2.2.2]octane-1-carboxylate. A Friedel-Crafts reaction between methyl 4-bromobicyclo[2.2.2]octane-1-carboxylate and a substituted benzene yields A-1a (Ref. *J. Org. Chem.* kee, Wis., USA). $^1$H-NMR spectra were recorded on a Bruker 400 MHz or 500 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electrospray spray ionization (ESI) mass spectrometry analysis was conducted on a Hewlett-Packard 1100 MSD electrospray mass spectrometer using the HP1 100 HPLC for sample delivery. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Normally the analyte was dissolved in methanol at 0.1 mg/mL and 5 microliter was infused with the delivery solvent into the mass spectrometer, which scanned from 100 to 1500 daltons. All compounds could be analyzed in the positive ESI mode, using an acetonitrile/water gradient (10%-90%) acetonitrile in water with 0.1% formic acid as delivery solvent. The compounds provided below could also be analyzed in the negative ESI mode, using 2 mM $NH_4OAc$ in acetonitrile/water as delivery solvent. Enantiomeric purity was determined using a Hewlett-Packard Series 1050 system equipped with a chiral HLPC column (ChiralPak AD, 4.6 mm×150 mm) and isocratic elution using 5:95 isopropanol-hexane as a mobile phase.

The compounds were named using ChemDraw program from Cambridge Soft Inc.

EXAMPLE 2

Synthesis of Compounds of Formula IVb

Compounds of formula IVb can be made by schemes 2-1 and 2-2.

Scheme 2-1

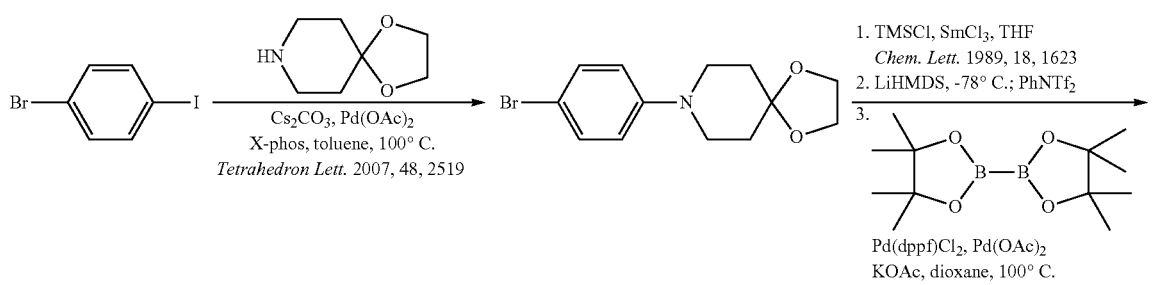

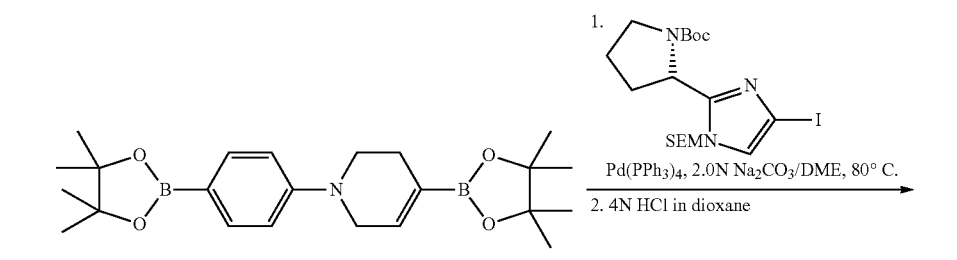

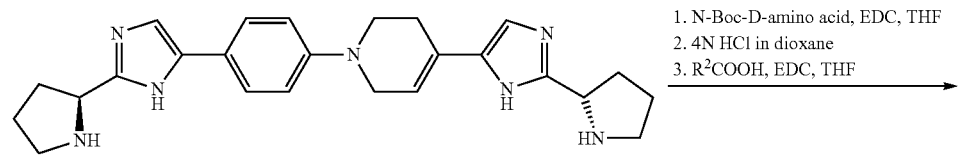

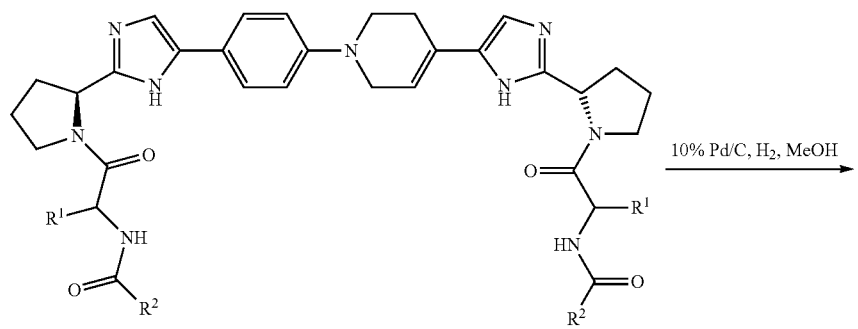

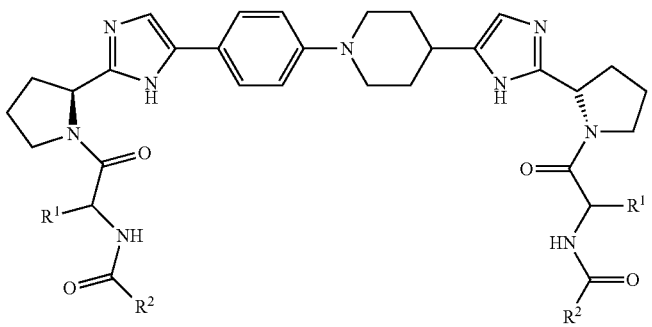
Scheme 2-2
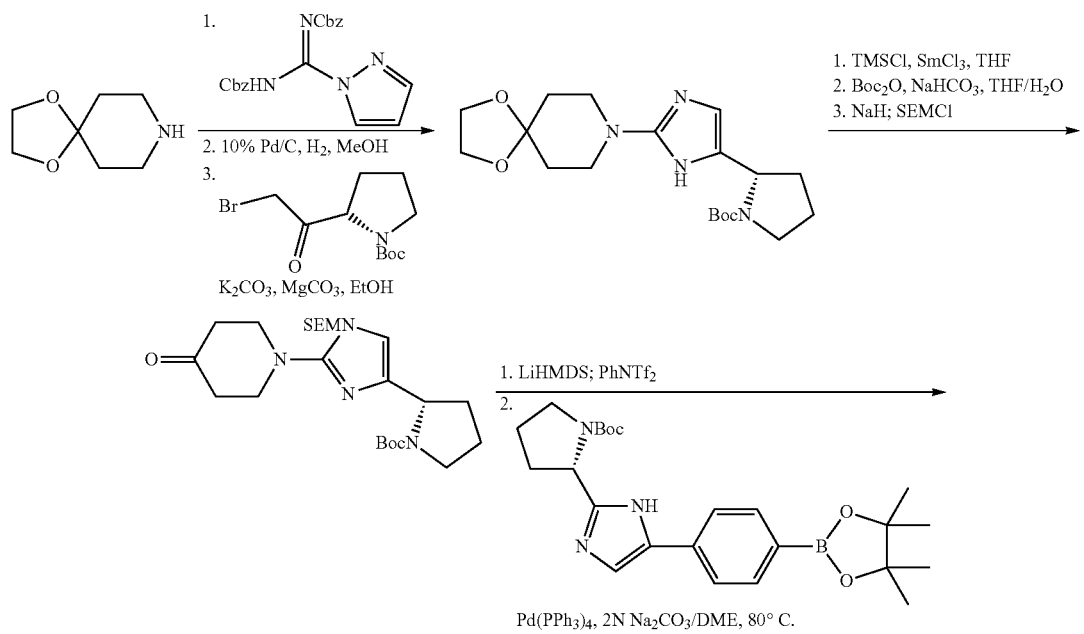
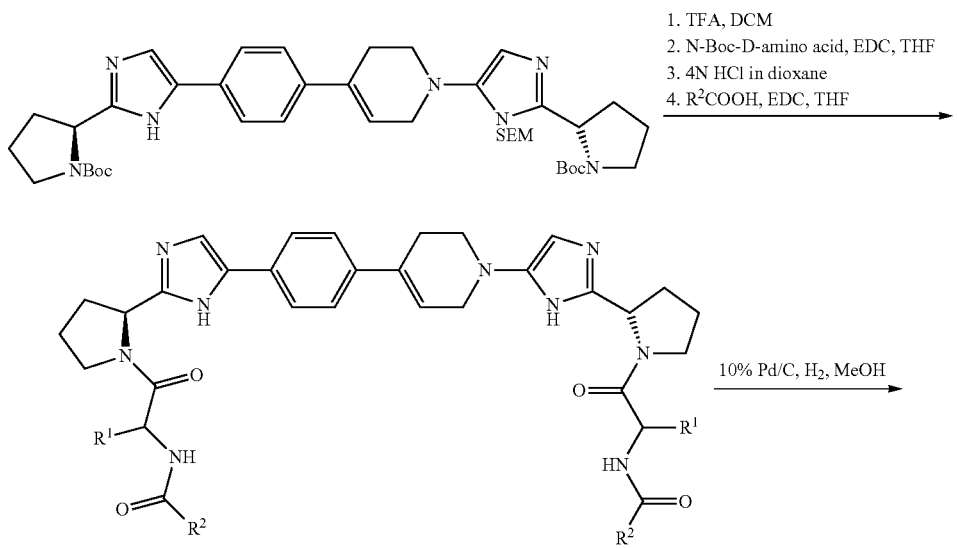

-continued
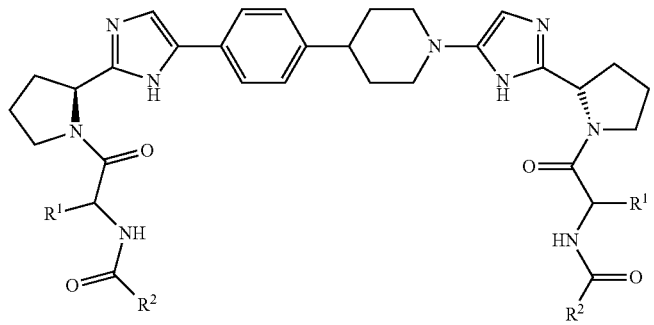
Scheme 2-3
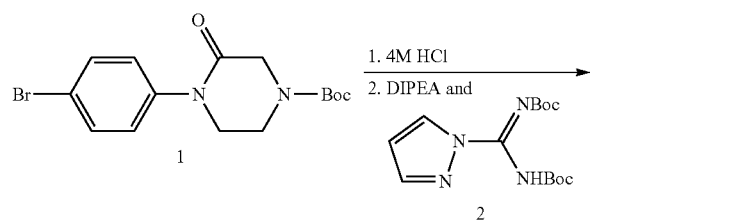
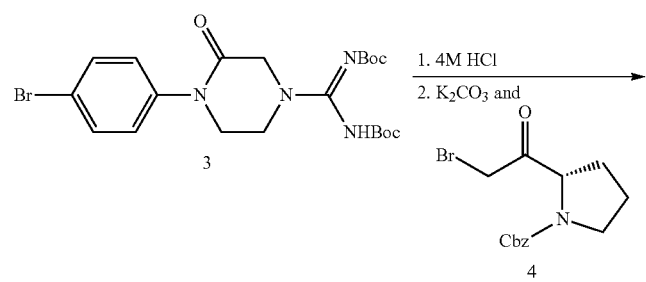
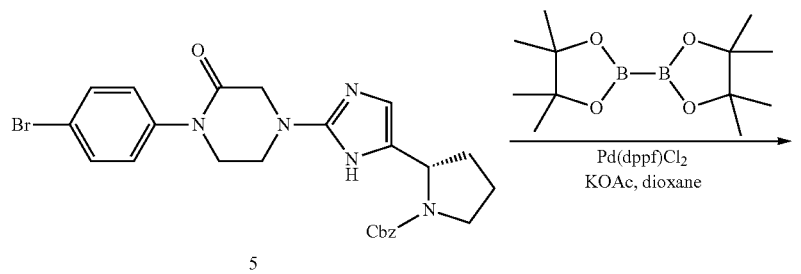
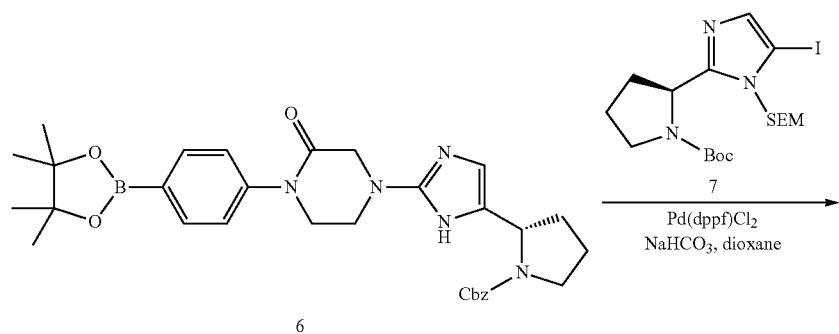

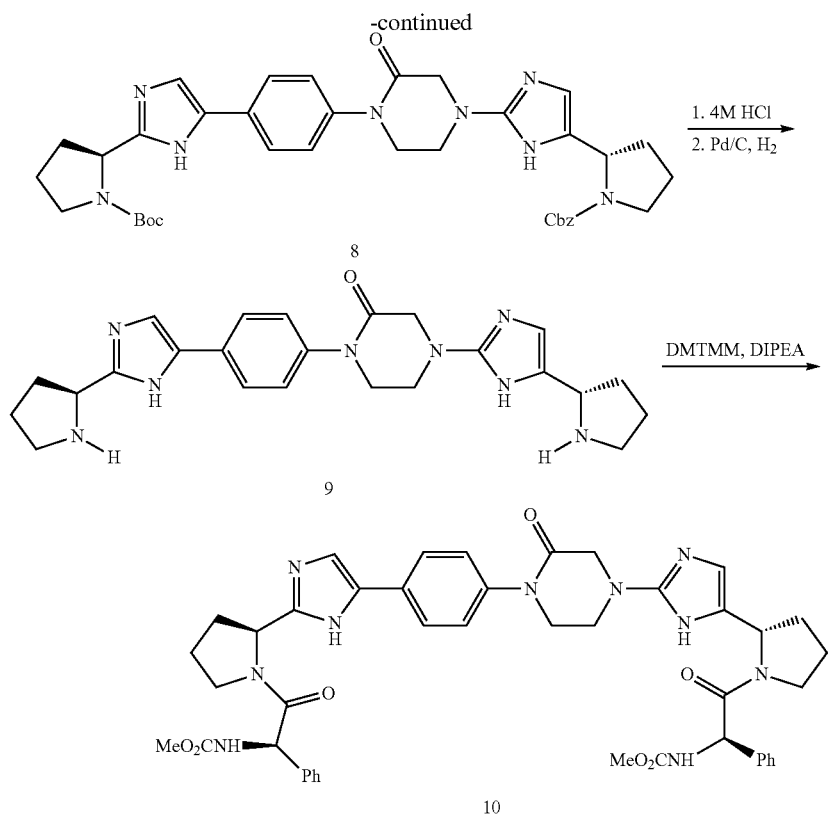

Step a.

Referring to Scheme 2-3, compound 1 was prepared following procedures described in *J. Med. Chem.* 2007, 50, 6706.

Step b.

A sample of compound 1 (1.0 g, 2.82 mmol) in dichloromethane was treated with excess 4N HCl in dioxane. At the completion of removal of Boc group as indicated by LCMS, solvents were removed and the residue was dried under vacuum. This material was taken up in acetonitrile (6 mL) and treated with tert-butyl (1H-pyrazol-1-yl)methylenedicarbamate (2) (1.01 g, 3.2 mmol) and DIPEA (0.60 g, 4.65 mmol) at rt overnight. The solvents were evaporated off and the crude product was purified by silica gel column chromatography with a gradient eluent consisting various ratio of EtOAc and hexanes to give compound 3 (0.59 g, 71% yield).

Step c.

A solution of 3 (1.34 g, 2.69 mmol, from combined runs) in THF (5 mL) was treated with excess 4N HCl in dioxane at rt overnight. Solvents were removed by evaporation, and residue was further dried under high vacuum. A portion of this de-Boc material (0.3 g, 1.0 mmol) was taken up in THF (4 mL) and water (0.34 mL). To this mixture was added $K_2CO_3$ (0.27 g, 2.02 mmol) followed by bromoketone compound 4 (0.33 g, 1.01 mmol, prepared following published procedures). The entire mixture was heated at reflux overnight. After cooling, the reaction mixture was added $CH_2Cl_2$ and washed with $H_2O$ and brine, respectively. After drying over $Na_2SO_4$, the solvent was removed and the residue was purified by silica gel column chromatography, eluted with 1-3% MeOH in EtOAc to afford 5 (0.32 g).

Step d.

A mixture of compound 5 (0.2 g, 0.38 mmol), bis(pinacolato)diboron (0.12 g, 0.46 mmol), potassium acetate (0.11 g, 1.1 mmol), and $Pd(dppf)Cl_2 \cdot CH_2Cl_2$ (30 mg, 0.038 mmol) in dioxane (5 mL) was stirred at 80° C. for 17 h under an atmosphere of Ar. Subsequently, the reaction mixture was filtered. The filtered cake was washed with EtOAc (5 mL×3). The filtrate was washed with $H_2O$ and dried with anhydrous $Na_2SO_4$. The solvent was removed and the residue was purified by silica gel column chromatography to give compound 6 (0.14 g).

Step e.

A solution of compound 6 (0.640 g, 1.1 mmol) in dioxane (24 mL) and water (2.4 mL) was sequentially added (S)-tert-butyl 2-(5-iodo-1-((2-(trimethylsilyl)ethoxy)methyl)-1H-imidazol-2-yl)pyrrolidine-1-carboxylate (1.10 g, 2.22 mmol), $NaHCO_3$ (0.37 g, 3.66 mmol), and $Pd(dppf)Cl_2 \cdot CH_2Cl_2$ (90 mg, 0.11 mmol) at rt under an atmosphere of Ar. After stirring at 80° C. overnight under an atmosphere of Ar, the reaction mixture was diluted with EtOAc (100 mL). The organic layer was isolated, washed with brine, and dried with anhydrous $Na_2SO_4$. The solvent was removed and the residue was purified by silica gel column chromatography to give compound 8 (0.2 g mg) as a yellow solid.

Step f.

A sample of compound 8 (34 mg) was treated 4N HCl in dioxane (0.5 mL) at rt overnight to remove both the Boc group and the SEM group. The Cbz group was removed under hydrogenolysis conditions (Pd/C, $H_2$).

Step g.

Compound 9 (29 mg, 0.05 mmol) was treated with N-Moc-D-Phg-OH (20.6 mg, 0.11 mmol), DMTMM (42 mg, 0.15 mmol) and DIPEA (52 mg, 0.42 mmol) in THF/DMF (0.5 mL/0.5 mL) to give compound 10. LC-MS (ESI): m/z 829 $(M+H)^+$.

Scheme 2-4
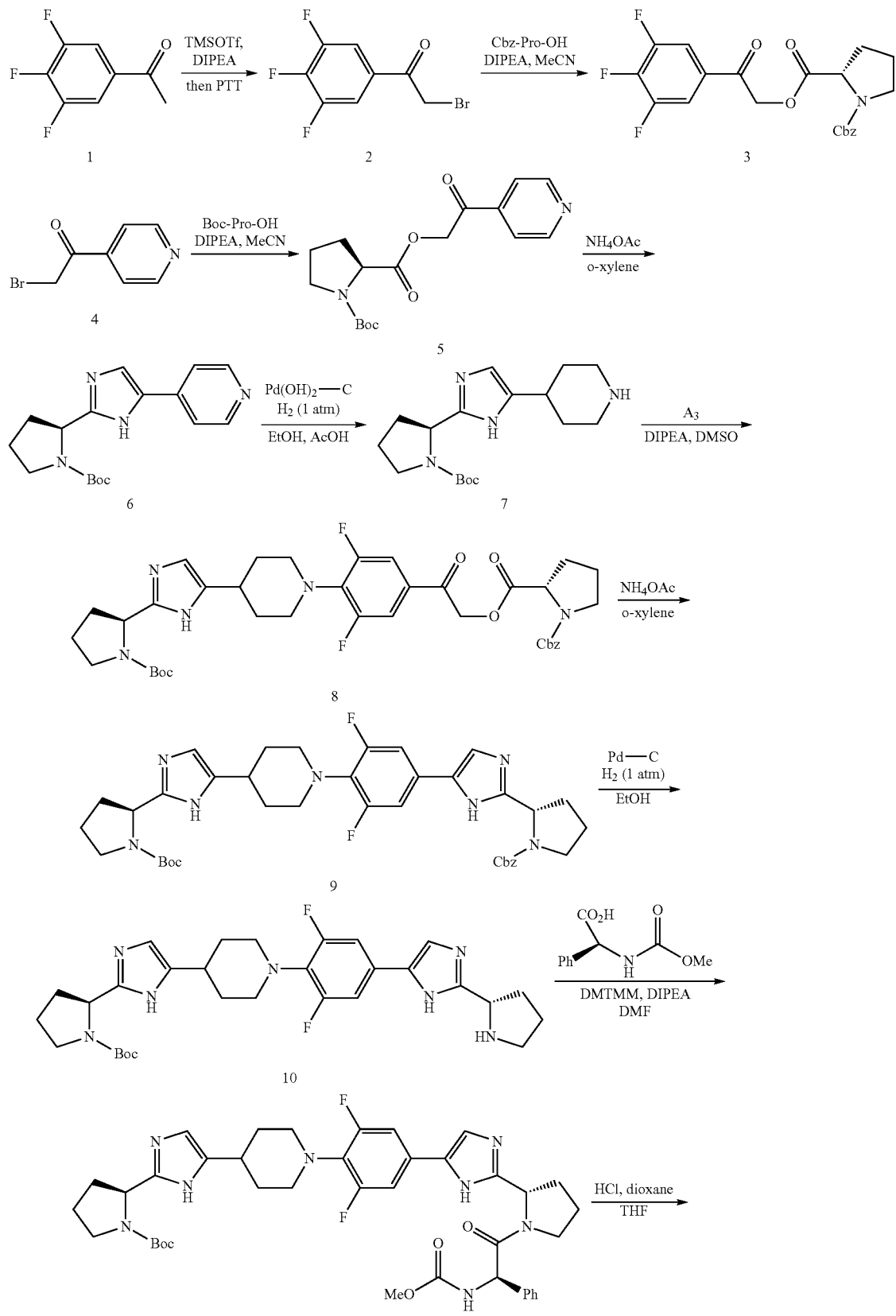

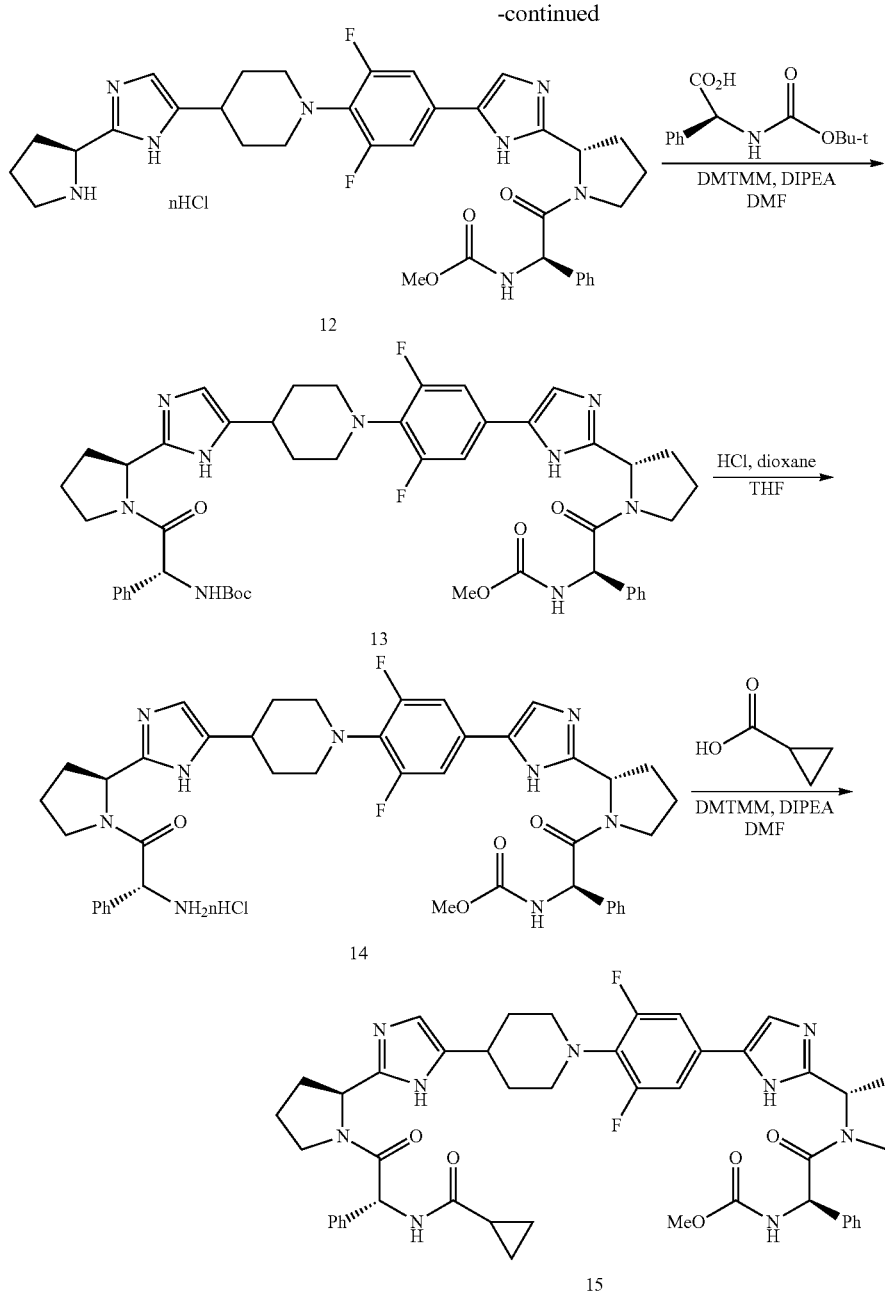

Step a.
Referring to Scheme 2-4, to a stirred solution of 1 (1 eq., 0.2 M) in CH₂Cl₂ was added DIPEA (1.2 eq.). The reaction flask was cooled with a water-ice bath, and TMSOTf (1.1 eq.) was slowly added over a 10 min period. The reaction was stirred at 0° C. for 10 min, then at rt until silylation was complete, as determined by TLC (1.5 h). PTT (1M in THF, 1.05 eq) was added over 10 min. The reaction was stirred at rt until bromination was complete, as judged by TLC (30 min). The reaction was partitioned between CH₂Cl₂ and NaHCO₃ with a 1/1 (v/v) ratio. The aqueous phase was extracted with CH₂Cl₂ (2×). The combined organic layers were dried over Na₂SO₄, filtered, and concentrated. The crude product 2 was used without further purification.

Step b.
To a stirred solution of 2 (1 eq., 0.3M) and N-Cbz-L-Pro-OH (1 eq.) in MeCN was added DIPEA (1.2 eq.). The reaction was stirred at rt for 16 h. The reaction was concentrated to dryness. The resulting crude product was purified by silica gel column chromatography (hexanes/EtOAc=100/0 to 70/30 (v/v), 5 step gradient) to provide 3.

Step c.
To a stirred solution of 4 (1 eq, 0.3M) and N-Boc-L-Pro-OH (1 eq.) in MeCN was added DIPEA (1.2 eq.). The reaction was stirred at rt for 16 h. The reaction was concentrated to dryness. The resulting crude product was purified by silica gel flash column chromatography (hexanes/EtOAc=100/0 to 70/30 (v/v), 5 step gradient) to provide 5.

Step d.

A stream of nitrogen was bubbled through a solution of 5 (1 eq., 0.3M) in o-xylene in a sealable reaction tube for 10 min. NH₄OAc (10 eq.) was added to the solution. The reaction tube was sealed and placed in a 150° C. oil bath. The reaction was stirred at this temperature for 1 h then cooled to rt. The reaction tube was carefully opened, and its contents partitioned between aqueous $Na_2CO_3$ and $CH_2Cl_2$/MeOH (10/1 (v/v)) with a 1:1 (v/v) ratio. The layers were separated, and the aqueous phase was extracted with $CH_2Cl_2$/MeOH (10/1) until the extracts were free of any uv-active component (as determined by TLC). The combined organic layers were dried over $Na_2SO_4$, filtered, and concentrated. The resulting crude product was purified by silica gel column chromatography (hexanes/EtOAc=50/50, 20/80, and 0/100, then MeOH/EtOAc=1/99 (v/v)) to provide 6.

Step e.

To a solution of 6 (1 eq.) in EtOH/AcOH (1/1, v/v) was added Pd(OH)₂ on carbon (10%). After sealing the reaction flask with a rubber septum, the system was evacuated and backfilled with 1 atm H₂ (2×). The vigorously stirred reaction was stirred at rt under H₂ (1 atm) for 16 h. The mixture was filtered through a pad of CELITE™545 (pre-washed with EtOH), and the separated solids were washed with EtOH (5×). The filtrate was concentrated to provide crude 7. Residual AcOH was removed by dissolving the crude product in H₂O then adjusting the pH to ~13 with 2N aqueous NaOH. The product was extracted with $CH_2Cl_2$ until the extracts were free of 7. The crude product was used without further purification.

Step f.

To a solution of 7 (1 eq., 0.3M) and 3 (1 eq.) in DMSO was added DIPEA (1.2 eq). The reaction was stirred at rt for 4 h then at 30° C. for 16 h. The reaction was then partitioned between aqueous $Na_2CO_3$ and $CH_2Cl_2$/MeOH (10/1 (v/v)) with a 1:1 (v/v) ratio. The layers were separated, and the aqueous phase was extracted with $CH_2Cl_2$/MeOH (10/1 (v/v)) until the extracts were free of any UV-active component. The combined organic layers were dried over $Na_2SO_4$, filtered, and concentrated by rotary evaporation. The resulting crude product was purified by silica gel column chromatography (hexanes/EtOAc=33/67 to 0/100 (v/v), 5 step gradient) to provide 8.

Step g.

A stream of nitrogen was bubbled through a solution of 8 (1 eq, 0.3M) in o-xylene in a sealable reaction tube for 10 min. NH₄OAc (10 eq) was added to the solution. The reaction tube was sealed and placed in a 150° C. oil bath. The reaction was stirred at this temperature for 1 h then cooled to rt. The reaction tube was carefully opened, and its contents were partitioned between aqueous $Na_2CO_3$ and $CH_2Cl_2$/MeOH (10/1 (v/v)) with a 1:1 (v/v) ratio. The layers were separated, and the aqueous phase was extracted with $CH_2Cl_2$/MeOH (10/1 (v/v)) until the extracts were free of any UV-active component. The combined organic layers were dried over $Na_2SO_4$, filtered, and concentrated by rotary evaporation. The resulting crude product was purified by silica gel flash column chromatography (hexanes/EtOAc=25/75 to 0/100 (v/v), then MeOH/EtOAc 1/99 to 3/97 (v/v)) to provide 9.

Step h.

To a solution of 9 (1 eq) in absolute EtOH was added Pd on carbon (10%, 50% H₂O). After sealing the reaction flask with a rubber septum, the system was evacuated and backfilled with 1 atm H₂ (2×). The vigorously stirred reaction was stirred at rt under H₂ (1 atm) for 4 h. The mixture was filtered through a pad of CELITE™545 (pre-washed with EtOH), and the separated solids were washed with EtOH (5×). The filtrate was concentrated to provide crude 10 that was used without further purification.

Step i.

To a stirred solution of 10 (1 eq, 0.1M) and N-Moc-D-Phg-OH (1 eq.) in DMF, DMTMM (1 eq.) and DIPEA (1 eq.) were sequentially added. The reaction was stirred at rt for 1 h and partitioned between aqueous $Na_2CO_3$ and $CH_2Cl_2$/MeOH (10/1) with a 1/1 (v/v) ratio. The layers were separated, and the aqueous phase was extracted with $CH_2Cl_2$/MeOH (10/1) until the extracts were free of any uv-active component. The combined organic layers were dried over $Na_2SO_4$, filtered, and concentrated by rotary evaporation. Residual DMF was removed by bulb-to-bulb distillation using gentle heating. The remaining crude product was purified by silica gel column chromatography (hexanes/EtOAc=25/75, 10/90, 0/100 (v/v), then MeOH/EtOAc=1/99 to 3/97 (v/v)) to provide 11.

Step j.

Compound 11 (1 eq.) was treated with THF (7 mL/mmol 11) followed by slow addition of 4N HCl in dioxane (14 mL/1 mmol of 11). The reaction was stirred at rt for 2 h. The reaction mixture was concentrated to dryness to provide 12.

Step k.

To a stirred solution of 12 (1 eq, 0.1M) and N-Boc-D-Phg-OH (1 eq.) in DMF were sequentially added DMTMM (1 eq.) and DIPEA (1 eq.). The reaction was stirred at rt for 1 h. The crude reaction mixture was purified on a C18-Luna preparative HPLC column (H₂O-MeCN, 0.1% HCO₂H) to give compound 13 as a white solid.

Step l.

Compound 13 (1 eq.) was treated with THF (7 mL/mmol) followed by slow addition of 4N HCl in dioxane (14 mL/1 mmol of 13). The reaction was stirred at rt for 3 h. The reaction mixture was concentrated to dryness to provide 14.

Step m.

To a stirred solution of 14 (1 eq, 0.1M) and cyclopropane carboxylic acid (1 eq.) in DMF were sequentially added DMTMM (1 eq.) and DIPEA (1 eq.). The reaction was stirred at rt until complete, as determined by LC-MS. The crude reaction mixture was purified on a C18-Luna preparative HPLC column (H₂O-MeCN, 0.1% HCO₂H) to give compound 15 as a white solid. $^1$H NMR (CDCl₃, 300 MHz) δ 7.37-7.49 (m, 12H), 7.22 (br s, 1H), 7.19 (br s, 1H), 7.16 (s, 1H), 6.84 (d, J=6.0 Hz, 1H), 6.27 (d, J=0.5 Hz, 1H), 5.94 (br d, J=6.0 Hz, 1H), 5.58 (d, J=6.0 Hz, 1H), 5.39 (d, J=6.5 Hz, 1H), 5.24-5.30 (m, 2H), 3.70-3.82 (m, 2H), 3.68 (s, 3H), 3.14-3.35 (m, 6H), 2.88 (br m, 1H), 2.65-2.78 (m, 2H), 1.75-2.15 (m, 10H), 1.47 (m, 1H), 0.97 (m, 2H), 0.79 (m, 2H). LC/MS (ESI) m/z 430.9 [(M+2H)/2]⁺. HPLC: Agilent Eclipse XDB-C18 4.6×150 mm, 5 μm; 5%-100% B over 15 min; A=H₂O+TFA (0.1%), B=MeCN+TFA (0.1%); 254 nm; 20 μL injection volume. RT=8.17 min; 97% pure.

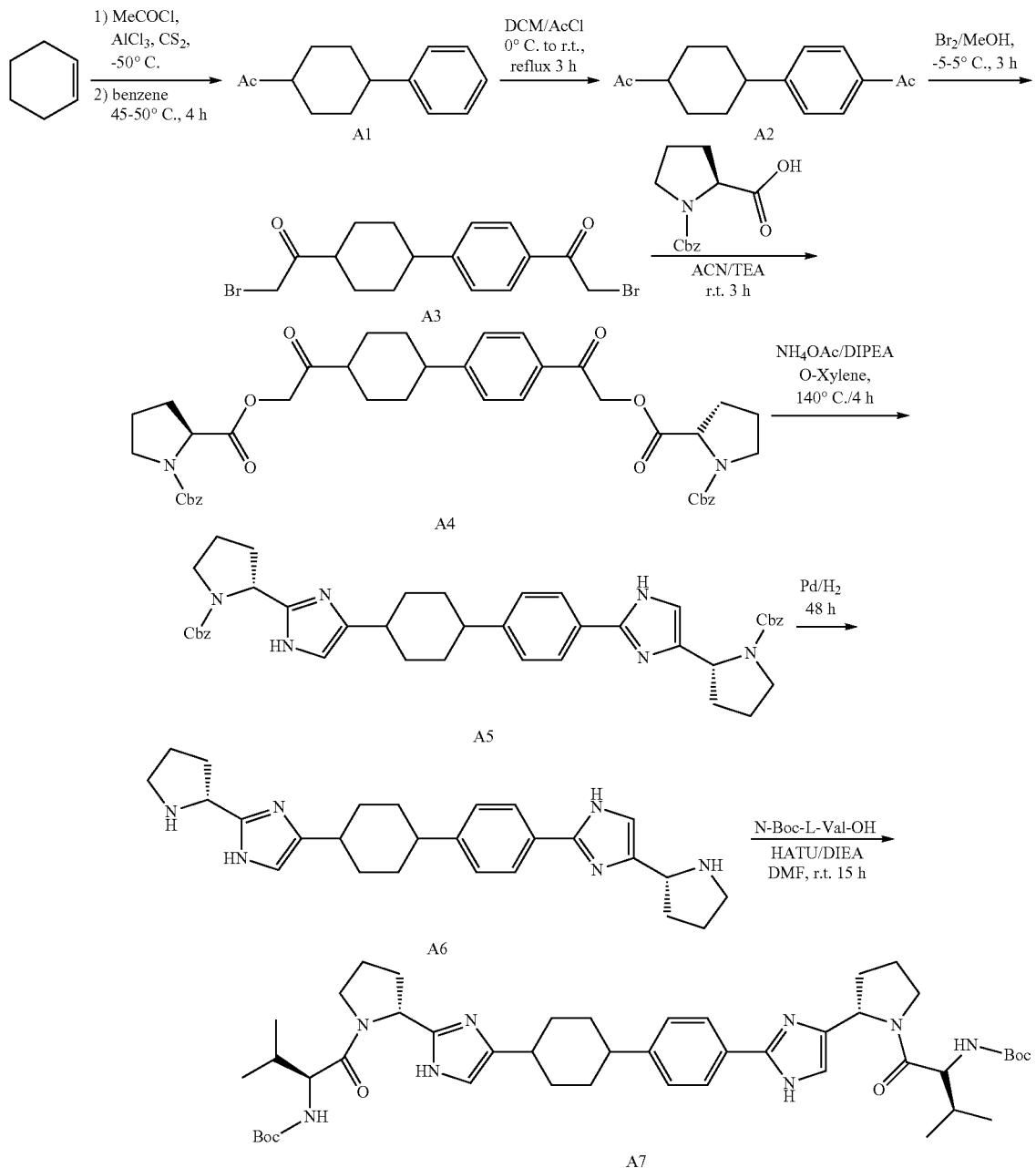

Scheme 2-6

Step a.

Referring to Scheme 2-6 to a suspension of AlCl₃ (19.5 g, 146 mmol) in CS₂ (40 mL) at −78° C. was added acetyl chloride (10.4 mL, 146 mmol) slowly over 10 min. The mixture was stirred vigorously for 15 min and cyclohexene (10 g, 122 mmol) was added dropwise over 20 min. The mixture was stirred below −20° C. for 30 min. The solvent was removed and the residue was re-dissolved in benzene. The mixture was heated at 40-50° C. 3-4 h, cooled to rt and poured into a mixture of ice and HCl (1N). The organic layer was collected, and aqueous layer was extracted with ethyl acetate (3×). The combined organic layers were concentrated and purified on a column (hexane:ethyl acetate, 8:2) to give 1-(4-phenylcyclohexyl)ethanone (A1) (9 g, 37% yield).

Step b.

To a suspension of AlCl₃ (5.9 g, 54 mmol) in DCM (200 mL) at 0° C. was added 1-(4-phenylcyclohexyl)ethanone (9 g in DCM), and acetyl chloride (10.4 mL, 146 mmol) dropwise over 30 min. The mixture was stirred to rt for 15 min. and heated at 45° C. for 4 h. After being cooled to rt, the mixture was poured it into ice-HCl (1N). The organic layer was collected, and the aqueous layer was extracted with ethyl acetate (3×). The combined organic layers were combined, concentrated and purified on column (hexane:ethyl acetate, 8:2) to give 1-(4-(4-acetylcyclohexyl)phenyl)ethanone (A2) as a mixture of two isomers (5 g, 46% yield).

Step c.

To a solution of 1-(4-(4-acetylcyclohexyl)phenyl)ethanone (A2) (900 mg, 3.7 mmol) in MeOH (20 mL) at 0° C. was added bromine (993 µL, 8.1 mmol) drop-wise and the reaction mixture was stirred below 5° C. for 3 h. The reaction was quenched by adding saturated aqueous NaHCO₃ solution and the mixture was extracted with ethyl acetate (3×). The extracts were combined and concentrated. The residue was purified by silica gel column chromatography (n-hexane/ethyl acetate=5/1 (v/v)) to afford 2-bromo-1-(4-(4-(2-bromoacetyl)cyclohexyl)phenyl)ethanone (A3) (400 mg, 27% yield).

Step d.

To a solution of N-Cbz-L-Pro-OH (1.36 g, 5.47 mmol) in acetonitrile (10 mL) was added triethyl amine (762 µL, 5.47 mmol) and 2-bromo-1-(4-(4-(2-bromoacetyl)cyclo hexyl)phenyl)ethanone (A3) (1 g, 2.49 mmol) in acetonitrile. The reaction mixture was stirred at rt overnight. The solvent was removed and product was diluted with ethyl acetate (3×), washed with NaHCO₃ (100 mL) and brine, and dried with Na₂SO₄. After removal of the solvent, the crude product (S)-1-benzyl 2-(2-(4-(4-(2-((S)-1-(benzyloxycarbonyl)pyrrolidine-2-carbonyloxy)acetyl)cyclohexyl)phenyl)-2-oxoethyl)pyrrolidine-1,2-dicarboxylate (A4) (2.5 g) was used for the next step directly.

Step e.

A solution of (S)-1-benzyl 2-(2-(4-(4-(2-((S)-1-(benzyloxycarbonyl)pyrrolidine-2-carbonyloxy)acetyl)cyclohexyl)phenyl)-2-oxoethyl)pyrrolidine-1,2-dicarboxylate (A4) (3.0 g, 4.06 mmol) in o-xylene (25 mL), ammonium acetate (3.76 g, 48.7 mmol) and diisopropylethylamine (48.7 mmol) was placed in a pressure resistant tube. The tube was sealed and heated to 140° C. for 4 h, cooled to rt. The volatile component was removed in vacuo and the residue was partitioned between water and CH₂Cl₂. The organic phase was dried, filtered and concentrated in vacuo. The resulting crude material was purified by a flash chromatography (CH₂Cl₂/MeOH=9/1 (v/v)) to provide (S)-benzyl 2-(4-(4-(4-(4-((S)-1-(benzyloxycarbonyl)pyrrolidin-2-yl)-1H-imidazol-2-yl)phenyl)cyclohexyl)-1H-imidazol-2-yl)pyrrolidine-1-carboxylate (A5) as yellow residue (200 mg).

Step f.

(S)-benzyl 2-(4-(4-(4-(4-((S)-1-(benzyloxycarbonyl)pyrrolidin-2-yl)-1H-imidazol-2-yl)phenyl)cyclohexyl)-1H-imidazol-2-yl)pyrrolidine-1-carboxylate (A5) (200 mg) and Pd/C (20 mg) in MeOH (20 mL) was purged with H₂. The reaction was stirred under hydrogen balloon for 48 h, filtered on CELITE™ and concentrated. The residue 2-((S)-pyrrolidin-2-yl)-4-(4-(4-(4-((S)-pyrrolidin-2-yl)-1H-imidazol-2-yl)phenyl)cyclohexyl)-1H-imidazole (A6) was directly used for next step without further purification.

Step g.

To a solution of 2-((S)-pyrrolidin-2-yl)-4-(4-(4-(4-((S)-pyrrolidin-2-yl)-1H-imidazol-2-yl)phenyl)cyclohexyl)-1H-imidazole (A6) (300 mg, 0.715 mmol) in DMF (20 mL) was added N-Boc-L-Val-OH (432 mg, 1.72 mmol), HATU (654 mg, 1.72 mmol) and diisopropylethylamine (590 µL, 3.58 mmol). The reaction was stirred at rt overnight. The solvent was removed under reduced pressure. The crude product was purified by silica gel column chromatography (CH₂Cl₂/MeOH=9/1 (v/v)) and preparative TLC to give A7 (500 mg) as a white solid. LC-MS (ESI): m/z 829 (M+H)⁺.

Scheme 2-7

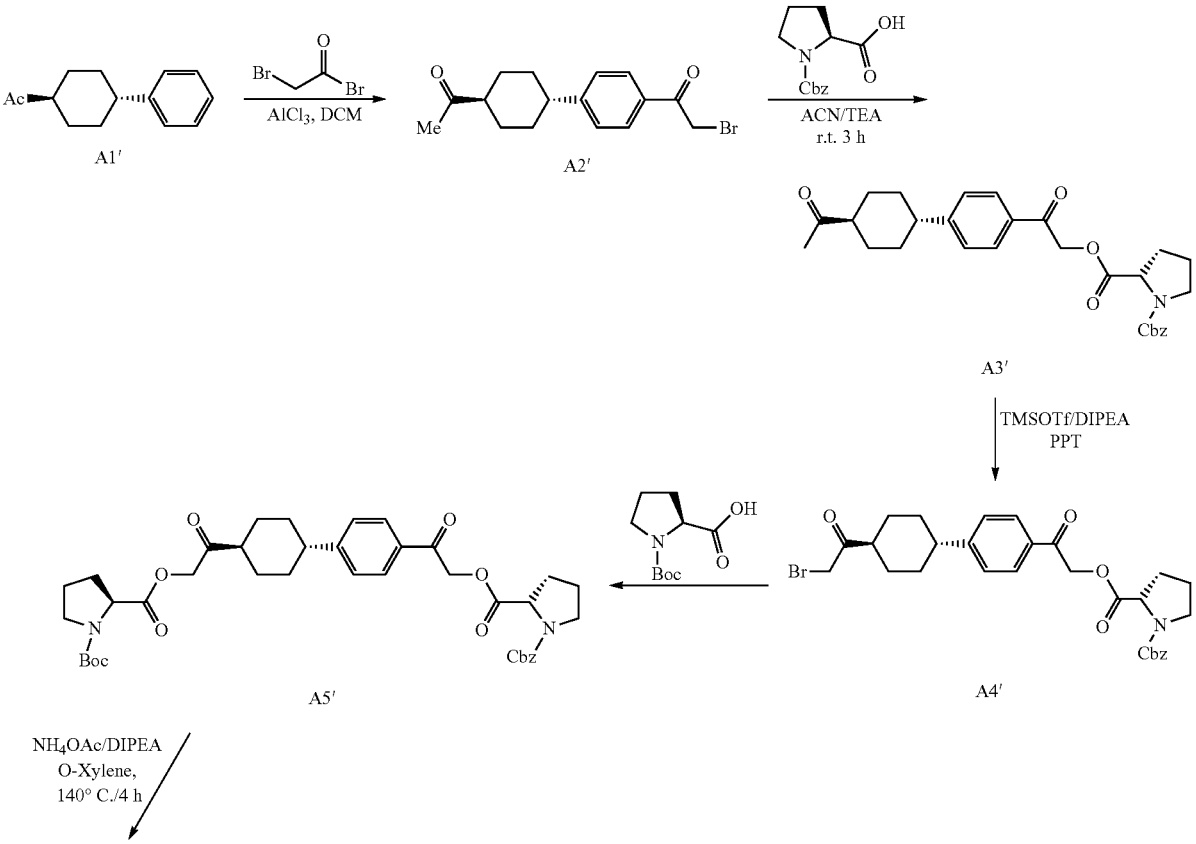

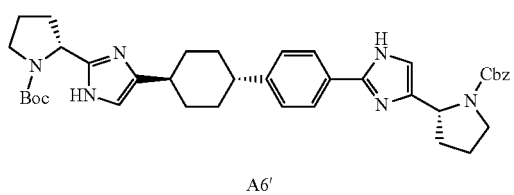

-continued

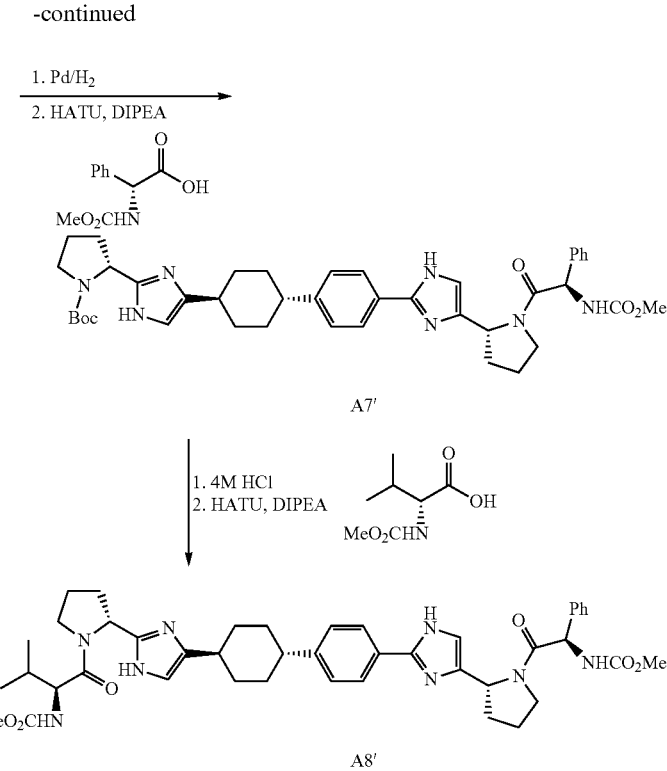

Step a.

Referring to Scheme 2-7 to a suspension of AlCl₃ (1.58 g, 12 mmol) in DCM (30 mL) at −78° C. was added 1-(4-phenylcyclohexyl)ethanone (A1') (1 g in DCM, 5.0 mmol), and bromoacetyl bromide (0.65 mL, 7.5 mmol) dropwise over 10 min. The mixture was stirred to rt for 15 min and heated at 40-50° C. for 3 h, cooled to rt and poured into a mixture of ice and HCl (1N). The organic layer was collected, and the aqueous layer was extracted with ethyl acetate (3×). The combined organic layers were concentrated on rotovap and purified silica gel column chromatography (Hexanes/EtOAc=8/2 (v/v)) to give the desired trans-isomer A2' (1 g, 62% yield) along with a small amount of cis-isomer.

Step b.

To a solution of the N-Cbz-L-Pro-OH (7.4 g, 29.7 mmol) in acetonitrile (30 mL) was added triethylamine (5.2 mL, 37 mmol) and A2' (8 g, 24.8 mmol) in acetonitrile. The reaction mixture was stirred at rt overnight. The solvent was removed and product was extracted with ethyl acetate (3×), washed with NaHCO₃ (200 mL) and brine, dried with Na₂SO₄. After removal of the solvent, the crude product was purified silica gel column chromatography (Hexanes/EtOAc=1/1 (v/v)) to give pure A3' as a light yellow oil (8 g, 66% yield).

Step c.

To a solution of A3' (20.0 g, 40.7 mmol) and diethylisopropylamine (20 mL) in DCM (200 mL) in a round bottom flask was added trimethylsilyl trifluoromethanesulfonate (TMSOTf, 20 mL, 122 mmol) at −78° C. The reaction was stirred at rt overnight. To the solution was added a solution of phenyltrimethylammonium tribromide (PTT, 16.8 g, 45 mmol) in THF (50 mL). The reaction was stirred at rt 2 h and quenched with saturated NaHCO₃ solution. The mixture was partitioned between water and CH₂Cl₂ (3×), and the organic layers were washed with brine, dried, filtered and concentrated in vacuum. The resulting crude material was purified by silica gel column chromatography (Hexanes/EtOAc=1/1 (v/v)) to provide A4' as yellow residue (17 g, 73% yield).

Using similar procedure as for compound A3' from A2', compound A5' was prepared from the corresponding bromide A4' in 80% yield.

Step d.

To a solution of A5' (2.5 g, 3.5 mmol) in o-xylene (25 mL) in a sealed tube was added ammonium acetate (4.1 g, 53 mmol). The mixture was sealed and heated at 140° C. for 3 h and then cooled to rt. The volatile component was removed in vacuo, and the residue was partitioned between H₂O and CH₂Cl₂, and the organic phase was dried, filtered and concentrated in vacuo. The resulting crude material was purified by silica gel column chromatography (CH₂Cl₂/MeOH=9/1 (v/v)) to provide A6' as a yellow solid (250 mg, 10% yield).

Step e.

Following the deprotection and amide formation operations described for similar systems and repeated the process twice, the differentially functionalized compound A8' was obtained. LC-MS (ESI): m/z 789 (M+H)⁺.

Scheme 3-1

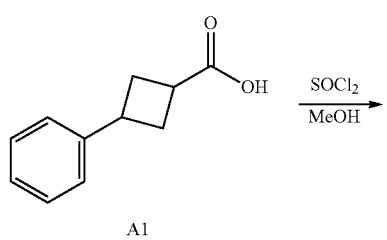

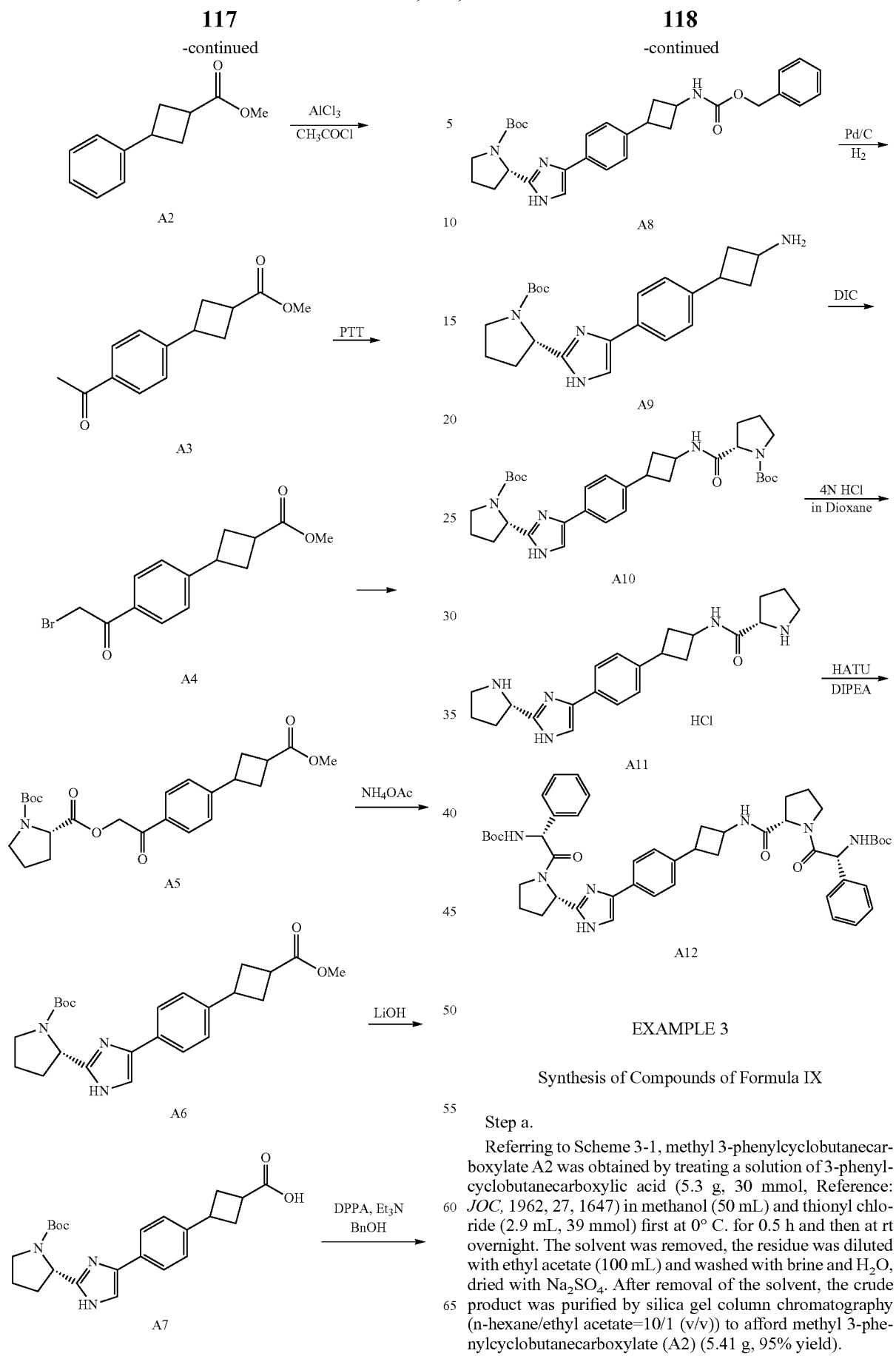

EXAMPLE 3

Synthesis of Compounds of Formula IX

Step a.

Referring to Scheme 3-1, methyl 3-phenylcyclobutanecarboxylate A2 was obtained by treating a solution of 3-phenylcyclobutanecarboxylic acid (5.3 g, 30 mmol, Reference: *JOC,* 1962, 27, 1647) in methanol (50 mL) and thionyl chloride (2.9 mL, 39 mmol) first at 0° C. for 0.5 h and then at rt overnight. The solvent was removed, the residue was diluted with ethyl acetate (100 mL) and washed with brine and H$_2$O, dried with Na$_2$SO$_4$. After removal of the solvent, the crude product was purified by silica gel column chromatography (n-hexane/ethyl acetate=10/1 (v/v)) to afford methyl 3-phenylcyclobutanecarboxylate (A2) (5.41 g, 95% yield).

Step b.

To a solution of methyl 3-phenylcyclobutanecarboxylate (A2) (5.41 g, 28 mmol) and $AlCl_3$ (9.5 g, 71 mmol) in methylene chloride (150 mL) at 0° C. was added acetyl chloride (4 mL) dropwise and the reaction mixture was stirred at rt overnight. The reaction mixture was diluted with 1N HCl (100 mL) and extracted with $CH_2Cl_2$, and the organic layer was dried with $Na_2SO_4$, filtered and concentrated. The crude product was purified by silica gel column chromatography (n-hexane/ethyl acetate=5:1) to afford methyl 3-(4-acetylphenyl)cyclobutanecarboxylate (A3) (6.0 g, 94% yield).

Step c.

To a solution of methyl 3-(4-acetylphenyl)cyclobutanecarboxylate (A3) (6.56 g, 28.2 mmol) in methylene chloride (250 mL) at 0° C. was added PTT (10.6 g, 28.2 mmol) and the reaction mixture was stirred at rt overnight. The reaction was quenched with $NaHCO_3$ (100 mL), washed with brine, and dried with $Na_2SO_4$. After removal of the solvent, crude product A4 (7.2 g, 82% yield) was directly used for the next step.

Step d.

A solution of crude methyl 3-(4-(2-bromoacetyl)phenyl)cyclobutanecarboxylate (A4) (8.8 g, 28.3 mmol), N-Boc-L-Pro-OH (6.7 g, 31.2 mmol) and triethylamine (4.34 mL) in $CH_3CN$ was stirred for 2 h. At the completion of reaction, the volatile components were removed in vacuo, and the residue was partitioned between $H_2O$ and $CH_2Cl_2$. The organic phase was dried, filtered and concentrated in vacuo. The residue was purified by silica gel column chromatography to provide (S)-1-tert-butyl 2-(2-(4-(3-(methoxycarbonyl)cyclobutyl)phenyl)-2-oxoethyl)pyrrolidine-1,2-dicarboxylate (A5) as a colorless oil (10.6 g, 84% yield).

Step e.

A mixture of ketoester (S)-1-tert-butyl 2-(2-(4-(3-(methoxycarbonyl)cyclobutyl)phenyl)-2-oxoethyl)pyrrolidine-1,2-dicarboxylate (A5) (3.7 g, 8.76 mmol) and $NH_4OAc$ (6.75 g, 87.6 mmol) in o-xylenes (10 mL) was heated in a sealed tube at 140° C. for 1 h. The volatile component was removed in vacuo, and the residue was partitioned between $H_2O$ and $CH_2Cl_2$. The organic phase was dried, filtered and concentrated in vacuo. The resulting crude material was purified by silica gel column chromatography to provide (S)-tert-butyl 2-(4-(4-(3-(methoxycarbonyl)cyclobutyl)phenyl)-1H-imidazol-2-yl)pyrrolidine-1-carboxylate (A6) as a colorless oil (1.76 g, 47.4% yield).

Step f.

To a solution of the compound (S)-tert-butyl 2-(4-(4-(3-(methoxycarbonyl)cyclobutyl)phenyl)-1H-imidazol-2-yl)pyrrolidine-1-carboxylate (A6) (1.76 g, 41.5 mmol) in THF (10 mL) and MeOH (10 mL), LiOH (1M, 10.0 mL) was added at 0° C. After 30 min of stirring, the reaction was quenched with saturated solution of $NH_4Cl$, extracted with EtOAc, dried over $Na_2SO_4$, and concentrated to obtain the crude product (S)-3-(4-(2-(1-(tert-butoxycarbonyl)pyrrolidin-2-yl)-1H-imidazol-4-yl)phenyl)cyclobutanecarboxylic acid (A7) (1.4 g, 82.4% yield), which was used without further purification.

Step g.

The mixture of (S)-3-(4-(2-(1-(tert-butoxycarbonyl)pyrrolidin-2-yl)-1H-imidazol-4-yl)phenyl)cyclobutanecarboxylic acid (A7) (822 mg, 2 mmol), DPPA (0.53 mL, 2.4 mmol), and triethylamine (0.34 mL) in benzyl alcohol (10 mL) was heated at 95° C. overnight. The volatile component was removed in vacuo, the residue was partitioned between $H_2O$ and $CH_2Cl_2$. The organic phase was dried, filtered and concentrated in vacuo. The resulting crude material was purified by a flash chromatography on silica gel to provide (S)-tert-butyl 2-(4-(4-(3-(benzyloxycarbonylamino)cyclobutyl)phenyl)-1H-imidazol-2-yl)pyrrolidine-1-carboxylateas (A8) as a yellow solid (449 mg, 44% yield).

Step h.

To a solution of (S)-tert-butyl 2-(4-(4-(3-(benzyloxycarbonylamino) cyclobutyl)phenyl)-1H-imidazol-2-yl)pyrrolidine-1-carboxylate (A8) (449 mg, 0.87 mmol) in methanol (10 mL) was added 10% Pd/C (50 mg) and the mixture was stirred overnight under $H_2$ atmosphere in a balloon. The mixture was filtrated and concentrated to obtain the crude product (S)-tert-butyl 2-(4-(4-(3-aminocyclobutyl)phenyl)-1H-imidazol-2-yl)pyrrolidine-1-carboxylate (A9) (330 mg, 99% yield) without further purification.

Step i.

To a solution of (S)-tert-butyl 2-(4-(4-(3-aminocyclobutyl)phenyl)-1H-imidazol-2-yl)pyrrolidine-1-carboxylate (A9) (330 mg, 0.86 mmol) in dichloromethane (60 mL), N-Boc-L-Pro-OH (204 mg, 0.95 mmol), and DIC (0.2 mL) were added at rt. After stirring overnight, the reaction mixture was diluted with methylene chloride (50 mL), and washed with saturated aqueous $NaHCO_3$, dried with $Na_2SO_4$. After removal of the solvent, the crude product was purified by silica gel column chromatography (n-hexane/ethyl acetate=2:1) to afford the product (S)-tert-butyl 2-(3-(4-(2-((S)-1-(tert-butoxycarbonyl)pyrrolidin-2-yl)-1H-imidazol-4-yl)phenyl)cyclobutylcarbamoyl)pyrrolidine-1-carboxylate (A10) (294 mg, 59% yield).

Step j.

To a solution of (S)-tert-butyl 2-(3-(4-(2-((S)-1-(tert-butoxycarbonyl)pyrrolidin-2-yl)-1H-1-imidazol-4-yl)phenyl)cyclobutylcarbamoyl)pyrrolidine-1-carboxylate (A10) (100 mg, 0.173 mmol) in THF (8 mL), 4N HCl in dioxane (2 mL) was added slowly at rt. After stirring for 1.5 h, the solvent was removed to give (S)—N-(3-(4-(2-((S)-pyrrolidin-2-yl)-1H-imidazol-4-yl)phenyl)cyclobutyl)pyrrolidine-2-carboxamide (A11) as an HCl salt. The white solid was used for the next step without further purification.

Step k.

To a solution of (S)—N-(3-(4-(2-((S)-pyrrolidin-2-yl)-1H-imidazol-4-yl)phenyl)cyclobutyl)pyrrolidine-2-carboxamide (A11) (100 mg, 0.98 mmol) in dichloromethane (20 mL), N-Boc-D-Phg-OH (87 mg, 0.35 mmol), DIPEA (144 µL, 0.34 mmol) and HATU (134 mg, 0.35 mmol) were added at rt. After stirring overnight, the reaction mixture was washed with brine and $H_2O$, dried with $Na_2SO_4$. After removal of the solvent, the crude product was purified by silica gel column chromatography (DCM/MeOH=10/1 (v/v)) to afford tert-butyl (R)-2-((S)-2-(3-(4-(2-((S)-1-((R)-2-(tert-butoxycarbonylamino)-2-phenylacetyl)pyrrolidin-2-yl)-1H-imidazol-4-yl)phenyl)cyclobutylcarbamoyl)pyrrolidin-1-yl)-2-oxo-1-phenylethylcarbamate (A12) (50 mg, 34% yield). LC-MS (ESI): m/z 846 (M+H)$^+$.

Scheme 3-2

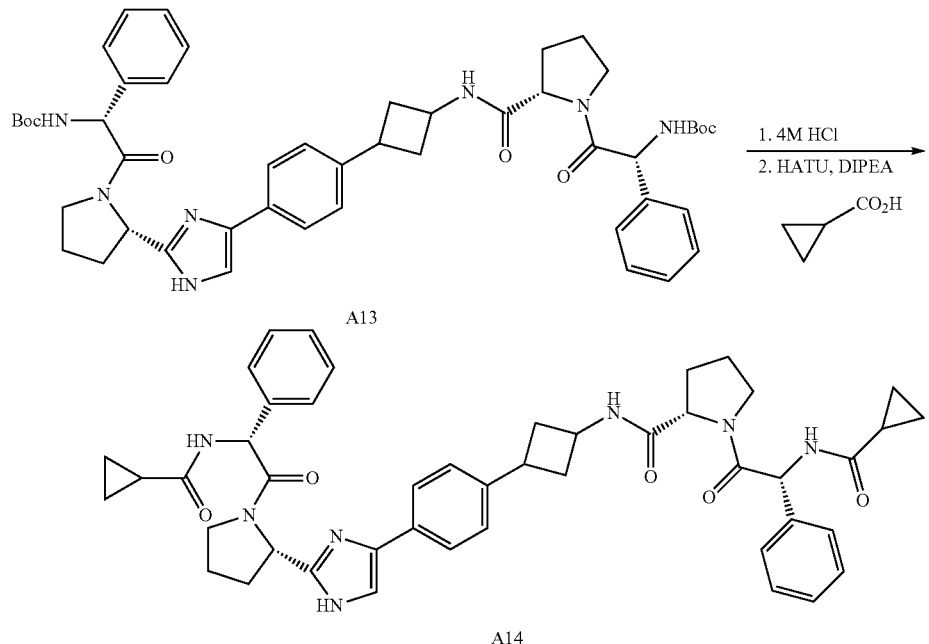

Additional examples of formula IX bearing varying capping groups were prepared following procedures described below, such as in the synthesis of compound A14, shown in Scheme 3-2.

Step a.

A sample of the product from Scheme 3-1, tert-butyl (R)-2-((S)-2-(3-(4-(2-((S)-1-((R)-2-(tert-butoxycarbonyl amino)-2-phenylacetyl)pyrrolidin-2-yl)-1H-imidazol-4-yl) phenyl)cyclobutylcarbamoyl)pyrrolidin-1-yl)-2-oxo-1-phenylethylcarbamate (A13) (222 mg, 0.262 mmol) in THF (10 mL) was treated with 4N HCl in dioxane (5 mL) at rt for 8 h. At the completion of the reaction, solvent was removed and the resulting white solid, (S)-1-((R)-2-amino-2-phenylacetyl)-N-(3-(4-(2-((S)-1-((R)-2-amino-2-phenylacetyl) pyrrolidin-2-yl)-1H-imidazol-4-yl)phenyl)cyclobutyl)pyrrolidine-2-carboxamide (300 mg) was used for the next step without further purification.

Step b.

To a solution of (S)-1-((R)-2-amino-2-phenylacetyl)-N-(3-(4-(2-((S)-1-((R)-2-amino-2-phenylacetyl)pyrrolidin-2-yl)-1H-imidazol-4-yl)phenyl)cyclobutyl)pyrrolidine-2-carboxamide (80 mg, 0.124 mmol) in dichloromethane (20 mL), cyclopropyl carboxylic acid (22 mg, 0.26 mmol), DIPEA (0.5 mL) and HATU (94 mg, 0.26 mmol) were added at rt. After stirring overnight, the reaction was washed with brine and $H_2O$, dried with $Na_2SO_4$. After removal of the solvent, the crude product was purified by silica gel column chromatography (DCM/MeOH=10/1 (v/v)) to afford (S)-1-((R)-2-(cyclopropanecarboxamido)-2-phenylacetyl)-N-(3-(4-(2-((S)-1-((R)-2-(cyclopropanecarboxamido)-2-phenylacetyl) pyrrolidin-2-yl)-1H-imidazol-4-yl)phenyl)cyclobutyl) pyrrolidine-2-carboxamide (A14) (25 mg).

EXAMPLE 4

Synthesis of Compounds of Formula V

Scheme 4-1

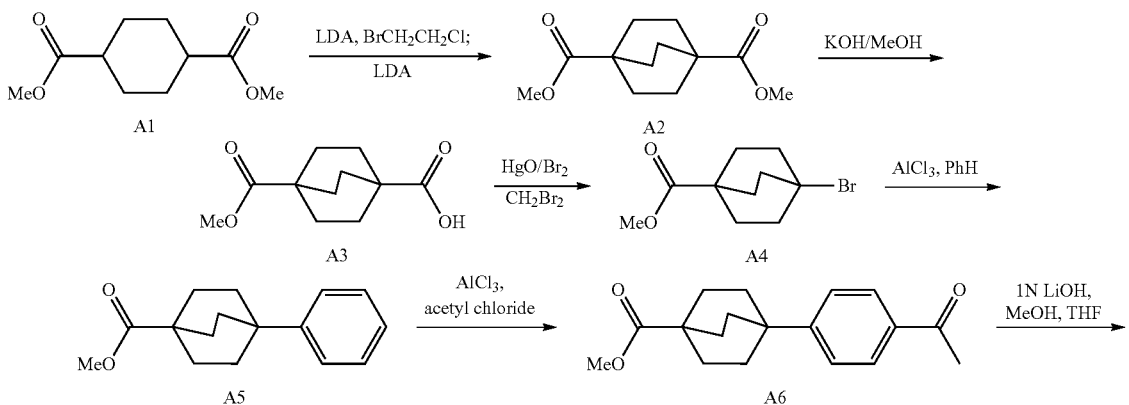

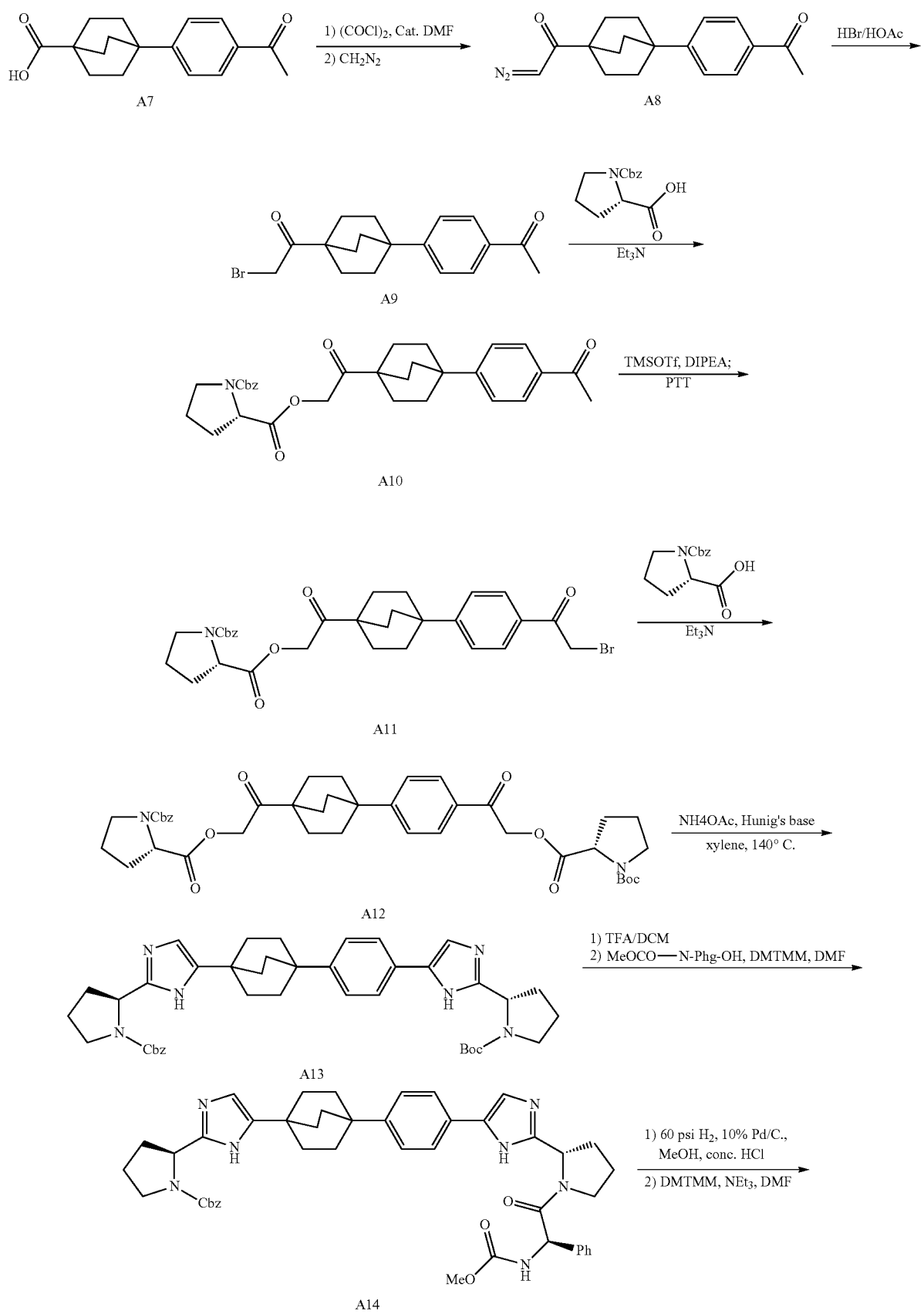
-continued

-continued

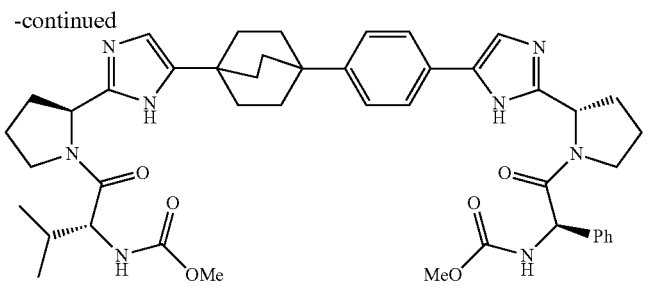

A15

Step a.

Referring to Scheme 4-1, the starting building blocks, A1, A2, A3, and A4 can be prepared following published conditions in the literature. References: 1). Chang, H.; Fiesman, W. F. and Petter, R. C. *Syn. Comm.* 2007, 37, 1267. 2). Champans, N. B.; Sotheeswar, S, and Tonyne, K. J. *J. Org. Chem.* 1970, 35, 917. 3). Della, E. W. and Tsanaktisidis, J. *Aust. J. Chem.* 1985, 38, 1705.

Step b.

To a solution of freshly prepared LDA (132 mL of n-butyl lithium, 2.5 M in hexane, 51 mL of diisopropylamine) in THF (anhydrous, 420 mL), DMPU (200 mL) at −78° C. was added a solution of A1 (60 g, 300 mmol) in THF (60 mL) at −78° C. After stirring for 40 min, 1-bromo-2-chloroethane (24.9 mL, 300 mmol) was added. After stirring for another 20 min at −78° C., the dry ice-acetone bath was removed and the reaction was slowly warmed up to rt. After stirring for an additional hour, the reaction mixture was cooled back to −78° C. and a solution of DMPU (200 mL) in THF (420 mL) was added. Another portion of freshly prepared LDA (120 mL of n-butyl lithium, 2.5 M in hexane, 47 mL of di-isopropylamine in THF (anhydrous, 420 ml)) was added into the reaction mixture by cannula at −78° C. After stirring for 1.5 h at −78° C., the dry ice-acetone bath was removed and the reaction was slowly warmed up to rt. After 5-6 h, the reaction was quenched with saturated aqueous ammonium chloride (300 mL) and concentrated. The residue was diluted with $H_2O$ (480 mL) and extracted with ethyl acetate/hexane (1:5 (v/v), 3×360 mL). The combined organic layers were washed with brine (500 mL) and then dried, filtered, and concentrated. The resulting crude product was purified by silica gel flash column chromatography (Hexanes/EtOAc=10/1 (v/v)) to provide A2 (35 g).

Step c.

To a solution of A2 (24.7 g) in MeOH (310 mL) was added potassium hydroxide (6.12 g) in $H_2O$ (62 mL) at rt. The reaction was warmed up to 95° C. and stirred overnight. The reaction was cooled to rt and concentrated. The residue was diluted with $H_2O$ (1000 mL) and extracted with ethyl acetate/hexane (1:10, 3×400 mL), which provided recycled A2 (4.8 g) after concentration. The remaining aqueous layer was acidified to pH=3 by concentrated HCl and then was extracted with ethyl acetate/methanol (10:1 (v/v), 3×500 mL). The combined organic layers were dried with sodium sulfate, filtered and concentrated to provide A3 (17.8 g).

Step d.

To a solution of A3 (17.8 g) in dibromomethane (1200 mL) was added mercury(II) oxide at rt. The reaction was warmed up to 80° C. and bromine (6.0 mL) was added dropwise during 25 min. After additional 3 h stirring, the reaction was cooled down to rt and filtered through a pad of CELITE™, washed with dichloromethane, concentrated to afford A4 (19.8 g). The crude product A4 was used without further purification.

Step e.

To a solution of A4 (19.8 g) in dichloromethane (500 mL) at −20° C. was added aluminum chloride (43 g) in several portions. The reaction was then warmed up to 0° C. After overnight stirring, the reaction was poured into a mixture of ethyl acetate (800 mL), 1M HCl (800 mL) along with some ice. After separating the ethyl acetate layer, the aqueous layer was extracted with ethyl acetate (3×300 mL). The combined organic layers were washed with brine, $H_2O$, dried over $Na_2SO_4$, filtered, and concentrated to afford A5 (19.2 g), which was used without further purification.

Step f.

To a solution of A5 (19.2 g) in dichloromethane (500 mL) at −20° C. was added acetyl chloride (16.8 mL), followed by aluminum chloride (43 g). The reaction was allowed to warm up to rt. After overnight stirring, the reaction was poured into a mixture of ethyl acetate (800 mL), 1M HCl (800 mL) along with some ice. After separating the organic layer, the aqueous layer was extracted with ethyl acetate (3×300 mL). The combined organic layers were washed with brine, $H_2O$, dried over $Na_2SO_4$, filtered, and concentrated to afford A6 (24 g), which was used for next reaction without further purification.

Step g.

To a solution of A6 (21 g) in MeOH (500 mL) and THF (500 mL) was added aqueous lithium hydroxide (1M, 365 mL) at rt. After overnight stirring, the reaction was concentrated. The residue was diluted with water (1400 mL) and extracted with diethyl ether (3×500 mL), ethyl acetate (2×400 mL). The combined organic layers were extracted with lithium hydroxide (1M, 500 mL). All aqueous basic layers were combined and acidified to pH 2 by concentrated HCl, extracted with ethyl acetate (3×800 mL). The combined organic layers were dried over $Na_2SO_4$, filtered and concentrated to provide A7 (14.8 g).

Step h.

To a solution of A7 (14.8 g) in dichloromethane (800 mL) was added oxalyl chloride (5.1 mL) at rt. DMF (209 µL) was added in three portions over 4 h. The reaction was concentrated and re-dissolved in dichloromethane (500 mL). The fresh made diazomethane (0.3M, 500 mL) was added at 0° C. The reaction was slowly warmed up to rt. After overnight stirring, the reaction was concentrated to obtain the crude A8 (17.8 g).

Step i.

To a suspension of A8 (17.8 g) in acetic acid (250 mL), hydrogen bromide (33% in acetic acid, 25 mL) was added dropwise at rt. After stirring for an additional hour, the reaction was filtered though a pad of CELITE™454, washed with ethyl acetate, concentrated to afford the crude product, which was purified by silica gel flash column chromatography (Hexanes/EtOAc=3/1 (v/v)) to provide A9 (18.5 g).

Step j.

To a stirred solution of A9 (18.5 g) and Cbz-Pro-OH (14.5 g) in MeCN was added Et$_3$N (8.1 mL). The reaction was stirred at rt overnight and concentrated. The resulting crude product was diluted by ethyl acetate (1000 mL) and washed with saturated sodium carbonate, brine, H$_2$O, dried over sodium sulfate and concentrated to provide A10 (27 g).

Step k.

To a stirred solution of A10 (10 g) in CH$_2$Cl$_2$ (400 mL) was added DIPEA (3.4 mL). The reaction flask was cooled down to −20° C. and TMSOTf (3.5 mL) was slowly added. The reaction was warmed up to rt and stirred for 2 h, then cooled back to −20° C. PTT (8.0 g) in THF (30 mL) was added over 10 min. The reaction was slowly warmed up to rt and stirred overnight. The reaction was poured into a mixture of dichloromethane (500 mL) and sodium disulfite (10% in H$_2$O, 500 mL). The organic layer was separated and washed with brine, H$_2$O, dried over sodium sulfate and concentrated to provide the crude product, which was purified by silica gel flash column chromatography (hexanes/EtOAc=4/1 (v/v)) to provide A11 (8.7 g).

Step l.

To a stirred solution of A11 (8.7 g) and N-Cbz-L-Pro-OH (3.45 g) in MeCN was added Et$_3$N (2.24 mL). The reaction was stirred at rt overnight and concentrated. The resulting crude product was diluted by ethyl acetate (500 mL) and washed with saturated sodium carbonate, brine, water, dried over sodium sulfate and concentrated to provide A12 (10.2 g).

Step m.

A12 (6.5 g) was dissolved in xylene (100 mL) in a sealed bottle. NH$_4$OAc (14.5 g) and N,N-diisopropylethylamine (33 mL) were added to the solution. The reaction tube was sealed and placed in an 140° C. oil bath. The reaction was stirred at this temperature for 1.5 h, then cooled to rt. The reaction tube was carefully opened, and reaction mixture was diluted with dichloromethane. The combine organic solution was washed with brine and H$_2$O, dried over Na$_2$SO$_4$, filtered, and concentrated. The resulting crude product was purified by silica gel flash column chromatography (EtOAc/Acetone/28% NH$_4$OH=100/1/1 (v/v/v)) to provide A13 (3.0 g).

Step n.

To a stirred solution of A13 (500 mg) in dichloromethane (50 mL) was added trifluoroacetic acid (5 mL). After 3 h, the reaction was concentrated to dryness to give a TFA salt, which was dissolved in DMF (20 mL). To the solution were added DIEA (490 µL), N-Moc-D-Phg-OH (98 mg) and 4-(4,6-dimethoxy-1,3,5-triazin-2-yl)-4-methylmorpholinium chloride (DMTMM, 156 mg) subsequently. After one h stirring, the reaction was diluted with H$_2$O. The suspension was filtered through a pad of CELITE™545 and washed with H$_2$O. The filtrate cake was rinsed with dichloromethane and concentrated to provide A14 (380 mg) without further purification.

Step 13. Step o. To a stirred solution of A14 (8 mg) in methanol (3 mL) was added 10% Pd/C (4 mg) and one drop of concentrated HCl. The reaction was in a Parr shaker at rt and under 60 psi of hydrogen for 12 hours. The reaction was filtered through a pad of CELITE™545 and washed with methanol. The filtrate was concentrated to dryness to provide a free amine, which was dissolved in DMF (1 mL). Subsequently, the mixture was added DIEA (6 µL), N-Moc-Val-OH (1.8 mg) and DMTMM (2.8 mg). After stirring for one h, the reaction was quenched by adding water. The suspension was filtered through CELITE™545 and washed with water. The filtrate cake was rinsed by dichloromethane and concentrated. The residue was purified by prep-HPLC (Phenomenex, C18-Luna column, H$_2$O-MeCN, 0.1% HCO$_2$H) to provide A15 (3.0 mg, 98% purity). $^1$H NMR (CDCl$_3$, 300 MHz). δ 8.01 (br s, 1H), 7.57 (d, J=8.0 Hz, 2H), 7.44-7.39 (m, 5H), 7.31 (d, J=8.0 Hz, 2H), 7.24 (s, 1H), 6.75 (s, 1H), 6.02 (br d, J=7.1 Hz, 1H), 5.48 (br d, J=5.8 Hz, 1H), 5.43-5.40 (m, 2H), 5.34 (br d, J=5.5 Hz, 1H), 4.15-4.10 (m, 1H), 3.97-3.95 (m, 1H), 3.83-3.80 (m, 1H), 3.71 (s, 3H), 3.65 (s, 3H), 3.25-3.22 (m, 1H), 2.77-2.62 (m, 2H), 2.35-2.20 (m, 1H), 2.20-2.00 (m, 4H), 2.05-1.85 (br m, 16H), 1.03 (d, J=4.4 Hz, 6H).

LLC-MS (ESI) m/z: 805.3 (M+H)$^+$, 803.3 (M−H)$^-$. HPLC: Agilent Eclipse XDB-C18 4.6×150 mm, 5 µm; 5%-100% B over 15 min; A=H$_2$O+TFA (0.1%), B=MeCN+TFA (0.1%); 254 nm; 20 µL injection volume. RT=8.86 min; 98%.

EXAMPLE 5

Synthesis of Additional Compounds of Formula I

Scheme 5-1

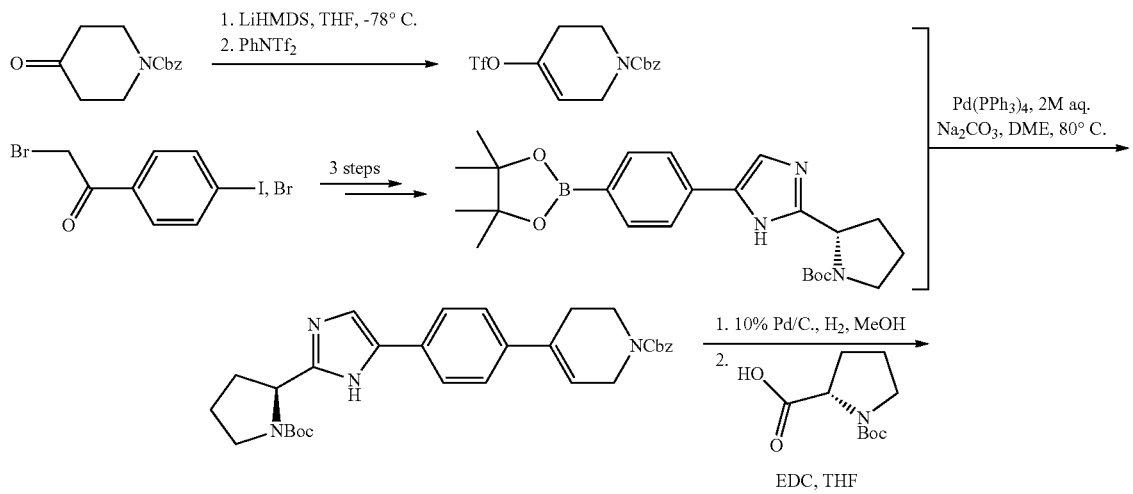

129 130
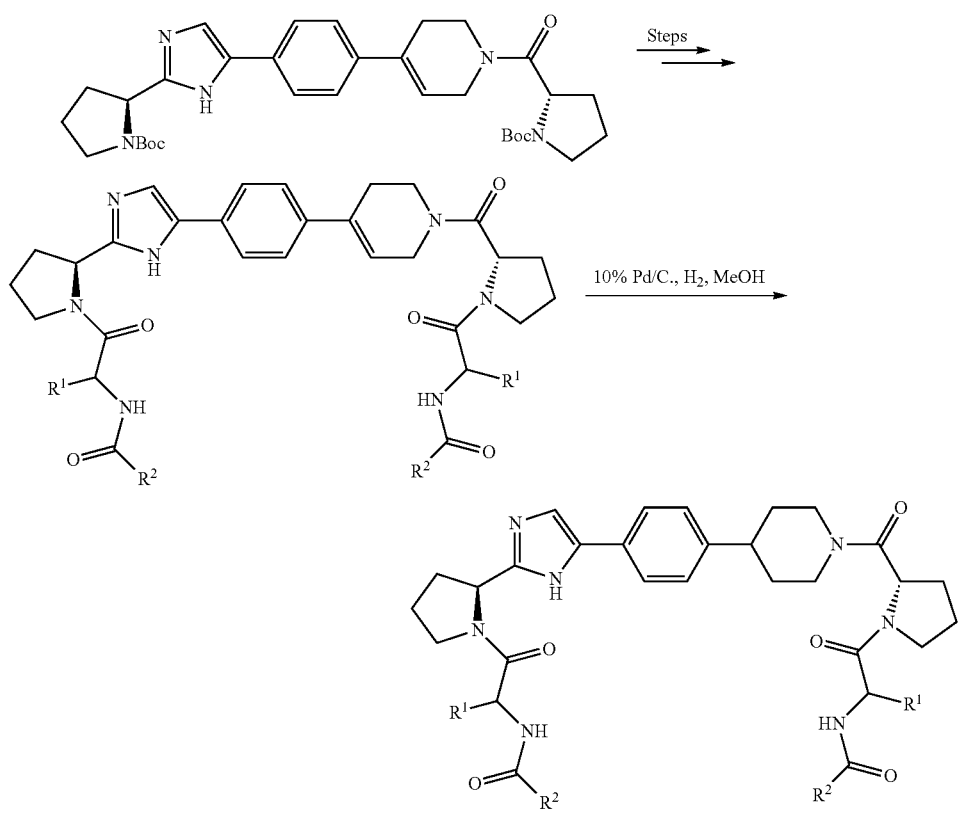
Scheme 5-2
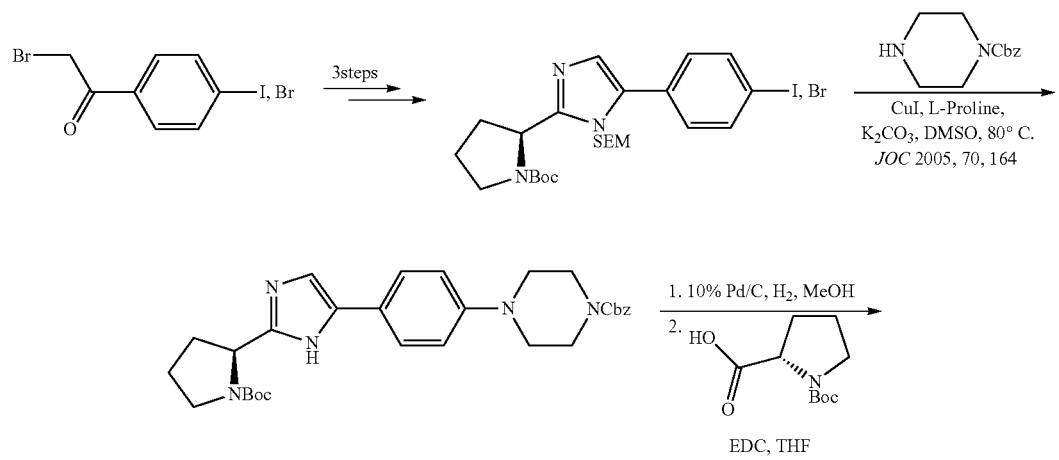
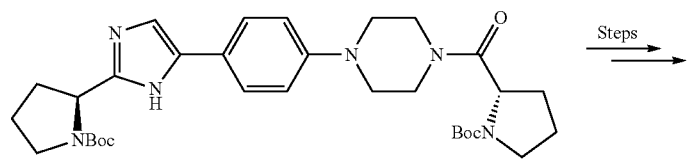

-continued
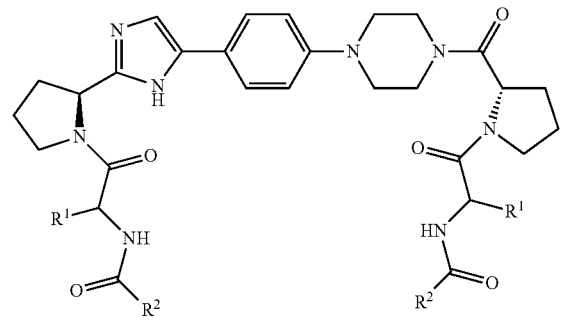

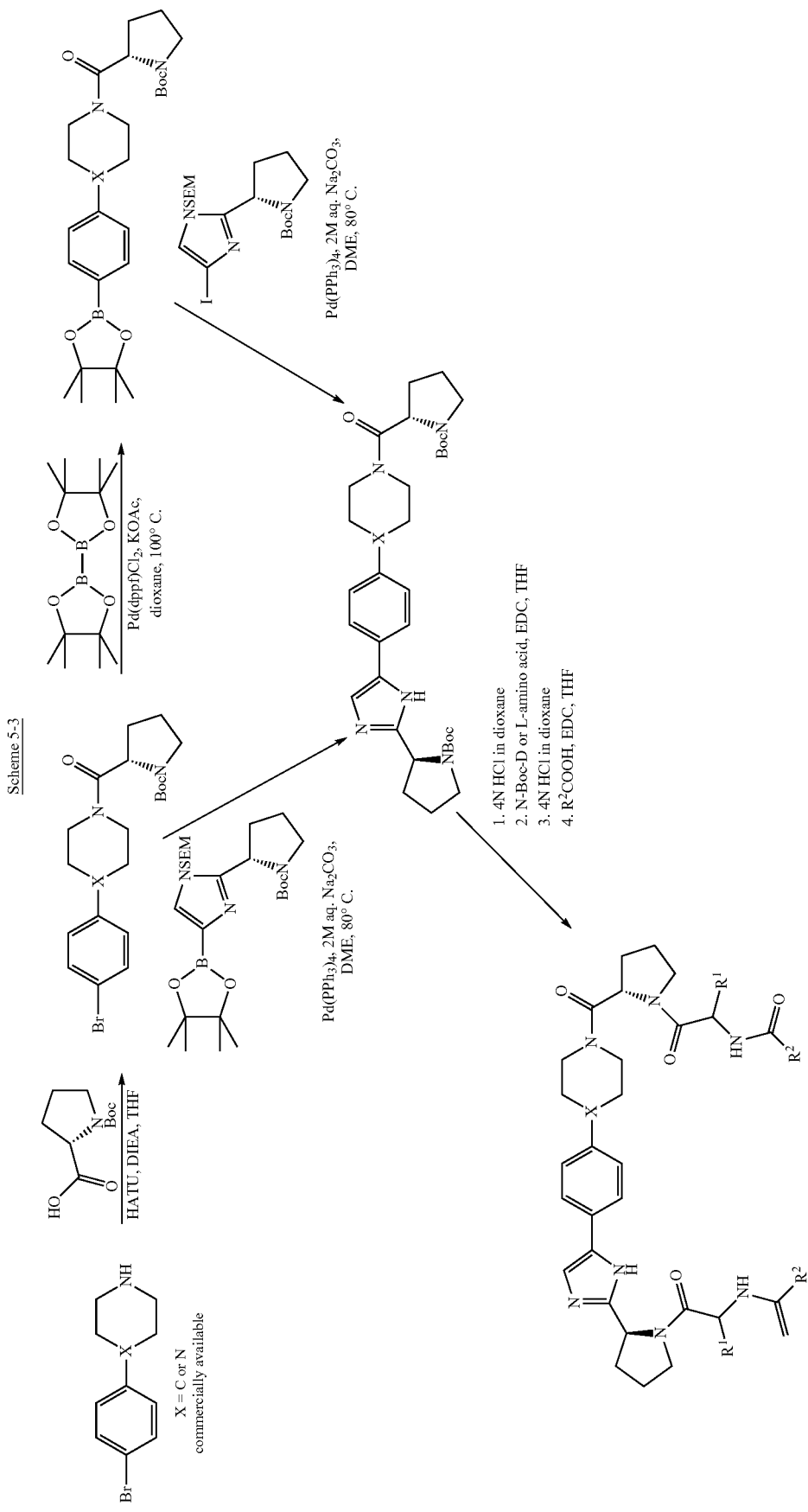

Scheme 5-4

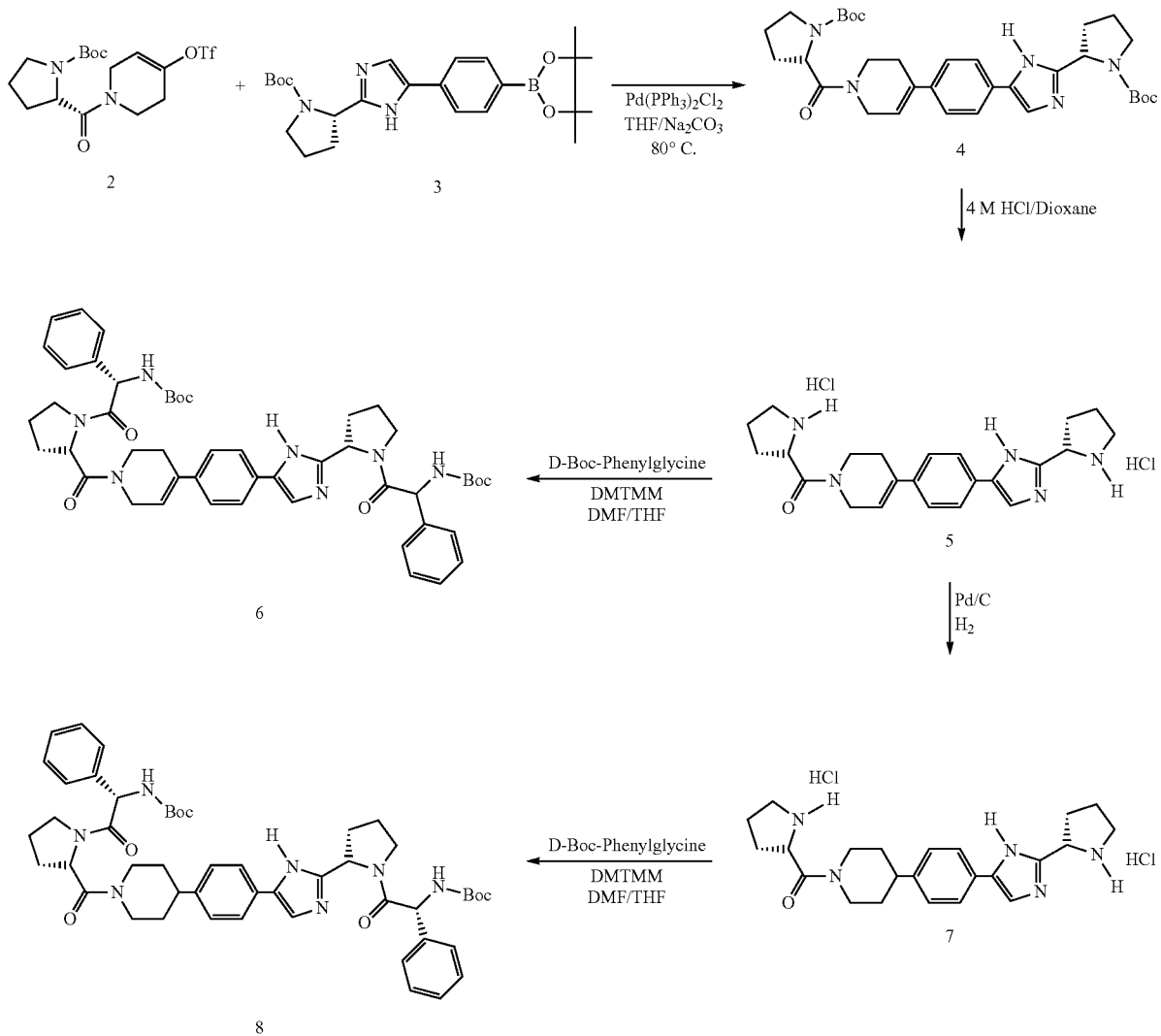

Step a.

Referring to Scheme 5-4, a mixture of triflate 2 (0.43 g, 2.34 mmol), borate 3 from above (1.01 g, 2.3 mmol) and Pd(PPh₃)₂Cl₂ (160 mg, 0.23 mmol) in THF (12 mL) and aqueous Na₂CO₃ (2 M, 2.4 mL) was degassed and filled with nitrogen. The mixture heated at 80° C. overnight. The reaction mixture was purified by column chromatography eluting with 1% methanol in ethyl acetate to give compound 4 (0.95 g, 70% yield).

Step b.

To a solution of 4 (0.95 g, 1.6 mmol) in DCM (32 mL) at 0° C. was add 4M HCl in dioxane. The mixture was stirred at 0° C. for 3 h and warmed to rt for 1 h. Solvent was removed to give a white solid 5.

Step c.

A mixture of 5 obtained above, DMTMM (0.89 g, 3.2 mmol), triethylamine (1.12 mL, 8.0 mmol) and N-Boc-D-Phg-OH (0.8 g, 3.2 mmol) in THF (16 mL) was stirred at rt for 14 h. The reaction was diluted with H₂O (50 mL), extracted with ethyl acetate (3×20 mL). The combined organic layers were washed with brine, dried over Na₂SO₄, and then concentrated to give a residue. The residue was purified with silica gel chromatography eluting with hexane/ethyl acetate (1/1 to 1/2 (v/v)) to afford 6 (32 mg, 14% yield). LCMS (ESI): m/z 858 (M+H)⁺.

Step d.

A mixture of 5 (400 mg, 1.0 mmol) and Pd/C (100 mg) in methanol (12 mL) was degassed, and filled with hydrogen (60 psi). The mixture was shaken for 16 h. The solution was filtered through a pad of CELITE™545. The filtrate was concentrated to give a pale yellow solid 7.

Step e.

A mixture of 7 (384 mg, 0.98 mmol), DMTMM (0.51 g, 1.86 mmol), triethylamine (0.54 mL, 3.9 mmol) and Boc-D-Phg-OH (466 mg, 1.86 mmol) in THF (10 mL) was stirred at rt for 14 h. The reaction was diluted with H₂O and extracted with ethyl acetate. The combined organic layers were washed with brine and dried over Na₂SO₄, concentrated to give a residue. The residue was purified by silica gel column chromatography eluting with hexane/ethyl acetate (1/1 to 1/2 (v/v)) to afford 8 (0.24 g, 29% yield). LC-MS (ESI): m/z 860 (M+H)⁺.

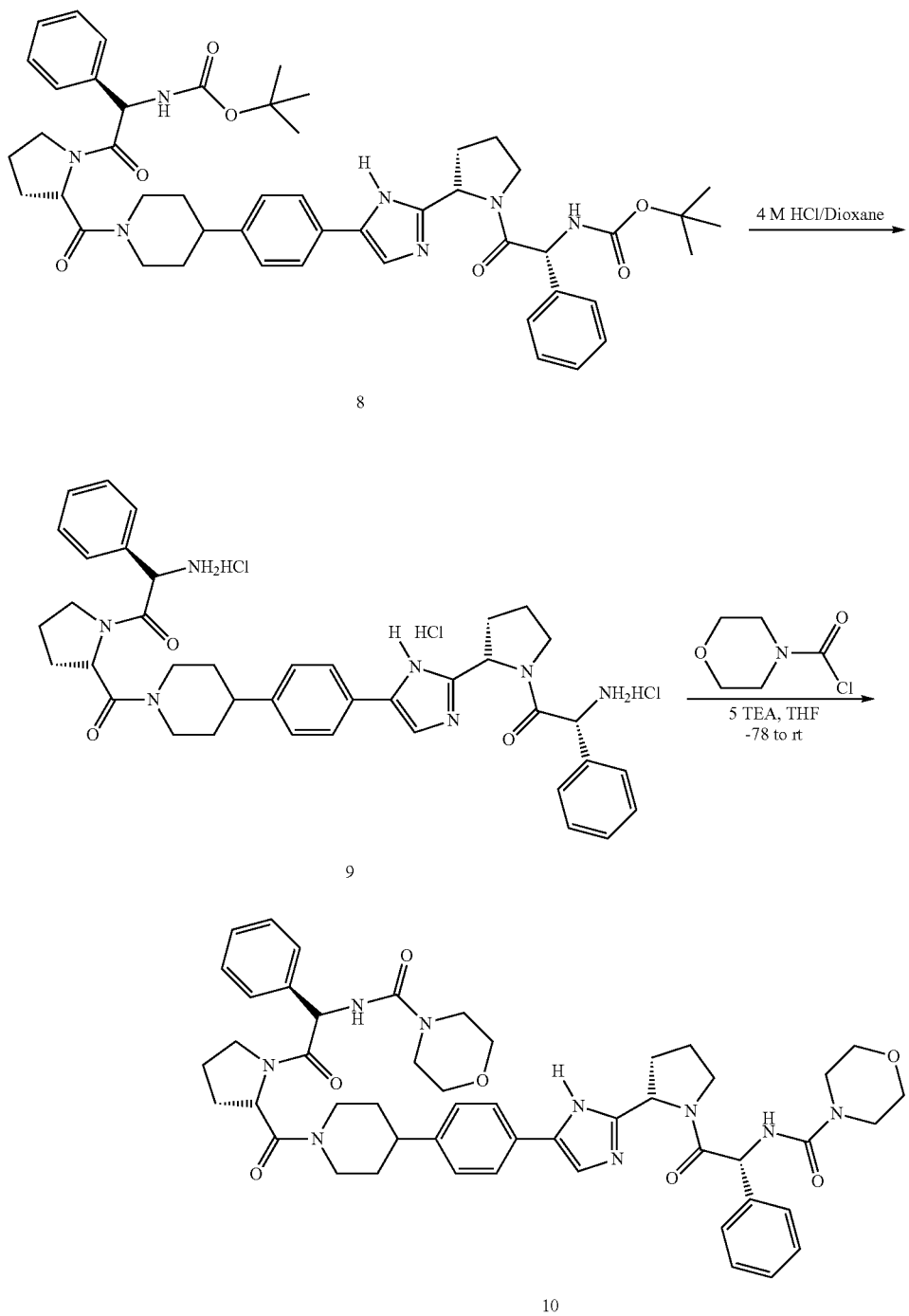

Scheme 5-5

Step a.

Referring to Scheme 5-5, to a solution of 8 (0.86 g, 1.0 mmol) in DCM (10 mL) at 0° C. was add TFA (2 mL). The mixture was stirred at rt for 3 h. Solvent was removed to give a white solid 9.

Step b.

To a solution of 9 (90 mg, 0.14 mmol) and triethylamine (95 μL, 0.68 mmol) in THF/DMF (2 mL, 1/1 (v/v)) at −78° C. was added morpholinyl chloroformate (30 μL, 0.26 mmol). The solution was stirred at rt overnight, diluted with H$_2$O and ethyl acetate. The organic layer was washed with H$_2$O and brine, dried over sodium sulfate, and then concentrated to give a residue. The residue was purified with silica gel chromatography eluting with 5% methanol in DCM to afford 10 (40 mg). LC-MS (ESI): m/z 884 (M−H)$^−$.

Scheme 5-6
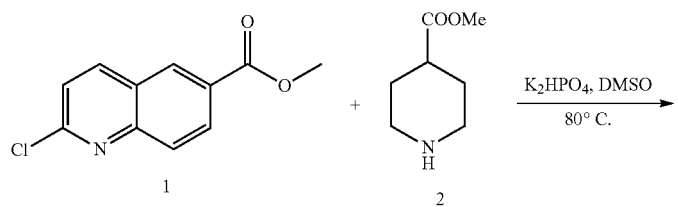
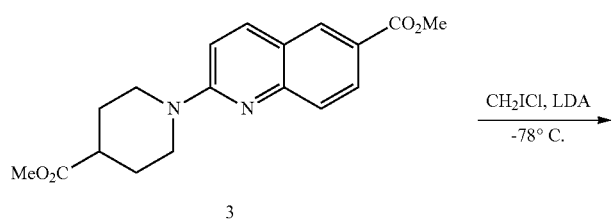
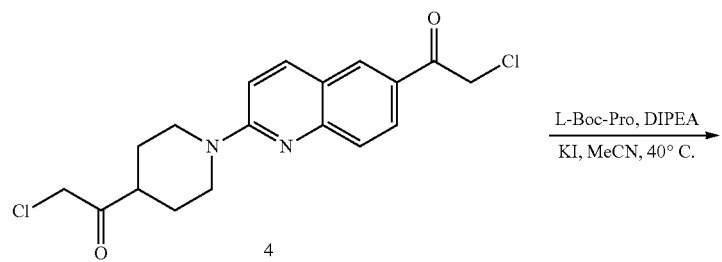
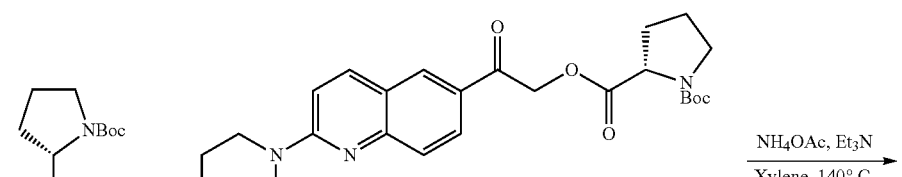
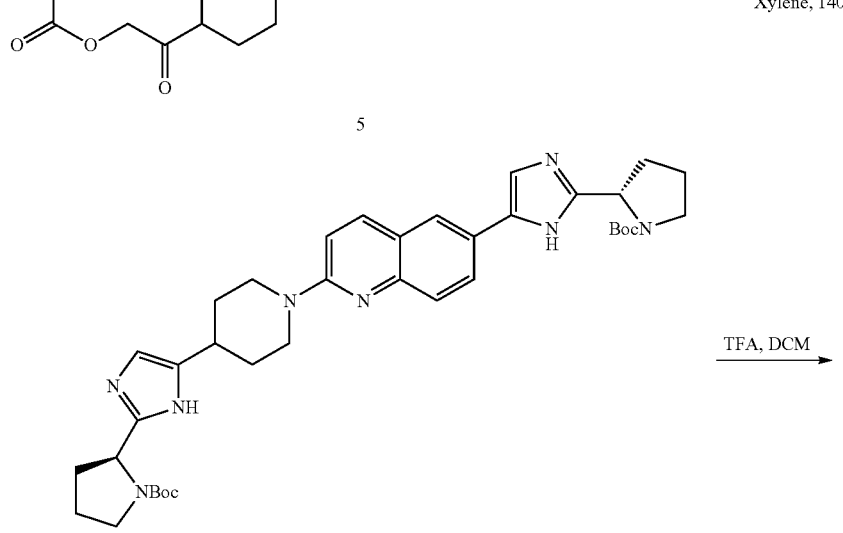

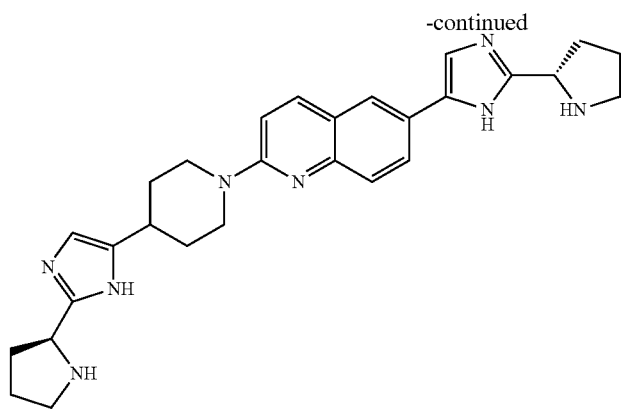

7

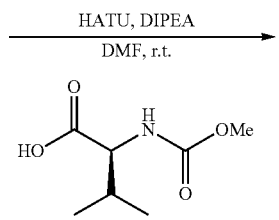

8

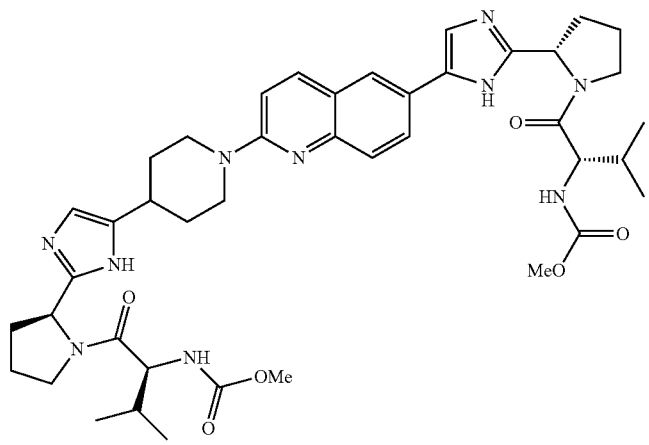

9

Step a.

Referring to Scheme 5-6, to prepare compound 1, to a solution of quinoline-6-carboxylic acid methyl ester (5.61 g, 30 mmol) in 100 mL of dichloromethane was added mCPBA (8.1 g, 36 mmol, 77% maximum purity) in four portions in 5 min at 0° C. The resulting mixture was warmed to rt and stirred for 2 h. The reaction mixture was diluted with 300 mL of dichloromethane and washed with aqueous $Na_2S_2O_3$ solution, saturated $NaHCO_3$ solution, $H_2O$ and brine. After the organic layer was dried and concentrated, an intermediate was obtained as yellow solid (6.2 g, 100% yield), which was used for next step without further purification. $^1$H NMR (300 MHz, $CDCl_3$) δ 8.81 (d, 1H), 8.59-8.65 (m, 2H), 8.36 (d, 1H), 7.86 (d, 1H), 7.40 (d, 1H), 3.98 (s, 3H) ppm.

Step b.

To the solution of quinoline N-oxide (6.7 g, 33 mmol) in dichloromethane (60 mL) was added $POCl_3$ (30 mL) dropwise at rt. The reaction mixture was stirred for 16 h at 50° C. in sealed vessel before it was concentrated to dryness. The residue was dissolved in dichloromethane and washed with saturated $NaHCO_3$, $H_2O$ and brine. The organic layer was dried over $Na_2SO_4$. After concentration, the residue was purified by the flash column chromatography (silica, hexanes/ethyl acetate, v/v, 3/1 to 1/1) to afford the title compound (1.75 g, 24% yield) as white solid which contained some unknown impurity. Pure product was obtained by recrystallization from EtOAc and hexanes for analytical purpose. $^1$H NMR (300 MHz, $CDCl_3$) δ 8.58 (d, 1H), 8.31 (d, 1H), 8.20 (d, 1H), 8.06 (d, 1H), 7.46 (d, 1H), 4.00 (s, 3H) ppm.

Step c.

The mixture of 1 (1.8 g, 8.1 mmol), methyl isonipecotate 2 (1.75 g, 12.2 mmol) and $K_2HPO_4$ (5.64 g, 32.4 mmol) in 15 mL of DMSO was stirred at 80° C. for 20 hours. After cooling down, the resulting mixture was partitioned between 500 mL of EtOAc and 500 mL of $H_2O$. The organic layer was washed with $H_2O$ and brine, and dried ($Na_2SO_4$). After concentration, the residue was purified by the flash column chromatography (silica, hexanes/ethyl acetate, v/v, 3/1 to 1/1) to afford compound 3 (1.95 g, 70% yield) as a white solid. $^1$H NMR (300 MHz, $CDCl_3$) δ 8.32 (d, 1H), 8.11 (dd, 1H), 7.92 (d, 1H), 7.65 (d, 1H), 7.01 (d, 1H), 4.45-4.55 (m, 2H), 3.93 (s, 3H), 3.70 (s, 3H), 3.10-3.24 (td, 2H), 2.58-2.68 (m, 1H), 2.00-2.10 (m, 2H), 1.75-1.87 (m, 2H) ppm.

Step d.

To the solution of 3 (1.81 g, 5.5 mmol) and chloroiodomethane (2.81 mL, 38.5 mmol) in THF (40 mL) was added LDA (pre-cooled to −78° C., freshly made from 10.9 mL of diisoproylamine and 28.6 mL of 2.5 M n-BuLi in hexanes in 40 mL of THF) at −78° C. via cannula over 20 minutes. The reaction mixture was stirred for two hours at −78° C. before it was quenched by dropwise addition of 60 mL AcOH/THF (v/v, 1/1). The resulting mixture was warmed up and partitioned in EtOAc and saturated $NaHCO_3$. The organic layer was washed with $H_2O$ and dried over $Na_2SO_4$. After concentration, the residue was purified by the flash column chromatography (silica, hexanes/ethyl acetate, v/v, 2/1 to 1/1) to afford the title compound 4 (1.48 g, 74% yield) as a yellow solid. $^1$H NMR (300 MHz, $CDCl_3$) δ 8.22 (d, 1H), 8.15 (dd, 1H), 7.94 (d, 1H), 7.68 (d, 1H), 7.01 (d, 1H), 4.78 (s, 2H), 4.61-4.72 (m, 2H), 4.20 (s, 2H), 3.10-3.22 (td, 2H), 2.98-3.12 (m, 1H), 1.96-2.08 (m, 2H), 1.67-1.85 (m, 2H) ppm.

Step e.

A solution of 4 (1.2 g, 3.3 mmol), N-Boc-L-Pro-OH (2.1 g, 9.9 mmol), DIPEA (2.96 mL, 19.8 mmol) and potassium iodide (1.66 g, 9.9 mmol) in MeCN (50 mL) was stirred at 40° C. for 14 h. After removing all solvent in vacuo, the residue was partitioned in EtOAc and saturated NaHCO$_3$. The organic layer was washed with H$_2$O and brine and dried over Na$_2$SO$_4$. After concentration, the residue was purified by silica gel column chromatography (hexanes/ethyl acetate, v/v, 1/1 to 1/2) to afford compound 5 (2.21 g, 93% yield) as a yellow solid. LC-MS (ESI): m/z (M+H)$^+$ 723.75; (M−H)$^−$ 721.85.

Step f.

A mixture of 5 (723 mg, 1.0 mmol), ammonium acetate (2.31 g, 30 mmol) and Et$_3$N (4.18 mL, 30 mmol) in xylene (30 mL) was stirred in sealed vessel at 140° C. for 1.5 h. After removing all solvent in vacuo, the residue was partitioned in 5% MeOH in dichloromethane and water. The organic layer was washed with H$_2$O and brine. The aqueous layers were extracted with 5% MeOH in dichloromethane twice. The combined organic layers were dried over Na$_2$SO$_4$. After concentration, the residue was purified by the flash column chromatography (silica, NH$_4$OH/acetone/ethyl acetate, v/v, 1/3/100) to afford compound 6 (320 mg). LC-MS (ESI): m/z (M+H)$^+$ 683.7; (M−H)$^−$ 681.8.

Step g.

The solution of 6 (320 mg) in 6 mL of dichloromethane and TFA (5 mL) was stirred at rt for 2 h. After removing solvent in vacuo, the residue was purified by reverse-phase preparative HPLC to afford compound 7 (120 mg) as a yellow solid. LC-MS (ESI): m/z (M+H)$^+$ 483.5; (M−H)$^−$ 481.6.

Step h.

To a solution of N-Moc-L-Val-OH (8) (77 mg, 0.44 mmol) and HATU (167 mg, 0.44 mmol) in 2 mL of DMF was added DIPEA (0.15 mL, 1.0 mmol). The resulting solution was stirred at rt for 20 min before 7 (97 mg, ca. 0.2 mmol) and DIPEA (0.15 mL, 1.0 mmol) in 3 mL of DMF was added. The reaction mixture was stirred at rt for another 2 h with determination of the completion of the reaction by LC-MS. The solution was partitioned between EtOAc and water and the organic layer was washed with H$_2$O and brine. The aqueous layer was extracted with EtOAc. The combined organic layers were dried over Na$_2$SO$_4$ before it was concentrated in vacuo. The residue was purified by reverse phase prep-HPLC to afford the title compound 9 (70 mg) as a yellow solid. $^1$H NMR (300 MHz, CDCl$_3$) δ 8.22 (d, 1H), 8.18 (d, 1H), 7.96 (d, 1H), 7.86 (dd, 1H), 7.55 (s, 1H), 7.24 (d, 1H), 6.96 (s, 1H), 5.10 (t, 1H), 5.01 (t, 1H), 4.38-4.52 (m, 2H), 4.19 (dd, 2H), 3.60-4.00 (m, 6H), 3.57 (s, 3H), 3.56 (s, 3H), 3.32-3.48 (m, 3H), 3.08-3.24 (m, 1H), 1.90-2.44 (m, 12H), 1.65-1.90 (m, 3H), 0.81 (t, 6H), 0.69 (t, 6H) ppm. LC-MS (ESI): m/z 399.7 (M+2H)$^{++}$; 795.9 (M−H)$^−$.

Scheme 5-7

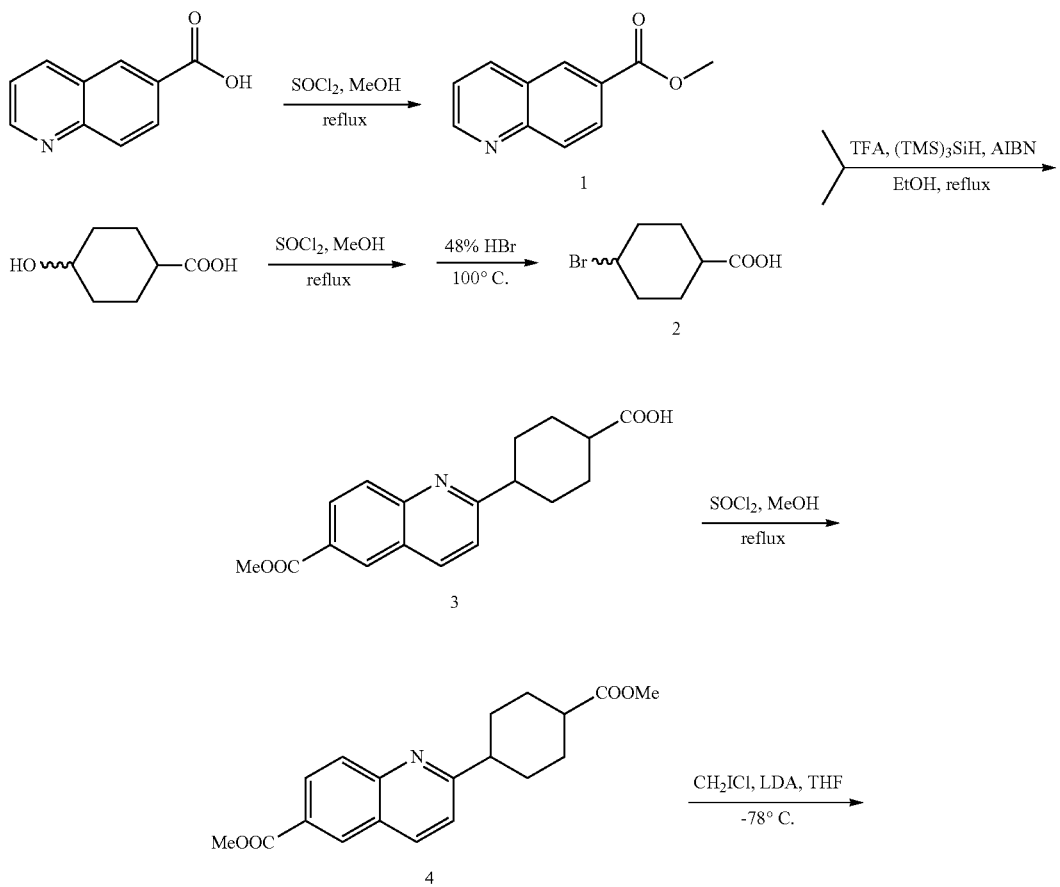

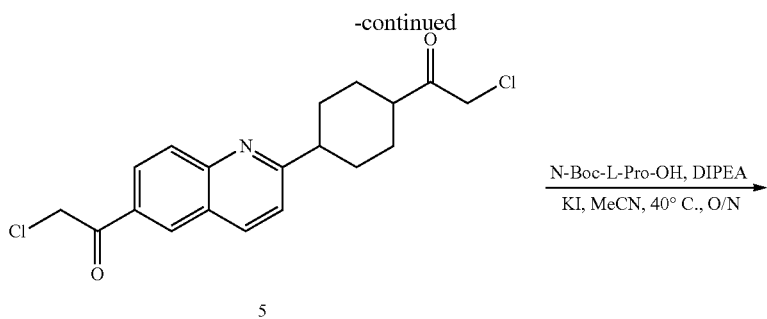
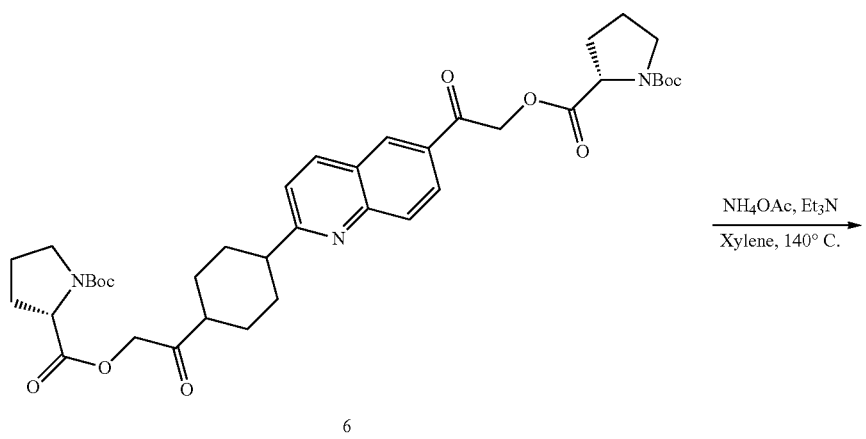
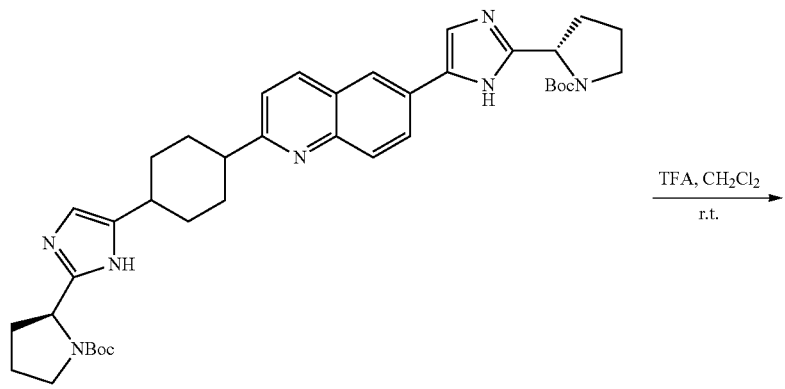
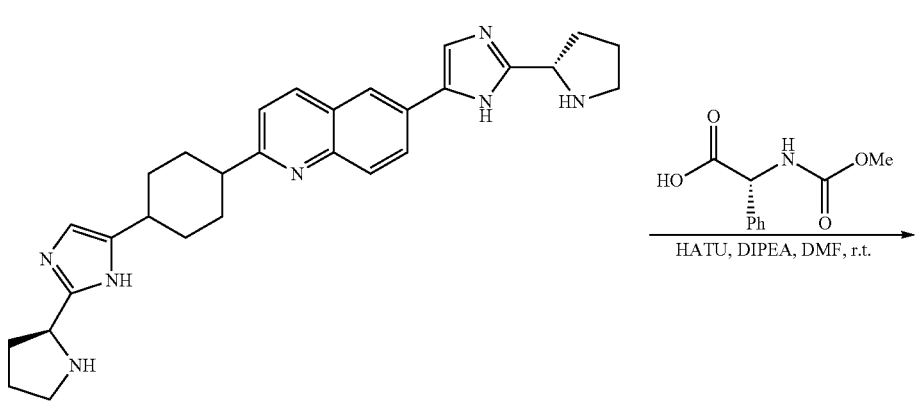

-continued

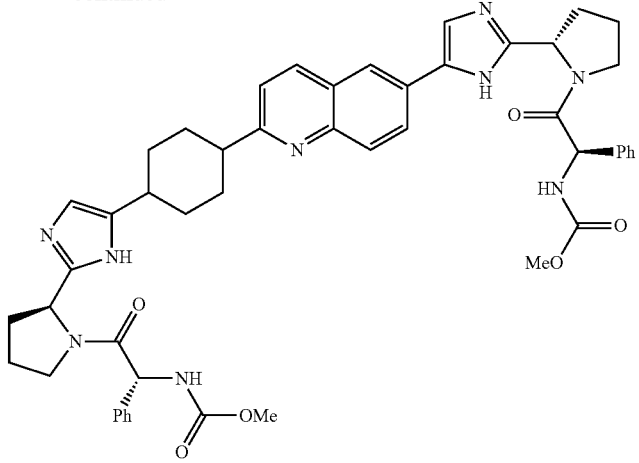

9

Step a.

Referring to Scheme 5-7, to a suspension of quinoline-6-carboxylic acid (13.2 g, 76.2 mmol) in MeOH (120 mL) was added thionyl chloride (16.6 mL, 229 mmol) dropwise at 0° C. over 10 minutes. The resulting mixture was refluxed for 3 h, then concentrated to remove all solvents in vacuo. The residue was partitioned between 300 mL of EtOAc and 500 mL of saturated NaHCO₃. The organic layer was washed with H₂O followed by brine and dried with Na₂SO₄. After concentration, the residue was purified by silica gel column chromatography (hexanes/ethyl acetate, v/v, 1/1 to 1/2) to afford the compound 1 (11.2 g, 79% yield) as a yellow solid. ¹H NMR (300 MHz, CDCl₃) 9.01 (dd, 1H), 8.60 (d, 1H), 8.24-8.34 (m, 2H), 8.15 (d, 1H), 7.48 (dd, 1H), 4.00 (s, 3H) ppm.

Step b.

To a solution of 4-hydroxy-cyclohexanecarboxylic acid (11.5 g, 80 mmol) in methanol (120 mL) was added thionyl chloride (16.5 mL, 224 mmol) dropwise at 0° C. The resulting mixture was then warmed to refluxing for 3 hours. All solvent was removed in vacuo and the residue was dissolved in EtOAc. The solution was washed with saturated aqueous NaHCO₃ solution, H₂O and brine. Column chromatography (EtOAc/Hexanes, v/v, 1/1 to 2/1) gave 8.5 g methyl ester as colorless oil. The methyl ester (6.2 g) was mixed with 60 mL of 48% HBr in sealed flask and heated up to 100° C. After 30 minutes, the clear solution was cooled down and partitioned between EtOAc and H₂O. The organic layer was washed with H₂O and dried over Na₂SO₄. After removing all solvent and cooling down, some crystal formed. Compound 2 (2.4 g) was obtained after filtration. ¹H NMR (300 MHz, CDCl₃) 3.98-4.08 (m, 1H), 2.25-2.45 (m, 3H), 1.99-2.16 (m, 2H), 1.72-1.94 (m, 2H), 1.50-1.65 (m, 1H) ppm.

Step c.

To a solution of compound 1 (3.45 g, 18.4 mmol) in absolute ethanol (100 mL) was added TFA (1.42 mL, 18.4 mmol) dropwise at rt, followed by compound 2 (3.18 g, 15.3 mmol). The reaction mixture was heated to reflux. (TMS)₃SiH (5.7 mL, 18.4 mmol) and AIBN (2.52 g, 15.3 mmol) were added into the mixture in four portions over a period of 6 h. After refluxing for 8 h, the resulting mixture was cooled down and all solvents were removed. The residue was purified by silica gel column chromatography (isopropyl alcohol/dichloromethane, v/v, 1/20 to 1/10) to afford compound 3 (470 mg) as a yellow solid. LC-MS (ESI): m/z 314 (M+1)⁺.

Step d.

To a solution of Intermediate 3 (470 g, 1.5 mmol) in methanol (20 mL) was added thionyl chloride (0.55 mL, 7.5 mmol) dropwise at 0° C. The resulting mixture was then heated to refluxing for 3 h. All solvent was removed in vacuo and the residue was dissolved in EtOAc. The solution was washed with saturated aqueous NaHCO₃ solution, water and brine, respectively. Column chromatography (EtOAc/Hexanes, v/v, 1/1) gave compound 4 (310 mg). LC-MS (ESI): m/z 328 (M+1)⁺.

Step e.

To a solution of Intermediate 4 (310 mg, 0.95 mmol) and chloroiodomethane (0.42 mL, 5.7 mmol) in THF (10 mL) was added LDA (precooled to −78° C., freshly made from 1.75 mL of diisoproylamine and 4.56 mL of 2.5 M n-BuLi in hexanes in 20 mL of THF) at −78° C. via cannula for 20 min. The reaction mixture was stirred for 2 h at −78° C. before it was quenched by dropwise addition of 3 mL of AcOH/THF (v/v, 1/1). The resulting mixture was warmed up and partitioned between EtOAc and saturated NaHCO₃. The organic layer was washed with H₂O and dried over Na₂SO₄. After concentration, the residue was purified by silica gel column chromatography (hexanes/ethyl acetate, v/v, 2/1 to 1/1) to afford compound 5 (330 mg) as a yellow solid. LC-MS (ESI): m/z 364 (M+1)⁺.

Step f.

A solution of Intermediate 5 (330 mg, 0.91 mmol), N-Boc-L-Pro-OH (0.58 g, 2.73 mmol), DIPEA (0.81 mL, 5.46 mmol) and potassium iodide (0.45 g, 2.7 mmol) in MeCN (20 mL) was stirred at 40° C. for 14 h. After removing all solvent in vacuo, the residue was partitioned in EtOAc and saturated NaHCO₃. The organic layer was washed with H₂O and brine and dried over Na₂SO₄. After concentration, the residue was purified by silica gel column chromatography (hexanes/ethyl acetate, v/v, 1/1 to 1/2) to afford compound 6 (450 mg) as yellow solid. LC-MS (ESI): m/z 722.75 (M+1)⁺.

Step g.

A mixture of Intermediate 6 (450 mg, 0.62 mmol), ammonium acetate (1.44 g, 18.7 mmol) and Et₃N (2.6 mL, 18.7 mmol) in xylene (20 mL) was stirred in sealed vessel at 140° C. for 1.5 h. After removing all solvent in vacuo, the residue was partitioned between 5% MeOH in dichloromethane and H₂O. The organic layer was washed with H₂O and brine. The aqueous layers were extracted with 5% MeOH in dichloromethane twice. The combined organic layers were dried over Na$_2$SO$_4$. After concentration, the residue was purified by silica gel column chromatography (isopropyl alcohol/dichloromethane, v/v, 1/10 to 1/7) to afford compound 7 (110 mg) as a yellow solid. LC-MS (ESI): m/z 682.7 (M+1)$^+$.

yellow solid. $^1$H NMR (300 MHz, CDCl$_3$) δ 8.00-8.30 (m, 4H), 7.93 (br, 2H), 7.16-7.42 (m, 13H), 6.84 (s, 1H), 6.64 (s, 1H), 5.06-5.44 (m, 4H), 3.40-3.98 (m, 10H), 2.85-3.35 (m, 2H), 1.30-2.60 (m, 16H) ppm. LC-MS (ESI): m/z 433.15 (M+2)$^{2+}$, 863.0 (M−1)$^−$.

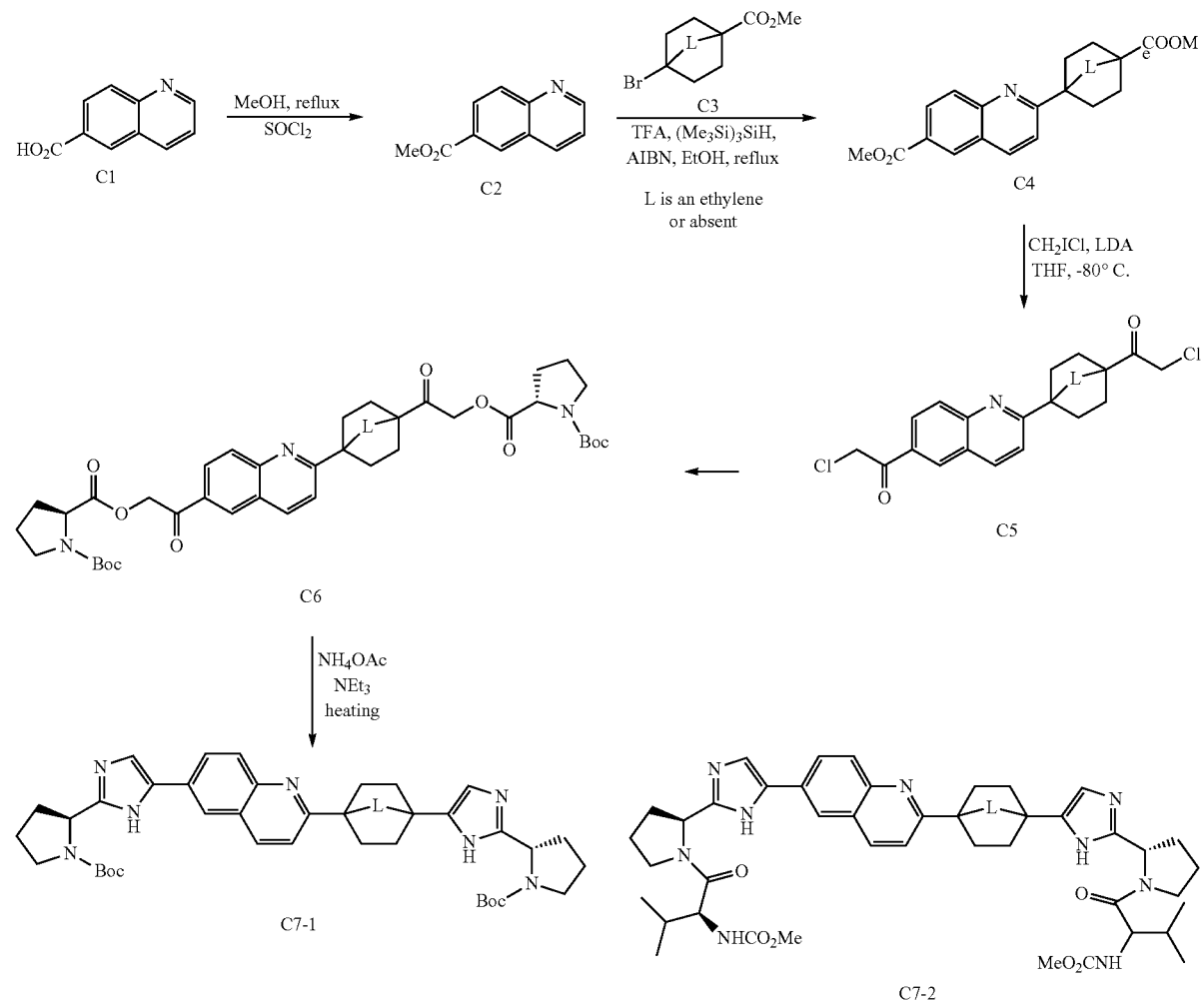

Scheme 5-8

Step h.

A solution of Intermediate 6 (110 mg) in dichloromethane (3 mL) and TFA (2 mL) was stirred at rt for 2 h. After removing all solvent in vacuo, compound 8 (122 mg) was obtained as a yellow TFA salt. LC-MS (ESI): m/z 482.5 (M+1)$^+$.

Step i.

To a solution of N-Moc-D-Phg-OH (25 mg) and compound 8 (~40 mg) in 0.75 mL of THF and 1.5 mL of DMF was added DIPEA (0.01 mL). The resulting solution was stirred at rt for 20 min before DMTMM (33 mg) was added. The reaction mixture was stirred at rt for another 2 h as LC-MS indicating the completion of reaction. The solution was partitioned in EtOAc and water, the organic layer was washed with water and brine. The aqueous layer was extracted with EtOAc. The combined organic layers were dried over Na$_2$SO$_4$ before it was concentrated in vacuo. The residue was purified by reverse phase prep-HPLC to afford compound 9 (8.8 mg) as Step a.

Referring to Scheme 5-8, to a suspension of quinoline-6-carboxylic acid (13.2 g, 76.2 mmol) in 120 mL MeOH was added thionyl chloride (16.6 mL, 229 mmol) dropwise at 0° C. in 10 min. After being heated at reflux for 3 h, the volatile solvents were removed by a rotary evaporator in vacuo. The residue was taken up in 300 mL EtOAc and was washed with 500 mL saturated NaHCO$_3$, H$_2$O and brine sequentially. The organic layer was dried over anhydrous Na$_2$SO$_4$. After filtration and concentration, the residue was purified by silica gel column chromatography (hexanes/ethyl acetate, v/v, 1/1 to 1/2) to afford compound C2 (11.2 g, 79% yield) as yellow solid. $^1$H NMR (300 MHz, CDCl$_3$) δ 9.01 (dd, 1H), 8.60 (d, 1H), 8.24-8.34 (m, 2H), 8.15 (d, 1H), 7.48 (dd, 1H), 4.00 (s, 3H) ppm.

Step b.

2-(4-Methoxycarbonyl-bicyclo[2.2.2]oct-1-yl)-quinoline-6-carboxylic acid methyl ester. To a solution of quinoline-6- carboxylic acid methyl ester C2 (9.5 g, 50.7 mmol) in 150 ml, EtOH was added TFA (3.91 mL, 50.7 mmol) dropwise at 0° C. To the resulting mixture was added 4-bromo-bicyclo [2.2.2]octane-1-carboxylic acid methyl ester (5.02 g, 20.3 mmol, this compound was prepared according to steps and conditions described previously) and tris(trimethylsilyl)silane (13.8 mL, 44.7 mmol) and heated to refluxing. To the refluxing mixture was added AIBN (2.67 g, 24.4 mmol) in four portions over 6 h. After the completion of addition, the reaction mixture was kept at refluxing for another 12 h. After cooling down, the mixture was partitioned between EtOAc and water. The organic layer was washed with brine and dried over anhydrous $Na_2SO_4$. After filtration and concentration, the residue was purified by the flash column chromatography (silica, hexanes/ethyl acetate, v/v, 4/1 to 2/1) to afford compound C4 (4.6 g, 64% yield) as a white solid. The product was further purified by recrystallization from a mixture of EtOAc and hexanes. $^1$H NMR (300 MHz, $CDCl_3$) δ 8.52 (d, 1H), 8.22 (dd, 1H), 8.15 (d, 1H), 8.04 (d, 1H), 7.48 (d, 1H), 3.98 (s, 3H), 3.69 (s, 3H), 1.88-2.18 (m, 12H) ppm.

Step c.

2-Chloro-1-{2-[4-(2-chloro-acetyl)-bicyclo[2.2.2]oct-1-yl]-quinolin-6-yl}-ethanone. To a solution of C4 (610 mg, 1.68 mmol) and chloroiodomethane (0.74 mL, 10.1 mmol) in THF (10 mL) was added LDA (pre-cooled to −78° C., freshly made from 3 mL of diisoproylamine and 8.06 mL of 2.5 M n-BuLi in hexanes in 10 mL of THF) at −78° C. via a cannula over 20 min. The reaction mixture was stirred for two h at −78° C. before it was quenched by dropwise addition of 12 mL of AcOH/THF (v/v, 1/1). The resulting mixture was warmed up and partitioned in EtOAc and saturated $NaHCO_3$. The organic layer was washed with water and dried over $Na_2SO_4$. After concentration, the residue was purified by the flash column chromatography (silica, hexanes/ethyl acetate, v/v, 8/1 to 2/1) to afford the compound C5 (445 mg, 68% yield) as a brown solid. $^1$H NMR (300 MHz, $CDCl_3$) δ 8.42 (d, 1H), 8.18-8.23 (m, 2H), 8.12 (d, 1H), 7.55 (d, 1H), 4.82 (s, 2H), 4.39 (s, 2H), 1.90-2.22 (m, 12H) ppm.

Step d.

The solution of compound C5 (445 mg, 1.14 mmol), N-Boc-L-Pro-OH (762 mg, 3.42 mmol), DIPEA (1.01 mL, 6.84 mmol) and potassium iodide (568 mg, 3.42 mmol) in MeCN (20 mL) was stirred at 50° C. for 4 h. After removing all solvent in vacuo, the residue was partitioned between EtOAc and saturated $NaHCO_3$. The organic layer was washed with $H_2O$ and brine, and dried over $Na_2SO_4$. After concentration, the residue was purified by silica gel column chromatography (hexanes/ethyl acetate, v/v, 1/1 to 1/2) to afford compound C6 (620 mg, 73% yield) as yellow solid. LC-MS (ESI) m/z: 747 (M−H)$^−$.

Step e.

The mixture of C6 (700 mg, 0.94 mmol), ammonium acetate (2.16 g, 28 mmol) and $Et_3N$ (3.9 mL, 28 mmol) in xylene (30 mL) was stirred in sealed vessel at 140° C. for 1.5 h. After removing all solvent in vacuo, the residue was partitioned in 5% MeOH in dichloromethane and water. The organic layer was washed with $H_2O$ and brine. The aqueous layers were extracted with 5% MeOH in dichloromethane twice. The combined organic layers were dried over $Na_2SO_4$. After concentration, the residue was purified by the flash column chromatography (silica, $NH_4OH$/acetone/ethyl acetate, v/v, 1/3/100) to afford compound C7-1 (300 mg, 47% yield) as yellow solid. LC-MS (ESI) m/z: 707 (M−H)$^−$.

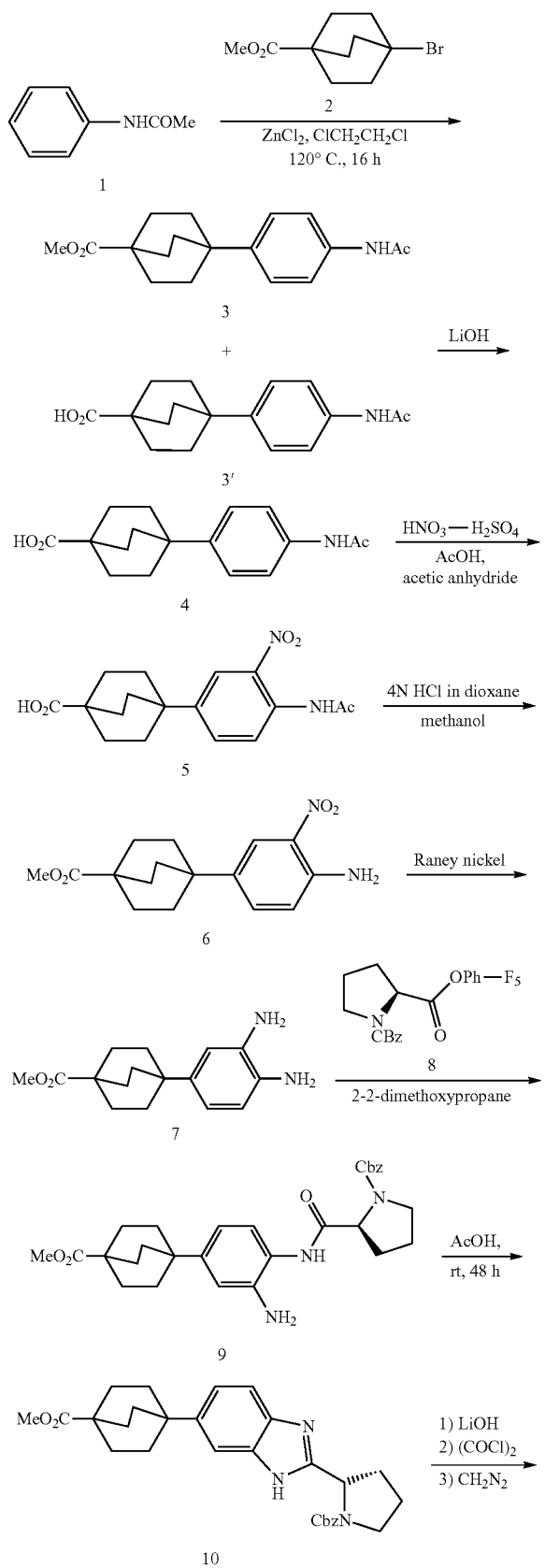

Scheme 5-9

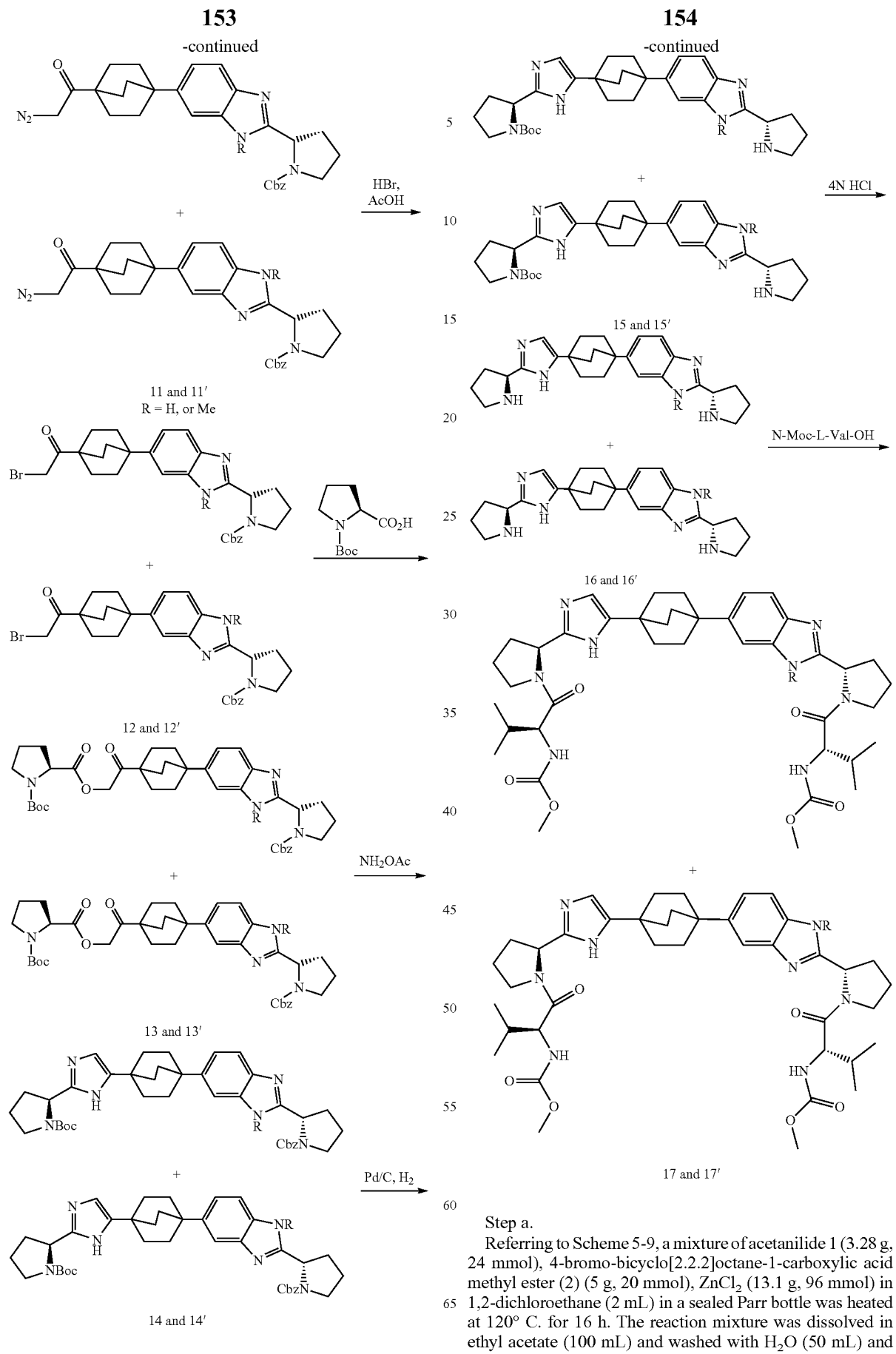
Step a.
Referring to Scheme 5-9, a mixture of acetanilide 1 (3.28 g, 24 mmol), 4-bromo-bicyclo[2.2.2]octane-1-carboxylic acid methyl ester (2) (5 g, 20 mmol), ZnCl$_2$ (13.1 g, 96 mmol) in 1,2-dichloroethane (2 mL) in a sealed Parr bottle was heated at 120° C. for 16 h. The reaction mixture was dissolved in ethyl acetate (100 mL) and washed with H$_2$O (50 mL) and brine (50 mL). The organic phase was dried over $Na_2SO_4$ and concentrated under reduced pressure to give a mixture of ester 3 and acid 3'.

Step b.

The resulting mixture of ester 3 and acid 3' was dissolved in methanol (60 mL) and treated with aqueous lithium hydroxide (10 g in 20 mL of water, 240 mmol). The reaction mixture was refluxed for 4 h. Methanol was evaporated under reduced pressure and the resulting aqueous solution was washed with ethyl acetate (20 mL). The aqueous solution was adjusted to pH 2 by the addition of 1 N HCl (aq) and extracted with ethyl acetate (2×100 mL). The combined organic phases were dried over $Na_2SO_4$ and concentrated in vacuo to give 4 (5.3 g, 92% yield) as a yellow solid.

Step c.

A nitrating mixture [1.17 mL, prepared from 67% $HNO_3$ (3.52 mmol) and $H_2SO_4$] was added dropwise to a cooled mixture of acid 4 (1.01 g, 3.52 mmol) in glacial acetic acid (8 mL) and acetic anhydride (4 mL). The mixture was stirred at rt for 12 h and poured into iced $H_2O$. The precipitate was filtered off, washed with $H_2O$ to neutral, and dried in vacuo to give 5 (0.72 g, 70% yield) as a yellow solid.

Step d.

A solution of 5 (2.7 g, 9.8 mmol) and 4 N HCl in dioxane (20 mL) in methanol (30 mL) was stirred at rt overnight. The solvent was evaporated, and the resulting residue was dissolved in ethyl acetate (50 mL) and washed with saturated $NaHCO_3$ and brine. The organic phase was concentrated and the resulting crude product was purified by silica gel column chromatography (ethyl acetate/hexane=15/85 (v/v)) to give 6 (1.64 g, 60% yield) as a yellow solid.

Step e.

A solution of 6 (1.64 g, 5.4 mmol) and Raney nickel (0.63 g, 10.8 mmol) in absolute ethanol (20 mL) was stirred under an atmosphere of hydrogen (15 psi) at rt for 12 h. The mixture was filtered and the filtrate was concentrated followed by purification silica gel column chromatography (ethyl acetate/hexane=75/25 (v/v)) to give compound 7 as an HCl salt (0.8 g, 49% yield).

Step f.

A solution of N-Cbz-L-Pro-OH (2 g, 8 mmol), pentafluorophenol (1.48 g, 8 mmol) and DCC (1.82 g, 8.8 mmol) in ethyl acetate (20 mL) was stirred at rt for 2 h. The reaction solution was filtered and the filtrate was concentrated in vacuo to give compound 8 (3.2 g, 96% yield) as a white solid. The mixture of compound 7 (0.44 g, 1.61 mmol) and activated ester 8 (0.8 g, 1.93 mmol) in 2,2-dimethoxypropane (30 mL) was stirred at rt overnight. The reaction solution was concentrated to give crude compound 9.

Step g.

Compound 9 was dissolved in acetic acid (2 mL) and heated at 60° C. for 5 h. The reaction solution was neutralized by saturated $NaHCO_3$ and extracted with ethyl acetate (2×20 mL). The combined organic phase was concentrated and the resulting crude product was purified by silica gel column chromatography (ethyl acetate/hexane, 65/35, v/v) to give compound 10 (0.4 g, 52% yield) as a yellow oil.

Step h.

To a solution of compound 10 (0.8 g, 1.68 mmol) in methanol (3 mL) was added aqueous lithium hydroxide (0.13 g in 1 mL of water, 3.4 mmol). The reaction mixture was then refluxed for 8 h. Methanol was evaporated and the resulting aqueous solution was washed by ethyl acetate and neutralized by 1 N HCl solution. After extraction with ethyl acetate (2×20 ml), concentration under reduced pressure, the crude product was purified by silica gel column chromatography (ethyl acetate/hexane=80/20 (v/v)) to give a free acid (0.32 g, 40% yield) as a yellow oil.

Step i.

A solution of acid obtained (0.57 g, 1.2 mmol) and oxalyl chloride (1.05 mL, 12 mmol) in dichloromethane (5 mL) was stirred at rt overnight. After concentrated under reduced pressure, the remaining residue was dissolved in ether (10 mL) followed by addition of diazomethane (20 mL, 0.33 N in ether, 6.8 mmol) at 0° C. The reaction mixture was stirred at 0° C. for 30 min. The reaction solution was concentrated and purified by silica gel column chromatography (ethyl acetate/hexane=75/25 (v/v)) to give an isomeric mixture (as a result of methylation on one of the benzimidazole nitrogens) of diazoketones 11 and 11' (0.2 g, 35% yield).

Step j.

Diazoketones 11 and 11' (0.2 g, 0.42 mmol) were dissolved in acetic acid (1 mL) followed by treatment with HBr (48% in water, 168 mg, 1.0 mmol) at 0° C. The reaction mixture was stirred at rt for 1 h. Saturated $NaHCO_3$ was added slowly into the reaction solution followed by extraction with ethyl acetate (2×10 mL). The organic phase was dried over $Na_2SO_4$, concentrated under reduced pressure, and purified by silica gel column chromatography (ethyl acetate/hexane=25/75 (v/v)) to give 12 and 12' (0.15 g, 65% yield).

Step k.

A solution of compounds 12 and 12' (0.37 g, 0.68 mmol), N-Boc-L-Pro-OH (0.29 g, 1.35 mmol) and DIPEA (0.47 mL, 2.7 mmol) in acetonitrile (3 mL) was stirred at rt overnight. Acetonitrile was evaporated and the remaining residue was dissolved in ethyl acetate (20 mL). The solution was washed with saturated $NaHCO_3$ and brine and then dried over $Na_2SO_4$. After concentration under reduced pressure, the crude product was purified by silica gel column chromatography (ethyl acetate/hexane=75/35 (v/v)) to give compounds 13 and 13' (0.3 g, 65% yield).

Step l.

A mixture of compounds 13 and 13' (140 mg, 0.2 mmol) and ammonium acetate (0.47 g, 6.14 mmol) in xylene (1.5 mL) in a sealed bottle was stirred at 140° C. for 90 min. After concentration, the reaction mixture was purified by silica gel column chromatography (ethyl acetate 100%, then ethyl acetate/methanol=90/10 (v/v)) to give compounds 14 and 14' (83.3 mg) as yellow solid in 59% yield.

Step m.

A mixture of compounds 14 and 14' (83.3 mg, 0.13 mmol), Pd/C (53.4 mg, 5% on carbon, 0.025 mmol) and one drop concentrated HCl in ethanol (3 mL) under an atmosphere of hydrogen (15 psi) was stirred at rt for 6 h. The reaction solution was then concentrated in vacuo to give compounds 15 and 15' (75 mg, 90% yield). To a solution of the amines obtained above (75 mg, 0.14 mmol) in THF (4 mL) was added 4N HCl in dioxane (1 mL) at rt. The reaction mixture was stirred at rt for 2 h. The solvent was evaporated and the residue was dried in vacuo to give compounds 16 and 16' (50 mg, 83% yield) as a yellow solid.

Step n.

To a solution of compounds 16 and 16' (44 mg, 0.1 mmol), N-Moc-L-Val-OH (43 mg, 0.25 mmol) and DMTMM (68 mg, 0.25 mmol) in a solvent mixture of DMF-THF (2 mL, 1:3) was added DIPEA (0.17 mL, 1.0 mmol) at rt. The reaction mixture was stirred at rt for 2 h. THF was evaporated and the remaining residue was purified by prep-HPLC to provide compounds 17 and 17' (4.6 mg, 5% yield). $^1$H NMR (300 MHz, $CD_3OD$) δ 7.33 (m, 4H), 6.92 (s, 1H), 5.30 (t, J=6.9 Hz, 1H), 5.12 (t, J=6.9 Hz, 1H), 4.22 (m, 2H), 3.99 (m, 4H), 3.94 (s, 3H), 3.64 (s, 3H), 3.59 (s, 3H), 2.36 (m, 4H), 2.03 (m, 4H), 1.93 (m, 12H), 0.92 (m, 12H) ppm. LC-MS (ESI): m/z 757 (M−H)⁻.

Scheme 6-1
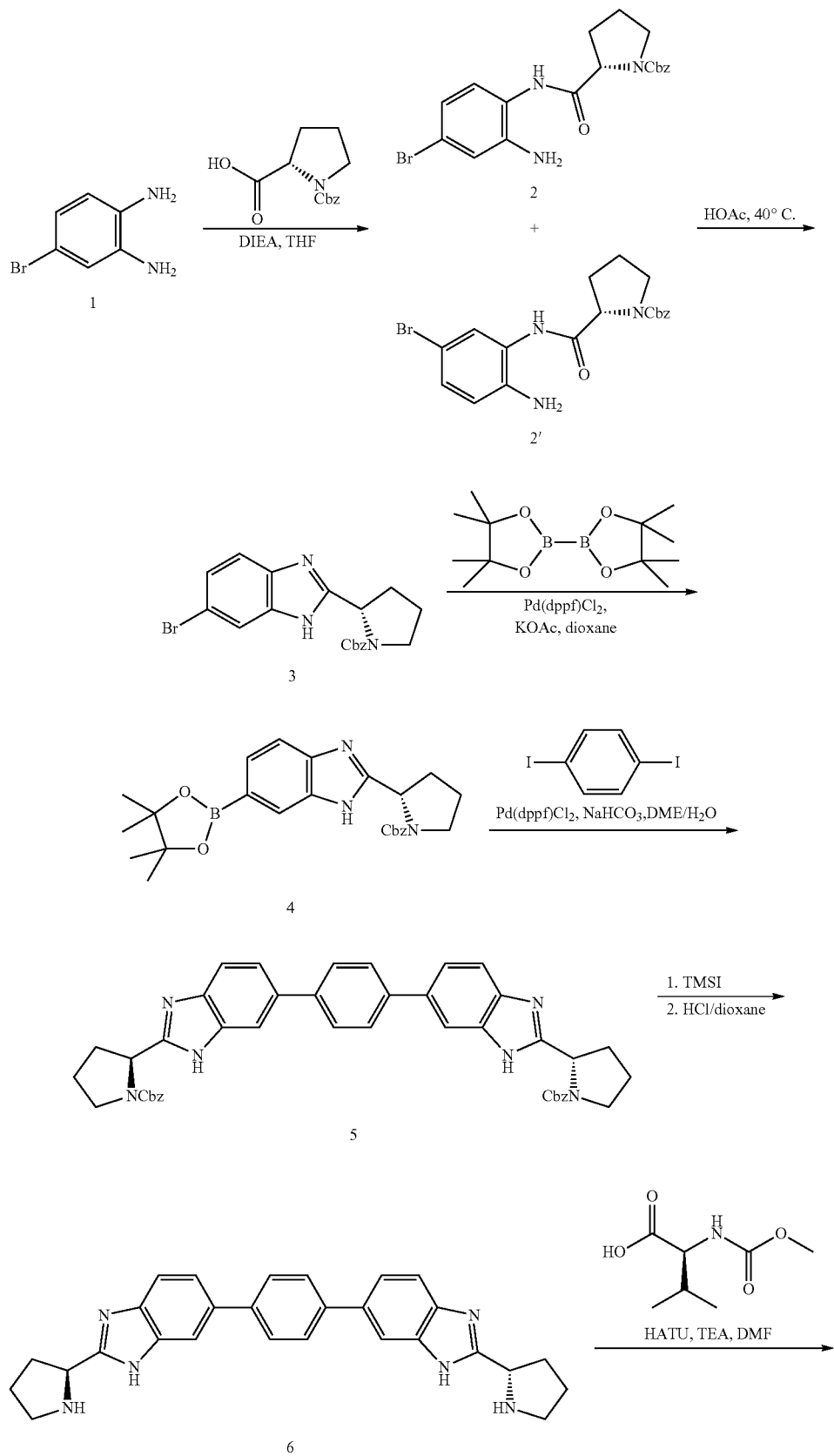

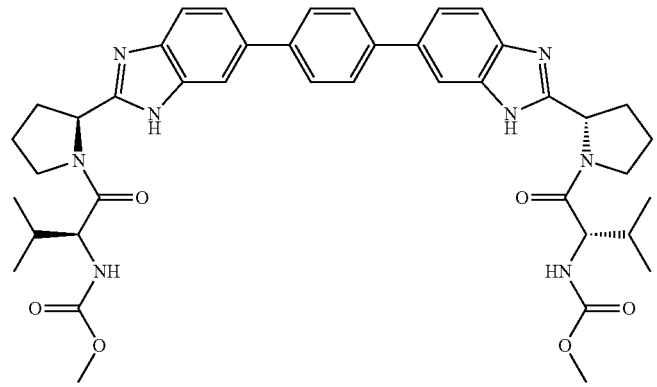

7

EXAMPLE 6

Synthesis of Compounds of Formula IIIb

Step a.

Referring to Scheme 6-1, to a solution of N-Cbz-L-Pro-OH (7.52 g, 30.0 mmol) and DIPEA (5.50 g, 54.0 mmol) in THF (200 mL) was added HATU (11.5 g, 30.0 mmol) at rt. After stirring for 10 min, 4-bromobenzene-1,2-diamine (1) (5.10 g, 27.0 mmol) was added and the reaction mixture was stirred at rt for 2 h. The mixture was concentrated and the residue was diluted with EtOAc (250 mL) and water (50 mL). The organic phase was washed with brine and dried with anhydrous $Na_2SO_4$. The solvent was removed and the residue was dried in vacuo to give crude compounds 2 and 2' (10.0 g), which were used for the next step without further purification. LC-MS (ESI) m/z 418.1 (M+H)$^+$.

Step b.

A mixture of compounds 2 and 2' (10.0 g) in AcOH (100 mL) was stirred at 40° C. for 12 h. The reaction mixture was then neutralized by carefully adding saturated aqueous $Na_2CO_3$ to adjust the pH value to 8. Subsequently, the reaction mixture was extracted with EtOAc (150 mL×3). The extracts were combined, washed with brine, and dried with anhydrous $Na_2SO_4$. The solvent was removed and the residue was purified by silica gel column chromatography (Petroleum ether/EtOAc=4/1 (v/v)) to give compound 3 (5.6 g, 70%) as a yellow solid. LC-MS (ESI) m/z 400.1 (M+H)$^+$.

Step c.

To a mixture of compound 3 (5.05 g, 12.5 mmol), bis(pinacolato)diboron (7.10 g, 26.3 mmol), and KOAc (3.20 g, 32.5 mmol) in 1,4-dioxane (100 mL) was added Pd(dppf)Cl$_2$ (400 mg, 0.5 mmol) at rt under an atmosphere of N$_2$. After stirring at 80° C. for 3 h under an atmosphere of N$_2$, the reaction mixture was filtered through CELITE™545 and the filtered cake was washed with EtOAc (100 mL×3). The filtrate was washed with brine and dried with anhydrous $Na_2SO_4$. The solvent was removed and the residue was purified by silica gel column chromatography (Petroleum ether/EtOAc=2/1 (v/v)) to give compound 4 (3.0 g, 53%) as a gray solid: LC-MS (ESI) m/z 448.2 (M+H)$^+$.

Step d.

To a mixture of compound 4 (1.04 g, 2.20 mmol), 1,4-diiodobenzene (360 mg, 1.1 mmol), and NaHCO$_3$ (650 mg, 7.7 mmol) in 1,2-dimethoxyethane (36 mL) and water (12 mL) was added Pd(dppf)Cl$_2$ (80.0 mg, 0.10 mmol) at rt under an atmosphere of N$_2$. After stirring at 80° C. overnight under an atmosphere of N$_2$, the reaction mixture was concentrated and the residue was diluted with EtOAc (100 mL) and water (25 mL). The organic phase was washed with brine and dried with anhydrous Na$_2$SO$_4$. The solvent was removed and the residue was purified by silica gel column chromatography (DCM/MeOH=50/1 (v/v)) to give compound 5 (350 mg, 44%) as a yellow solid. LC-MS (ESI) m/z 717.3 (M+H)$^+$.

Step e.

To a solution of compound 5 (200 mg, 0.28 mmol) in CHCl$_3$ (5 mL) was added TMSI (168 mg, 0.84 mmol) at rt. After stirring at rt overnight, the reaction was quenched by adding MeOH (3.0 mL), followed by 4N HCl in dioxane (2.0 mL). The resulting mixture was stirred at rt for 30 min and concentrated. The residue was washed with DCM (10 mL) and dried in vacuo to give crude compound 6 (220 mg), which was used for the next step without further purification. LC-MS (ESI) m/z 449.2 (M+H)$^+$.

Step f.

To a solution of crude compound 6 (150 mg, 0.20 mmol) in DMF (2 mL) was added Et$_3$N (0.22 mL, 2.10 mmol), followed by N-Moc-L-Val-OH (87.0 mg, 0.50 mmol) and HATU (190 mg, 0.50 mmol). After stirring at rt for 1 h, the reaction mixture was concentrated and the residue was diluted with DCM (50 mL) and water (10 mL). The organic phase was washed with brine and dried with anhydrous Na$_2$SO$_4$. The solvent was removed and the residue was purified by silica gel column chromatography (DCM/MeOH=50/1 (v/v)) to give compound 7 (40 mg, 26%) as a white powder. $^1$H NMR (500 MHz, CDCl$_3$) δ 7.68-7.26 (m, 10H), 5.55-5.45 (m, 4H), 4.41-4.38 (m, 2H), 3.93-3.90 (m, 2H), 3.85-3.77 (m, 2H), 3.72 (s, 6H), 2.97-2.95 (m, 2H), 2.43-2.41 (m, 2H), 2.28-2.00 (m, 2H), 2.18-2.14 (m, 2H), 2.08-2.06 (m, 2H), 0.93-0.89 (m, 12H) ppm; LC-MS (ESI) m/z 763.4 (M+H)$^+$.

Scheme 6-2
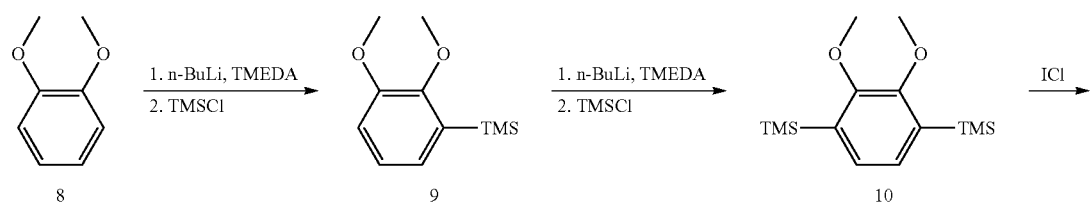
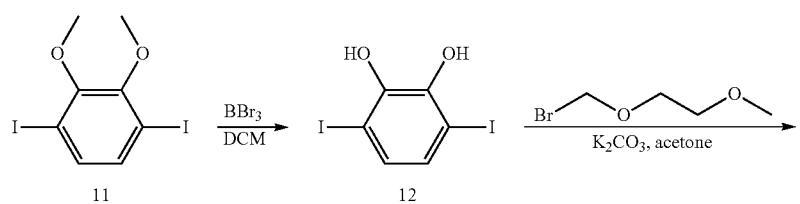
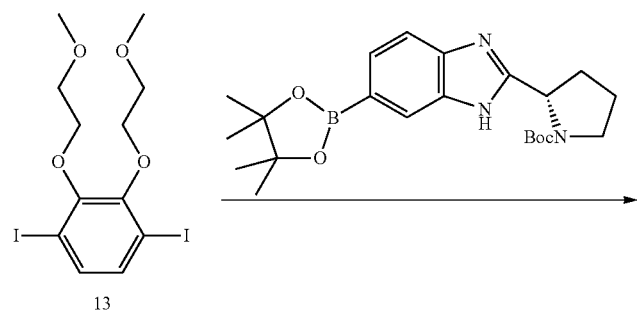
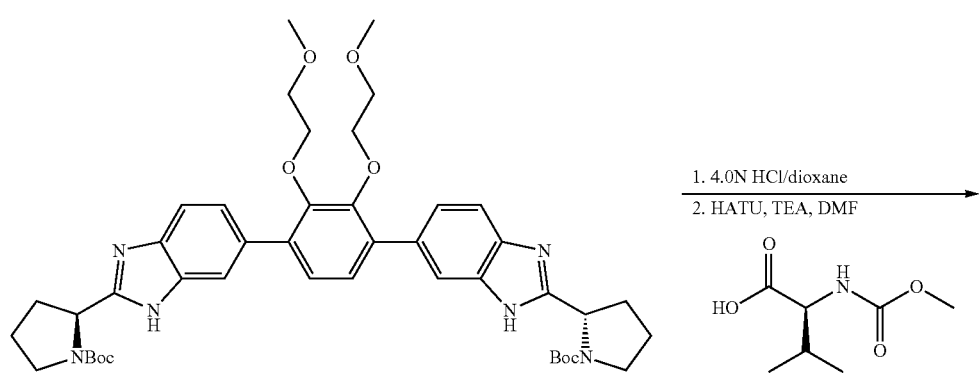

-continued

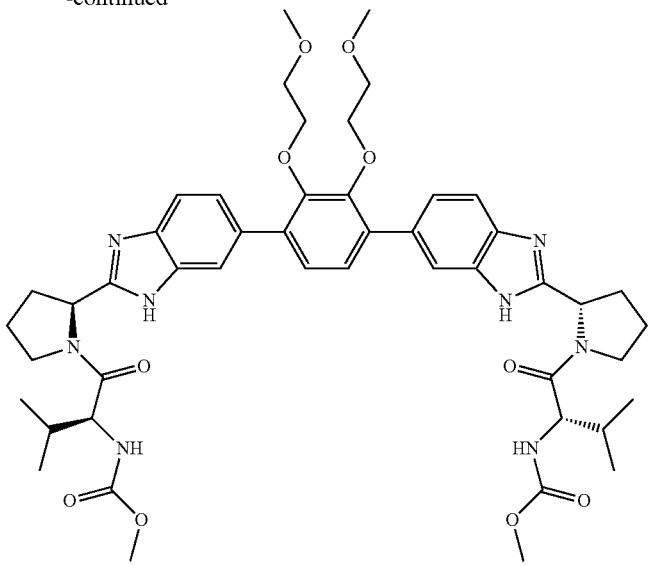

15

Step a.

Referring to Scheme 6-2, to a solution of veratrol (8) (40.0 g, 0.29 mol) in anhydrous THF (100 mL) and TMEDA (40 mL) was added n-BuLi (2.5 M in hexanes, 128 mL, 0.32 mol) dropwise at rt under an atmosphere of $N_2$. After stirring at rt for 28 h under an atmosphere of $N_2$, the reaction mixture was cooled to −78° C., followed by adding TMSCl (45 mL). The reaction mixture was stirred at rt for 5 h and then added water (20 mL). The reaction mixture was concentrated and the residue was extracted with hexane (100 mL×3). The extracts were combined, washed with brine, and dried with anhydrous $Na_2SO_4$. The solvent was removed and the residue was purified by silica gel column chromatography to give compound 9 (42 g, 69%) as a colorless oil. LC-MS: (ESI) m/z 211.1 $(M+H)^+$.

Step b.

To a solution of compound 9 (40 g, 0.20 mol) in anhydrous TMEDA (40 mL) was added n-BuLi in hexanes (2.5 M, 120 mL, 0.24 mol) dropwise at 0° C. under an atmosphere of $N_2$. After stirring at rt for 25 h, the reaction mixture was cooled to −78° C., followed by adding TMSCl (40 mL). The reaction mixture was stirred at rt for 5 h and then added water (50 mL). The mixture was concentrated and the residue was extracted with hexanes (100 mL×3). The extracts were combined, washed with brine, and dried with anhydrous $Na_2SO_4$. The solvent was removed and the residue was purified by silica gel column chromatography to give compound 10 (52 g, 85%) as colorless oil. LC-MS: (ESI) m/z 283.1 $(M+H)^+$.

Step c.

A mixture of compound 10 (19.0 g, 68.1 mmol) in dichloromethane (100 mL) was added a solution of ICl (23.0 g, 142 mmol) in dichloromethane (100 mL) at 0° C. After stirring at rt for 30 min, the reaction was quenched by adding saturated aqueous $Na_2S_2O_3$. The organic phase was washed with brine and dried with anhydrous $Na_2SO_4$. The solvent was removed and the residue was purified by silica gel column chromatography ($CH_2Cl_2$/petroleum ether=1/10 (v/v)) to give compound 11 (18.0 g, 75%). $^1$H NMR ($CDCl_3$, 500 MHz): δ 7.24 (s, 2H), 3.87 (s, 6H) ppm. LC-MS: (ESI) m/z 390.9 $(M+H)^+$.

Step d.

To a solution of compound 11 (3.89 g, 10.0 mmol) in $CH_2Cl_2$ (20 mL) was added $BBr_3$ (2.5 M in DCM, 15 mL, 60 mmol) at −78° C. After stirring at rt for 14 h, the reaction mixture was poured into water and the aqueous layer was extracted with $CH_2Cl_2$ (50 mL×2). The organic phase was washed with brine and dried with anhydrous $Na_2SO_4$. The solvent was removed and the residue was purified by silica gel column chromatography to give compound 12 as a white solid (3.1 g, 85%). $^1$H NMR ($CDCl_3$, 500 MHz): δ 7.00 (s, 2H), 5.61 (s, 2H) ppm. LC-MS: (ESI) m/z 362.8 $(M+H)^+$.

Step e.

A mixture of compound 12 (1.5 g, 4.2 mmol), $K_2CO_3$ (4.60 g, 33.2 mmol), and 1-bromo-2-methoxyethane (2.30 g, 16.6 mmol) in acetone (100 mL) was refluxed overnight. The reaction mixture was concentrated and the residue was diluted with $H_2O$ (50 mL) and EtOAc (150 mL). The organic phase was washed with brine and dried with anhydrous $Na_2SO_4$. The solvent was removed and the residue was purified by silica gel column chromatography (DCM/petroleum ether=1/10 (v/v)) to give compound 13 (1.5 g, 65%). $^1$H NMR ($CDCl_3$, 500 MHz): δ 7.23 (s, 2H), 3.99 (t, J=6.8 Hz, 4H), 1.81 (m, 4H), 1.55 (m, 4H), 1.28 (m, 32H), 3.99 (t, J=6.8 Hz, 6H). LC-MS: (ESI) m/z 478.9 $(M+H)^+$.

Step f.

To a solution of compound 13 (200 mg, 0.42 mmol) in 40 mL $DME/H_2O$ (3/1 (v/v)), (S)-tert-butyl 2-(6-(4,4,5,5-tetramethyl-1,3,2-dioxaborolan-2-yl)-1H-benzo[c/]imidazol-2-yl)pyrrolidine-1-carboxylate (434 mg, 1.05 mmol), $Pd(dppf)Cl_2$ (69 mg, 0.084 mmol), and $NaHCO_3$ (212 mg, 2.52 mmol) were respectively added at rt under an atmosphere of $N_2$. After stirring at 80° C. for 17 h, the reaction mixture was concentrated and the residue was diluted with EtOAc (100 mL) and water (20 mL). The organic phase was washed with brine and dried with anhydrous $Na_2SO_4$. The solvent was removed and the residue was purified by silica gel column chromatography (Petroleum ether/acetone=2/1 (v/v)) to give compound 14 (250 mg, 75%) as a yellowish solid. LC-MS: (ESI) m/z 797.4 $(M+H)^+$.

Step g.

A mixture of compound 14 (150 mg, 0.21 mmol) in dioxane (2 mL) was added 4N HCl in dioxane (2 mL) at rt. After stirring at rt for 2 h, the reaction mixture was concentrated and the residue was dried in vacuo to give an HCl salt, which was used for the next step without further purification. LC-MS: (ESI) m/z 597.3 (M+H)⁺.

Step h.

Subsequently, the HCl salt was dissolved in DMF (2 mL) and the resulting solution was respectively added DIPEA (0.34 mL, 2.1 mmol), N-Boc-L-Val-OH (90 mg, 0.51 mmol), and HATU (192 mg, 0.210 mmol). After stirring at rt for 30 min, the reaction mixture was poured into ice H₂O. The solid was collected by filtration and purified by preparative HPLC to give compound 15. LC-MS (ESI): m/z 911.5 (M+H)⁺.

EXAMPLE 7

Synthesis of Compounds of Formula X

Scheme 7-1

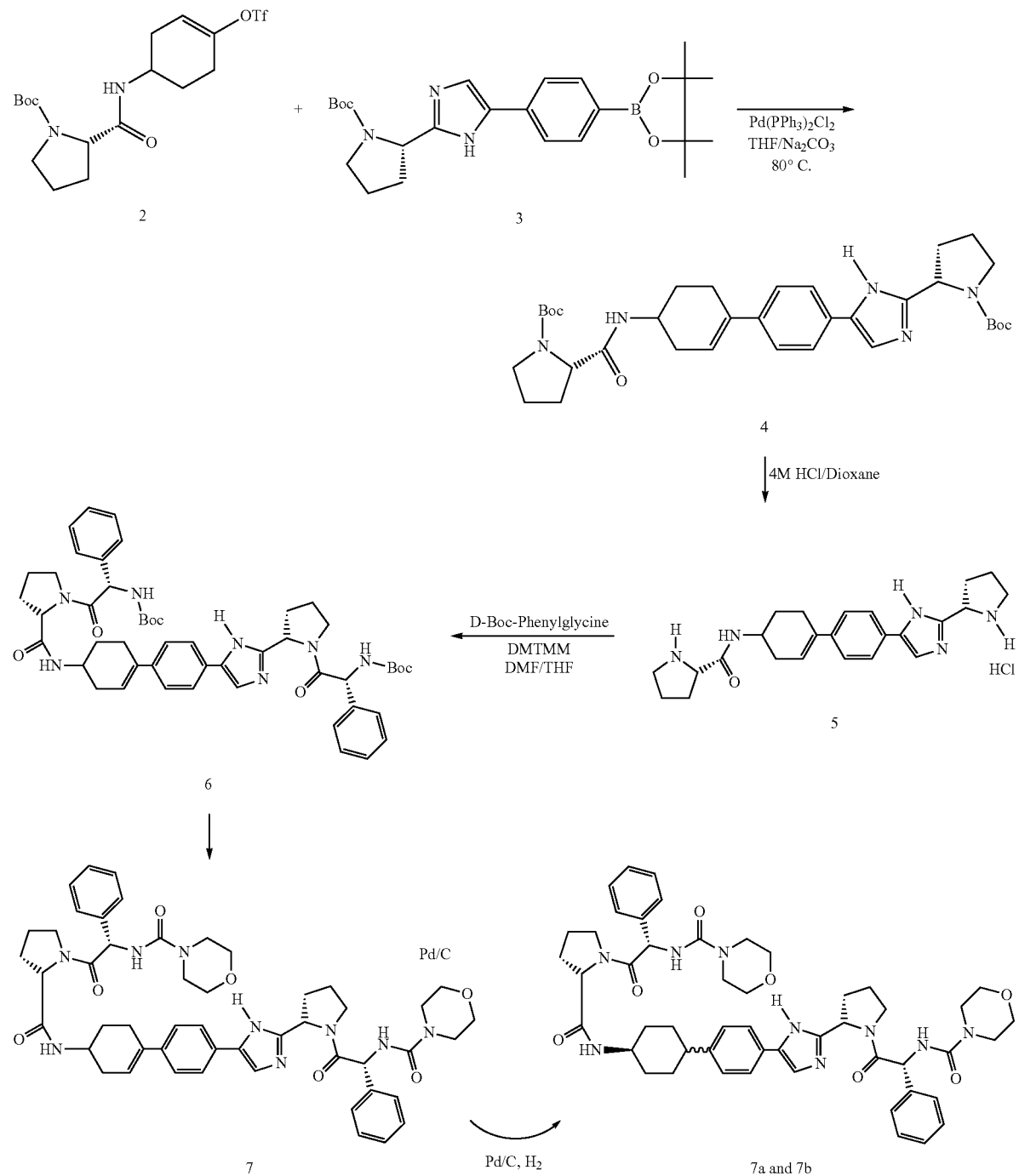

Step a.

To prepare compound 2 of Scheme 7-1, tert-Butyl 4-oxocyclohexylcarbamate (9.0 g, 42.5 mmol) was treated with HCl (4N in 1,4-dioxane, 60 mL) at rt. After 4 h stirring, the reaction was concentrated to obtain the crude product (6.3 g), which was dissolved in anhydrous DMF (200 mL). N-Boc-L-Pro-OH (9.1 g, 42.3 mmol)), HATU (17.7 g, 46.6 mmol) and DIEA (22.8 mL, 131 mmol) were added at rt. After stirring overnight, the reaction was quenched by brine, extracted by ethyl acetate. The combined organic phases were washed with brine and H$_2$O, dried with Na$_2$SO$_4$. After removal of the solvents, the crude product was purified by silica gel column chromatography (ethyl acetate) to afford (S)-tert-butyl 2-(4-oxocyclohexylcarbamoyl)pyrrolidine-1-carboxylate (7.5 g, 57% yield).

Step b.

To a solution of (S)-tert-butyl 2-(4-oxocyclohexylcarbamoyl)pyrrolidine-1-carboxylate (4.3 g, 13.87 mmol) in dichloromethane (350 mL) at −78° C. was slowly added LHMDS (29.1 mL, 1M in THF, 29.1 mmol). After stirring for 2 h, 1,1,1-trifluoro-N-phenyl-N-(trifluoromethylsulfonyl)methanesulfonamide (10.4 g, 29.1 mmol) was added as solid at −78° C. The reaction was slowly warmed up to rt over 4 h and quenched by adding sat. NaHCO$_3$, extracted with ethyl acetate. The combined organic phases were washed with brine and H$_2$O, dried with Na$_2$SO$_4$. After removal of the solvent, the crude product was purified by silica gel column chromatography (n-hexane/ethyl acetate, 1:1) to afford (2S)-tert-butyl 2-(4-(trifluoromethylsulfonyloxy)-cyclohex-3-enyl carbamoyl)pyrrolidine-1-carboxylate (2) (3.6 g, 59% yield).

Step c.

To a solution of (2S)-tert-butyl 2-(4-(trifluoromethylsulfonyloxy)cyclohex-3-enyl carbamoyl)pyrrolidine-1-carboxylate (2) (1.65 g, 3.73 mmol) and (S)-tert-butyl 2-(5-(4-(4,4,5,5-tetramethyl-1,3,2-dioxaborolan-2-yl)phenyl)-1H-imidazol-2-yl)pyrrolidine-1-carboxylate (3) (1.95 g, 4.44 mmol) in THF (19 mL), Pd(PPh$_3$)$_2$Cl$_2$ (130 mg, 0.185 mmol) and aqueous Na$_2$CO$_3$ (2M, 7.5 mL, 15 mmol) were added under N$_2$ protection at rt. The reaction mixture was heated at 80° C. overnight, and cooled to rt. The mixture was then filtered through a CELITE™ pad and washed with ethyl acetate. The combined organic phases were concentrated to provide the crude product, which was purified by silica gel column chromatography (n-hexane/ethyl acetate, 1:2) to afford (2S)-tert-butyl 2-(4-(4-(2-((S)-1-(tert-butoxycarbonyl)pyrrolidin-2-yl)-1H-imidazol-5-yl)phenyl)cyclohex-3-enylcarbamoyl)pyrrolidine-1-carboxylate (4) (2.1 g, 93% yield).

Step d.

To a solution of (2S)-tert-butyl 2-(4-(4-(2-((S)-1-(tert-butoxycarbonyl)pyrrolidin-2-yl)-1H-imidazol-5-yl)phenyl)cyclohex-3-enylcarbamoyl)pyrrolidine-1-carboxylate (50 mg, 0.082 mmol) in DCM (15 mL), was added TFA (1 mL) at rt. After 1.5 h stirring, the reaction was concentrated to give a TFA salt (5) (75 mg), which was dissolved in anhydrous THF (5 mL). N-Boc-D-Phg-OH (51 mg, 0.21 mmol), DMTMM (57 mg, 0.21 mmol) and Et$_3$N (57 µL, 0.41 mmol) were added at rt. After three days of stirring, the reaction was quenched with brine and extracted with ethyl acetate. The combined organic phases were washed with brine and H$_2$O and dried over Na$_2$SO$_4$. After removal of the solvent, the crude product was purified by prep-TLC (DCM/MeOH=10/1 (v/v)) to afford compound 6 (40 mg, 56% yield).

Step e.

To a solution of the compound 6 (210 mg, 0.24 mmol) in DCM (10 mL) was added TFA (1 mL) at rt. After 1.5 h stirring, the reaction was concentrated to give the crude product, which was dissolved in anhydrous THF (20 mL). 4-Morpholinecarbonyl chloride (62 µL, 0.54 mmol) and Et$_3$N (206 µL, 1.48 mmol) were added at rt. After overnight stirring, the reaction was quenched by water, extracted by ethyl acetate. After removal of the solvent, the crude product was purified by silica gel column chromatography (DCM/MeOH=20/1 (v/v)) to afford compound 7 (110 mg, 51% yield) LC-MS (ESI): m/z 898 (M+H)$^+$.

Step f.

A mixture of compound 7 (20 mg, 0.022 mmol) and 10% Pd/C (5 mg) in MeOH (2 mL) was hydrogenated (60 psi) for 2 days. The reaction was filtered through a CELITE™ pad and washed with MeOH. The combined organic phases was concentrated to give a crude product, which was purified by prep-TLC (DCM/MeOH=20/1 (v/v)) to afford a less polar product (7a) (9 mg, 45% yield), LC-MS (ESI): m/z 900 (M+H)$^+$ and a polar product (7b) (9 mg, 45% yield), LC-MS (ESI): m/z 900 (M+H)$^+$.

Biological Activity

Biological activity of the compounds of the invention was determined using an HCV replicon assay. The 1b_Huh-Luc/Neo-ET cell line persistently expressing a bicistronic genotype 1b replicon in Huh 7 cells was obtained from R$^e$BLikon GMBH. This cell line was used to test compound inhibition using luciferase enzyme activity readout as a measurement of compound inhibition of replicon levels.

On Day 1 (the day after plating), each compound is added in triplicate to the cells. Plates incubated for 72 h prior to running the luciferase assay. Enzyme activity was measured using a Bright-Glo Kit (cat. number E2620) manufactured by Promega Corporation. The following equation was used to generate a percent control value for each compound.

% Control=(Average Compound Value/Average Control)*100

The EC$_{50}$ value was determined using GraphPad Prism and the following equation:

Y=Bottom+(Top−Bottom)/(1+10^((Log IC50−X)*Hill-Slope))

EC$_{50}$ values of compounds are repeated several times in the replicon assay.

Example compounds of the disclosed invention are illustrated in Tables 1-9 attached as appendices. The tables show inhibitory activity of many of the example compounds with respect to HCV 1b. The biological activity is indicated as being *, , *, or ****, which corresponds to EC$_{50}$ ranges of >1000 nM, 999 nM to 10 nM, 9.9 nM to 1 nM, or <1 nM respectively. The tables further provide mass spectrometry results for the synthesized example compounds.

Pharmaceutical Compositions

The sixteenth aspect of the invention provides a pharmaceutical composition comprising the compounds of the invention. In a first embodiment, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, basic compounds such as free bases. A thorough discussion of pharmaceutically acceptable excipients and salts is available in Remington's Pharmaceutical Sciences, 18th Edition (Easton, Pa.: Mack Publishing Company, 1990).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

The seventeenth aspect of the invention provides the use of the compounds of the invention in the manufacture of a medicament.

In a first embodiment of the seventeenth aspect, the medicament is for the treatment of hepatitis C.

The eighteenth aspect of the invention provides a method of treating hepatitis C comprising administering to a subject in need thereof, a therapeutically effective amount of a compound of the invention, optionally in a pharmaceutical composition. A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject may be administered as many doses as is required to reduce and/or alleviate the signs, symptoms or causes of the disorder in question, or bring about any other desired alteration of a biological system. One of ordinary skill in the art of treating such diseases will be able, without undue experimentation and in reliance upon personal knowledge and the disclosure of this application, to ascertain a therapeutically effective amount of the compounds of this invention for a given disease.

Combination Therapy

The compounds of the present invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention may include, without limitation, all classes of HCV antivirals. For combination therapies, mechanistic classes of agents that may be useful when combined with the compounds of the present invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-813, PHX-1766, PHX2054, IDX-136, IDX-316, ABT-450 EP-013420 (and congeners) and VBY-376; the Nucleosidic HCV polymerase (replicase) inhibitors useful in the invention include, but are not limited to, R7128, PSI-7851, IDX-184, IDX-102, R1479, UNX-08189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nuclosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, NS5A inhibitors of the present invention may be used in combination with cyclophyllin and immunophyllin antagonists (eg, without limitation, DEBIO compounds, NM-811 as well as cyclosporine and its derivatives), kinase inhibitors, of heat shock proteins (e.g., HSP90 and HSP70), other immunomodulatory agents that may include, without limitation, interferons (-alpha, -beta, -omega, -gamma, -lambda or synthetic) such as Intron A™, Roferon-A™, Canferon-A300™, Advaferon™, Infergen™, Humoferon™, Sumiferon MP™, Alfaferone™, IFN-β™, Feron™ and the like; polyethylene glycol derivatized (pegylated) interferon compounds, such as PEG interferon-α-2a (Pegasys™), PEG interferon-α-2b (PEGIntron™), pegylated IFN-α-con1 and the like; long acting formulations and derivatizations of interferon compounds such as the albumin-fused interferon, Albuferon™, Locteron™ and the like; interferons with various types of controlled delivery systems (e.g. ITCA-638, omega-interferon delivered by the DUROS™ subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL™, REMICADE™ and HUMIRA™.

In addition, NS5A inhibitors of the present invention may be used in combination with antiprotozoans and other antivirals thought to be effective in the treatment of HCV infection, such as, without limitation, the prodrug nitazoxanide. Nitazoxanide can be used as an agent in combination the compounds disclosed in this invention as well as in combination with other agents useful in treating HCV infection such as peginterferon alfa-2a and ribavarin (see, for example, Rossignol, J F and Keeffe, E B, Future Microbiol. 3:539-545, 2008).

NS5A inhibitors of the present invention may also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. No. 5,807,876; U.S. Pat. No. 6,498,178; U.S. Pat. No. 6,344,465; U.S. Pat. No. 6,054,472; WO97/40028; WO98/40381; WO00/56331, WO 02/04425; WO 03/007945; WO 03/010141; WO 03/000254; WO 01/32153; WO 00/06529; WO 00/18231; WO 00/10573; WO 00/13708; WO 01/85172; WO 03/037893; WO 03/037894; WO 03/037895; WO 02/100851; WO 02/100846; EP 1256628; WO 99/01582; WO 00/09543; WO02/18369; WO98/17679, WO00/056331; WO 98/22496; WO 99/07734; WO 05/073216, WO 05/073195 and WO 08/021,927.

Additionally, combinations of, for example, ribavirin and interferon, may be administered as multiple combination therapy with at least one of the compounds of the present invention. The present invention is not limited to the aforementioned classes or compounds and contemplates known and new compounds and combinations of biologically active agents (see, Strader, D. B., Wright, T., Thomas, D. L. and Seeff, L. B., AASLD Practice Guidelines. 1-22, 2009 and Manns, M. P., Foster, G. R., Rockstroh, J. K., Zeuzem, S., Zoulim, F. and Houghton, M., Nature Reviews Drug Discovery. 6:991-1000, 2007, Pawlotsky, J-M., Chevaliez, S, and McHutchinson, J. G., Gastroenterology. 132:179-1998, 2007, Lindenbach, B. D. and Rice, C. M., Nature 436:933-938, 2005, Klebl, B. M., Kurtenbach, A., Salassidis, K., Daub, H. and Herget, T., Antiviral Chemistry & Chemotherapy. 16:69-90, 2005, Beaulieu, P. L., Current Opinion in Investigational Drugs. 8:614-634, 2007, Kim, S-J., Kim, J-H., Kim, Y-G., Lim, H-S, and Oh, W-J., The Journal of Biological Chemistry. 48:50031-50041, 2004. Okamoto, T., Nishimura, Y., Ichimura, T., Suzuki, K., Miyamura, T., Suzuki, T., Moriishi, K. and Matsuura, Y., The EMBO Journal. 1-11, 2006, Soriano, V., Peters, M. G. and Zeuzem, S. Clinical Infectious Diseases. 48:313-320, 2009, Huang, Z., Murray, M. G. and Secrist, J. A., Antiviral Research. 71:351-362, 2006 and Neyts, J., Antiviral Research. 71:363-371, 2006, each of which is incorporated by reference in their entirety herein). It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the professional judgment of the person administering or supervising the administration of the combination therapy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

TABLE 1

| Compound # | Structure | Inhibition of HCV genotype 1b | MS (M + H+) |
|---|---|---|---|
| 350 | 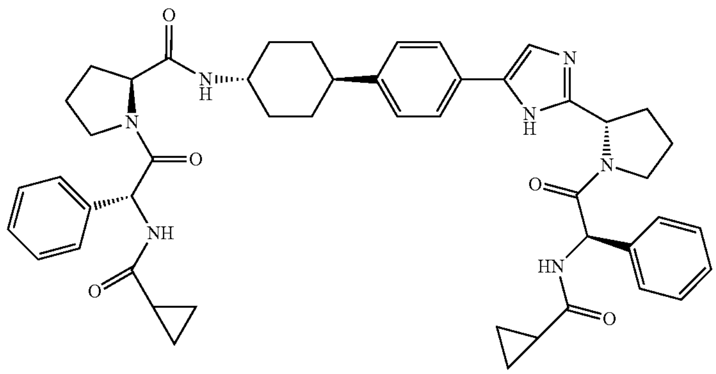 [SMILES: O=C(N[C@@H](C(=O)N1CCC[C@H]1C(=O)N[C@H]1CC[C@H](c2ccc(-c3cnc([C@@H]4CCCN4C(=O)[C@H](NC(=O)C4CC4)c4ccccc4)[nH]3)cc2)CC1)c1ccccc1)C1CC1] | **** | 810.4 |
| 351 | 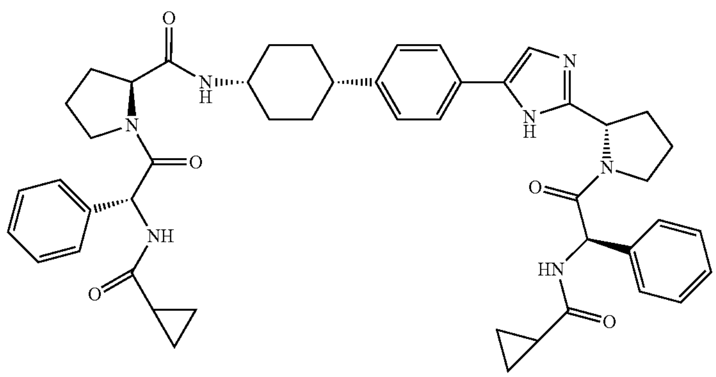 [SMILES: O=C(N[C@@H](C(=O)N1CCC[C@H]1C(=O)N[C@H]1CC[C@@H](c2ccc(-c3cnc([C@@H]4CCCN4C(=O)[C@H](NC(=O)C4CC4)c4ccccc4)[nH]3)cc2)CC1)c1ccccc1)C1CC1] | **** | 810.4 |
| 352 | 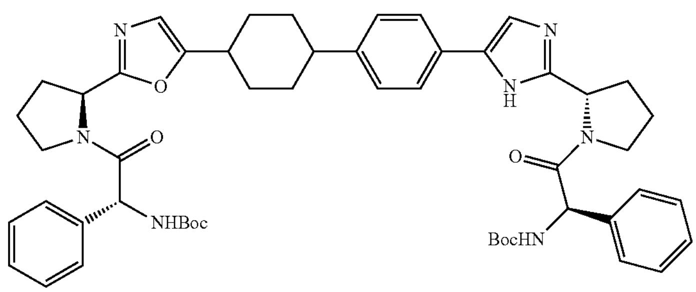 [SMILES: CC(C)(C)OC(=O)N[C@@H](C(=O)N1CCC[C@H]1c1ncc(-c2ccc(C3CCC(c4cnc([C@@H]5CCCN5C(=O)[C@H](NC(=O)OC(C)(C)C)c5ccccc5)o4)CC3)cc2)[nH]1)c1ccccc1] | *** | 898.5 |
| 353 | 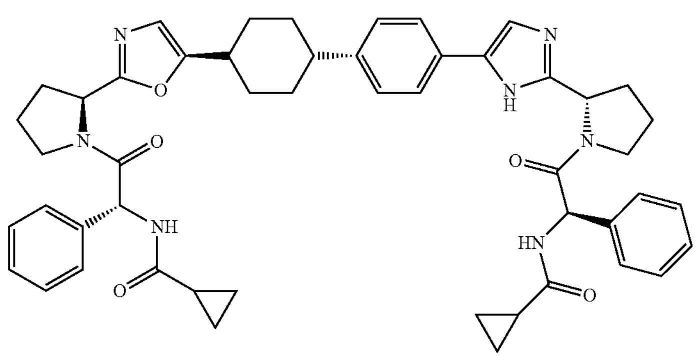 | **** | 834.4 |

TABLE 1-continued

| Compound # | Structure | Inhibition of HCV genotype 1b | MS (M + H+) |
|---|---|---|---|
| 354 | 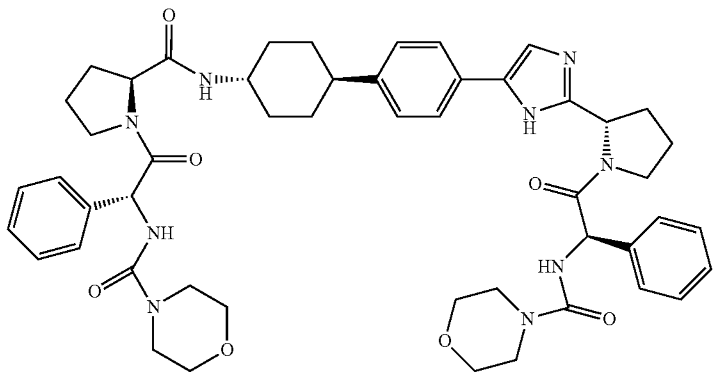 [SMILES: O=C(N[C@H]1CC[C@H](c2ccc(-c3cnc([C@@H]4CCCN4C(=O)[C@H](NC(=O)N4CCOCC4)c4ccccc4)[nH]3)cc2)CC1)[C@@H]1CCCN1C(=O)[C@H](NC(=O)N1CCOCC1)c1ccccc1] | *** | 900.5 |
| 355 | 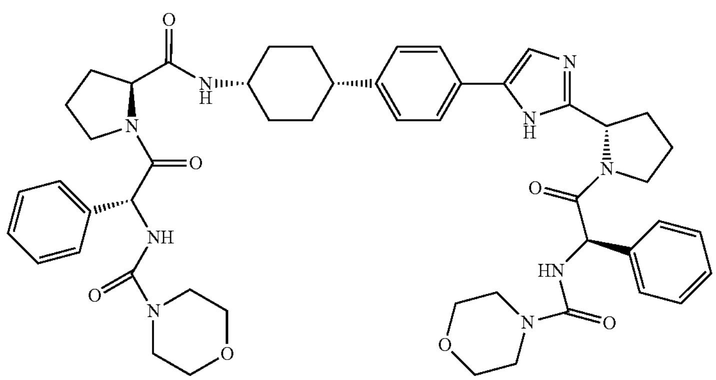 [SMILES: O=C(N[C@H]1CC[C@@H](c2ccc(-c3cnc([C@@H]4CCCN4C(=O)[C@H](NC(=O)N4CCOCC4)c4ccccc4)[nH]3)cc2)CC1)[C@@H]1CCCN1C(=O)[C@H](NC(=O)N1CCOCC1)c1ccccc1] | *** | 900.5 |
| 356 | 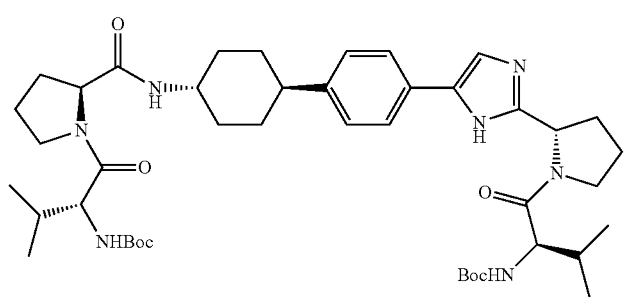 [SMILES: CC(C)[C@@H](NC(=O)OC(C)(C)C)C(=O)N1CCC[C@H]1C(=O)N[C@H]1CC[C@H](c2ccc(-c3cnc([C@@H]4CCCN4C(=O)[C@H](NC(=O)OC(C)(C)C)C(C)C)[nH]3)cc2)CC1] | ** | 806.5 |
| 357 | 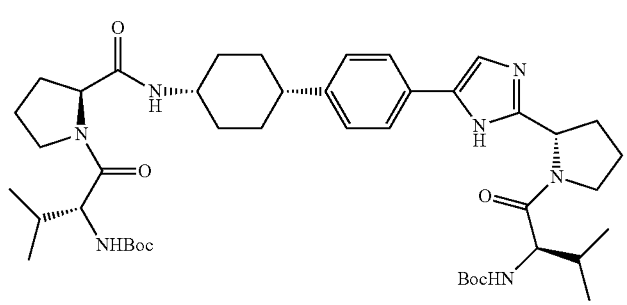 [SMILES: CC(C)[C@@H](NC(=O)OC(C)(C)C)C(=O)N1CCC[C@H]1C(=O)N[C@H]1CC[C@@H](c2ccc(-c3cnc([C@@H]4CCCN4C(=O)[C@H](NC(=O)OC(C)(C)C)C(C)C)[nH]3)cc2)CC1] | ** | 806.5 |

TABLE 1-continued

| Compound # | Structure | Inhibition of HCV genotype 1b | MS (M + H+) |
| --- | --- | --- | --- |
| 358 | 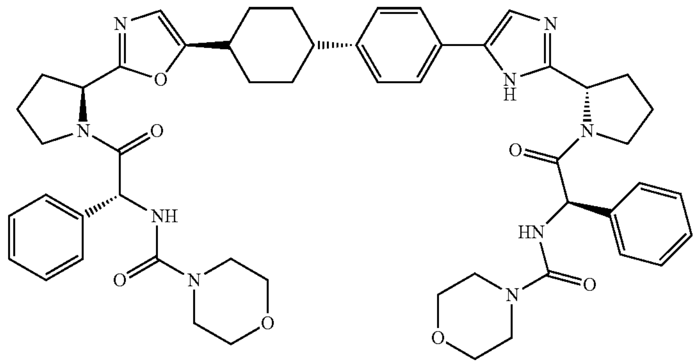 | **** | 924.5 |
| 359 | 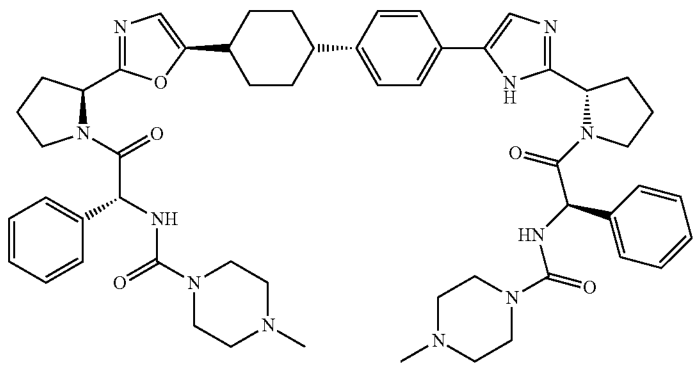 | *** | 950.5 |
| 360 | 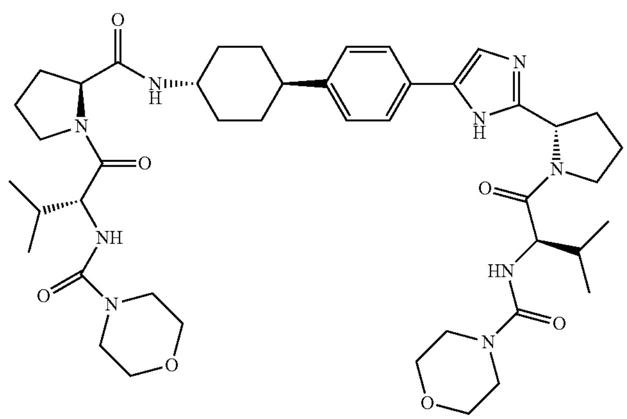 [SMILES: CC(C)[C@@H](NC(=O)N1CCOCC1)C(=O)N1CCC[C@H]1C(=O)N[C@H]1CC[C@H](c2ccc(-c3cnc([C@@H]4CCCN4C(=O)[C@H](NC(=O)N4CCOCC4)C(C)C)[nH]3)cc2)CC1] | ** | 832.5 |
| 361 | 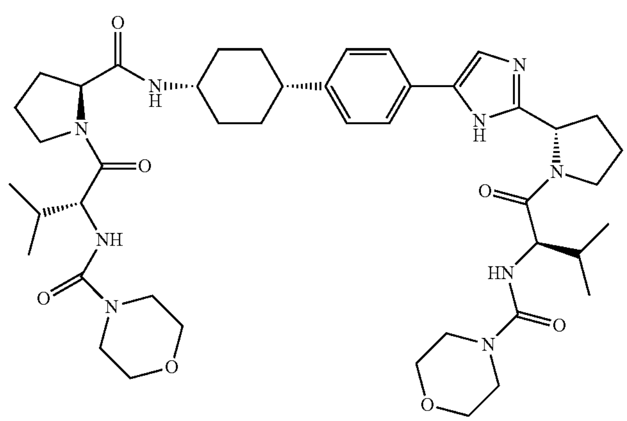 [SMILES: CC(C)[C@@H](NC(=O)N1CCOCC1)C(=O)N1CCC[C@H]1C(=O)N[C@H]1CC[C@@H](c2ccc(-c3cnc([C@@H]4CCCN4C(=O)[C@H](NC(=O)N4CCOCC4)C(C)C)[nH]3)cc2)CC1] | ** | 832.5 |

TABLE 1-continued

| Compound # | Structure | Inhibition of HCV genotype 1b | MS (M + H+) |
|---|---|---|---|
| 362 | 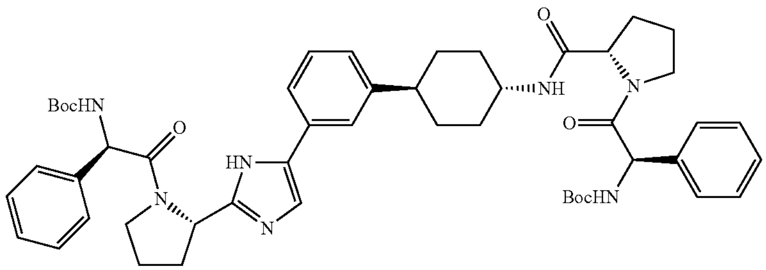 [SMILES: CC(C)(C)OC(=O)N[C@@H](C(=O)N1CCC[C@H]1C(=O)N[C@H]1CC[C@H](c2cccc(-c3cnc([C@@H]4CCCN4C(=O)[C@H](NC(=O)OC(C)(C)C)c4ccccc4)[nH]3)c2)CC1)c1ccccc1] | *** | 874.5 |
| 363 | 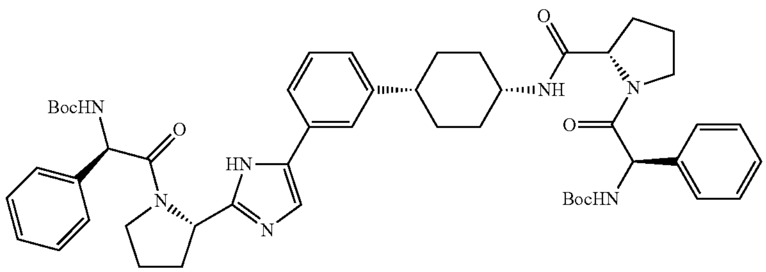 [SMILES: CC(C)(C)OC(=O)N[C@@H](C(=O)N1CCC[C@H]1C(=O)N[C@H]1CC[C@@H](c2cccc(-c3cnc([C@@H]4CCCN4C(=O)[C@H](NC(=O)OC(C)(C)C)c4ccccc4)[nH]3)c2)CC1)c1ccccc1] | **** | 874.5 |
| 364 | 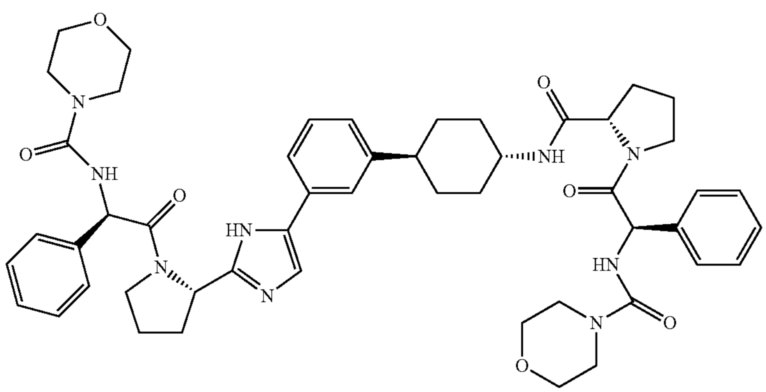 [SMILES: O=C(N[C@H]1CC[C@H](c2cccc(-c3cnc([C@@H]4CCCN4C(=O)[C@H](NC(=O)N4CCOCC4)c4ccccc4)[nH]3)c2)CC1)[C@@H]1CCCN1C(=O)[C@H](NC(=O)N1CCOCC1)c1ccccc1] | *** | 900.5 |
| 365 | 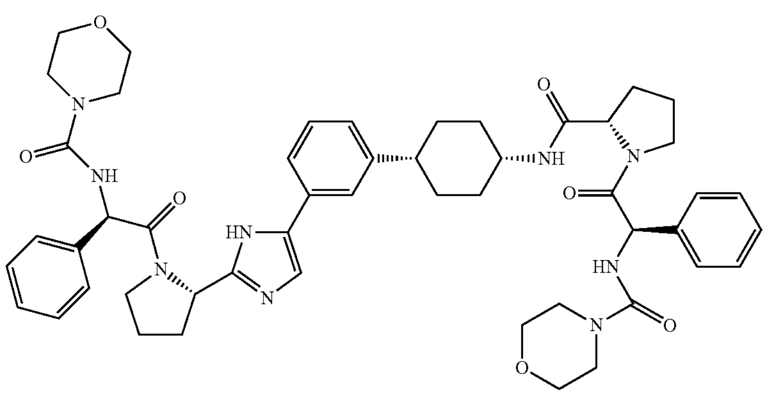 [SMILES: O=C(N[C@H]1CC[C@@H](c2cccc(-c3cnc([C@@H]4CCCN4C(=O)[C@H](NC(=O)N4CCOCC4)c4ccccc4)[nH]3)c2)CC1)[C@@H]1CCCN1C(=O)[C@H](NC(=O)N1CCOCC1)c1ccccc1] | *** | 900.5 |
| 366 | 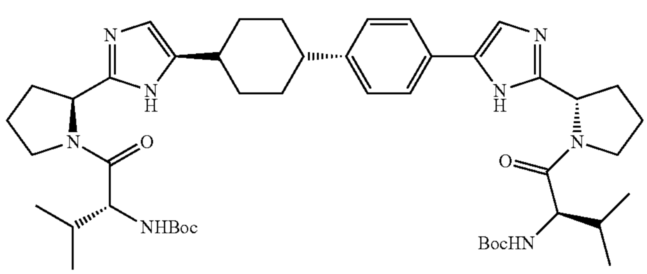 | ** | 829.5 |

TABLE 1-continued
| Compound # | Structure | Inhibition of HCV genotype 1b | MS (M + H+) |
|---|---|---|---|
| 367 | 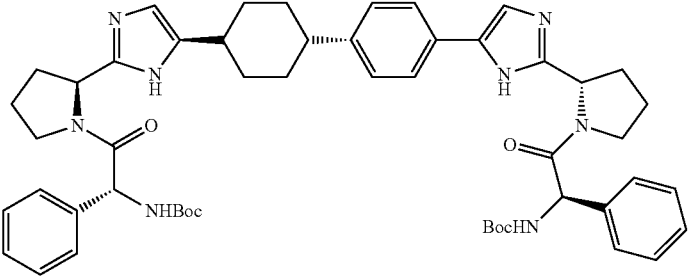 | **** | 897.5 |
| 368 | 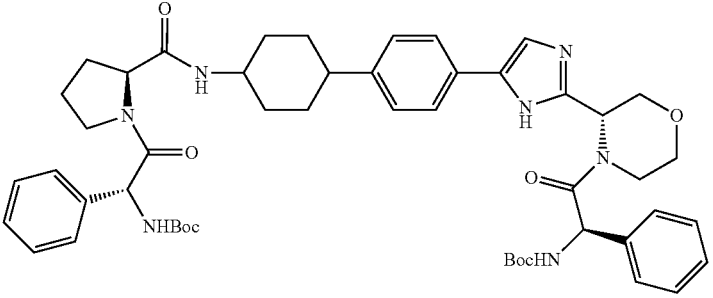 [SMILES: CC(C)(C)OC(=O)N[C@@H](C(=O)N1CCC[C@H]1C(=O)NC1CCC(c2ccc(-c3cnc([C@@H]4COCCN4C(=O)[C@H](NC(=O)OC(C)(C)C)c4ccccc4)[nH]3)cc2)CC1)c1ccccc1] | **** | 890.5 |
| 369 | 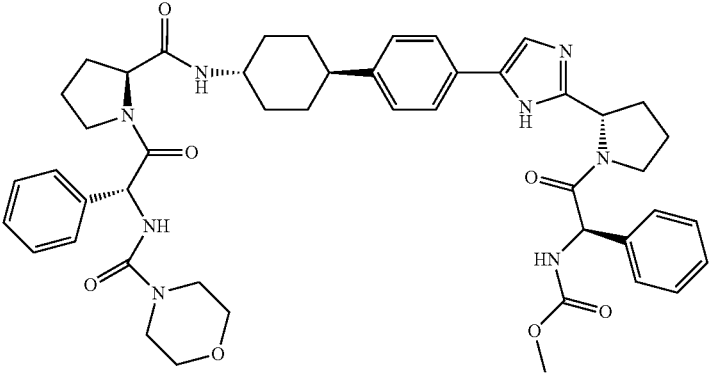 [SMILES: COC(=O)N[C@@H](C(=O)N1CCC[C@H]1c1ncc(-c2ccc([C@H]3CC[C@H](NC(=O)[C@@H]4CCCN4C(=O)[C@H](NC(=O)N4CCOCC4)c4ccccc4)CC3)cc2)[nH]1)c1ccccc1] | *** | 845.4 |
| 370 | 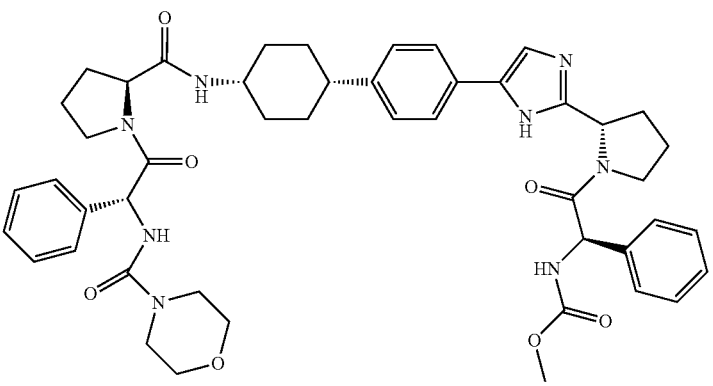 [SMILES: COC(=O)N[C@@H](C(=O)N1CCC[C@H]1c1ncc(-c2ccc([C@H]3CC[C@@H](NC(=O)[C@@H]4CCCN4C(=O)[C@H](NC(=O)N4CCOCC4)c4ccccc4)CC3)cc2)[nH]1)c1ccccc1] | *** | 845.4 |

TABLE 1-continued

| Compound # | Structure | Inhibition of HCV genotype 1b | MS (M + H+) |
|---|---|---|---|
| 371 | 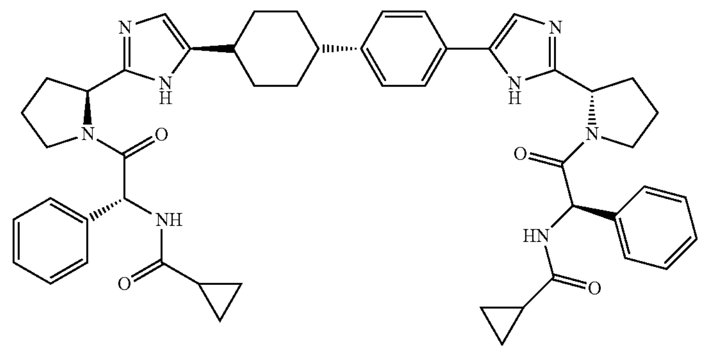 | **** | 833.4 |
| 372 | 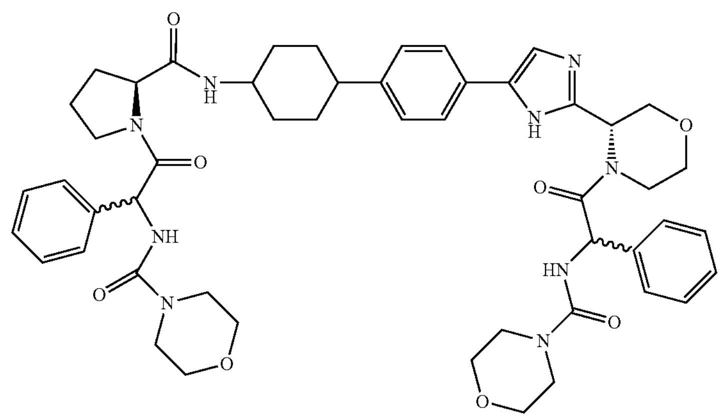 [SMILES: O=C(NC1CCC(c2ccc(-c3cnc([C@@H]4COCCN4C(=O)C(NC(=O)N4CCOCC4)c4ccccc4)[nH]3)cc2)CC1)[C@@H]1CCCN1C(=O)C(NC(=O)N1CCOCC1)c1ccccc1] | *** | 916.5 |
| 373 | 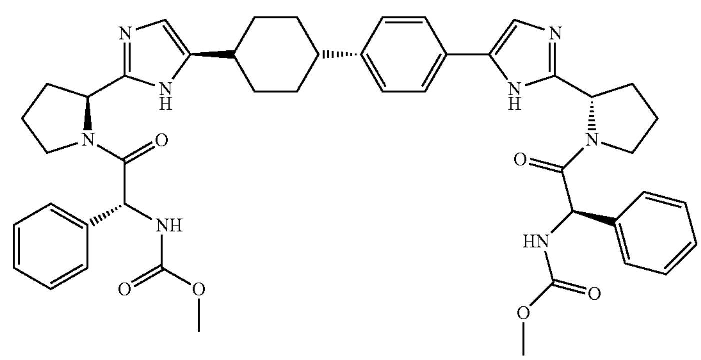 | **** | 813.4 |
| 374 | 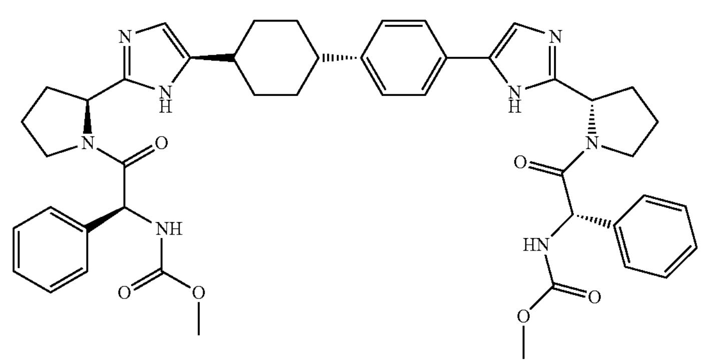 | **** | 813.4 |

TABLE 1-continued

| Compound # | Structure | Inhibition of HCV genotype 1b | MS (M + H+) |
|---|---|---|---|
| 375 | 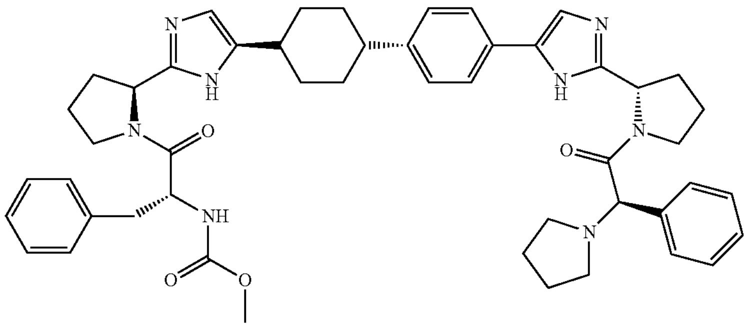 | **** | 823.5 |
| 376 | 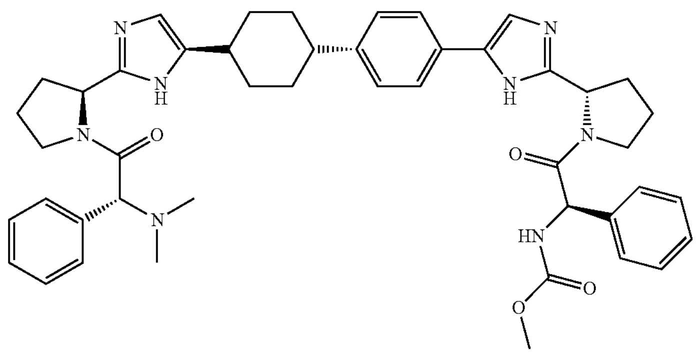 | **** | 783.4 |
| 377 | 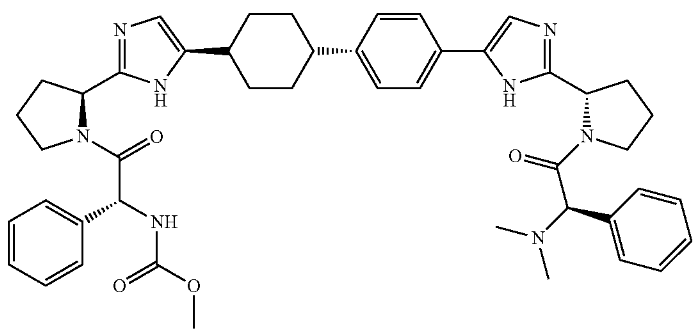 | **** | 783.4 |
| 378 | 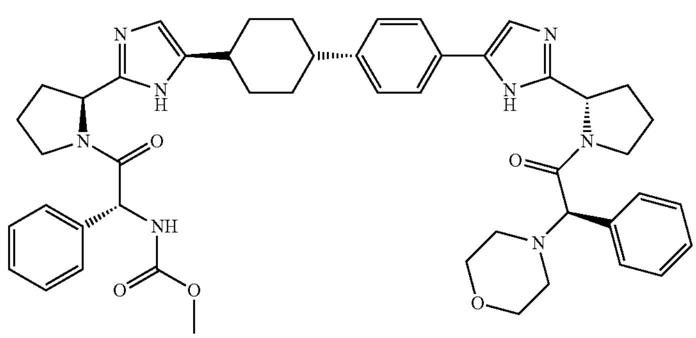 | **** | 825.4 |

TABLE 1-continued

| Compound # | Structure | Inhibition of HCV genotype 1b | MS (M + H+) |
|---|---|---|---|
| 379 | 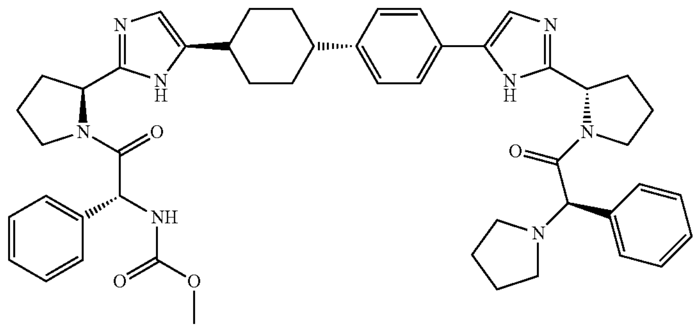 | **** | 809.4 |
| 380 | 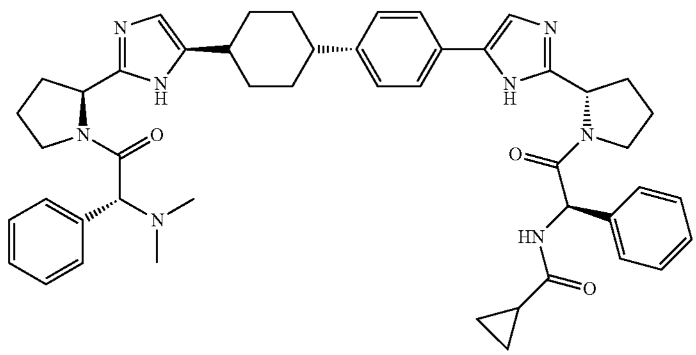 | **** | 793.4 |
| 381 | 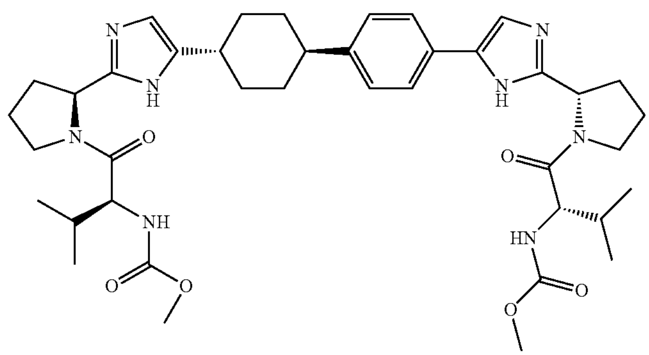 [SMILES: COC(=O)N[C@H](C(=O)N1CCC[C@H]1c1ncc(-c2ccc([C@H]3CC[C@H](c4cnc([C@@H]5CCCN5C(=O)[C@@H](NC(=O)OC)C(C)C)[nH]4)CC3)cc2)[nH]1)C(C)C] | **** | 745.4 |
| 382 | 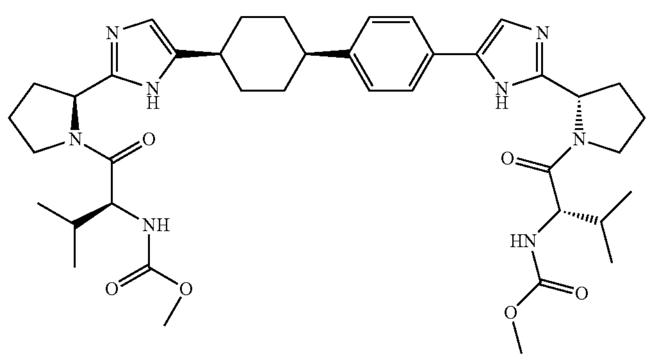 [SMILES: COC(=O)N[C@H](C(=O)N1CCC[C@H]1c1ncc(-c2ccc([C@H]3CC[C@@H](c4cnc([C@@H]5CCCN5C(=O)[C@@H](NC(=O)OC)C(C)C)[nH]4)CC3)cc2)[nH]1)C(C)C] | **** | 745.4 |

TABLE 1-continued

| Compound # | Structure | Inhibition of HCV genotype 1b | MS (M + H+) |
|---|---|---|---|
| 383 | 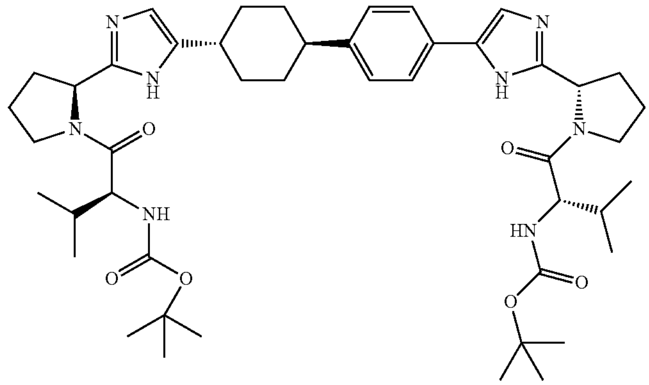 [SMILES: CC(C)[C@H](NC(=O)OC(C)(C)C)C(=O)N1CCC[C@H]1c1ncc(-c2ccc([C@H]3CC[C@H](c4cnc([C@@H]5CCCN5C(=O)[C@@H](NC(=O)OC(C)(C)C)C(C)C)[nH]4)CC3)cc2)[nH]1] | ** | 829.5 |
| 384 | 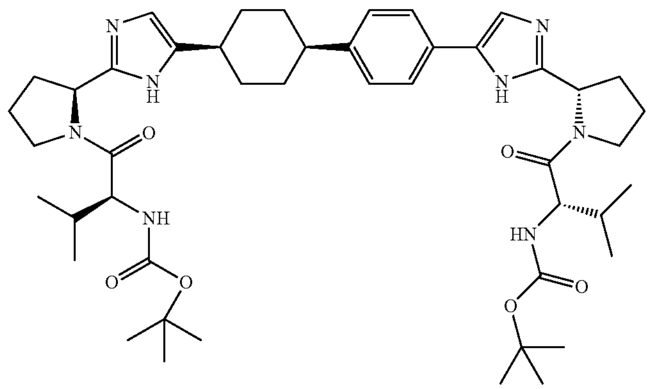 [SMILES: CC(C)[C@H](NC(=O)OC(C)(C)C)C(=O)N1CCC[C@H]1c1ncc(-c2ccc([C@H]3CC[C@@H](c4cnc([C@@H]5CCCN5C(=O)[C@@H](NC(=O)OC(C)(C)C)C(C)C)[nH]4)CC3)cc2)[nH]1] | ** | 829.5 |
| 385 | 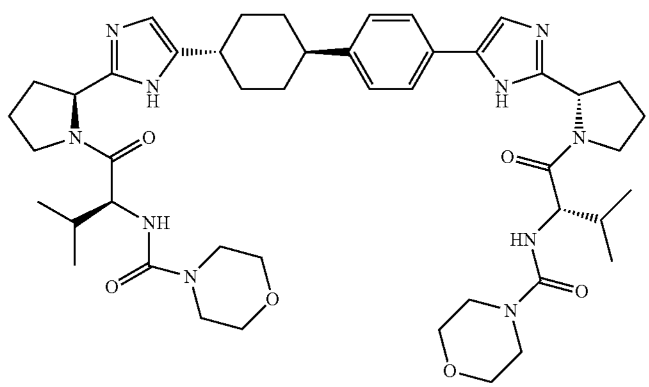 [SMILES: CC(C)[C@H](NC(=O)N1CCOCC1)C(=O)N1CCC[C@H]1c1ncc(-c2ccc([C@H]3CC[C@H](c4cnc([C@@H]5CCCN5C(=O)[C@@H](NC(=O)N5CCOCC5)C(C)C)[nH]4)CC3)cc2)[nH]1] | ** | 855.5 |
| 386 | 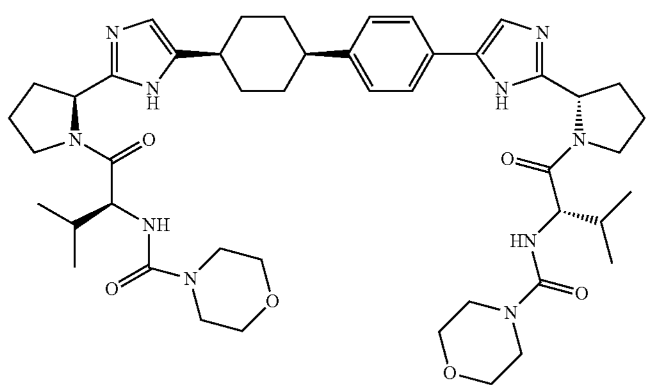 [SMILES: CC(C)[C@H](NC(=O)N1CCOCC1)C(=O)N1CCC[C@H]1c1ncc(-c2ccc([C@H]3CC[C@@H](c4cnc([C@@H]5CCCN5C(=O)[C@@H](NC(=O)N5CCOCC5)C(C)C)[nH]4)CC3)cc2)[nH]1] | ** | 855.5 |

TABLE 1-continued

| Compound # | Structure | Inhibition of HCV genotype 1b | MS (M + H+) |
|---|---|---|---|
| 387 | 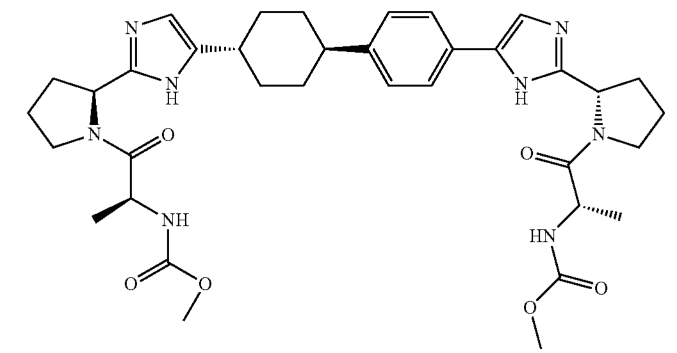 [SMILES: COC(=O)N[C@@H](C)C(=O)N1CCC[C@H]1c1ncc(-c2ccc([C@H]3CC[C@H](c4cnc([C@@H]5CCCN5C(=O)[C@H](C)NC(=O)OC)[nH]4)CC3)cc2)[nH]1] | **** | 689.4 |
| 388 | 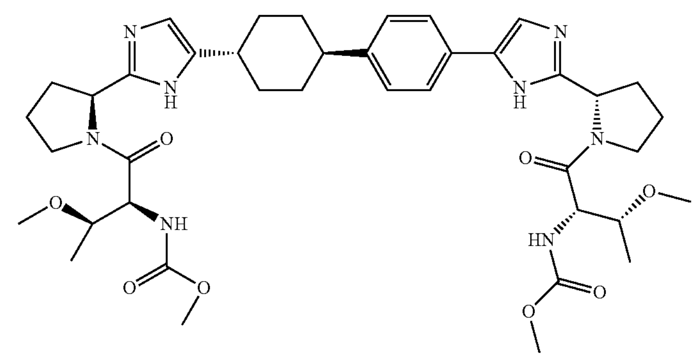 | **** | 777.4 |
| 940 | 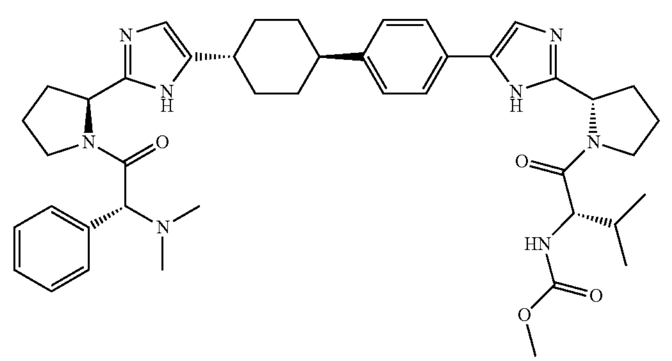 [SMILES: COC(=O)N[C@H](C(=O)N1CCC[C@H]1c1ncc(-c2ccc([C@H]3CC[C@H](c4cnc([C@@H]5CCCN5C(=O)[C@@H](c5ccccc5)N(C)C)[nH]4)CC3)cc2)[nH]1)C(C)C] | **** | 749.4 |
| 941 | 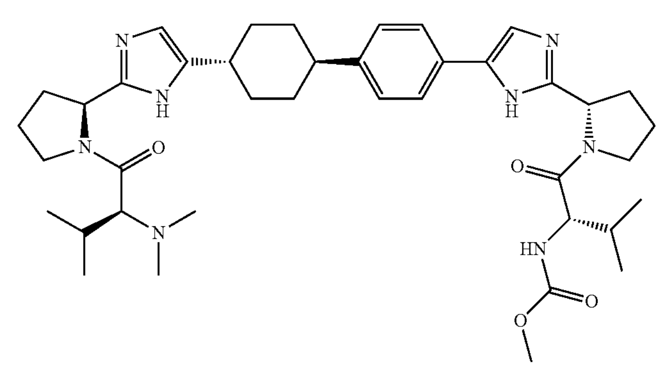 [SMILES: COC(=O)N[C@H](C(=O)N1CCC[C@H]1c1ncc(-c2ccc([C@H]3CC[C@H](c4cnc([C@@H]5CCCN5C(=O)[C@H](C(C)C)N(C)C)[nH]4)CC3)cc2)[nH]1)C(C)C] | **** | 715.5 |

TABLE 1-continued

| Compound # | Structure | Inhibition of HCV genotype 1b | MS (M + H+) |
|---|---|---|---|
| 942 | 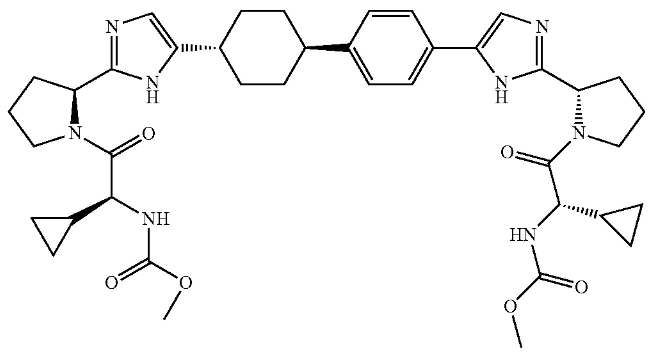 [SMILES: COC(=O)N[C@H](C(=O)N1CCC[C@H]1c1ncc(-c2ccc([C@H]3CC[C@H](c4cnc([C@@H]5CCCN5C(=O)[C@@H](NC(=O)OC)C5CC5)[nH]4)CC3)cc2)[nH]1)C1CC1] | **** | 741.4 |
| 943 | 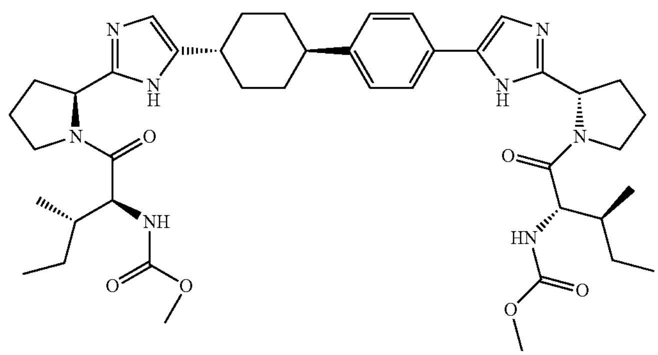 [SMILES: CC[C@H](C)[C@H](NC(=O)OC)C(=O)N1CCC[C@H]1c1ncc(-c2ccc([C@H]3CC[C@H](c4cnc([C@@H]5CCCN5C(=O)[C@@H](NC(=O)OC)[C@@H](C)CC)[nH]4)CC3)cc2)[nH]1] | **** | 773.5 |
| 944 | 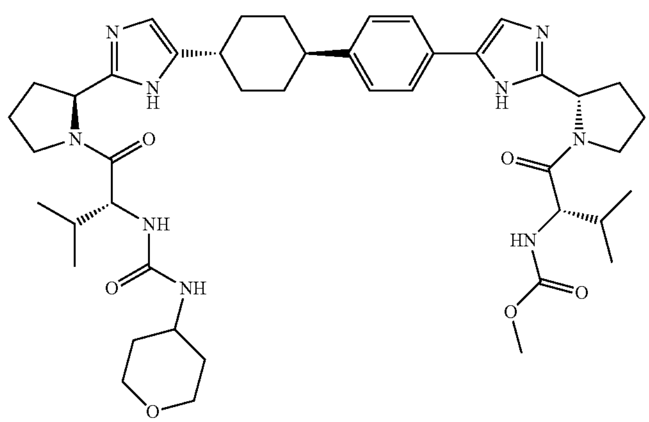 [SMILES: COC(=O)N[C@H](C(=O)N1CCC[C@H]1c1ncc(-c2ccc([C@H]3CC[C@H](c4cnc([C@@H]5CCCN5C(=O)[C@H](NC(=O)NC5CCOCC5)C(C)C)[nH]4)CC3)cc2)[nH]1)C(C)C] | **** | 814.5 |
| 945 | 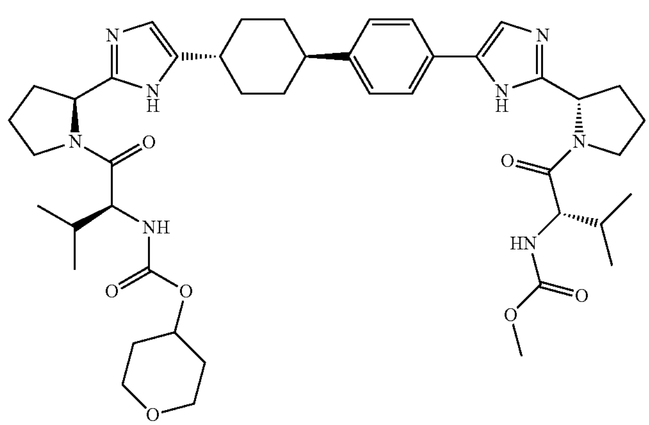 [SMILES: COC(=O)N[C@H](C(=O)N1CCC[C@H]1c1ncc(-c2ccc([C@H]3CC[C@H](c4cnc([C@@H]5CCCN5C(=O)[C@@H](NC(=O)OC5CCOCC5)C(C)C)[nH]4)CC3)cc2)[nH]1)C(C)C] | **** | 815.5 |

TABLE 1-continued

| Compound # | Structure | Inhibition of HCV genotype 1b | MS (M + H+) |
|---|---|---|---|
| 946 | 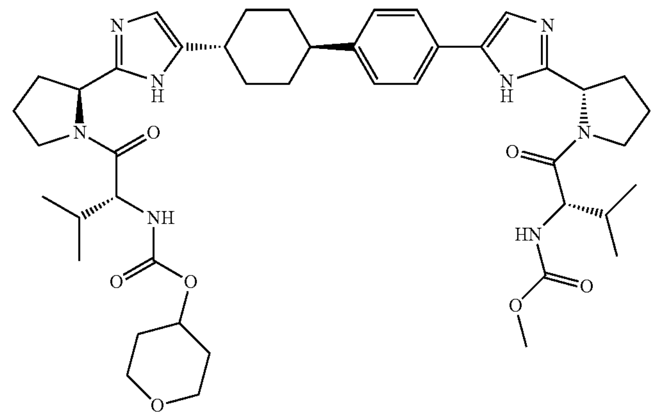 [SMILES: COC(=O)N[C@H](C(=O)N1CCC[C@H]1c1ncc(-c2ccc([C@H]3CC[C@H](c4cnc([C@@H]5CCCN5C(=O)[C@H](NC(=O)OC5CCOCC5)C(C)C)[nH]4)CC3)cc2)[nH]1)C(C)C] | **** | 815.5 |
| 947 | 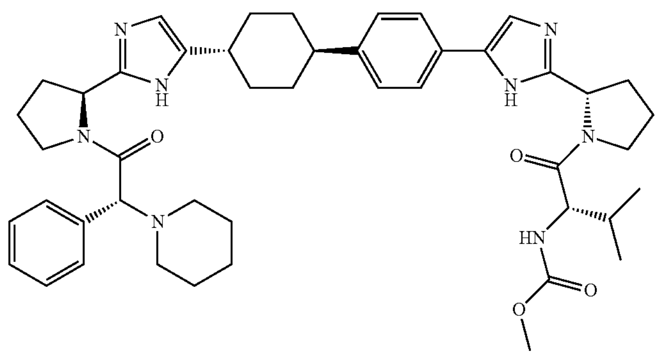 [SMILES: COC(=O)N[C@H](C(=O)N1CCC[C@H]1c1ncc(-c2ccc([C@H]3CC[C@H](c4cnc([C@@H]5CCCN5C(=O)[C@@H](c5ccccc5)N5CCCCC5)[nH]4)CC3)cc2)[nH]1)C(C)C] | **** | 789.5 |
| 2001 | 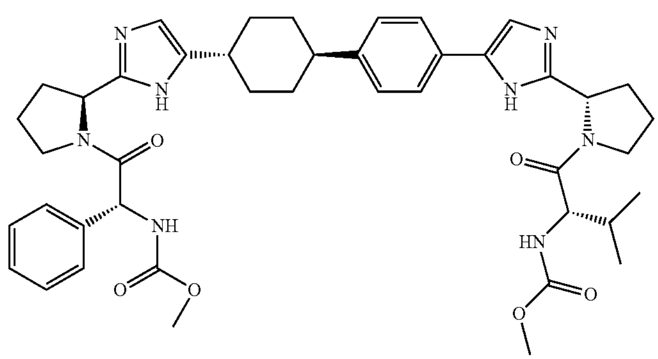 [SMILES: COC(=O)N[C@H](C(=O)N1CCC[C@H]1c1ncc(-c2ccc([C@H]3CC[C@H](c4cnc([C@@H]5CCCN5C(=O)[C@H](NC(=O)OC)c5ccccc5)[nH]4)CC3)cc2)[nH]1)C(C)C] | **** | 779.4 |
| 2002 | 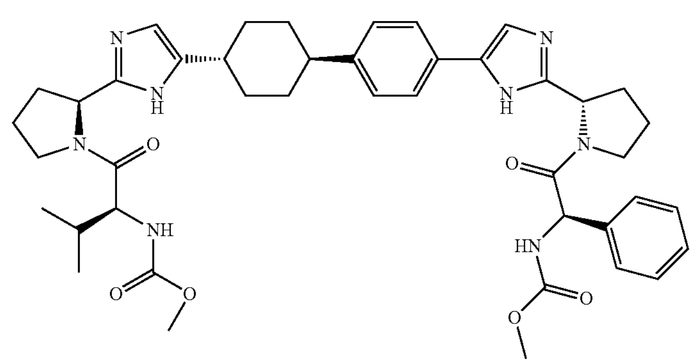 [SMILES: COC(=O)N[C@H](C(=O)N1CCC[C@H]1c1ncc([C@H]2CC[C@H](c3ccc(-c4cnc([C@@H]5CCCN5C(=O)[C@H](NC(=O)OC)c5ccccc5)[nH]4)cc3)CC2)[nH]1)C(C)C] | **** | 779.4 |

TABLE 1-continued

| Compound # | Structure | Inhibition of HCV genotype 1b | MS (M + H+) |
|---|---|---|---|
| 2003 | 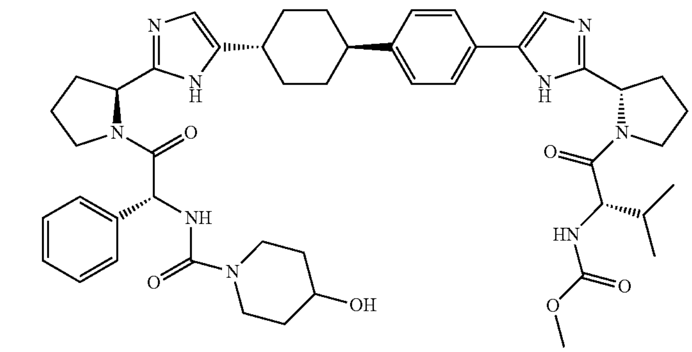 [SMILES: COC(=O)N[C@H](C(=O)N1CCC[C@H]1c1ncc(-c2ccc([C@H]3CC[C@H](c4cnc([C@@H]5CCCN5C(=O)[C@H](NC(=O)N5CCC(O)CC5)c5ccccc5)[nH]4)CC3)cc2)[nH]1)C(C)C] | **** | 848.5 |
| 2004 | 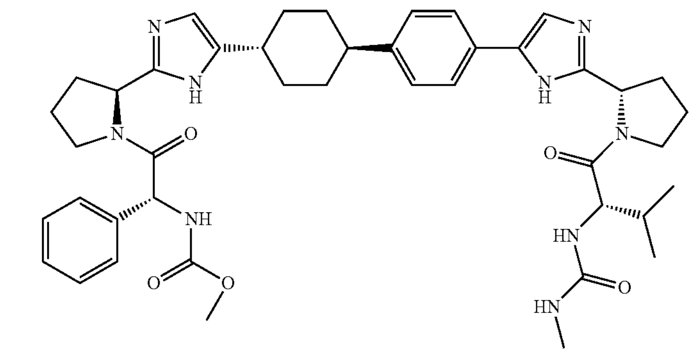 [SMILES: CNC(=O)N[C@H](C(=O)N1CCC[C@H]1c1ncc(-c2ccc([C@H]3CC[C@H](c4cnc([C@@H]5CCCN5C(=O)[C@H](NC(=O)OC)c5ccccc5)[nH]4)CC3)cc2)[nH]1)C(C)C] | **** | 778.4 |
| 2005 | 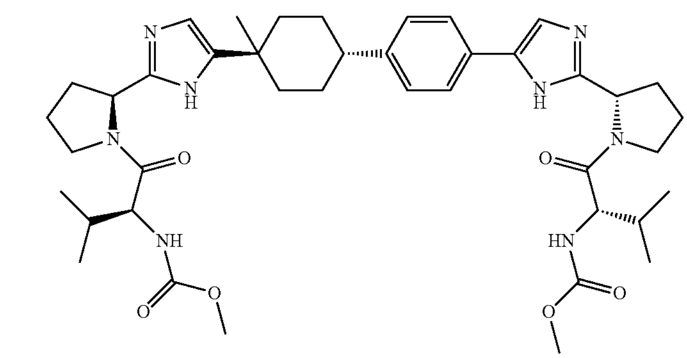 [SMILES: COC(=O)N[C@H](C(=O)N1CCC[C@H]1c1ncc(-c2ccc([C@H]3CC[C@](C)(c4cnc([C@@H]5CCCN5C(=O)[C@@H](NC(=O)OC)C(C)C)[nH]4)CC3)cc2)[nH]1)C(C)C] | **** | 759.4 |
| 2006 | 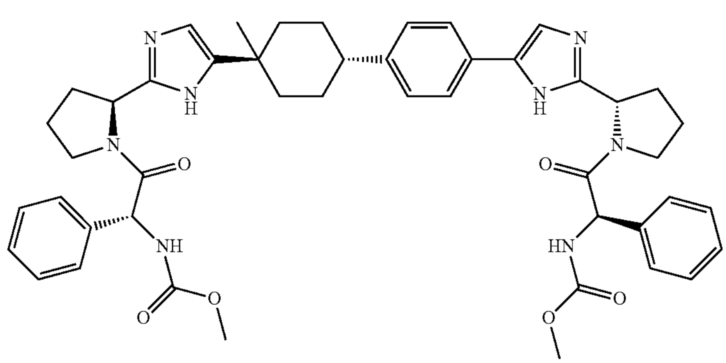 [SMILES: COC(=O)N[C@@H](C(=O)N1CCC[C@H]1c1ncc(-c2ccc([C@H]3CC[C@](C)(c4cnc([C@@H]5CCCN5C(=O)[C@H](NC(=O)OC)c5ccccc5)[nH]4)CC3)cc2)[nH]1)c1ccccc1] | **** | 827.4 |

TABLE 1-continued

| Compound # | Structure | Inhibition of HCV genotype 1b | MS (M + H+) |
|---|---|---|---|
| 2007 | 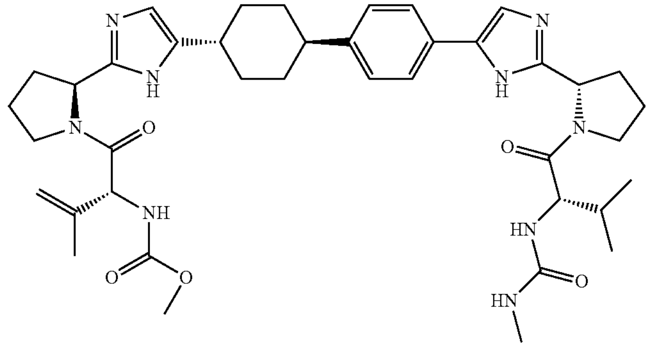 [SMILES: C=C(C)[C@@H](NC(=O)OC)C(=O)N1CCC[C@H]1c1ncc([C@H]2CC[C@H](c3ccc(-c4cnc([C@@H]5CCCN5C(=O)[C@@H](NC(=O)NC)C(C)C)[nH]4)cc3)CC2)[nH]1] | | |
| 2008 | 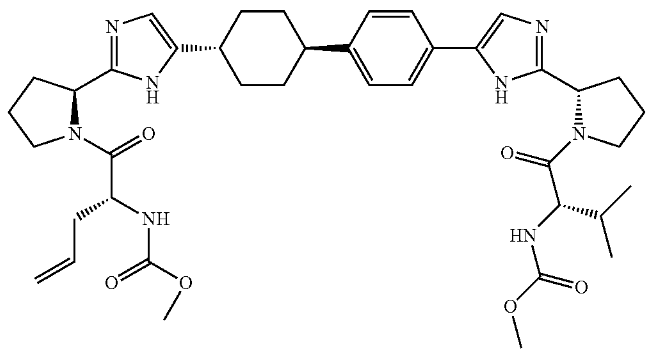 [SMILES: C=CC[C@@H](NC(=O)OC)C(=O)N1CCC[C@H]1c1ncc([C@H]2CC[C@H](c3ccc(-c4cnc([C@@H]5CCCN5C(=O)[C@@H](NC(=O)OC)C(C)C)[nH]4)cc3)CC2)[nH]1] | | |
| 2009 | 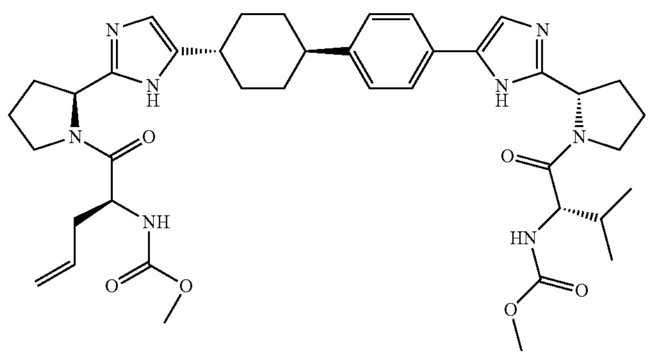 [SMILES: C=CC[C@H](NC(=O)OC)C(=O)N1CCC[C@H]1c1ncc([C@H]2CC[C@H](c3ccc(-c4cnc([C@@H]5CCCN5C(=O)[C@@H](NC(=O)OC)C(C)C)[nH]4)cc3)CC2)[nH]1] | | |
| 2010 | 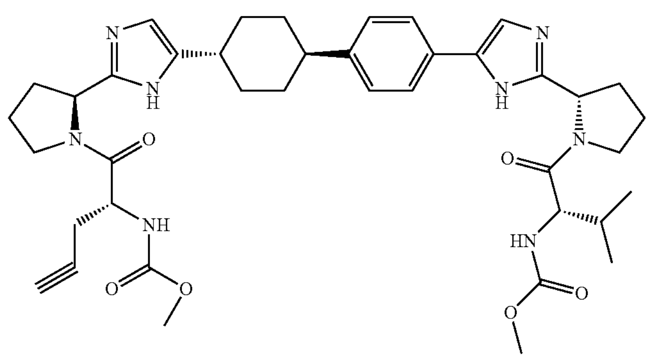 [SMILES: C#CC[C@@H](NC(=O)OC)C(=O)N1CCC[C@H]1c1ncc([C@H]2CC[C@H](c3ccc(-c4cnc([C@@H]5CCCN5C(=O)[C@@H](NC(=O)OC)C(C)C)[nH]4)cc3)CC2)[nH]1] | | |

TABLE 1-continued

| Compound # | Structure | Inhibition of HCV genotype 1b | MS (M + H+) |
|---|---|---|---|
| 2011 | 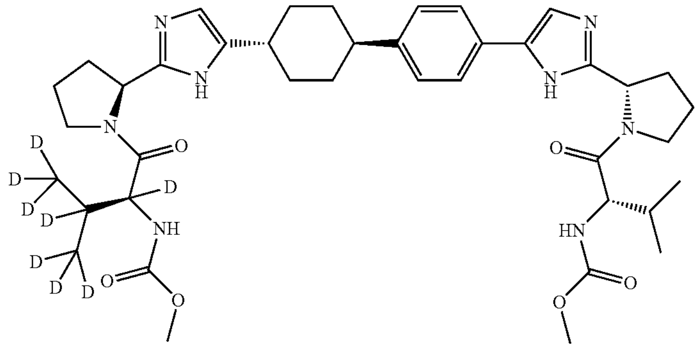 [SMILES: [2H]C([2H])([2H])C([2H])(C([2H])([2H])[2H])[C@@]([2H])(NC(=O)OC)C(=O)N1CCC[C@H]1c1ncc([C@H]2CC[C@H](c3ccc(-c4cnc([C@@H]5CCCN5C(=O)[C@@H](NC(=O)OC)C(C)C)[nH]4)cc3)CC2)[nH]1] | | |
| 2012 | 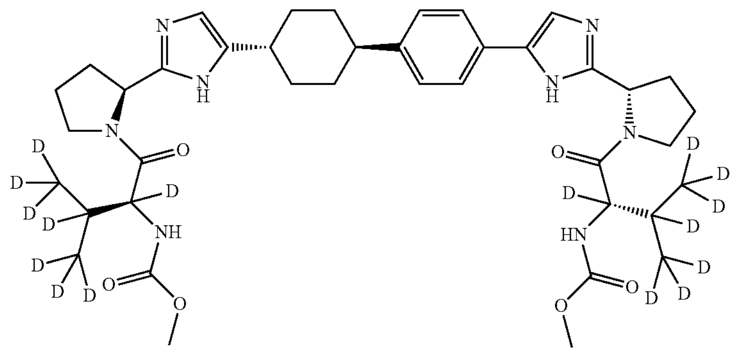 [SMILES: [2H]C([2H])([2H])C([2H])(C([2H])([2H])[2H])[C@@]([2H])(NC(=O)OC)C(=O)N1CCC[C@H]1c1ncc(-c2ccc([C@H]3CC[C@H](c4cnc([C@@H]5CCCN5C(=O)[C@]([2H])(NC(=O)OC)C([2H])(C([2H])([2H])[2H])C([2H])([2H])[2H])[nH]4)CC3)cc2)[nH]1] | | |
| 2013 | 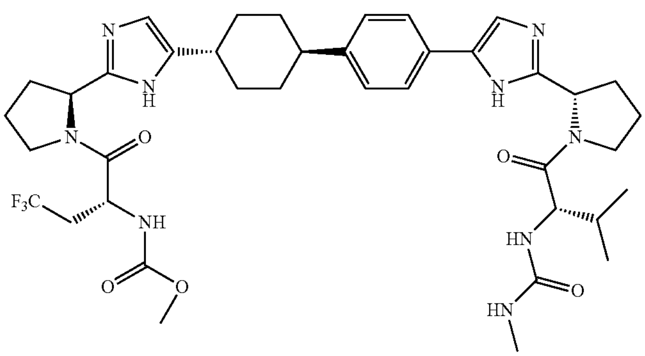 [SMILES: CNC(=O)N[C@H](C(=O)N1CCC[C@H]1c1ncc(-c2ccc([C@H]3CC[C@H](c4cnc([C@@H]5CCCN5C(=O)[C@@H](CC(F)(F)F)NC(=O)OC)[nH]4)CC3)cc2)[nH]1)C(C)C] | | |
| 2014 | 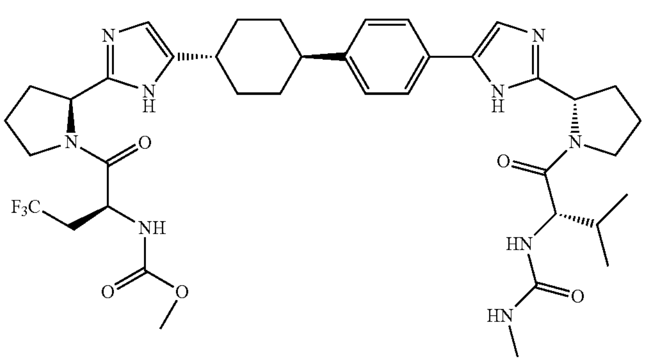 [SMILES: CNC(=O)N[C@H](C(=O)N1CCC[C@H]1c1ncc(-c2ccc([C@H]3CC[C@H](c4cnc([C@@H]5CCCN5C(=O)[C@H](CC(F)(F)F)NC(=O)OC)[nH]4)CC3)cc2)[nH]1)C(C)C] | | |

TABLE 1-continued

| Compound # | Structure | Inhibition of HCV genotype 1b | MS (M + H+) |
|---|---|---|---|
| 2015 | 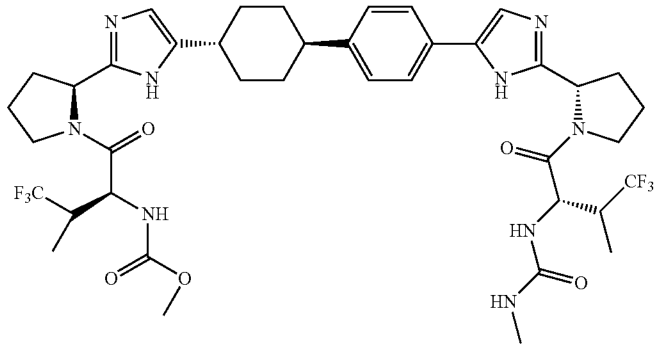 [SMILES: CNC(=O)N[C@H](C(=O)N1CCC[C@H]1c1ncc(-c2ccc([C@H]3CC[C@H](c4cnc([C@@H]5CCCN5C(=O)[C@@H](NC(=O)OC)C(C)C(F)(F)F)[nH]4)CC3)cc2)[nH]1)C(C)C(F)(F)F] | | |

TABLE 2

| Compound # | Structure | Inhibition of HCV genotype 1b | MS (M + H+) |
|---|---|---|---|
| 400 | 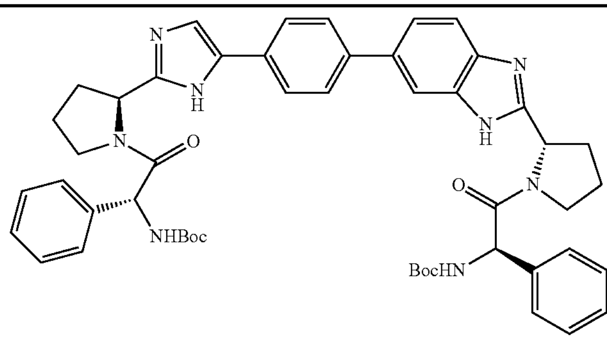 | **** | 865.4 |
| 401 | 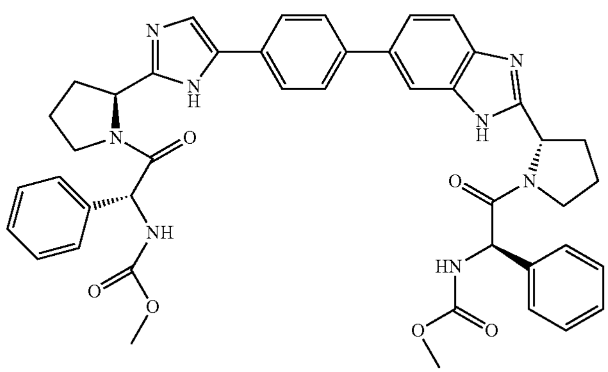 [SMILES: COC(=O)N[C@@H](C(=O)N1CCC[C@H]1c1ncc(-c2ccc(-c3ccc4nc([C@@H]5CCCN5C(=O)[C@H](NC(=O)OC)c5ccccc5)[nH]c4c3)cc2)[nH]1)c1ccccc1] | **** | 781.3 |
| 402 | 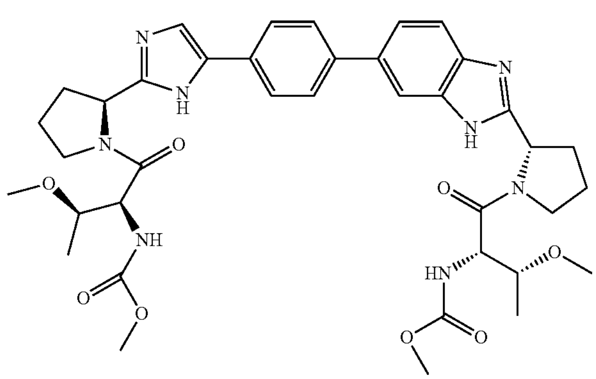 | **** | 745.4 |

TABLE 2-continued

| Compound # | Structure | Inhibition of HCV genotype 1b | MS (M + H⁺) |
|---|---|---|---|
| 403 | 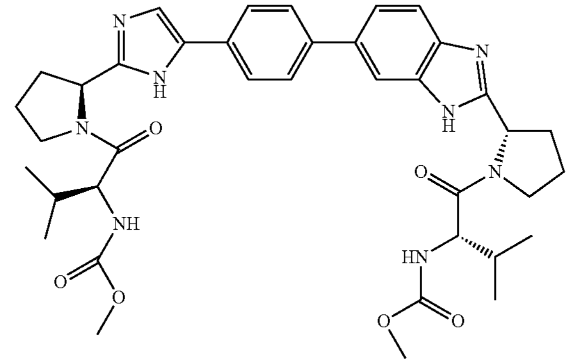 [SMILES: COC(=O)N[C@H](C(=O)N1CCC[C@H]1c1ncc(-c2ccc(-c3ccc4nc([C@@H]5CCCN5C(=O)[C@@H](NC(=O)OC)C(C)C)[nH]c4c3)cc2)[nH]1)C(C)C] | **** | 713.4 |
| 404 | 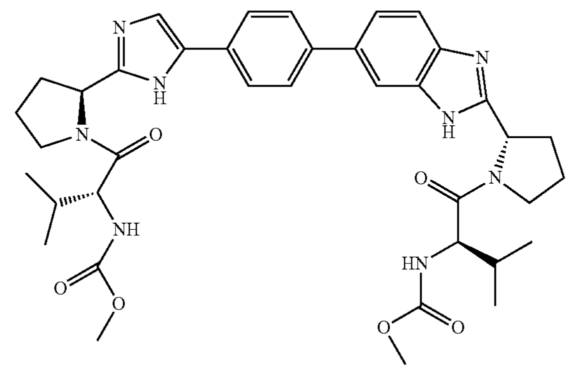 [SMILES: COC(=O)N[C@@H](C(=O)N1CCC[C@H]1c1ncc(-c2ccc(-c3ccc4nc([C@@H]5CCCN5C(=O)[C@H](NC(=O)OC)C(C)C)[nH]c4c3)cc2)[nH]1)C(C)C] | *** | 713.4 |
| 2019 | 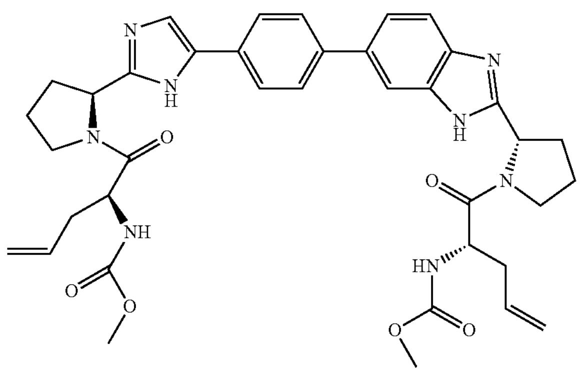 [SMILES: C=CC[C@H](NC(=O)OC)C(=O)N1CCC[C@H]1c1ncc(-c2ccc(-c3ccc4nc([C@@H]5CCCN5C(=O)[C@H](CC=C)NC(=O)OC)[nH]c4c3)cc2)[nH]1] | | |
| 2020 | 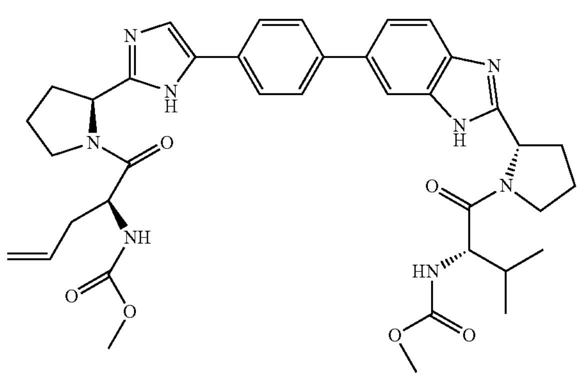 [SMILES: C=CC[C@H](NC(=O)OC)C(=O)N1CCC[C@H]1c1ncc(-c2ccc(-c3ccc4nc([C@@H]5CCCN5C(=O)[C@@H](NC(=O)OC)C(C)C)[nH]c4c3)cc2)[nH]1] | | |

TABLE 2-continued

| Compound # | Structure | Inhibition of HCV genotype 1b | MS (M + H⁺) |
|---|---|---|---|
| 2021 | 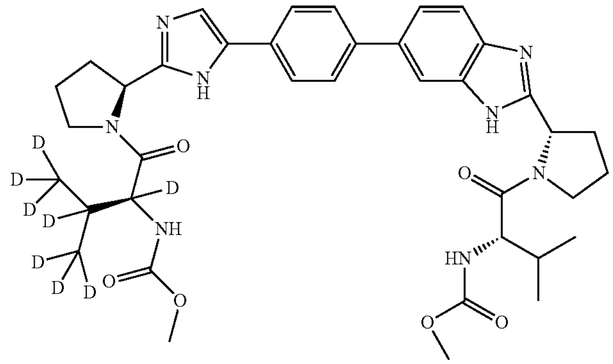 [SMILES: [2H]C([2H])([2H])C([2H])(C([2H])([2H])[2H])[C@@]([2H])(NC(=O)OC)C(=O)N1CCC[C@H]1c1ncc(-c2ccc(-c3ccc4nc([C@@H]5CCCN5C(=O)[C@@H](NC(=O)OC)C(C)C)[nH]c4c3)cc2)[nH]1] | | |
| 2022 | 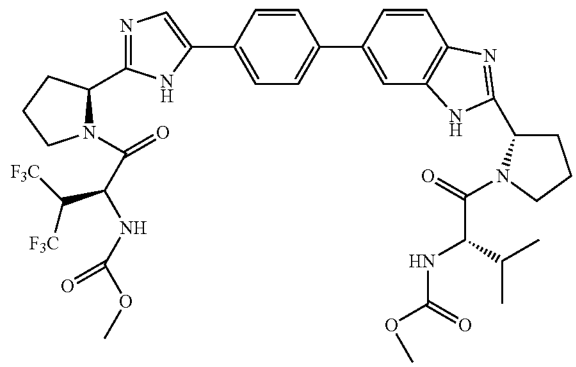 [SMILES: COC(=O)N[C@H](C(=O)N1CCC[C@H]1c1nc2ccc(-c3ccc(-c4cnc([C@@H]5CCCN5C(=O)[C@@H](NC(=O)OC)C(C(F)(F)F)C(F)(F)F)[nH]4)cc3)cc2[nH]1)C(C)C] | | |
| 2023 | 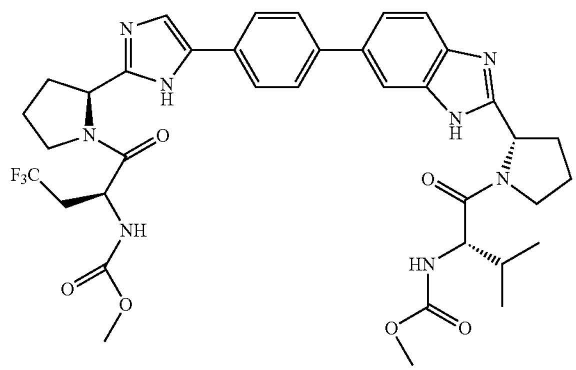 [SMILES: COC(=O)N[C@@H](CC(F)(F)F)C(=O)N1CCC[C@H]1c1ncc(-c2ccc(-c3ccc4nc([C@@H]5CCCN5C(=O)[C@@H](NC(=O)OC)C(C)C)[nH]c4c3)cc2)[nH]1] | | |
| 2024 | 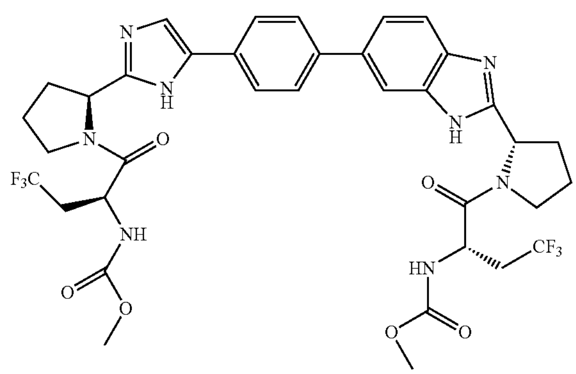 [SMILES: COC(=O)N[C@@H](CC(F)(F)F)C(=O)N1CCC[C@H]1c1ncc(-c2ccc(-c3ccc4nc([C@@H]5CCCN5C(=O)[C@H](CC(F)(F)F)NC(=O)OC)[nH]c4c3)cc2)[nH]1] | | |

TABLE 2-continued

| Compound # | Structure | Inhibition of HCV genotype 1b | MS (M + H+) |
|---|---|---|---|
| 2025 | 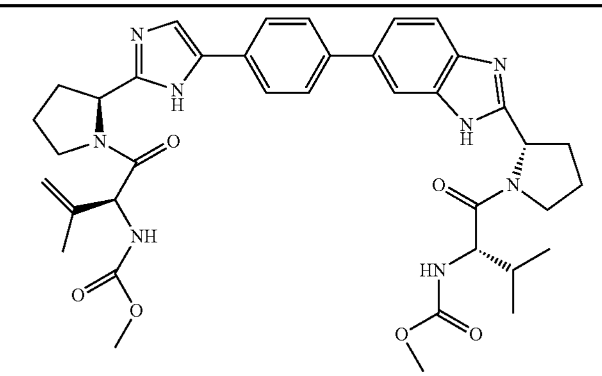 | | |
| 2026 | 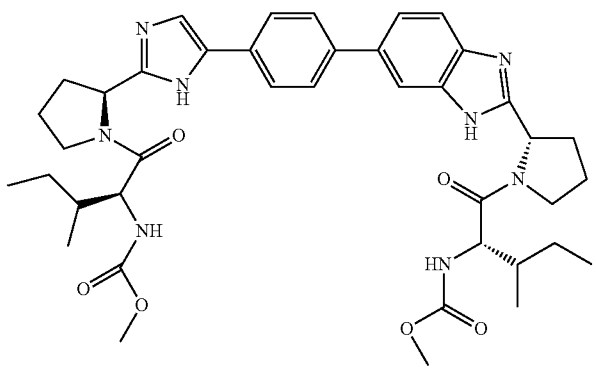 [SMILES: CCC(C)[C@H](NC(=O)OC)C(=O)N1CCC[C@H]1c1ncc(-c2ccc(-c3ccc4nc([C@@H]5CCCN5C(=O)[C@@H](NC(=O)OC)C(C)CC)[nH]c4c3)cc2)[nH]1] | | |

TABLE 3

| Compound # | Structure | Inhibition of HCV genotype 1b | MS (M + H+) |
|---|---|---|---|
| 450 | 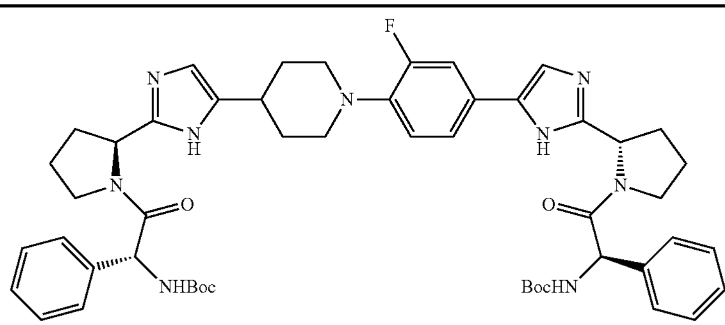 | **** | 916.5 |
| 451 | 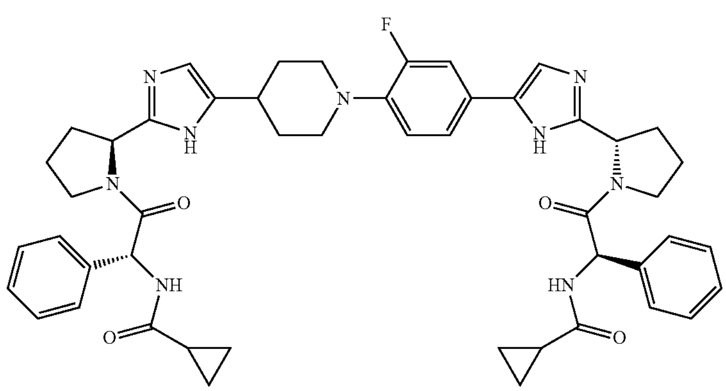 [SMILES: O=C(N[C@@H](C(=O)N1CCC[C@H]1c1ncc(-c2ccc(N3CCC(c4cnc([C@@H]5CCCN5C(=O)[C@H](NC(=O)C5CC5)c5ccccc5)[nH]4)CC3)c(F)c2)[nH]1)c1ccccc1)C1CC1] | **** | 852.4 |

TABLE 3-continued

| Compound # | Structure | Inhibition of HCV genotype 1b | MS (M + H⁺) |
|---|---|---|---|
| 452 | 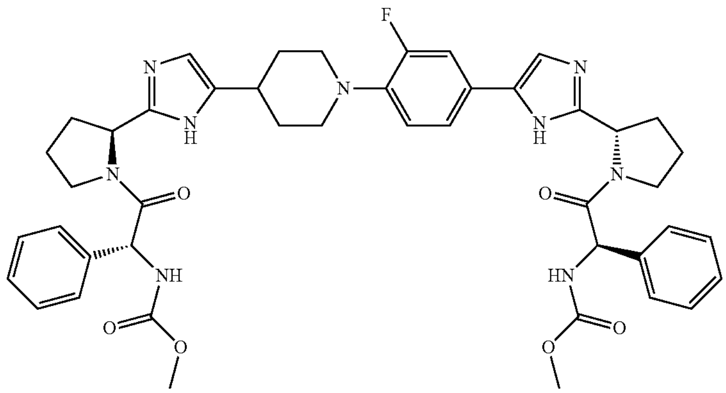 [SMILES: COC(=O)N[C@@H](C(=O)N1CCC[C@H]1c1ncc(-c2ccc(N3CCC(c4cnc([C@@H]5CCCN5C(=O)[C@H](NC(=O)OC)c5ccccc5)[nH]4)CC3)c(F)c2)[nH]1)c1ccccc1] | **** | 832.4 |
| 453 | 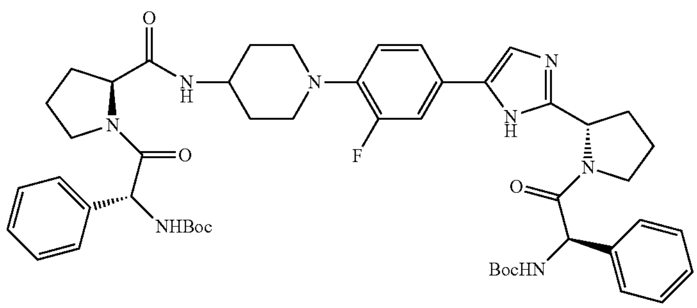 [SMILES: CC(C)(C)OC(=O)N[C@@H](C(=O)N1CCC[C@H]1C(=O)NC1CCN(c2ccc(-c3cnc([C@@H]4CCCN4C(=O)[C@H](NC(=O)OC(C)(C)C)c4ccccc4)[nH]3)cc2F)CC1)c1ccccc1] | **** | 893.5 |
| 454 | 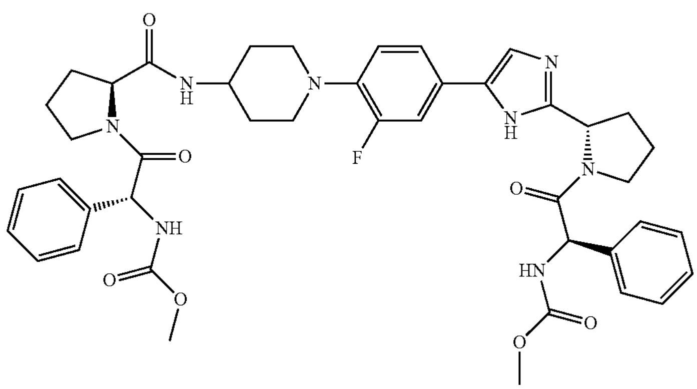 [SMILES: COC(=O)N[C@@H](C(=O)N1CCC[C@H]1C(=O)NC1CCN(c2ccc(-c3cnc([C@@H]4CCCN4C(=O)[C@H](NC(=O)OC)c4ccccc4)[nH]3)cc2F)CC1)c1ccccc1] | **** | 809.4 |
| 455 | 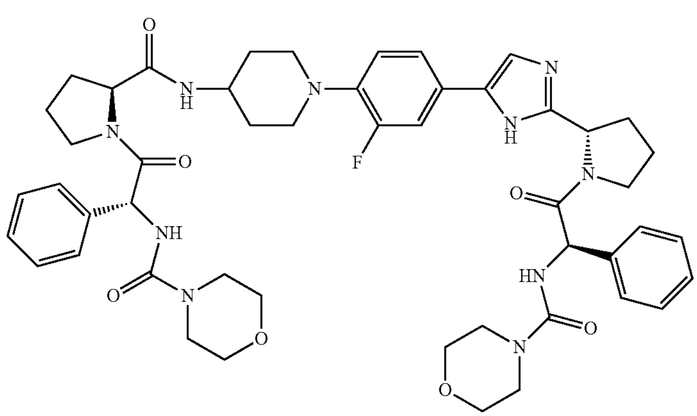 [SMILES: O=C(NC1CCN(c2ccc(-c3cnc([C@@H]4CCCN4C(=O)[C@H](NC(=O)N4CCOCC4)c4ccccc4)[nH]3)cc2F)CC1)[C@@H]1CCCN1C(=O)[C@H](NC(=O)N1CCOCC1)c1ccccc1] | *** | 919.5 |

TABLE 3-continued

| Compound # | Structure | Inhibition of HCV genotype 1b | MS (M + H⁺) |
|---|---|---|---|
| 456 | 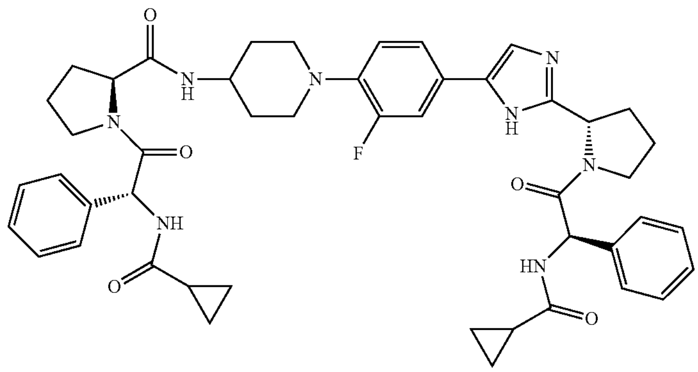 [SMILES: O=C(N[C@@H](C(=O)N1CCC[C@H]1C(=O)NC1CCN(c2ccc(-c3cnc([C@@H]4CCCN4C(=O)[C@H](NC(=O)C4CC4)c4ccccc4)[nH]3)cc2F)CC1)c1ccccc1)C1CC1] | **** | 829.4 |
| 457 | 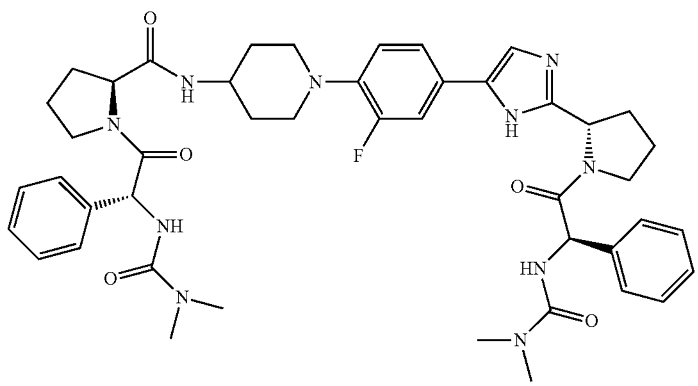 [SMILES: CN(C)C(=O)N[C@@H](C(=O)N1CCC[C@H]1C(=O)NC1CCN(c2ccc(-c3cnc([C@@H]4CCCN4C(=O)[C@H](NC(=O)N(C)C)c4ccccc4)[nH]3)cc2F)CC1)c1ccccc1] | **** | 835.4 |
| 458 | 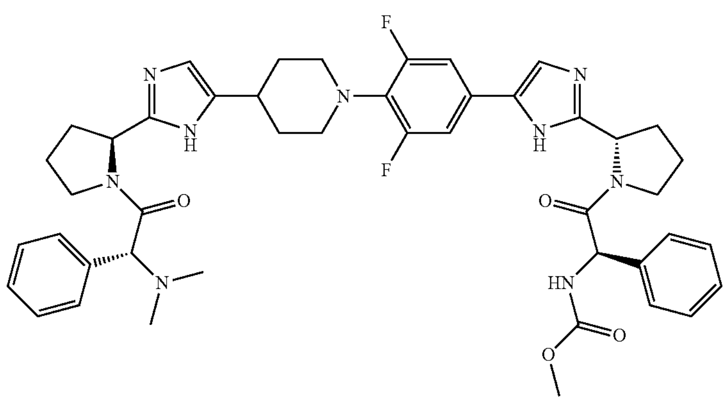 [SMILES: COC(=O)N[C@@H](C(=O)N1CCC[C@H]1c1ncc(-c2cc(F)c(N3CCC(c4cnc([C@@H]5CCCN5C(=O)[C@@H](c5ccccc5)N(C)C)[nH]4)CC3)c(F)c2)[nH]1)c1ccccc1] | **** | 820.4 |
| 459 | 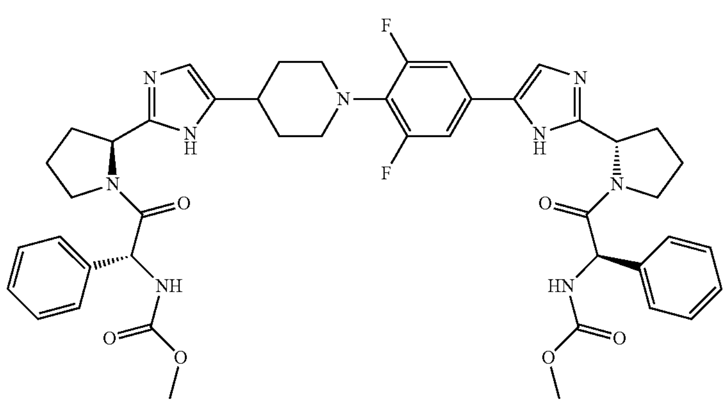 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)OC)c5ccccc5)[nH]4)CC3)c(F)c2)[nH]1)c1ccccc1] | **** | 850.4 |

TABLE 3-continued

| Compound # | Structure | Inhibition of HCV genotype 1b | MS (M + H+) |
|---|---|---|---|
| 460 | 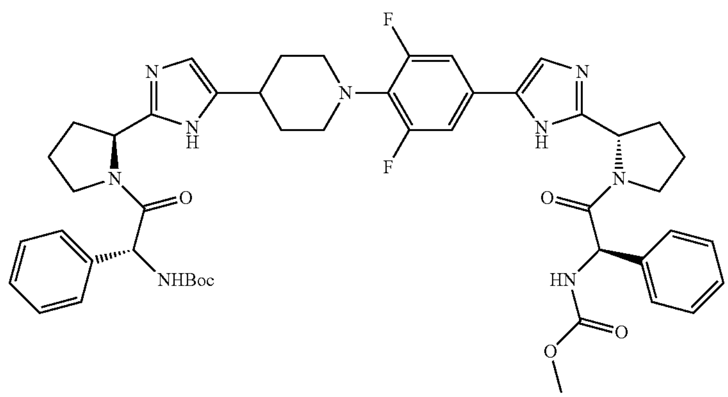 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)OC(C)(C)C)c5ccccc5)[nH]4)CC3)c(F)c2)[nH]1)c1ccccc1] | **** | 892.4 |
| 461 | 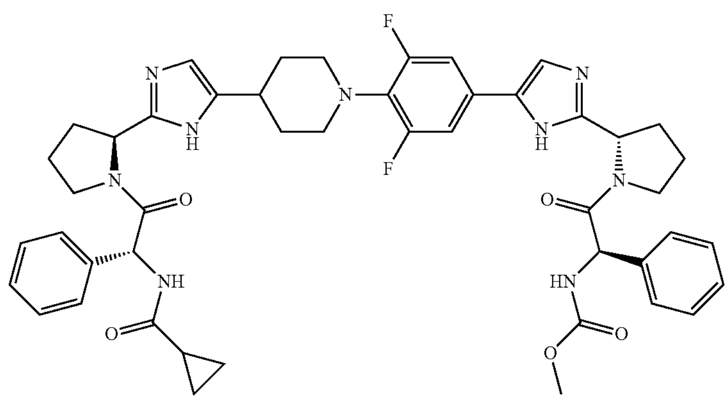 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)C5CC5)c5ccccc5)[nH]4)CC3)c(F)c2)[nH]1)c1ccccc1] | **** | 860.4 |
| 462 | 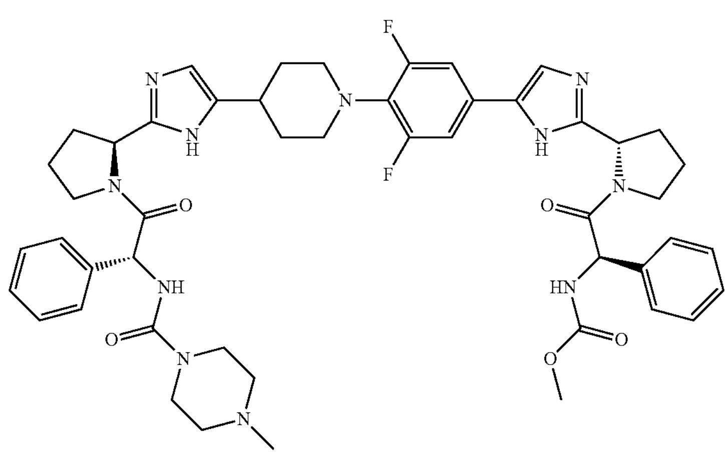 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)N5CCN(C)CC5)c5ccccc5)[nH]4)CC3)c(F)c2)[nH]1)c1ccccc1] | **** | 918.5 |

TABLE 3-continued

| Compound # | Structure | Inhibition of HCV genotype 1b | MS (M + H+) |
|---|---|---|---|
| 463 | 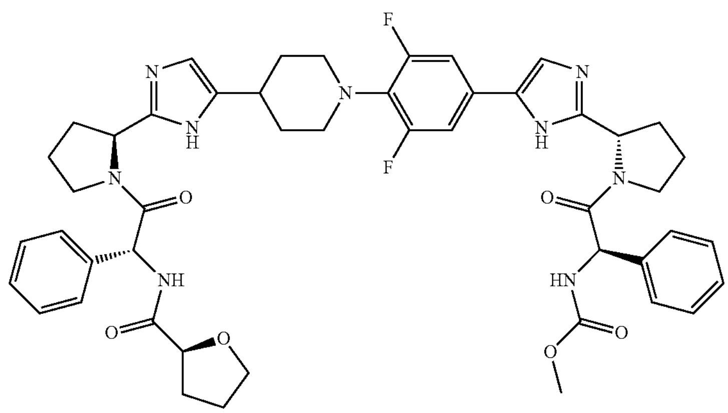 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)[C@@H]5CCCO5)c5ccccc5)[nH]4)CC3)c(F)c2)[nH]1)c1ccccc1] | 0.03 | 890.4 |
| 464 | 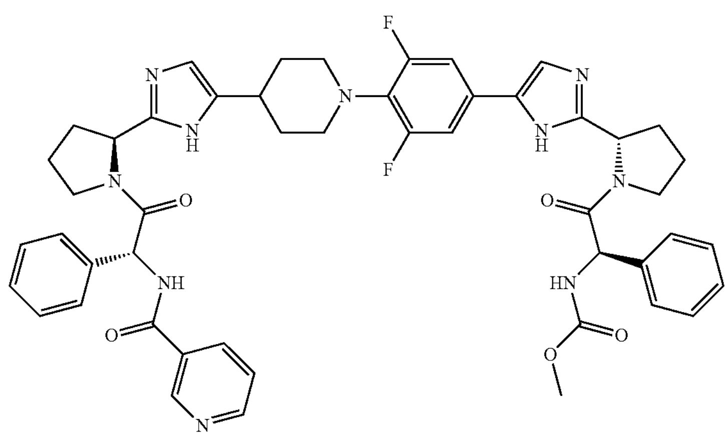 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)c5cccnc5)c5ccccc5)[nH]4)CC3)c(F)c2)[nH]1)c1ccccc1] | 0.03 | 897.4 |
| 465 | 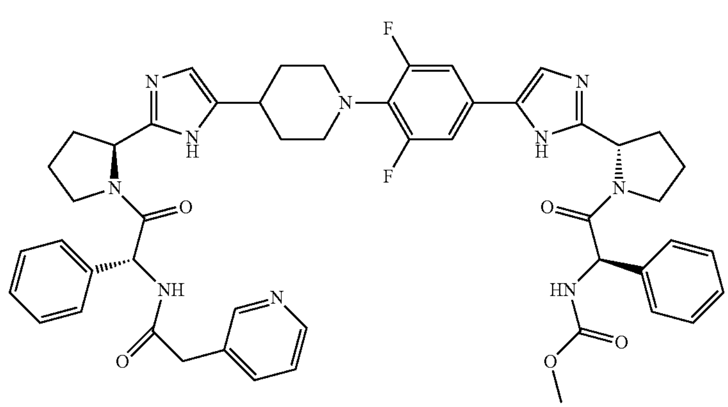 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)Cc5cccnc5)c5ccccc5)[nH]4)CC3)c(F)c2)[nH]1)c1ccccc1] | 0.08 | 911.4 |

TABLE 3-continued

| Compound # | Structure | Inhibition of HCV genotype 1b | MS (M + H+) |
|---|---|---|---|
| 466 | 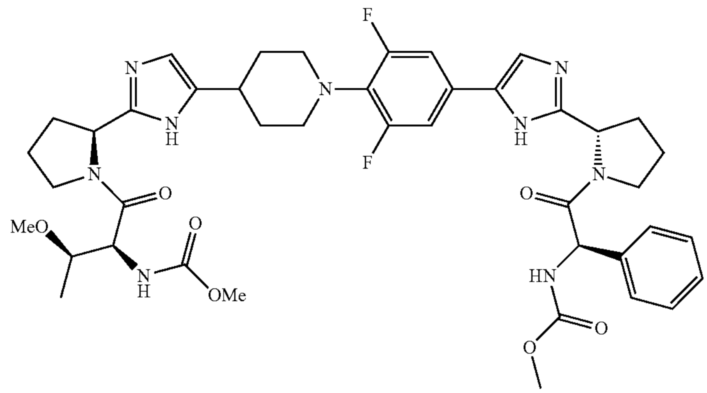 [SMILES: COC(=O)N[C@H](C(=O)N1CCC[C@H]1c1ncc(C2CCN(c3c(F)cc(-c4cnc([C@@H]5CCCN5C(=O)[C@H](NC(=O)OC)c5ccccc5)[nH]4)cc3F)CC2)[nH]1)[C@@H](C)OC] | **** | 832.4 |
| 467 | 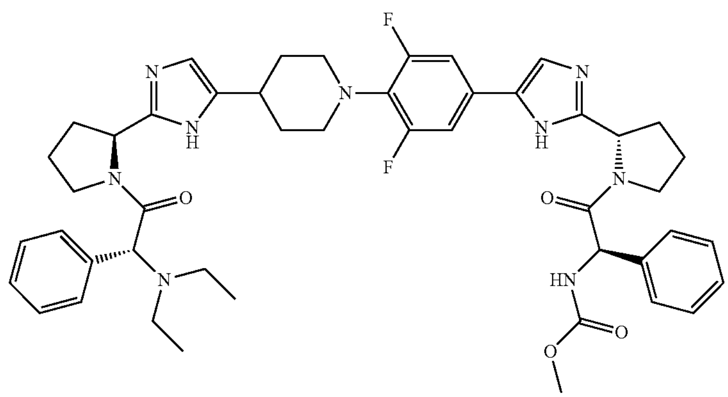 [SMILES: CCN(CC)[C@@H](C(=O)N1CCC[C@H]1c1ncc(C2CCN(c3c(F)cc(-c4cnc([C@@H]5CCCN5C(=O)[C@H](NC(=O)OC)c5ccccc5)[nH]4)cc3F)CC2)[nH]1)c1ccccc1] | **** | 848.4 |
| 468 | 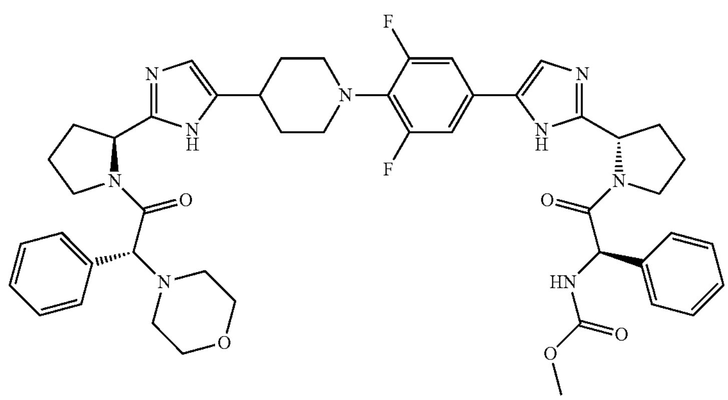 [SMILES: COC(=O)N[C@@H](C(=O)N1CCC[C@H]1c1ncc(-c2cc(F)c(N3CCC(c4cnc([C@@H]5CCCN5C(=O)[C@@H](c5ccccc5)N5CCOCC5)[nH]4)CC3)c(F)c2)[nH]1)c1ccccc1] | **** | 862.4 |
| 469 | 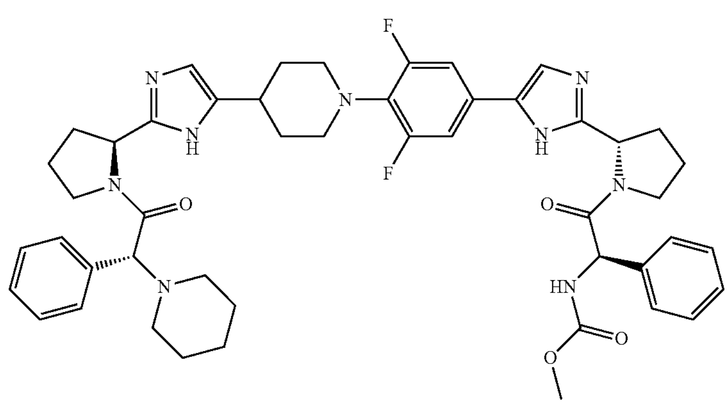 [SMILES: COC(=O)N[C@@H](C(=O)N1CCC[C@H]1c1ncc(-c2cc(F)c(N3CCC(c4cnc([C@@H]5CCCN5C(=O)[C@@H](c5ccccc5)N5CCCCC5)[nH]4)CC3)c(F)c2)[nH]1)c1ccccc1] | **** | 860.4 |

TABLE 3-continued

| Compound # | Structure | Inhibition of HCV genotype 1b | MS (M + H+) |
| --- | --- | --- | --- |
| 470 | 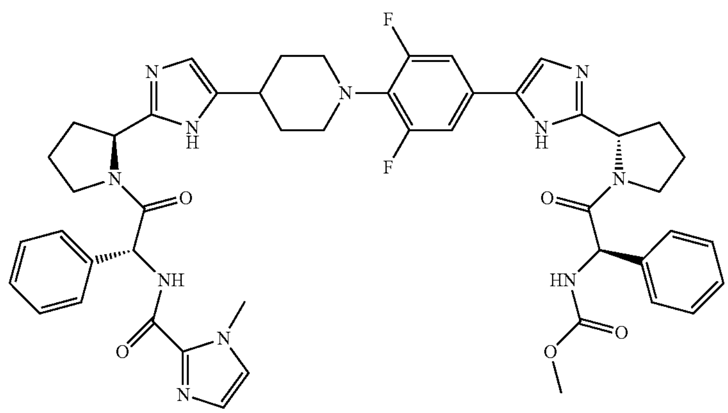 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)c5nccn5C)c5ccccc5)[nH]4)CC3)c(F)c2)[nH]1)c1ccccc1] | **** | 890.4 |
| 471 | 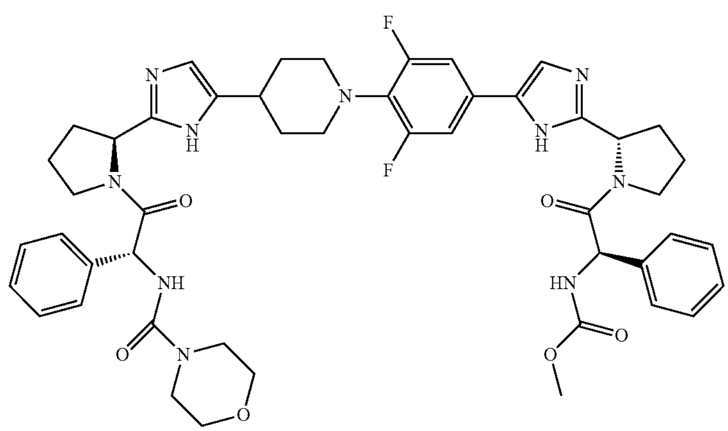 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)N5CCOCC5)c5ccccc5)[nH]4)CC3)c(F)c2)[nH]1)c1ccccc1] | *** | 905.4 |
| 472 | 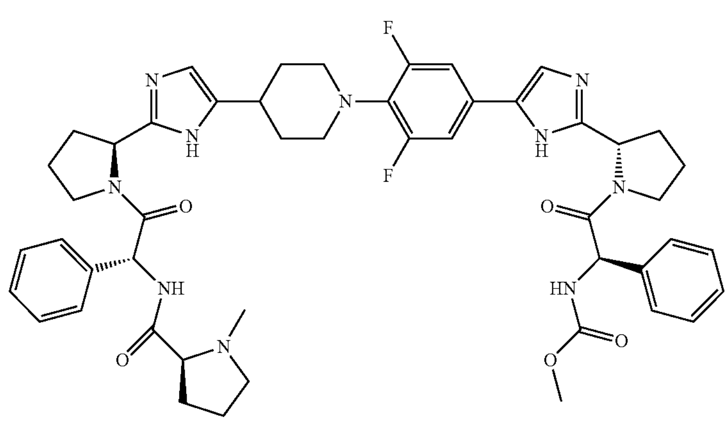 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)[C@@H]5CCCN5C)c5ccccc5)[nH]4)CC3)c(F)c2)[nH]1)c1ccccc1] | **** | 903.4 |

TABLE 3-continued

| Compound # | Structure | Inhibition of HCV genotype 1b | MS (M + H⁺) |
|---|---|---|---|
| 473 | 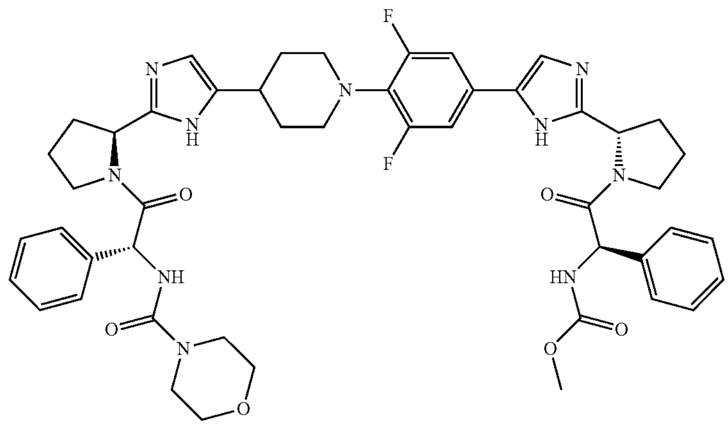 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)N5CCOCC5)c5ccccc5)[nH]4)CC3)c(F)c2)[nH]1)c1ccccc1] | **** | 905.4 |
| 474 | 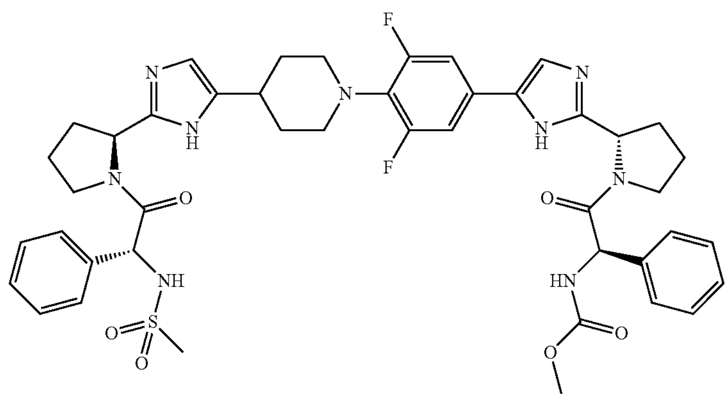 [SMILES: COC(=O)N[C@@H](C(=O)N1CCC[C@H]1c1ncc(-c2cc(F)c(N3CCC(c4cnc([C@@H]5CCCN5C(=O)[C@H](NS(C)(=O)=O)c5ccccc5)[nH]4)CC3)c(F)c2)[nH]1)c1ccccc1] | **** | 870.3 |
| 475 | 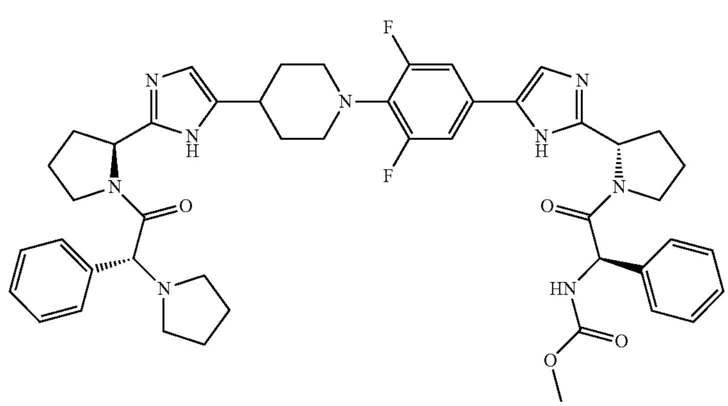 [SMILES: COC(=O)N[C@@H](C(=O)N1CCC[C@H]1c1ncc(-c2cc(F)c(N3CCC(c4cnc([C@@H]5CCCN5C(=O)[C@@H](c5ccccc5)N5CCCC5)[nH]4)CC3)c(F)c2)[nH]1)c1ccccc1] | **** | 846.4 |

TABLE 3-continued

| Compound # | Structure | Inhibition of HCV genotype 1b | MS (M + H+) |
|---|---|---|---|
| 476 | 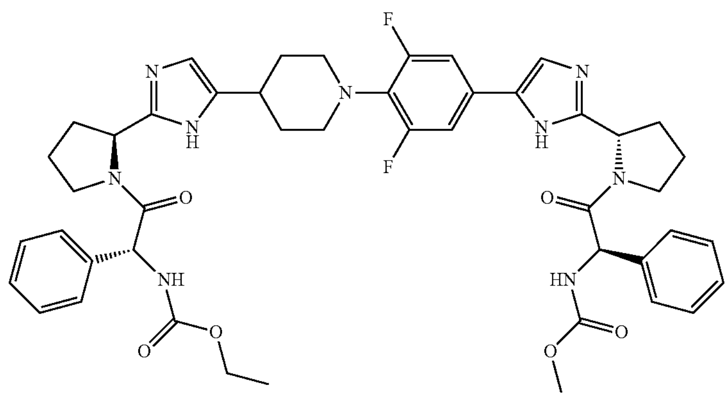 [SMILES: CCOC(=O)N[C@@H](C(=O)N1CCC[C@H]1c1ncc(C2CCN(c3c(F)cc(-c4cnc([C@@H]5CCCN5C(=O)[C@H](NC(=O)OC)c5ccccc5)[nH]4)cc3F)CC2)[nH]1)c1ccccc1] | **** | 864.4 |
| 477 | 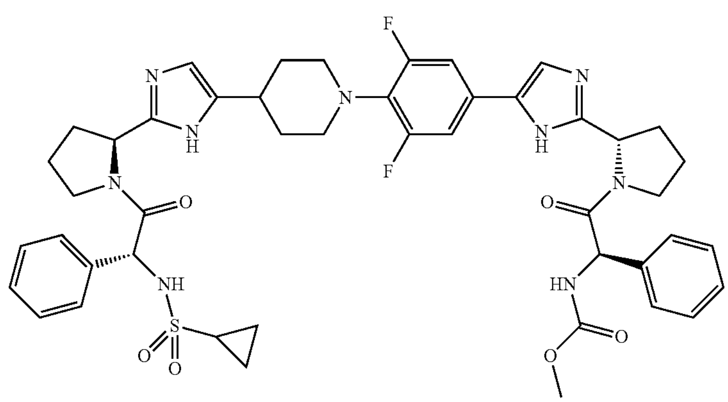 [SMILES: COC(=O)N[C@@H](C(=O)N1CCC[C@H]1c1ncc(-c2cc(F)c(N3CCC(c4cnc([C@@H]5CCCN5C(=O)[C@H](NS(=O)(=O)C5CC5)c5ccccc5)[nH]4)CC3)c(F)c2)[nH]1)c1ccccc1] | **** | 896.4 |
| 478 | 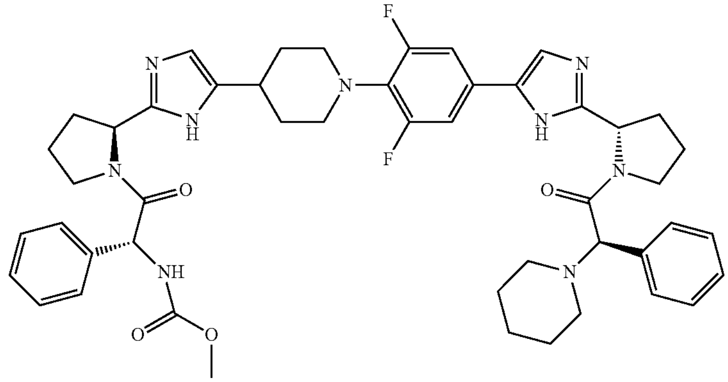 [SMILES: COC(=O)N[C@@H](C(=O)N1CCC[C@H]1c1ncc(C2CCN(c3c(F)cc(-c4cnc([C@@H]5CCCN5C(=O)[C@@H](c5ccccc5)N5CCCCC5)[nH]4)cc3F)CC2)[nH]1)c1ccccc1] | **** | 960.4 |

TABLE 3-continued

| Compound # | Structure | Inhibition of HCV genotype 1b | MS (M + H+) |
|---|---|---|---|
| 479 | 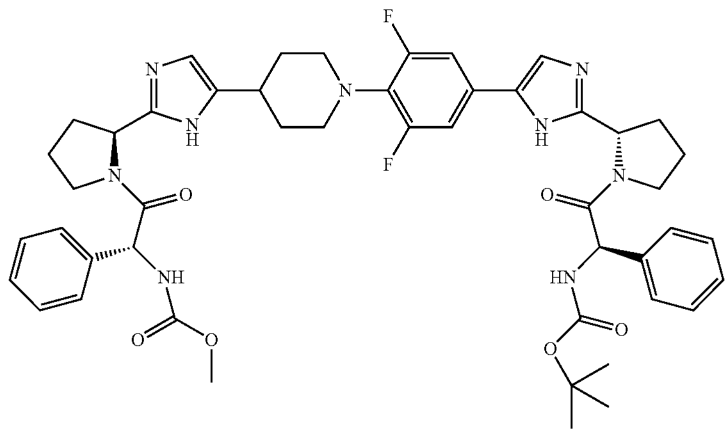 [SMILES: COC(=O)N[C@@H](C(=O)N1CCC[C@H]1c1ncc(C2CCN(c3c(F)cc(-c4cnc([C@@H]5CCCN5C(=O)[C@H](NC(=O)OC(C)(C)C)c5ccccc5)[nH]4)cc3F)CC2)[nH]1)c1ccccc1] | **** | 892.4 |
| 480 | 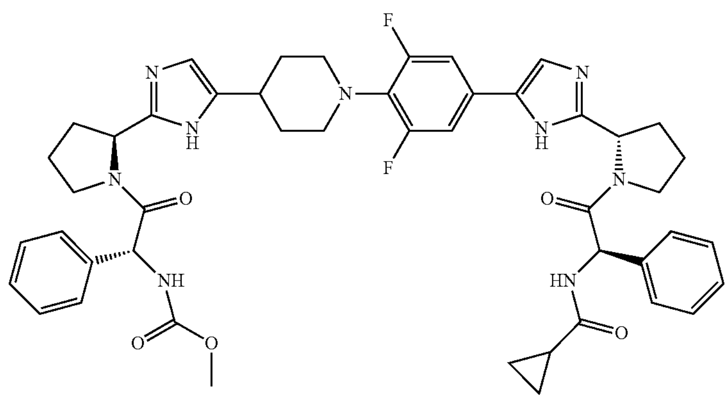 [SMILES: COC(=O)N[C@@H](C(=O)N1CCC[C@H]1c1ncc(C2CCN(c3c(F)cc(-c4cnc([C@@H]5CCCN5C(=O)[C@H](NC(=O)C5CC5)c5ccccc5)[nH]4)cc3F)CC2)[nH]1)c1ccccc1] | **** | 860.4 |
| 481 | 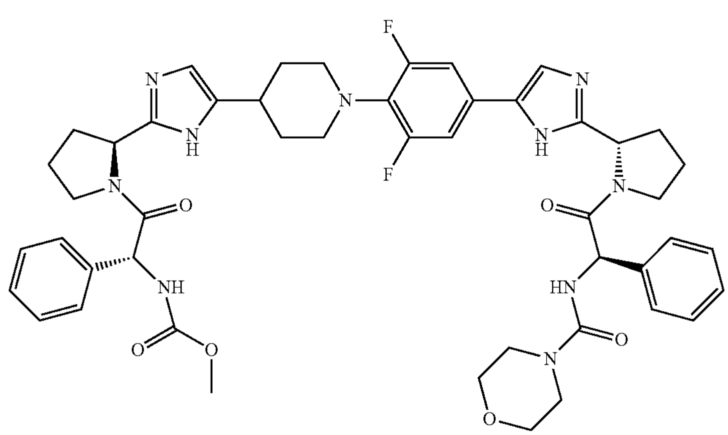 [SMILES: COC(=O)N[C@@H](C(=O)N1CCC[C@H]1c1ncc(C2CCN(c3c(F)cc(-c4cnc([C@@H]5CCCN5C(=O)[C@H](NC(=O)N5CCOCC5)c5ccccc5)[nH]4)cc3F)CC2)[nH]1)c1ccccc1] | **** | 905.4 |

TABLE 3-continued
| Compound # | Structure | Inhibition of HCV genotype 1b | MS (M + H⁺) |
|---|---|---|---|
| 482 | 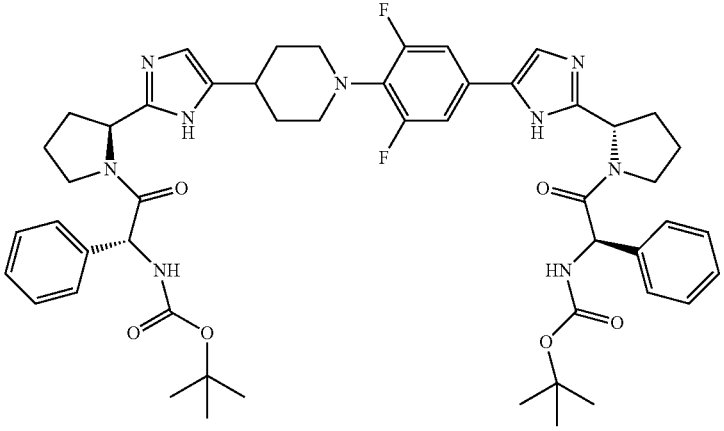 [SMILES: CC(C)(C)OC(=O)N[C@@H](C(=O)N1CCC[C@H]1c1ncc(-c2cc(F)c(N3CCC(c4cnc([C@@H]5CCCN5C(=O)[C@H](NC(=O)OC(C)(C)C)c5ccccc5)[nH]4)CC3)c(F)c2)[nH]1)c1ccccc1] | **** | 934.5 |
| 483 | 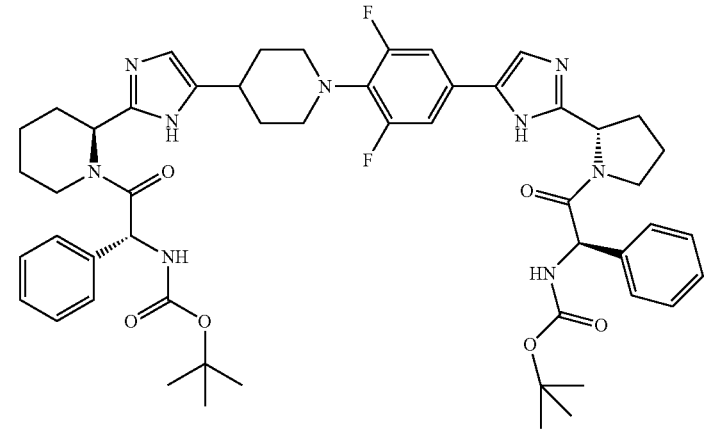 [SMILES: CC(C)(C)OC(=O)N[C@@H](C(=O)N1CCC[C@H]1c1ncc(-c2cc(F)c(N3CCC(c4cnc([C@@H]5CCCCN5C(=O)[C@H](NC(=O)OC(C)(C)C)c5ccccc5)[nH]4)CC3)c(F)c2)[nH]1)c1ccccc1] | **** | 948.5 |
| 484 | 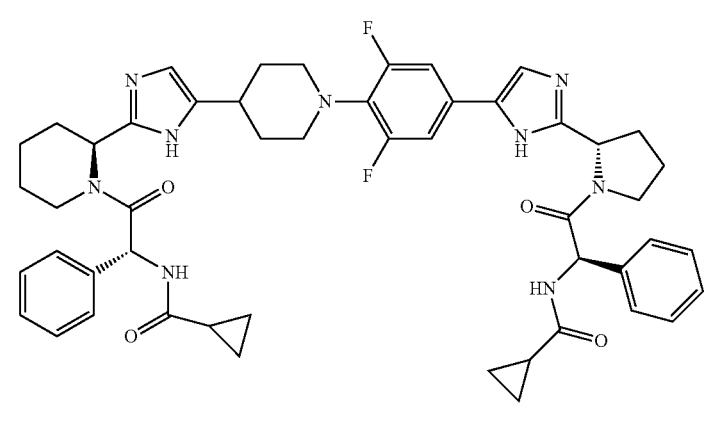 [SMILES: O=C(N[C@@H](C(=O)N1CCC[C@H]1c1ncc(-c2cc(F)c(N3CCC(c4cnc([C@@H]5CCCCN5C(=O)[C@H](NC(=O)C5CC5)c5ccccc5)[nH]4)CC3)c(F)c2)[nH]1)c1ccccc1)C1CC1] | **** | 884.4 |

TABLE 3-continued

| Compound # | Structure | Inhibition of HCV genotype 1b | MS (M + H⁺) |
|---|---|---|---|
| 485 | 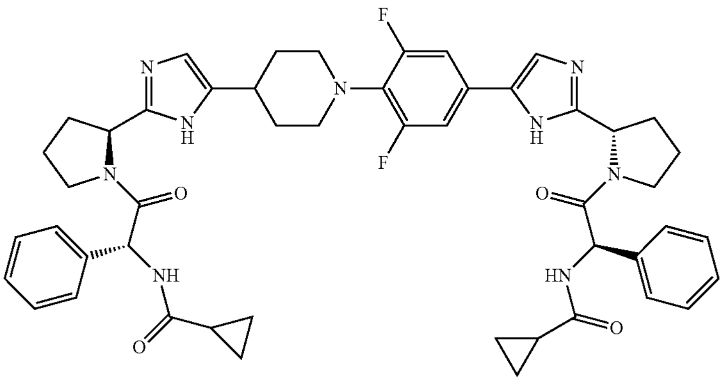 [SMILES: O=C(N[C@@H](C(=O)N1CCC[C@H]1c1ncc(-c2cc(F)c(N3CCC(c4cnc([C@@H]5CCCN5C(=O)[C@H](NC(=O)C5CC5)c5ccccc5)[nH]4)CC3)c(F)c2)[nH]1)c1ccccc1)C1CC1] | **** | 870.4 |
| 486 | 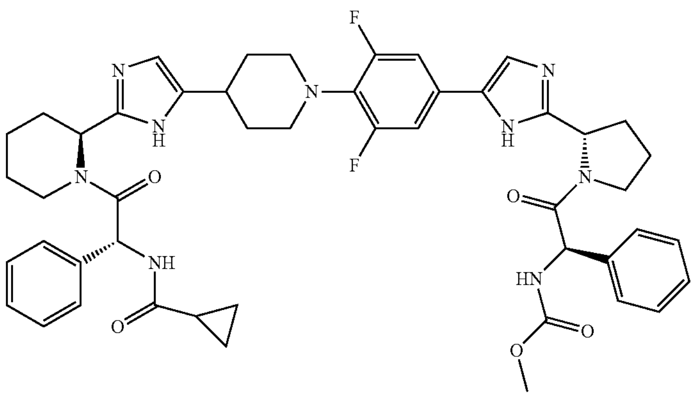 [SMILES: COC(=O)N[C@@H](C(=O)N1CCC[C@H]1c1ncc(-c2cc(F)c(N3CCC(c4cnc([C@@H]5CCCCN5C(=O)[C@H](NC(=O)C5CC5)c5ccccc5)[nH]4)CC3)c(F)c2)[nH]1)c1ccccc1] | **** | 874.4 |
| 487 | 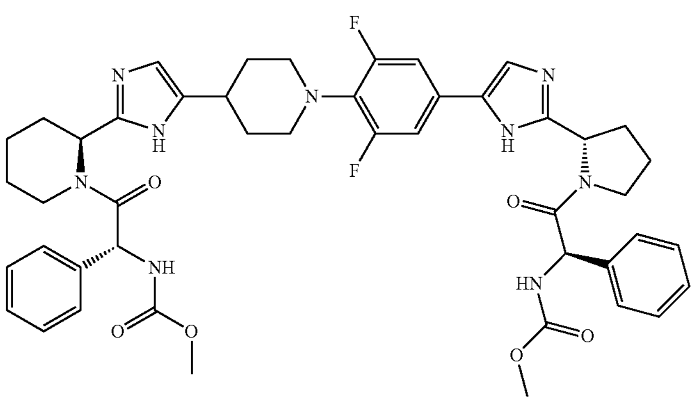 [SMILES: COC(=O)N[C@@H](C(=O)N1CCC[C@H]1c1ncc(-c2cc(F)c(N3CCC(c4cnc([C@@H]5CCCCN5C(=O)[C@H](NC(=O)OC)c5ccccc5)[nH]4)CC3)c(F)c2)[nH]1)c1ccccc1] | **** | 864.4 |
| 488 | 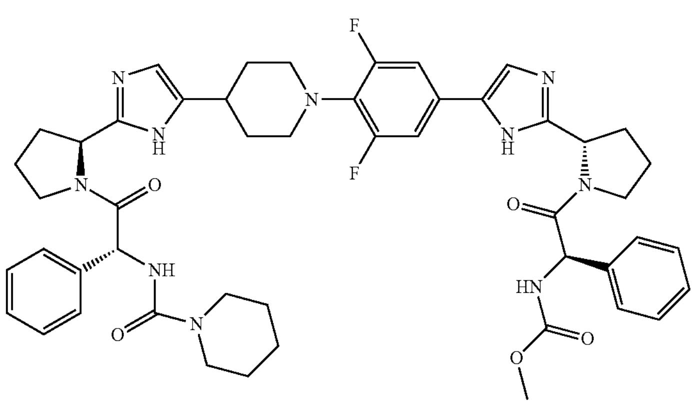 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)N5CCCCC5)c5ccccc5)[nH]4)CC3)c(F)c2)[nH]1)c1ccccc1] | **** | 903.4 |

TABLE 3-continued

| Compound # | Structure | Inhibition of HCV genotype 1b | MS (M + H⁺) |
|---|---|---|---|
| 489 | 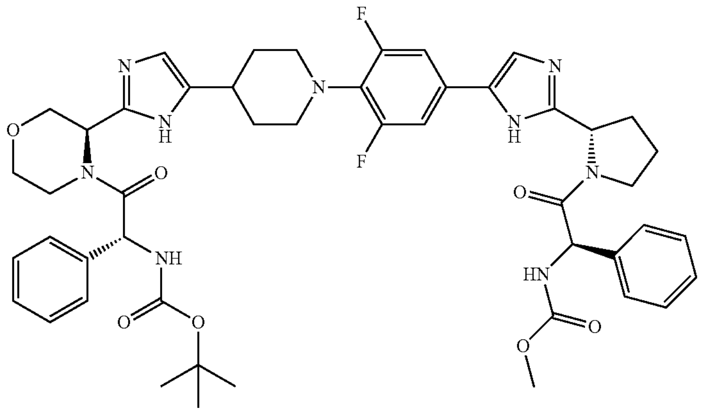 [SMILES: COC(=O)N[C@@H](C(=O)N1CCC[C@H]1c1ncc(-c2cc(F)c(N3CCC(c4cnc([C@@H]5COCCN5C(=O)[C@H](NC(=O)OC(C)(C)C)c5ccccc5)[nH]4)CC3)c(F)c2)[nH]1)c1ccccc1] | **** | 908.4 |
| 490 | 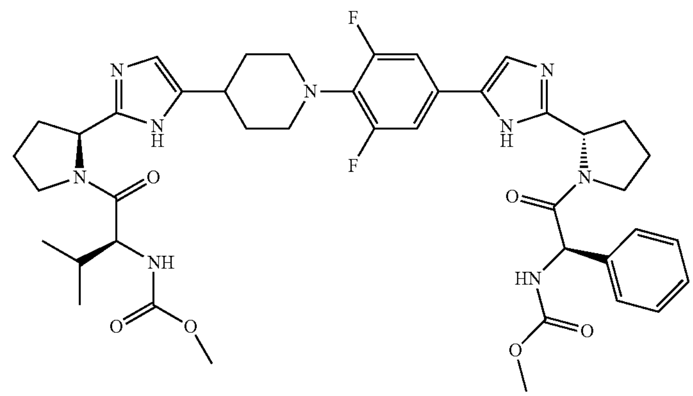 [SMILES: COC(=O)N[C@H](C(=O)N1CCC[C@H]1c1ncc(C2CCN(c3c(F)cc(-c4cnc([C@@H]5CCCN5C(=O)[C@H](NC(=O)OC)c5ccccc5)[nH]4)cc3F)CC2)[nH]1)C(C)C] | **** | 816.4 |
| 491 | 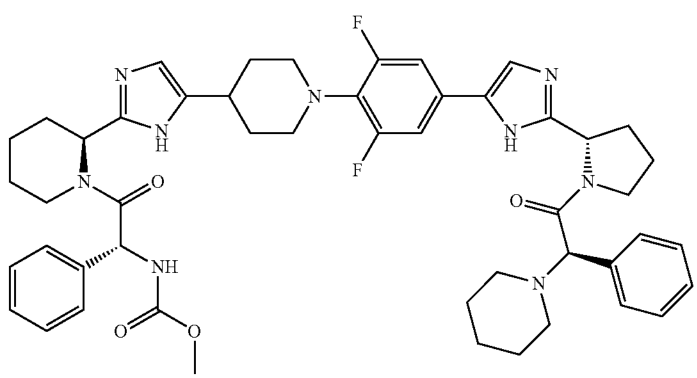 [SMILES: COC(=O)N[C@@H](C(=O)N1CCCC[C@H]1c1ncc(C2CCN(c3c(F)cc(-c4cnc([C@@H]5CCCN5C(=O)[C@@H](c5ccccc5)N5CCCCC5)[nH]4)cc3F)CC2)[nH]1)c1ccccc1] | **** | 874.5 |
| 492 | 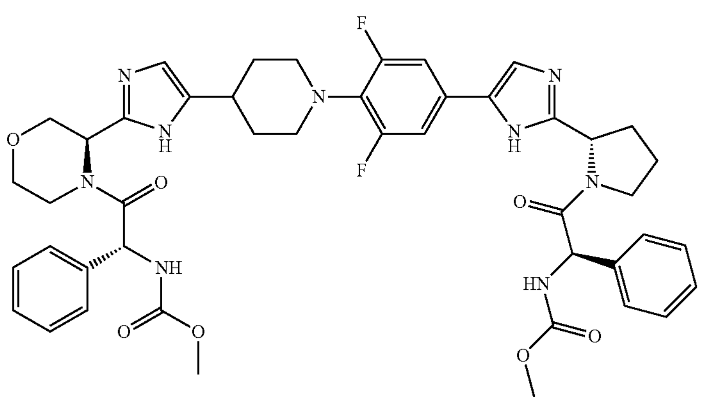 [SMILES: COC(=O)N[C@@H](C(=O)N1CCC[C@H]1c1ncc(-c2cc(F)c(N3CCC(c4cnc([C@@H]5COCCN5C(=O)[C@H](NC(=O)OC)c5ccccc5)[nH]4)CC3)c(F)c2)[nH]1)c1ccccc1] | **** | 866.4 |

TABLE 3-continued

| Compound # | Structure | Inhibition of HCV genotype 1b | MS (M + H+) |
|---|---|---|---|
| 493 | 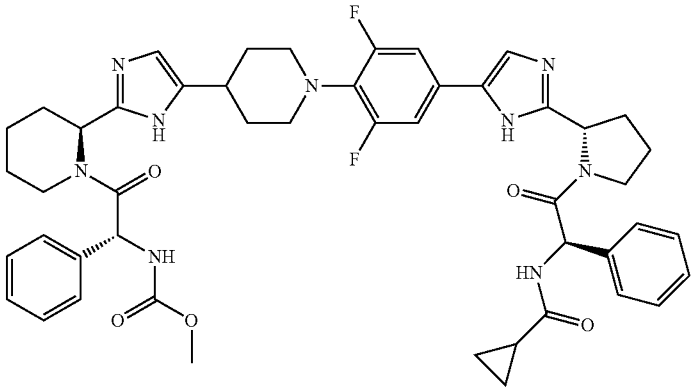 [SMILES: COC(=O)N[C@@H](C(=O)N1CCCC[C@H]1c1ncc(C2CCN(c3c(F)cc(-c4cnc([C@@H]5CCCN5C(=O)[C@H](NC(=O)C5CC5)c5ccccc5)[nH]4)cc3F)CC2)[nH]1)c1ccccc1] | **** | 874.4 |
| 494 | 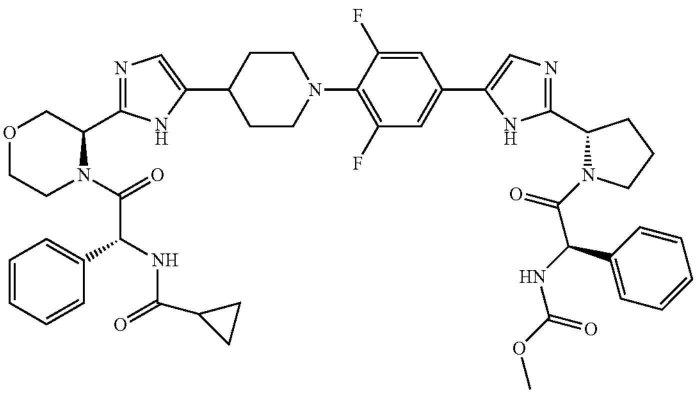 [SMILES: COC(=O)N[C@@H](C(=O)N1CCC[C@H]1c1ncc(-c2cc(F)c(N3CCC(c4cnc([C@@H]5COCCN5C(=O)[C@H](NC(=O)C5CC5)c5ccccc5)[nH]4)CC3)c(F)c2)[nH]1)c1ccccc1] | **** | 876.4 |
| 495 | 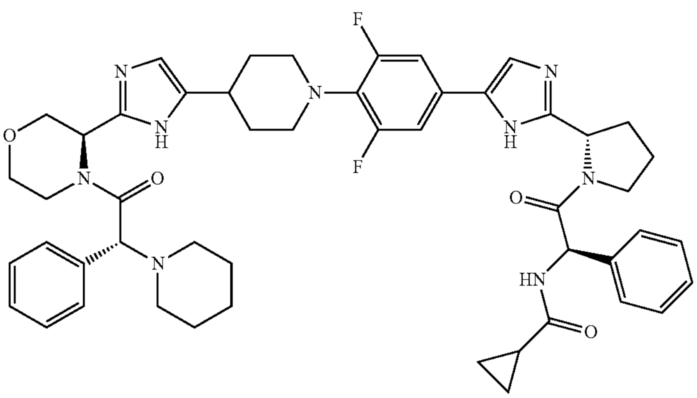 [SMILES: O=C(N[C@@H](C(=O)N1CCC[C@H]1c1ncc(-c2cc(F)c(N3CCC(c4cnc([C@@H]5COCCN5C(=O)[C@@H](c5ccccc5)N5CCCCC5)[nH]4)CC3)c(F)c2)[nH]1)c1ccccc1)C1CC1] | **** | 886.5 |
| 496 | 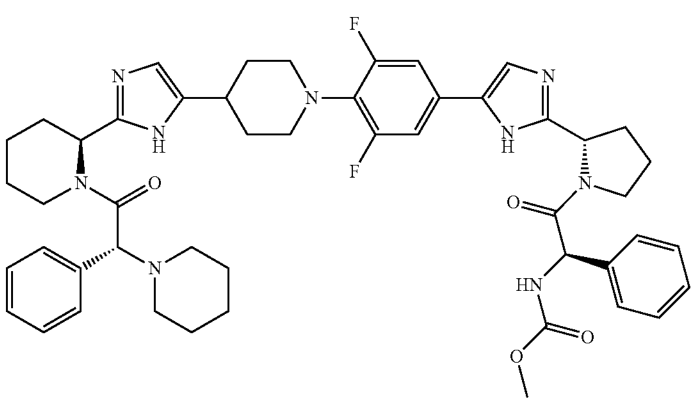 [SMILES: COC(=O)N[C@@H](C(=O)N1CCC[C@H]1c1ncc(-c2cc(F)c(N3CCC(c4cnc([C@@H]5CCCCN5C(=O)[C@@H](c5ccccc5)N5CCCCC5)[nH]4)CC3)c(F)c2)[nH]1)c1ccccc1] | **** | 874.5 |

TABLE 3-continued

| Compound # | Structure | Inhibition of HCV genotype 1b | MS (M + H⁺) |
|---|---|---|---|
| 497 | 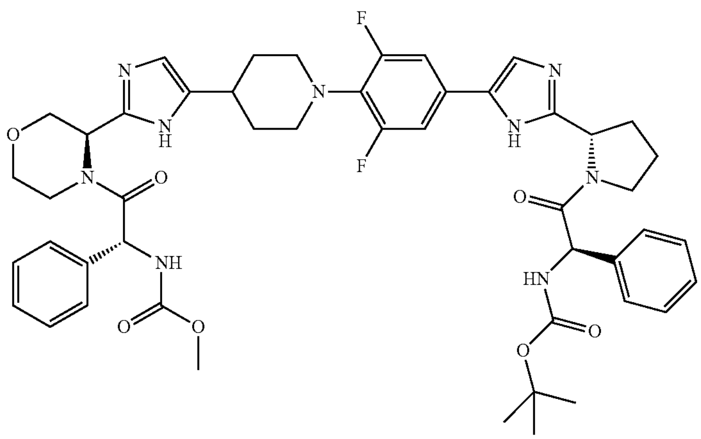 [SMILES: COC(=O)N[C@@H](C(=O)N1CCOC[C@H]1c1ncc(C2CCN(c3c(F)cc(-c4cnc([C@@H]5CCCN5C(=O)[C@H](NC(=O)OC(C)(C)C)c5ccccc5)[nH]4)cc3F)CC2)[nH]1)c1ccccc1] | **** | 908.4 |
| 498 | 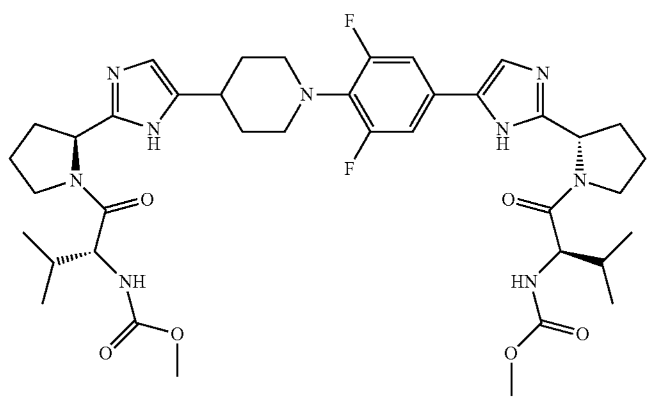 [SMILES: COC(=O)N[C@@H](C(=O)N1CCC[C@H]1c1ncc(-c2cc(F)c(N3CCC(c4cnc([C@@H]5CCCN5C(=O)[C@H](NC(=O)OC)C(C)C)[nH]4)CC3)c(F)c2)[nH]1)C(C)C] | *** | 782.4 |
| 499 | 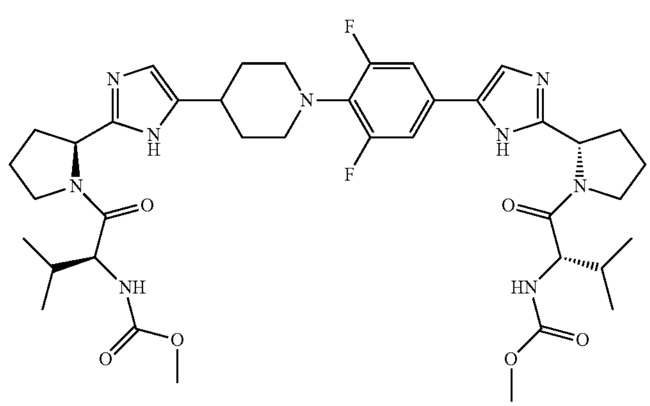 [SMILES: COC(=O)N[C@H](C(=O)N1CCC[C@H]1c1ncc(-c2cc(F)c(N3CCC(c4cnc([C@@H]5CCCN5C(=O)[C@@H](NC(=O)OC)C(C)C)[nH]4)CC3)c(F)c2)[nH]1)C(C)C] | **** | 782.4 |

TABLE 3-continued

| Compound # | Structure | Inhibition of HCV genotype 1b | MS (M + H⁺) |
|---|---|---|---|
| 500 | 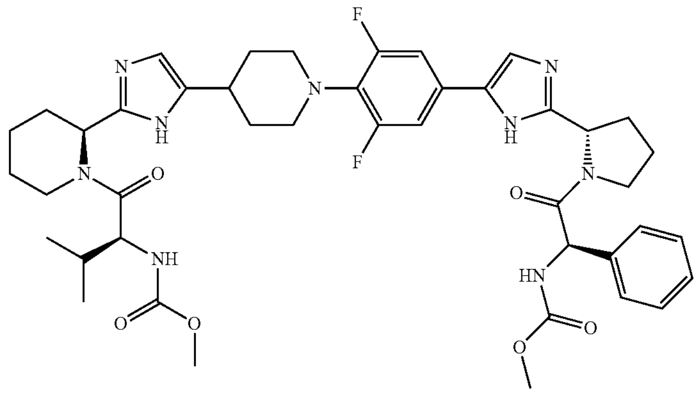 [SMILES: COC(=O)N[C@H](C(=O)N1CCCC[C@H]1c1ncc(C2CCN(c3c(F)cc(-c4cnc([C@@H]5CCCN5C(=O)[C@H](NC(=O)OC)c5ccccc5)[nH]4)cc3F)CC2)[nH]1)C(C)C] | **** | 830.4 |
| 501 | 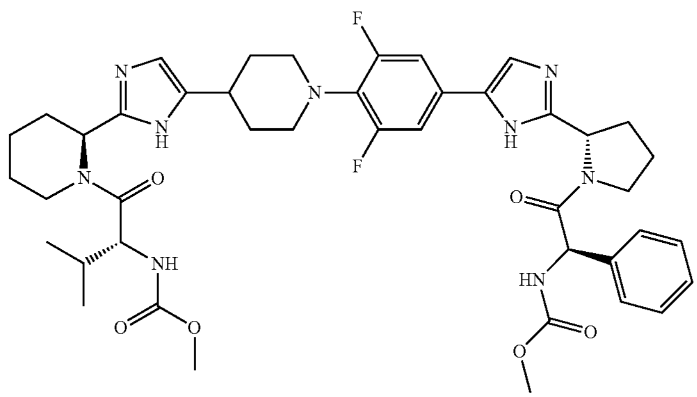 [SMILES: COC(=O)N[C@@H](C(=O)N1CCC[C@H]1c1ncc(-c2cc(F)c(N3CCC(c4cnc([C@@H]5CCCCN5C(=O)[C@H](NC(=O)OC)C(C)C)[nH]4)CC3)c(F)c2)[nH]1)c1ccccc1] | **** | 830.4 |
| 502 | 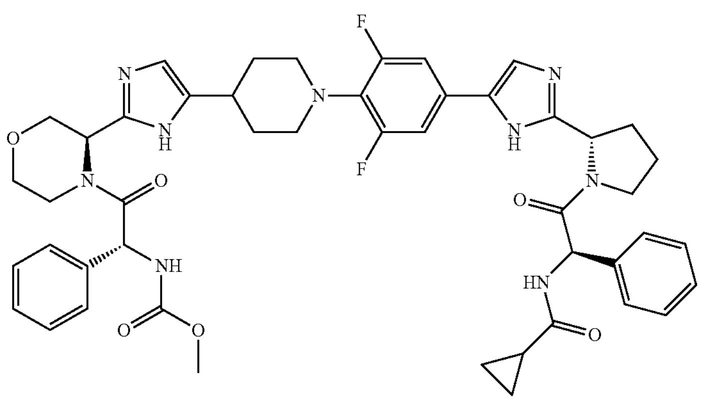 [SMILES: COC(=O)N[C@@H](C(=O)N1CCOC[C@H]1c1ncc(C2CCN(c3c(F)cc(-c4cnc([C@@H]5CCCN5C(=O)[C@H](NC(=O)C5CC5)c5ccccc5)[nH]4)cc3F)CC2)[nH]1)c1ccccc1] | **** | 876.4 |
| 503 | 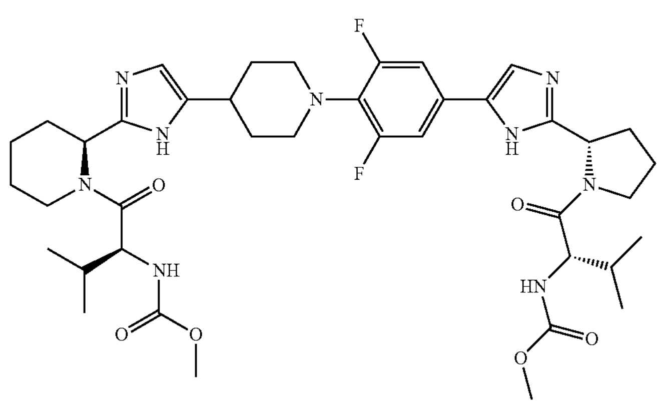 [SMILES: COC(=O)N[C@H](C(=O)N1CCC[C@H]1c1ncc(-c2cc(F)c(N3CCC(c4cnc([C@@H]5CCCCN5C(=O)[C@@H](NC(=O)OC)C(C)C)[nH]4)CC3)c(F)c2)[nH]1)C(C)C] | **** | 796.4 |

TABLE 3-continued

| Compound # | Structure | Inhibition of HCV genotype 1b | MS (M + H⁺) |
|---|---|---|---|
| 504 | 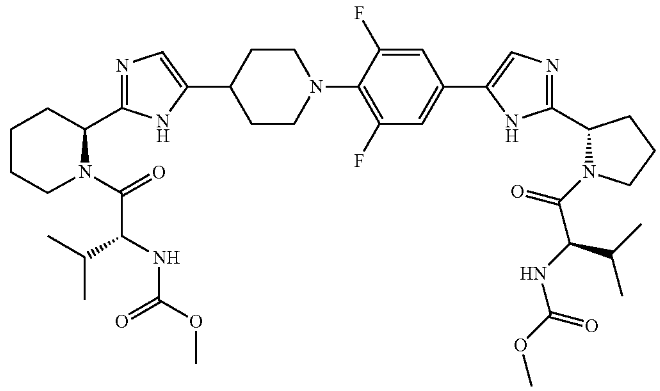 [SMILES: COC(=O)N[C@@H](C(=O)N1CCC[C@H]1c1ncc(-c2cc(F)c(N3CCC(c4cnc([C@@H]5CCCCN5C(=O)[C@H](NC(=O)OC)C(C)C)[nH]4)CC3)c(F)c2)[nH]1)C(C)C] | * | 796.4 |
| 505 | 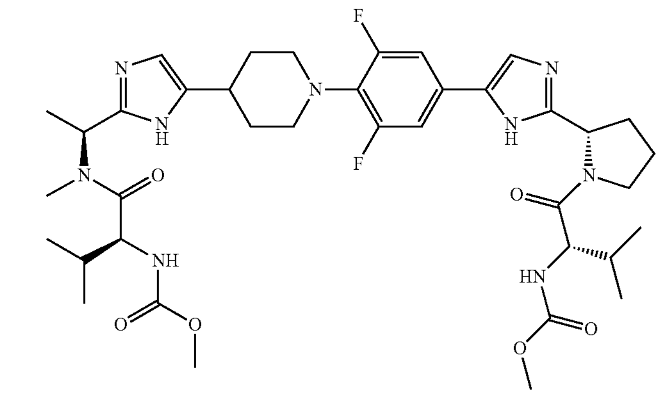 [SMILES: COC(=O)N[C@H](C(=O)N(C)[C@@H](C)c1ncc(C2CCN(c3c(F)cc(-c4cnc([C@@H]5CCCN5C(=O)[C@@H](NC(=O)OC)C(C)C)[nH]4)cc3F)CC2)[nH]1)C(C)C] | **** | 770.4 |
| 506 | 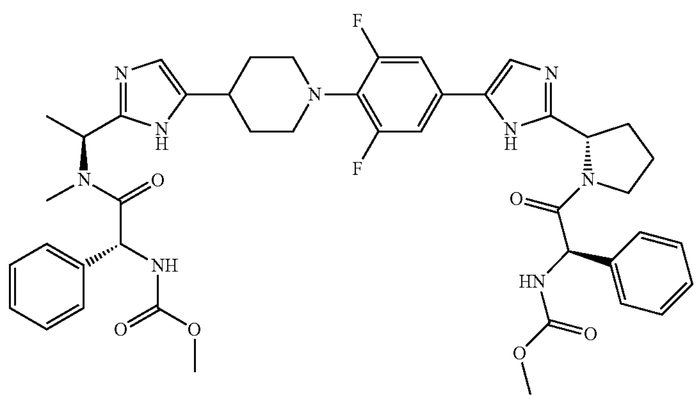 [SMILES: COC(=O)N[C@@H](C(=O)N(C)[C@@H](C)c1ncc(C2CCN(c3c(F)cc(-c4cnc([C@@H]5CCCN5C(=O)[C@H](NC(=O)OC)c5ccccc5)[nH]4)cc3F)CC2)[nH]1)c1ccccc1] | **** | 838.4 |
| 507 | 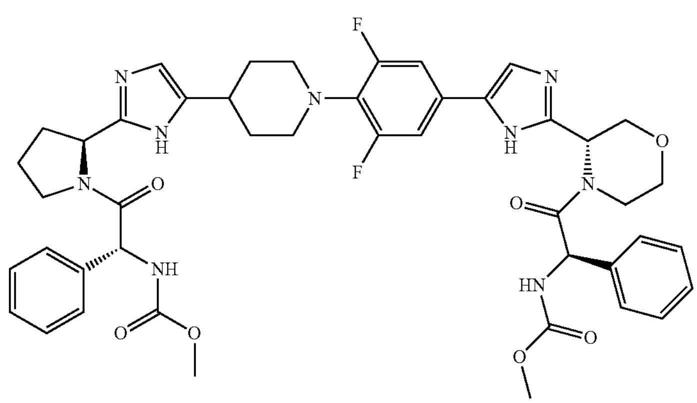 [SMILES: COC(=O)N[C@@H](C(=O)N1CCOC[C@H]1c1ncc(-c2cc(F)c(N3CCC(c4cnc([C@@H]5CCCN5C(=O)[C@H](NC(=O)OC)c5ccccc5)[nH]4)CC3)c(F)c2)[nH]1)c1ccccc1] | **** | 866.4 |

TABLE 3-continued
| Compound # | Structure | Inhibition of HCV genotype 1b | MS (M + H+) |
| --- | --- | --- | --- |
| 508 | 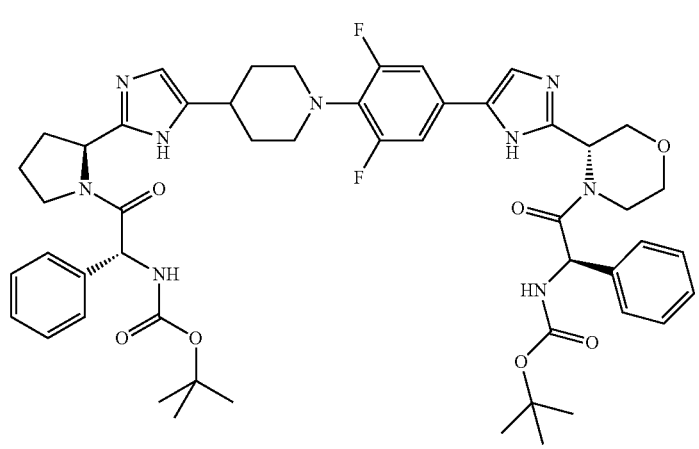 [SMILES: CC(C)(C)OC(=O)N[C@@H](C(=O)N1CCOC[C@H]1c1ncc(-c2cc(F)c(N3CCC(c4cnc([C@@H]5CCCN5C(=O)[C@H](NC(=O)OC(C)(C)C)c5ccccc5)[nH]4)CC3)c(F)c2)[nH]1)c1ccccc1] | **** | 950.5 |
| 509 | 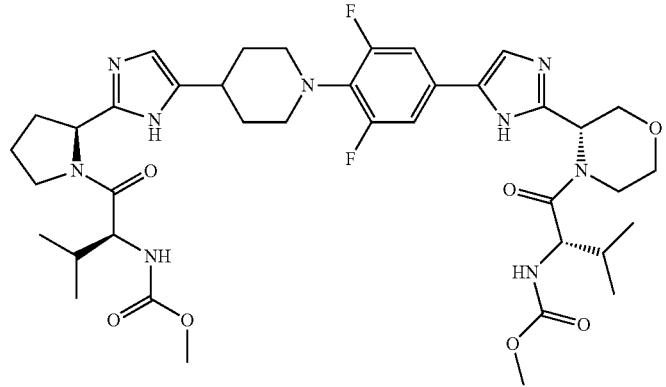 [SMILES: COC(=O)N[C@H](C(=O)N1CCOC[C@H]1c1ncc(-c2cc(F)c(N3CCC(c4cnc([C@@H]5CCCN5C(=O)[C@@H](NC(=O)OC)C(C)C)[nH]4)CC3)c(F)c2)[nH]1)C(C)C] | **** | 798.4 |
| 510 | 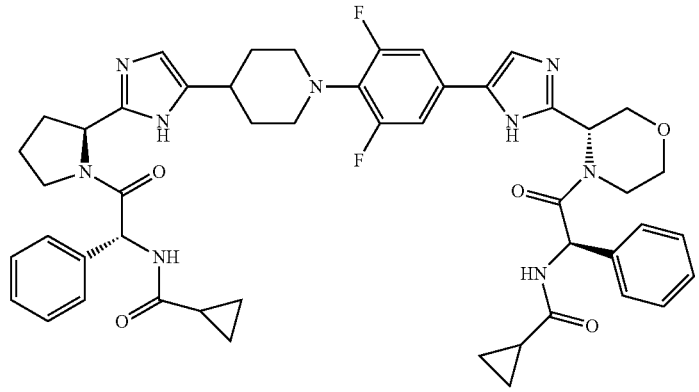 [SMILES: O=C(N[C@@H](C(=O)N1CCOC[C@H]1c1ncc(-c2cc(F)c(N3CCC(c4cnc([C@@H]5CCCN5C(=O)[C@H](NC(=O)C5CC5)c5ccccc5)[nH]4)CC3)c(F)c2)[nH]1)c1ccccc1)C1CC1] | **** | 886.4 |

TABLE 3-continued

| Compound # | Structure | Inhibition of HCV genotype 1b | MS (M + H⁺) |
|---|---|---|---|
| 511 | 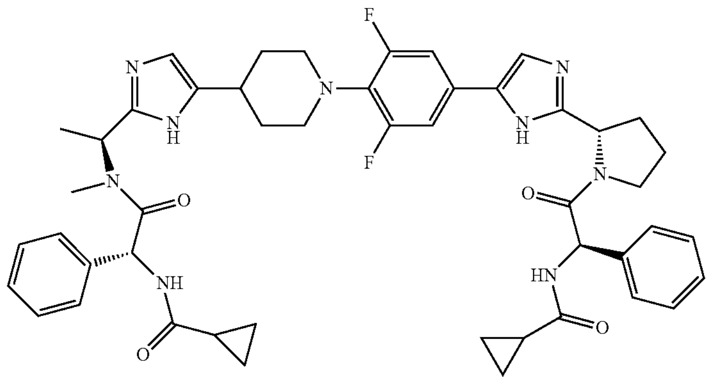 [SMILES: C[C@@H](c1ncc(C2CCN(c3c(F)cc(-c4cnc([C@@H]5CCCN5C(=O)[C@H](NC(=O)C5CC5)c5ccccc5)[nH]4)cc3F)CC2)[nH]1)N(C)C(=O)[C@H](NC(=O)C1CC1)c1ccccc1] | **** | 858.4 |
| 512 | 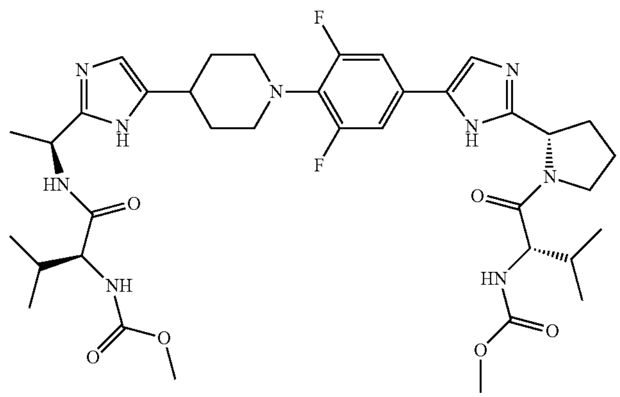 [SMILES: COC(=O)N[C@H](C(=O)N[C@@H](C)c1ncc(C2CCN(c3c(F)cc(-c4cnc([C@@H]5CCCN5C(=O)[C@@H](NC(=O)OC)C(C)C)[nH]4)cc3F)CC2)[nH]1)C(C)C] | **** | 756.4 |
| 513 | 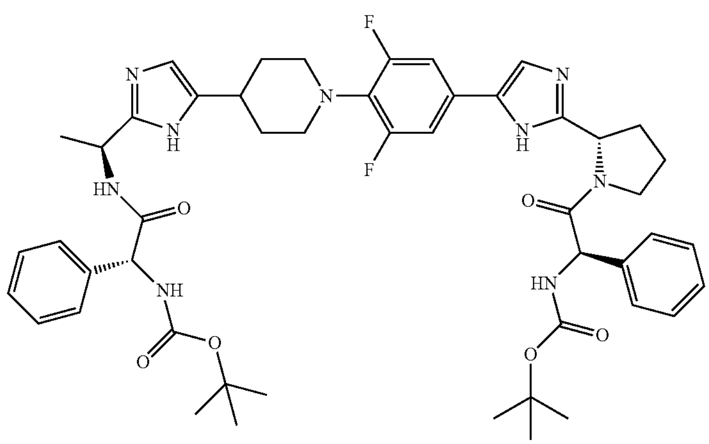 [SMILES: C[C@H](NC(=O)[C@H](NC(=O)OC(C)(C)C)c1ccccc1)c1ncc(C2CCN(c3c(F)cc(-c4cnc([C@@H]5CCCN5C(=O)[C@H](NC(=O)OC(C)(C)C)c5ccccc5)[nH]4)cc3F)CC2)[nH]1] | **** | 908.5 |
| 514 | 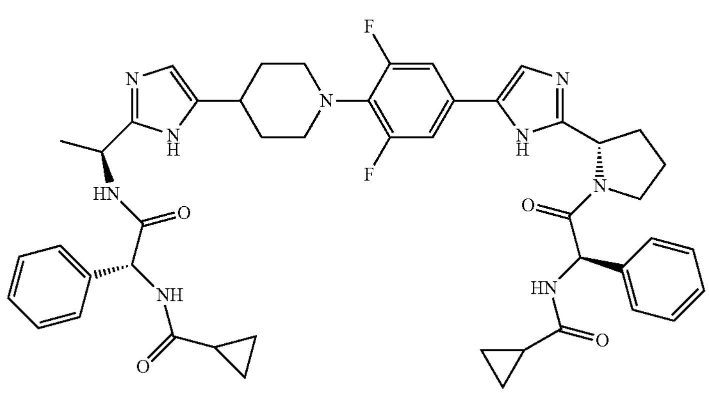 [SMILES: C[C@H](NC(=O)[C@H](NC(=O)C1CC1)c1ccccc1)c1ncc(C2CCN(c3c(F)cc(-c4cnc([C@@H]5CCCN5C(=O)[C@H](NC(=O)C5CC5)c5ccccc5)[nH]4)cc3F)CC2)[nH]1] | **** | 844.4 |

TABLE 3-continued

| Compound # | Structure | Inhibition of HCV genotype 1b | MS (M + H⁺) |
|---|---|---|---|
| 515 | 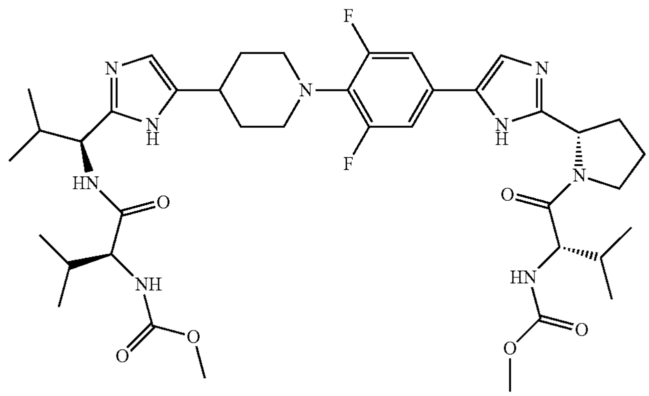 [SMILES: COC(=O)N[C@H](C(=O)N[C@H](c1ncc(C2CCN(c3c(F)cc(-c4cnc([C@@H]5CCCN5C(=O)[C@@H](NC(=O)OC)C(C)C)[nH]4)cc3F)CC2)[nH]1)C(C)C)C(C)C] | **** | 784.4 |
| 516 | 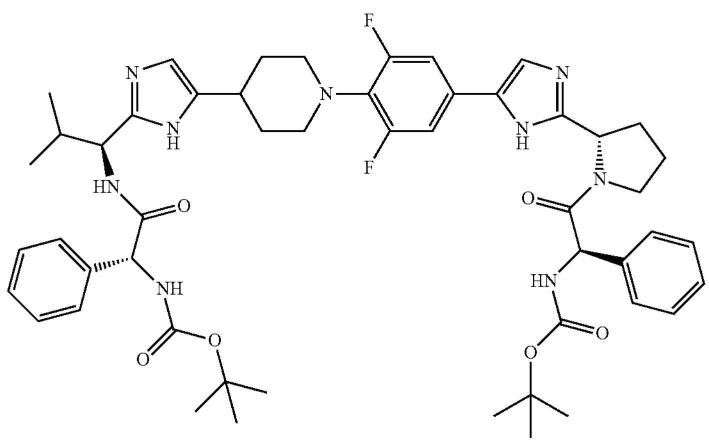 [SMILES: CC(C)[C@H](NC(=O)[C@H](NC(=O)OC(C)(C)C)c1ccccc1)c1ncc(C2CCN(c3c(F)cc(-c4cnc([C@@H]5CCCN5C(=O)[C@H](NC(=O)OC(C)(C)C)c5ccccc5)[nH]4)cc3F)CC2)[nH]1] | **** | 935.5 |
| 517 | 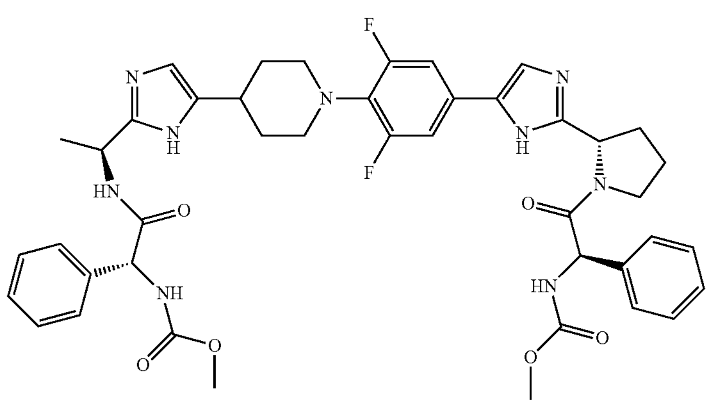 [SMILES: COC(=O)N[C@@H](C(=O)N[C@@H](C)c1ncc(C2CCN(c3c(F)cc(-c4cnc([C@@H]5CCCN5C(=O)[C@H](NC(=O)OC)c5ccccc5)[nH]4)cc3F)CC2)[nH]1)c1ccccc1] | **** | 824.4 |

TABLE 3-continued

| Compound # | Structure | Inhibition of HCV genotype 1b | MS (M + H⁺) |
|---|---|---|---|
| 518 | 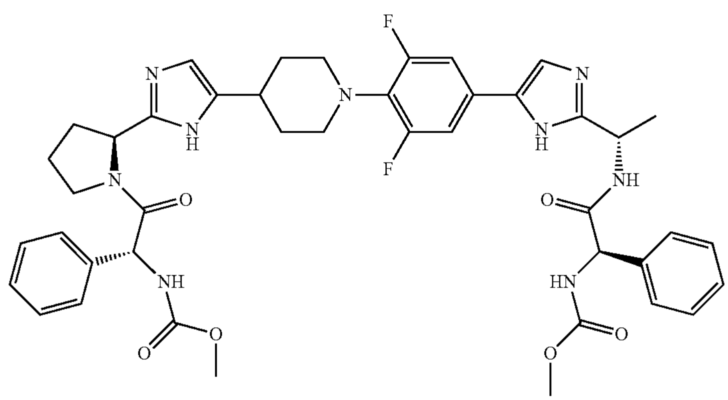 [SMILES: COC(=O)N[C@@H](C(=O)N[C@@H](C)c1ncc(-c2cc(F)c(N3CCC(c4cnc([C@@H]5CCCN5C(=O)[C@H](NC(=O)OC)c5ccccc5)[nH]4)CC3)c(F)c2)[nH]1)c1ccccc1] | **** | 824.4 |
| 519 | 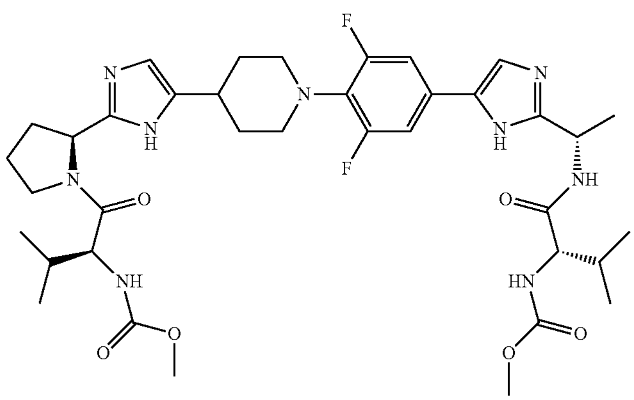 [SMILES: COC(=O)N[C@H](C(=O)N[C@@H](C)c1ncc(-c2cc(F)c(N3CCC(c4cnc([C@@H]5CCCN5C(=O)[C@@H](NC(=O)OC)C(C)C)[nH]4)CC3)c(F)c2)[nH]1)C(C)C] | **** | 756.4 |
| 520 | 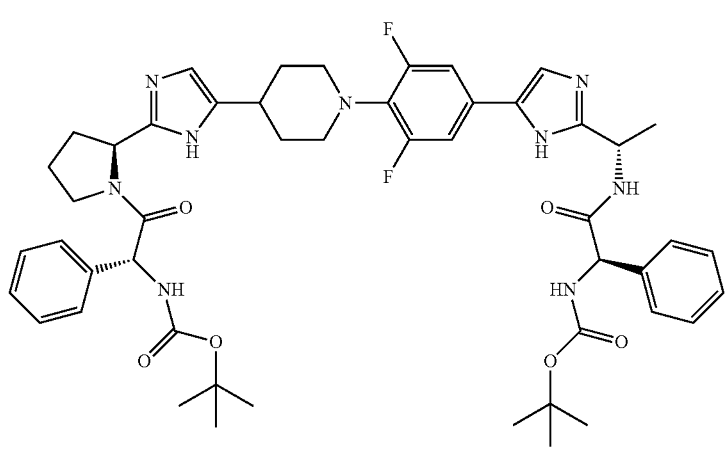 [SMILES: C[C@H](NC(=O)[C@H](NC(=O)OC(C)(C)C)c1ccccc1)c1ncc(-c2cc(F)c(N3CCC(c4cnc([C@@H]5CCCN5C(=O)[C@H](NC(=O)OC(C)(C)C)c5ccccc5)[nH]4)CC3)c(F)c2)[nH]1] | **** | 908.5 |

TABLE 3-continued
| Compound # | Structure | Inhibition of HCV genotype 1b | MS (M + H+) |
|---|---|---|---|
| 2027 | 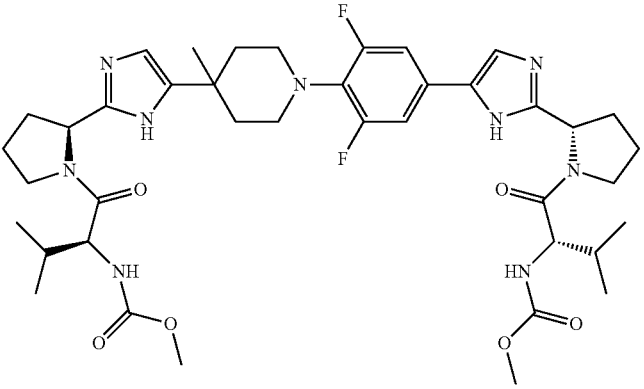 [SMILES: COC(=O)N[C@H](C(=O)N1CCC[C@H]1c1ncc(-c2cc(F)c(N3CCC(C)(c4cnc([C@@H]5CCCN5C(=O)[C@@H](NC(=O)OC)C(C)C)[nH]4)CC3)c(F)c2)[nH]1)C(C)C] | **** | 769.4 |
| 2028 | 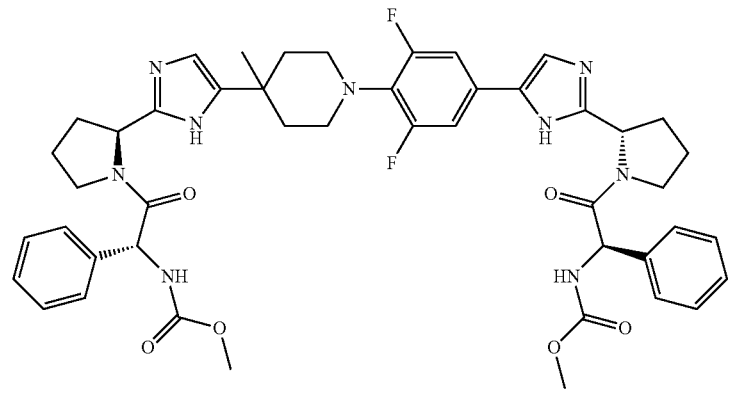 [SMILES: COC(=O)N[C@@H](C(=O)N1CCC[C@H]1c1ncc(-c2cc(F)c(N3CCC(C)(c4cnc([C@@H]5CCCN5C(=O)[C@H](NC(=O)OC)c5ccccc5)[nH]4)CC3)c(F)c2)[nH]1)c1ccccc1] | **** | 864.4 |
| 2029 | 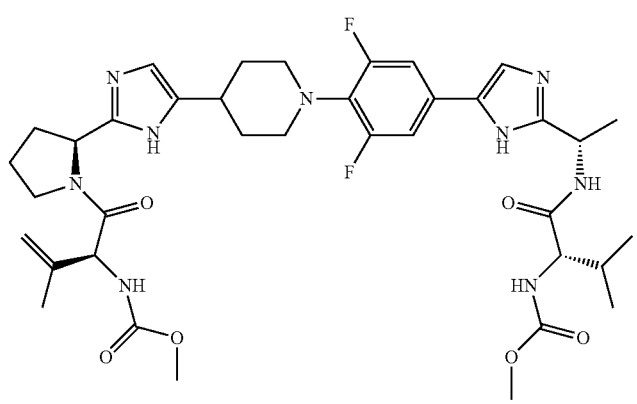 | | |
| 2030 | 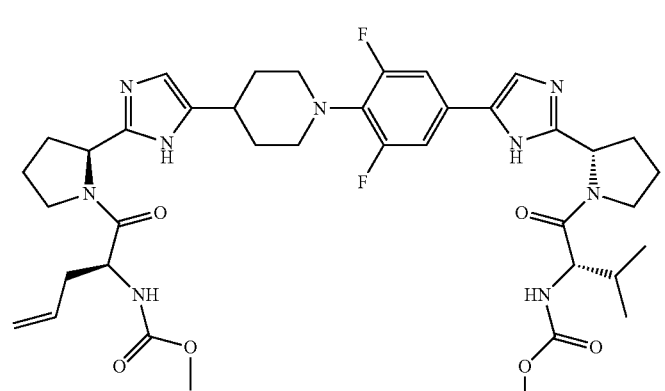 | | |

TABLE 3-continued

| Compound # | Structure | Inhibition of HCV genotype 1b | MS (M + H+) |
|---|---|---|---|
| 2031 | 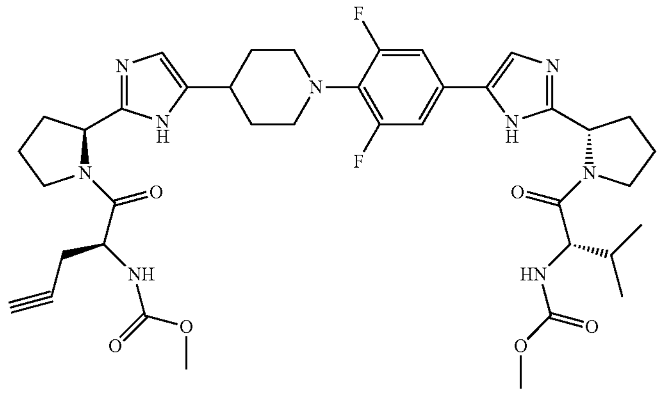 [SMILES: C#CC[C@H](NC(=O)OC)C(=O)N1CCC[C@H]1c1ncc(C2CCN(c3c(F)cc(-c4cnc([C@@H]5CCCN5C(=O)[C@@H](NC(=O)OC)C(C)C)[nH]4)cc3F)CC2)[nH]1] | | |
| 2032 | 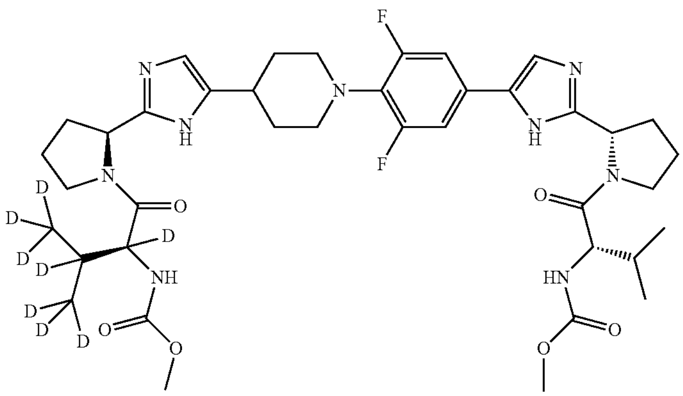 [SMILES: [2H]C([2H])([2H])C([2H])(C([2H])([2H])[2H])[C@@]([2H])(NC(=O)OC)C(=O)N1CCC[C@H]1c1ncc(C2CCN(c3c(F)cc(-c4cnc([C@@H]5CCCN5C(=O)[C@@H](NC(=O)OC)C(C)C)[nH]4)cc3F)CC2)[nH]1] | | |
| 2033 | 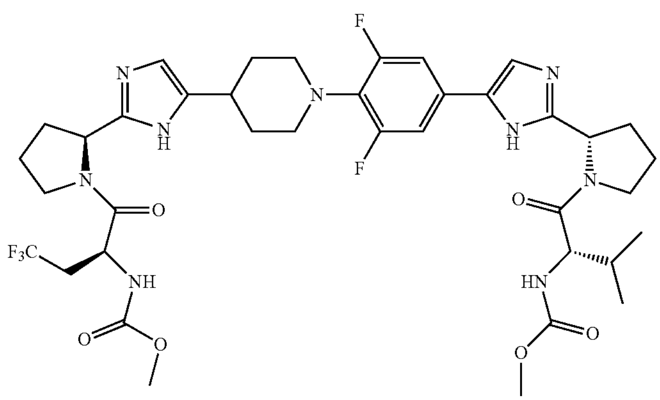 [SMILES: COC(=O)N[C@@H](CC(F)(F)F)C(=O)N1CCC[C@H]1c1ncc(C2CCN(c3c(F)cc(-c4cnc([C@@H]5CCCN5C(=O)[C@@H](NC(=O)OC)C(C)C)[nH]4)cc3F)CC2)[nH]1] | | |
| 2034 | 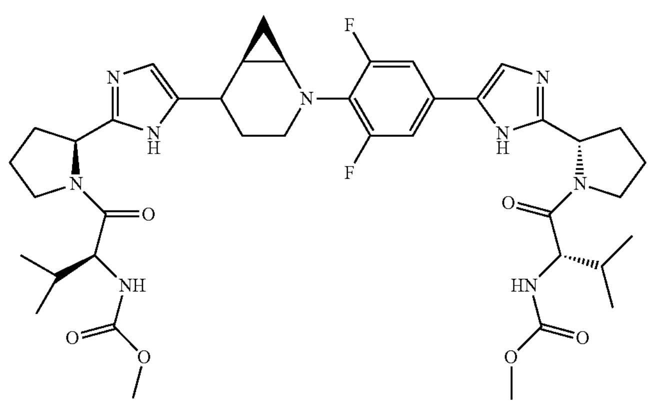 [SMILES: COC(=O)N[C@H](C(=O)N1CCC[C@H]1c1ncc(-c2cc(F)c(N3CCC(c4cnc([C@@H]5CCCN5C(=O)[C@@H](NC(=O)OC)C(C)C)[nH]4)[C@H]4C[C@H]43)c(F)c2)[nH]1)C(C)C] | | |

TABLE 4

| Compound # | Structure | Inhibition of HCV genotype 1b | MS (M + H+) |
| --- | --- | --- | --- |
| 550 | 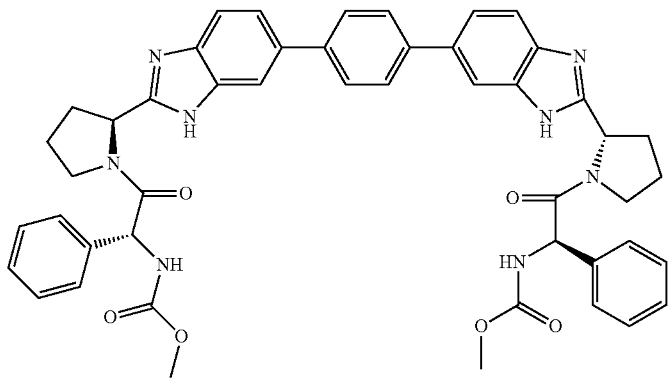 [SMILES: COC(=O)N[C@@H](C(=O)N1CCC[C@H]1c1nc2ccc(-c3ccc(-c4ccc5nc([C@@H]6CCCN6C(=O)[C@H](NC(=O)OC)c6ccccc6)[nH]c5c4)cc3)cc2[nH]1)c1ccccc1] | **** | 831.4 |
| 551 | 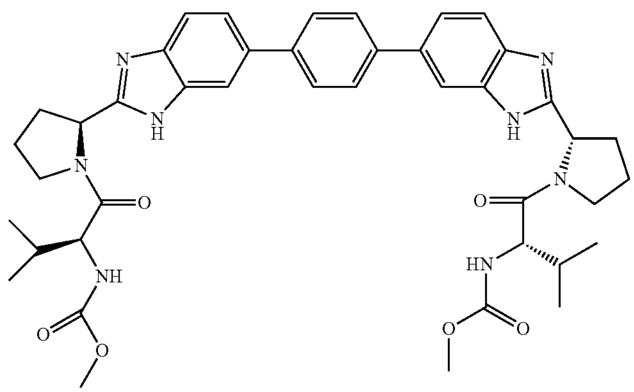 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)cc3)cc2[nH]1)C(C)C] | **** | 763.4 |
| 552 | 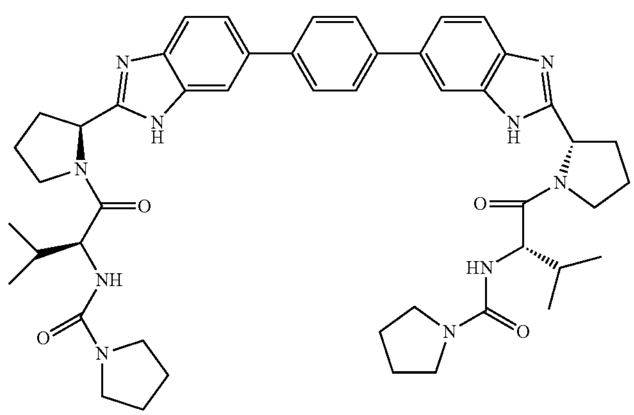 [SMILES: CC(C)[C@H](NC(=O)N1CCCC1)C(=O)N1CCC[C@H]1c1nc2ccc(-c3ccc(-c4ccc5nc([C@@H]6CCCN6C(=O)[C@@H](NC(=O)N6CCCC6)C(C)C)[nH]c5c4)cc3)cc2[nH]1] | * | 841.5 |

TABLE 4-continued

| Compound # | Structure | Inhibition of HCV genotype 1b | MS (M + H+) |
|---|---|---|---|
| 553 | 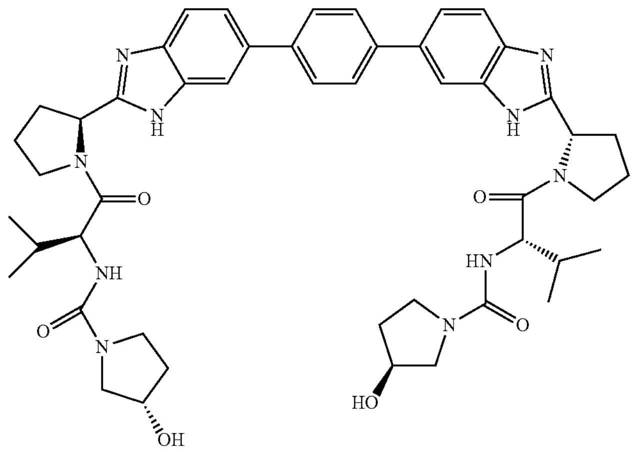 [SMILES: CC(C)[C@H](NC(=O)N1CC[C@H](O)C1)C(=O)N1CCC[C@H]1c1nc2ccc(-c3ccc(-c4ccc5nc([C@@H]6CCCN6C(=O)[C@@H](NC(=O)N6CC[C@H](O)C6)C(C)C)[nH]c5c4)cc3)cc2[nH]1] | * | 873.5 |
| 554 | 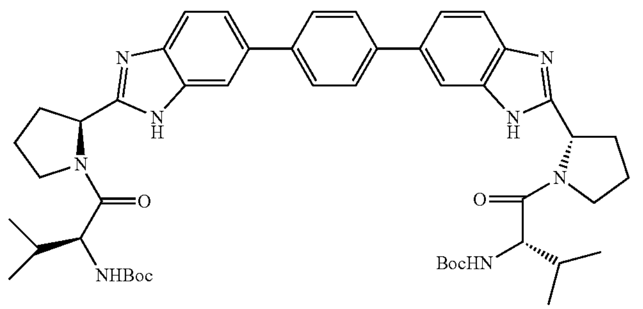 [SMILES: CC(C)[C@H](NC(=O)OC(C)(C)C)C(=O)N1CCC[C@H]1c1nc2ccc(-c3ccc(-c4ccc5nc([C@@H]6CCCN6C(=O)[C@@H](NC(=O)OC(C)(C)C)C(C)C)[nH]c5c4)cc3)cc2[nH]1] | * | 847.5 |
| 555 | 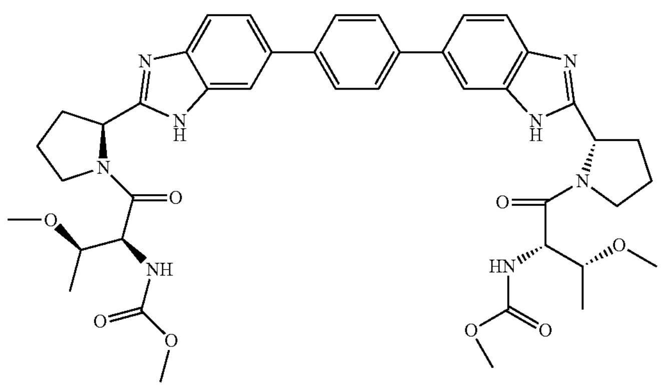 | **** | 795.4 |
| 556 | 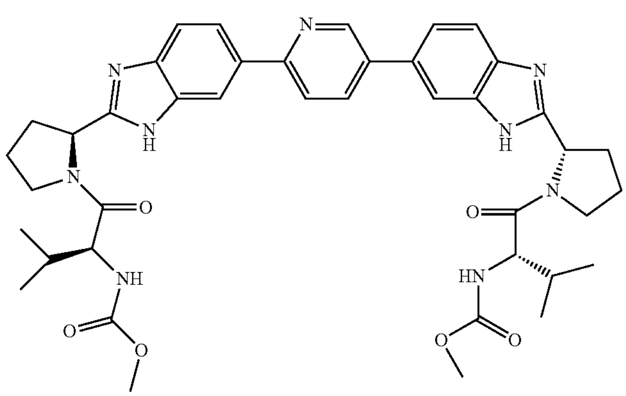 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)nc3)cc2[nH]1)C(C)C] | **** | 764.4 |

TABLE 4-continued

| Compound # | Structure | Inhibition of HCV genotype 1b | MS (M + H⁺) |
|---|---|---|---|
| 2035 | 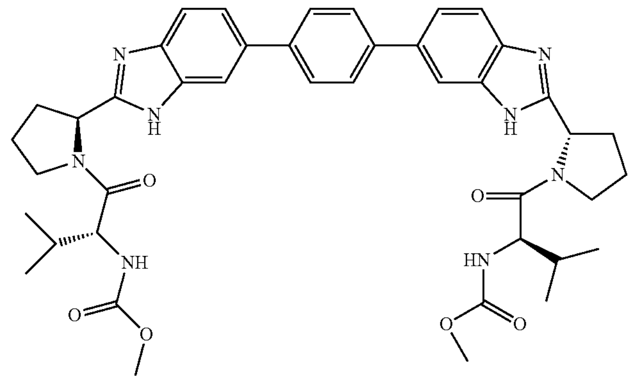 [SMILES: COC(=O)N[C@@H](C(=O)N1CCC[C@H]1c1nc2ccc(-c3ccc(-c4ccc5nc([C@@H]6CCCN6C(=O)[C@H](NC(=O)OC)C(C)C)[nH]c5c4)cc3)cc2[nH]1)C(C)C] | ** | 763.4 |
| 557 | 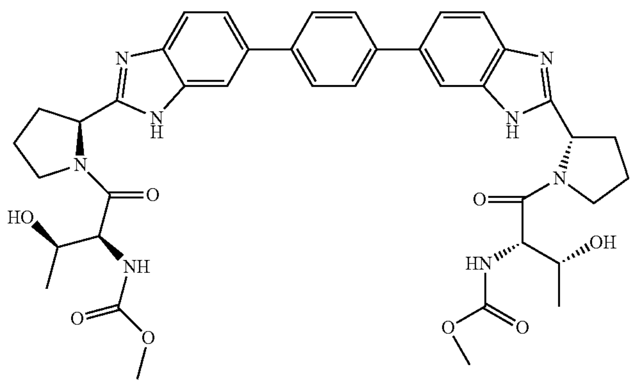 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)[C@@H](C)O)[nH]c5c4)cc3)cc2[nH]1)[C@@H](C)O] | **** | 767.3 |
| 930 | 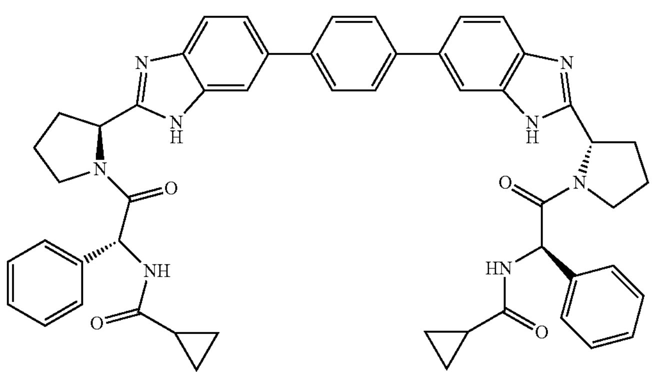 [SMILES: O=C(N[C@@H](C(=O)N1CCC[C@H]1c1nc2ccc(-c3ccc(-c4ccc5nc([C@@H]6CCCN6C(=O)[C@H](NC(=O)C6CC6)c6ccccc6)[nH]c5c4)cc3)cc2[nH]1)c1ccccc1)C1CC1] | **** | 851.4 |
| 931 | 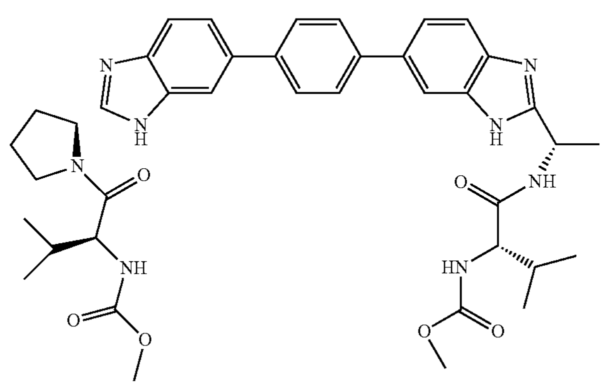 | **** | 737.4 |

TABLE 4-continued

| Compound # | Structure | Inhibition of HCV genotype 1b | MS (M + H+) |
|---|---|---|---|
| 932 | 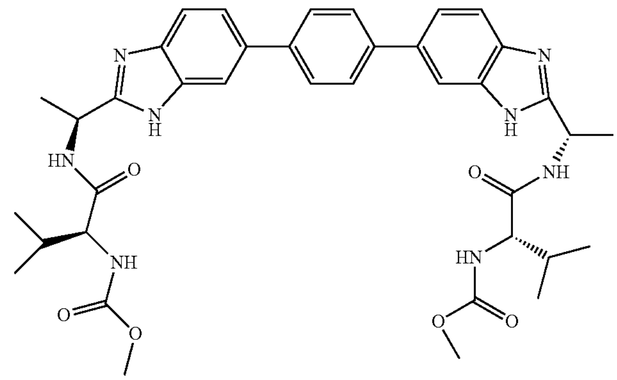 [SMILES: COC(=O)N[C@H](C(=O)N[C@@H](C)c1nc2ccc(-c3ccc(-c4ccc5nc([C@H](C)NC(=O)[C@@H](NC(=O)OC)C(C)C)[nH]c5c4)cc3)cc2[nH]1)C(C)C] | **** | 711.4 |
| 933 | 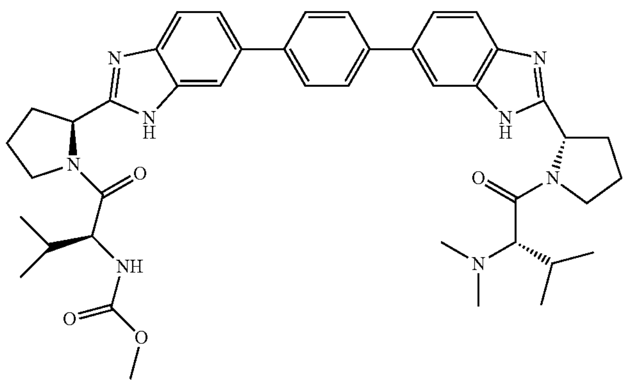 [SMILES: COC(=O)N[C@H](C(=O)N1CCC[C@H]1c1nc2ccc(-c3ccc(-c4ccc5nc([C@@H]6CCCN6C(=O)[C@H](C(C)C)N(C)C)[nH]c5c4)cc3)cc2[nH]1)C(C)C] | **** | 733.4 |
| 934 | 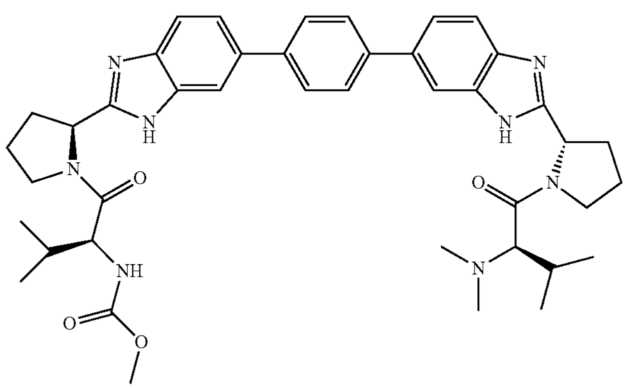 [SMILES: COC(=O)N[C@H](C(=O)N1CCC[C@H]1c1nc2ccc(-c3ccc(-c4ccc5nc([C@@H]6CCCN6C(=O)[C@@H](C(C)C)N(C)C)[nH]c5c4)cc3)cc2[nH]1)C(C)C] | **** | 733.4 |
| 935 | 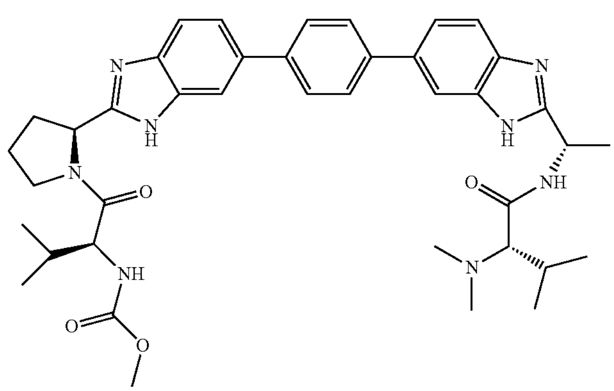 [SMILES: COC(=O)N[C@H](C(=O)N1CCC[C@H]1c1nc2ccc(-c3ccc(-c4ccc5nc([C@H](C)NC(=O)[C@H](C(C)C)N(C)C)[nH]c5c4)cc3)cc2[nH]1)C(C)C] | **** | 707.4 |

TABLE 4-continued

| Compound # | Structure | Inhibition of HCV genotype 1b | MS (M + H+) |
|---|---|---|---|
| 936 | 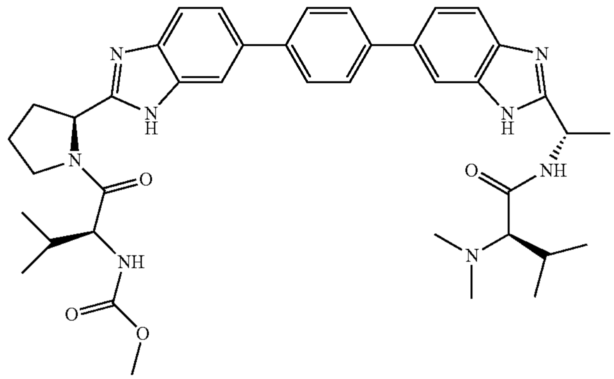 [SMILES: COC(=O)N[C@H](C(=O)N1CCC[C@H]1c1nc2ccc(-c3ccc(-c4ccc5nc([C@H](C)NC(=O)[C@@H](C(C)C)N(C)C)[nH]c5c4)cc3)cc2[nH]1)C(C)C] | **** | 707.4 |
| 937 | 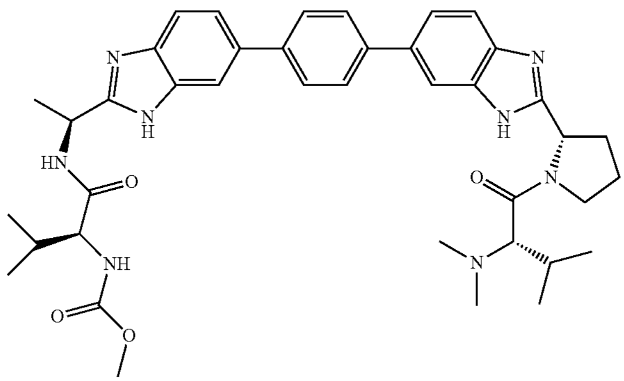 [SMILES: COC(=O)N[C@H](C(=O)N[C@@H](C)c1nc2ccc(-c3ccc(-c4ccc5nc([C@@H]6CCCN6C(=O)[C@H](C(C)C)N(C)C)[nH]c5c4)cc3)cc2[nH]1)C(C)C] | *** | 707.4 |
| 938 | 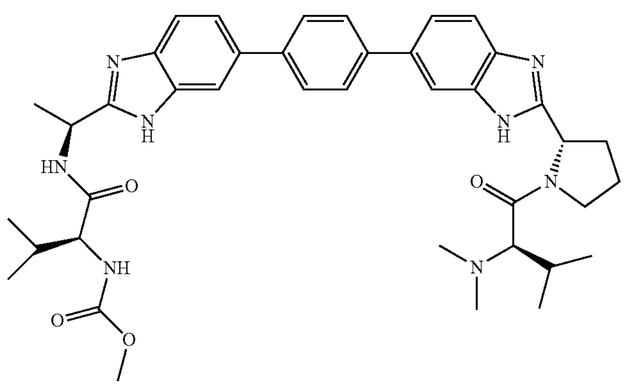 [SMILES: COC(=O)N[C@H](C(=O)N[C@@H](C)c1nc2ccc(-c3ccc(-c4ccc5nc([C@@H]6CCCN6C(=O)[C@@H](C(C)C)N(C)C)[nH]c5c4)cc3)cc2[nH]1)C(C)C] | **** | 707.4 |
| 939 | 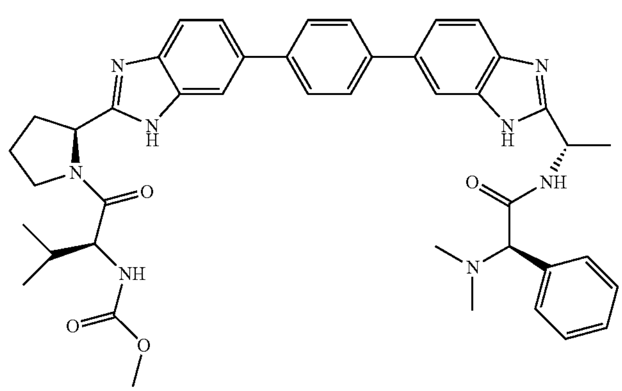 [SMILES: COC(=O)N[C@H](C(=O)N1CCC[C@H]1c1nc2ccc(-c3ccc(-c4ccc5nc([C@H](C)NC(=O)[C@@H](c6ccccc6)N(C)C)[nH]c5c4)cc3)cc2[nH]1)C(C)C] | **** | 741.4 |

TABLE 4-continued

| Compound # | Structure | Inhibition of HCV genotype 1b | MS (M + H⁺) |
|---|---|---|---|
| 2036 | 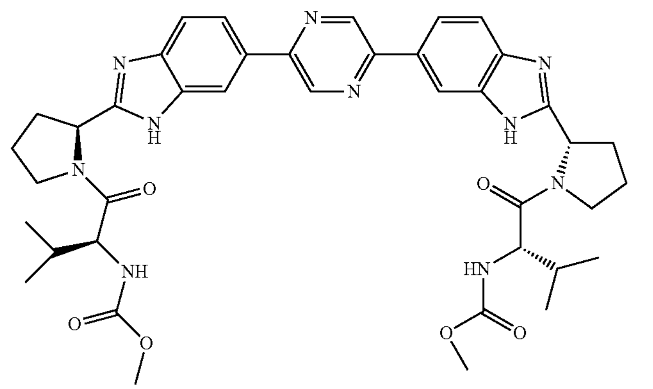 [SMILES: COC(=O)N[C@H](C(=O)N1CCC[C@H]1c1nc2ccc(-c3cnc(-c4ccc5nc([C@@H]6CCCN6C(=O)[C@@H](NC(=O)OC)C(C)C)[nH]c5c4)cn3)cc2[nH]1)C(C)C] | **** | 765.4 |
| 2037 | 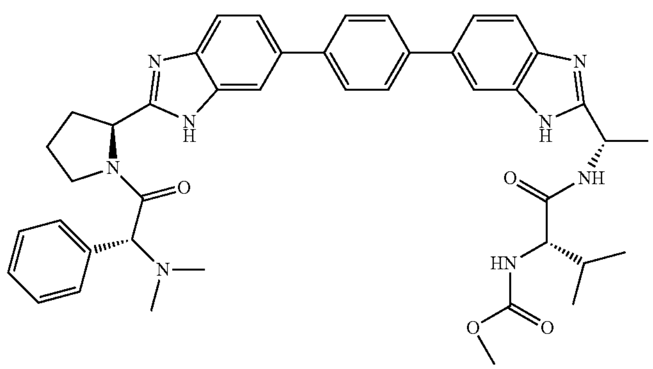 [SMILES: COC(=O)N[C@H](C(=O)N[C@@H](C)c1nc2ccc(-c3ccc(-c4ccc5nc([C@@H]6CCCN6C(=O)[C@@H](c6ccccc6)N(C)C)[nH]c5c4)cc3)cc2[nH]1)C(C)C] | **** | 741.4 |
| 2038 | 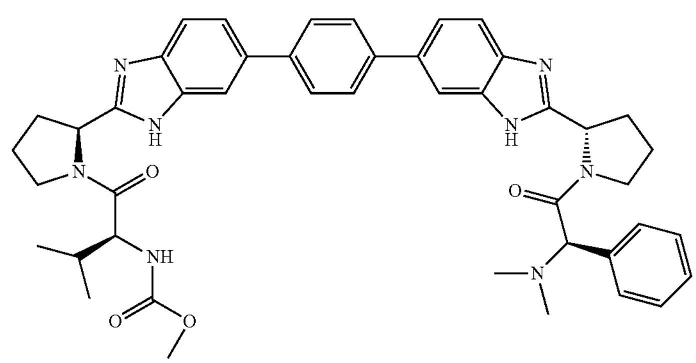 [SMILES: COC(=O)N[C@H](C(=O)N1CCC[C@H]1c1nc2ccc(-c3ccc(-c4ccc5nc([C@@H]6CCCN6C(=O)[C@@H](c6ccccc6)N(C)C)[nH]c5c4)cc3)cc2[nH]1)C(C)C] | **** | 767.4 |
| 2039 | 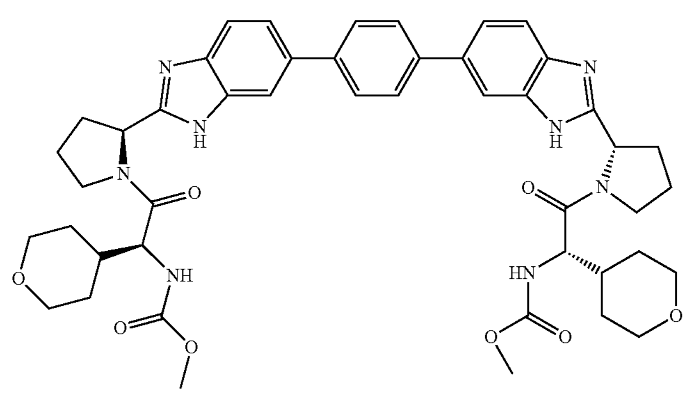 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C6CCOCC6)[nH]c5c4)cc3)cc2[nH]1)C1CCOCC1] | **** | 847.4 |

TABLE 4-continued

| Compound # | Structure | Inhibition of HCV genotype 1b | MS (M + H+) |
|---|---|---|---|
| 2040 | 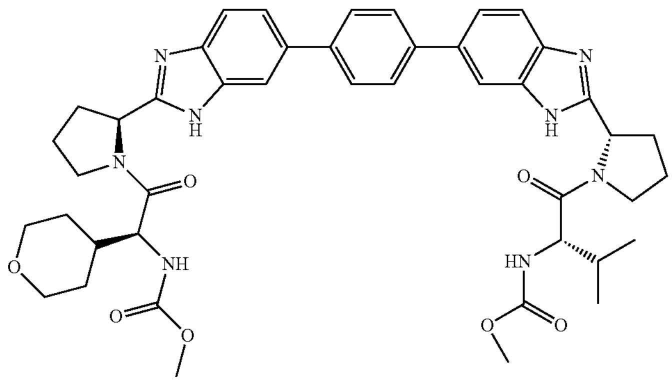 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C6CCOCC6)[nH]c5c4)cc3)cc2[nH]1)C(C)C] | **** | 805.4 |
| 2041 | 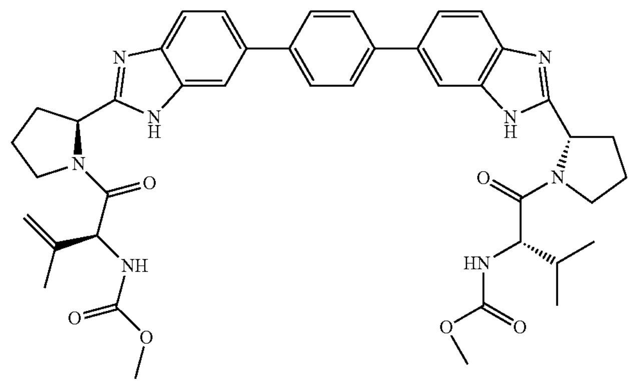 [SMILES: C=C(C)[C@H](NC(=O)OC)C(=O)N1CCC[C@H]1c1nc2ccc(-c3ccc(-c4ccc5nc([C@@H]6CCCN6C(=O)[C@@H](NC(=O)OC)C(C)C)[nH]c5c4)cc3)cc2[nH]1] | | |
| 2042 | 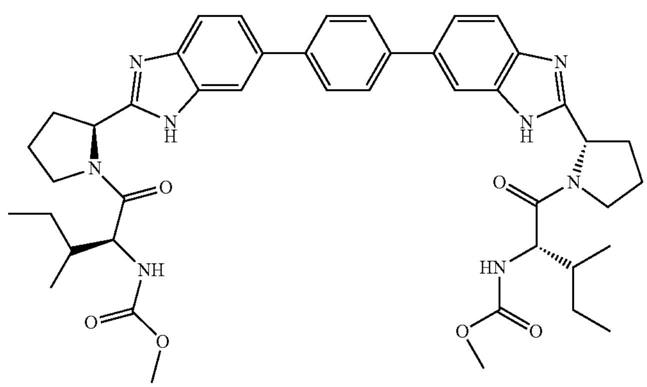 [SMILES: CCC(C)[C@H](NC(=O)OC)C(=O)N1CCC[C@H]1c1nc2ccc(-c3ccc(-c4ccc5nc([C@@H]6CCCN6C(=O)[C@@H](NC(=O)OC)C(C)CC)[nH]c5c4)cc3)cc2[nH]1] | | |
| 2043 | 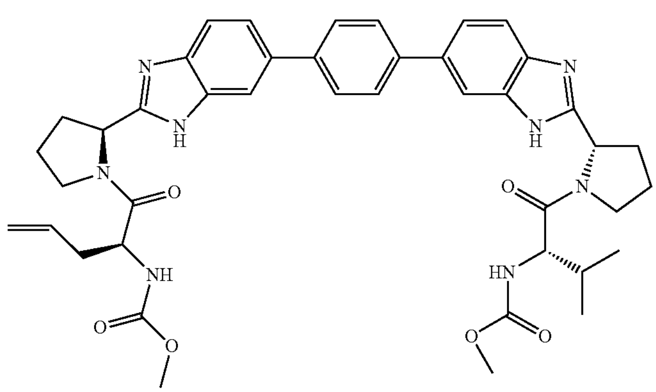 [SMILES: C=CC[C@H](NC(=O)OC)C(=O)N1CCC[C@H]1c1nc2ccc(-c3ccc(-c4ccc5nc([C@@H]6CCCN6C(=O)[C@@H](NC(=O)OC)C(C)C)[nH]c5c4)cc3)cc2[nH]1] | | |

TABLE 4-continued

| Compound # | Structure | Inhibition of HCV genotype 1b | MS (M + H+) |
|---|---|---|---|
| 2044 | 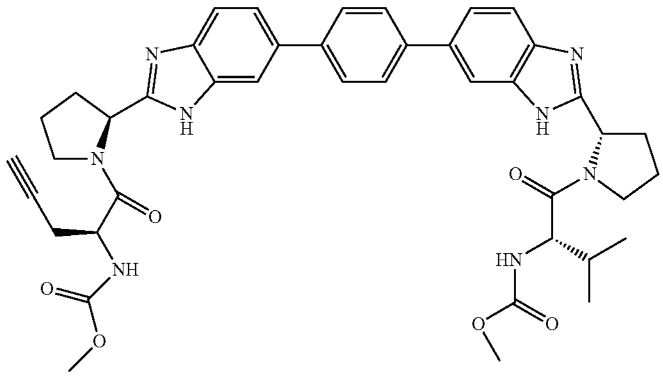 [SMILES: C#CC[C@H](NC(=O)OC)C(=O)N1CCC[C@H]1c1nc2ccc(-c3ccc(-c4ccc5nc([C@@H]6CCCN6C(=O)[C@@H](NC(=O)OC)C(C)C)[nH]c5c4)cc3)cc2[nH]1] | | |
| 2045 | 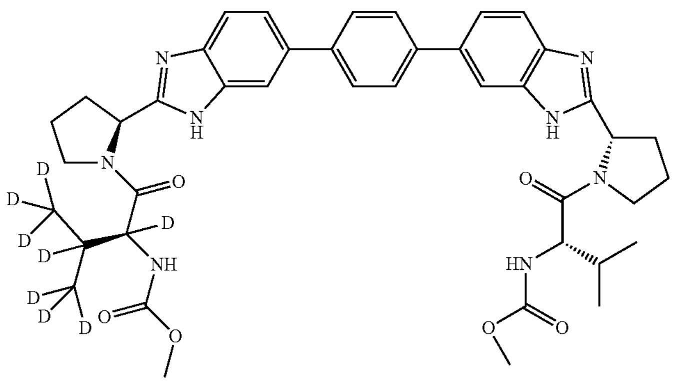 [SMILES: [2H]C([2H])([2H])C([2H])(C([2H])([2H])[2H])[C@@]([2H])(NC(=O)OC)C(=O)N1CCC[C@H]1c1nc2ccc(-c3ccc(-c4ccc5nc([C@@H]6CCCN6C(=O)[C@@H](NC(=O)OC)C(C)C)[nH]c5c4)cc3)cc2[nH]1] | | |
| 2046 | 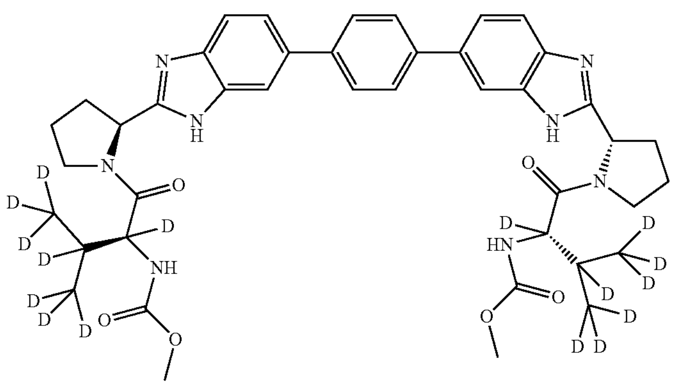 [SMILES: [2H]C([2H])([2H])C([2H])(C([2H])([2H])[2H])[C@@]([2H])(NC(=O)OC)C(=O)N1CCC[C@H]1c1nc2ccc(-c3ccc(-c4ccc5nc([C@@H]6CCCN6C(=O)[C@]([2H])(NC(=O)OC)C([2H])(C([2H])([2H])[2H])C([2H])([2H])[2H])[nH]c5c4)cc3)cc2[nH]1] | | |
| 2047 | 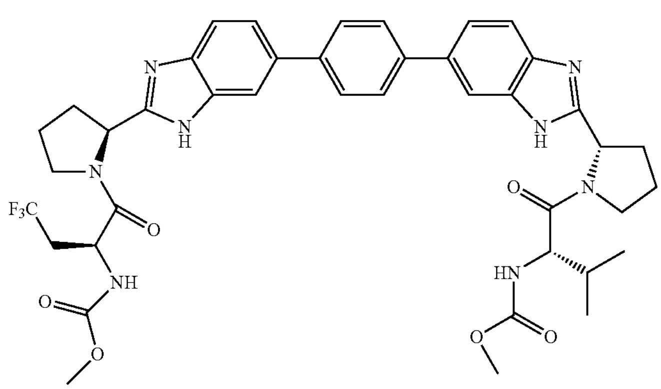 [SMILES: COC(=O)N[C@@H](CC(F)(F)F)C(=O)N1CCC[C@H]1c1nc2ccc(-c3ccc(-c4ccc5nc([C@@H]6CCCN6C(=O)[C@@H](NC(=O)OC)C(C)C)[nH]c5c4)cc3)cc2[nH]1] | | |

TABLE 4-continued

| Compound # | Structure | Inhibition of HCV genotype 1b | MS (M + H+) |
|---|---|---|---|
| 2048 | 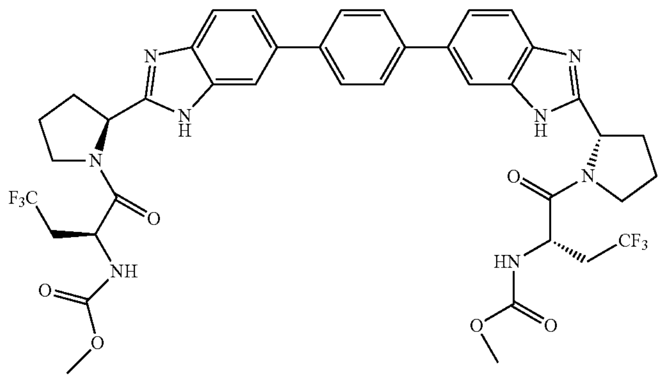 [SMILES: COC(=O)N[C@@H](CC(F)(F)F)C(=O)N1CCC[C@H]1c1nc2ccc(-c3ccc(-c4ccc5nc([C@@H]6CCCN6C(=O)[C@H](CC(F)(F)F)NC(=O)OC)[nH]c5c4)cc3)cc2[nH]1] | | |
| 2049 | 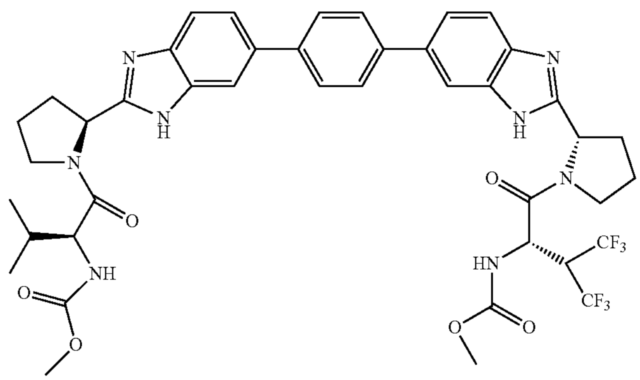 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C(F)(F)F)C(F)(F)F)[nH]c5c4)cc3)cc2[nH]1)C(C)C] | | |

TABLE 5

| Compound # | Structure | Inhibition of HCV genotype 1b | MS (M + H+) |
|---|---|---|---|
| 600 | 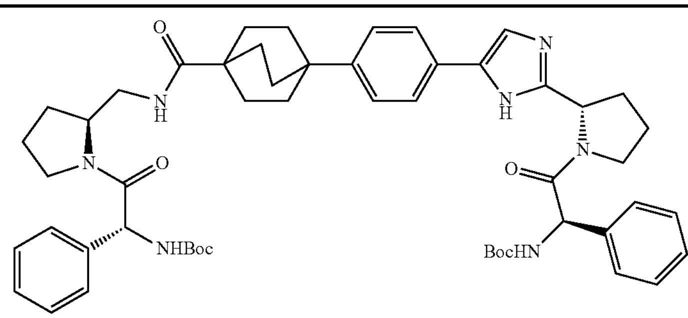 | *** | 914.5 |
| 601 | 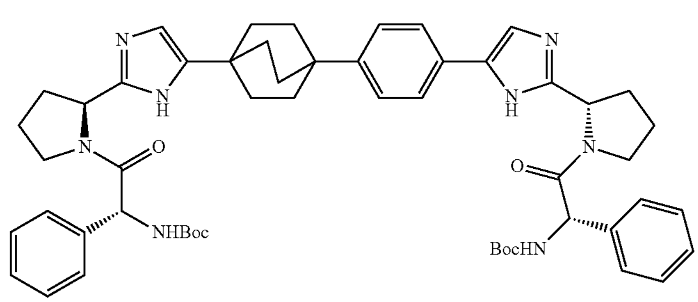 [SMILES: CC(C)(C)OC(=O)N[C@H](C(=O)N1CCC[C@H]1c1ncc(-c2ccc(C34CCC(c5cnc([C@@H]6CCCN6C(=O)[C@H](NC(=O)OC(C)(C)C)c6ccccc6)[nH]5)(CC3)CC4)cc2)[nH]1)c1ccccc1] | **** | 923.5 |

TABLE 5-continued

| Compound # | Structure | Inhibition of HCV genotype 1b | MS (M + H⁺) |
|---|---|---|---|
| 602 | 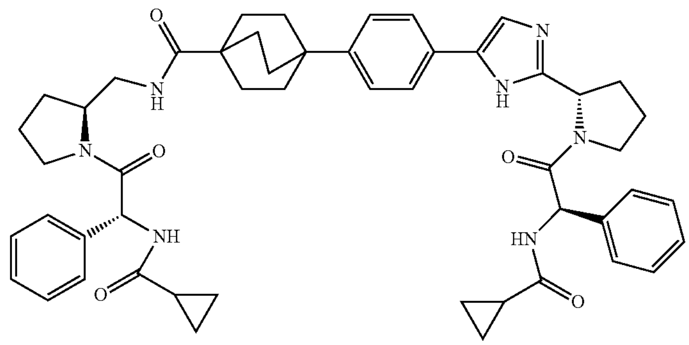 [SMILES: O=C(N[C@@H](C(=O)N1CCC[C@H]1CNC(=O)C12CCC(c3ccc(-c4cnc([C@@H]5CCCN5C(=O)[C@H](NC(=O)C5CC5)c5ccccc5)[nH]4)cc3)(CC1)CC2)c1ccccc1)C1CC1] | **** | 850.5 |
| 603 | 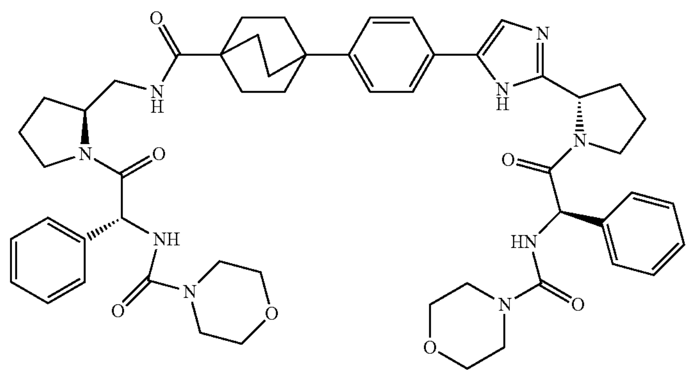 [SMILES: O=C(N[C@@H](C(=O)N1CCC[C@H]1CNC(=O)C12CCC(c3ccc(-c4cnc([C@@H]5CCCN5C(=O)[C@H](NC(=O)N5CCOCC5)c5ccccc5)[nH]4)cc3)(CC1)CC2)c1ccccc1)N1CCOCC1] | *** | 940.5 |
| 604 | 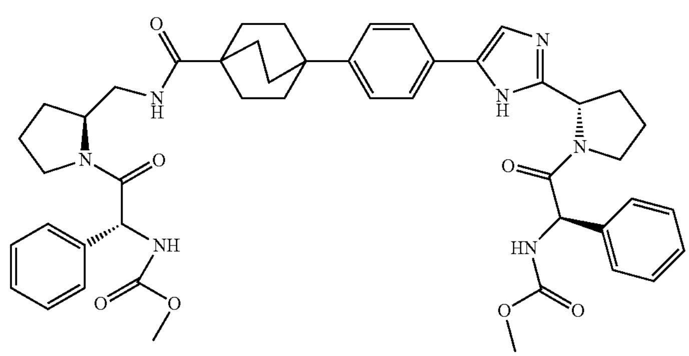 [SMILES: COC(=O)N[C@@H](C(=O)N1CCC[C@H]1CNC(=O)C12CCC(c3ccc(-c4cnc([C@@H]5CCCN5C(=O)[C@H](NC(=O)OC)c5ccccc5)[nH]4)cc3)(CC1)CC2)c1ccccc1] | **** | 830.4 |
| 605 | 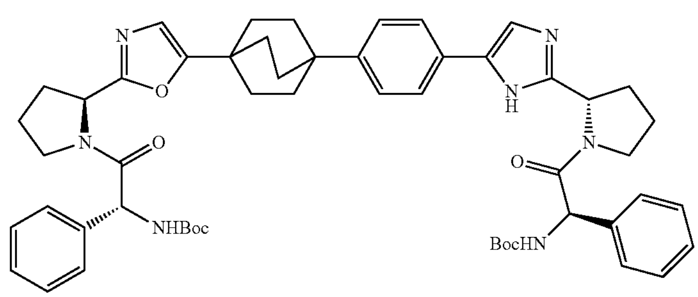 [SMILES: CC(C)(C)OC(=O)N[C@@H](C(=O)N1CCC[C@H]1c1ncc(-c2ccc(C34CCC(c5cnc([C@@H]6CCCN6C(=O)[C@H](NC(=O)OC(C)(C)C)c6ccccc6)o5)(CC3)CC4)cc2)[nH]1)c1ccccc1] | *** | 924.5 |

TABLE 5-continued

| Compound # | Structure | Inhibition of HCV genotype 1b | MS (M + H⁺) |
|---|---|---|---|
| 606 | 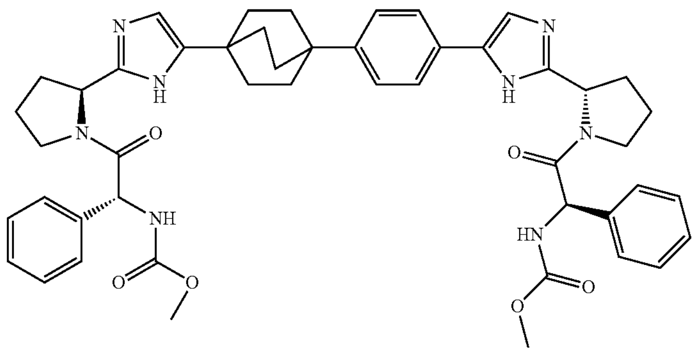 [SMILES: COC(=O)N[C@@H](C(=O)N1CCC[C@H]1c1ncc(-c2ccc(C34CCC(c5cnc([C@@H]6CCCN6C(=O)[C@H](NC(=O)OC)c6ccccc6)[nH]5)(CC3)CC4)cc2)[nH]1)c1ccccc1] | **** | 839.4 |
| 607 | 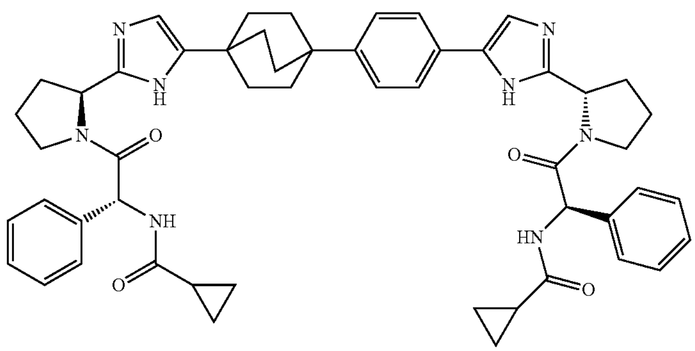 [SMILES: O=C(N[C@@H](C(=O)N1CCC[C@H]1c1ncc(-c2ccc(C34CCC(c5cnc([C@@H]6CCCN6C(=O)[C@H](NC(=O)C6CC6)c6ccccc6)[nH]5)(CC3)CC4)cc2)[nH]1)c1ccccc1)C1CC1] | **** | 859.5 |
| 608 | 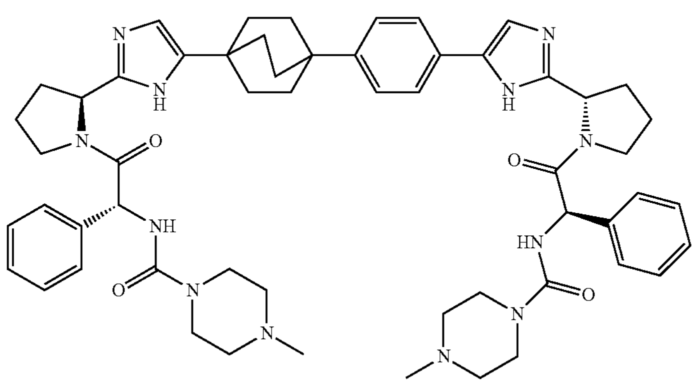 [SMILES: CN1CCN(C(=O)N[C@@H](C(=O)N2CCC[C@H]2c2ncc(-c3ccc(C45CCC(c6cnc([C@@H]7CCCN7C(=O)[C@H](NC(=O)N7CCN(C)CC7)c7ccccc7)[nH]6)(CC4)CC5)cc3)[nH]2)c2ccccc2)CC1] | ** | 875.6 |
| 609 | 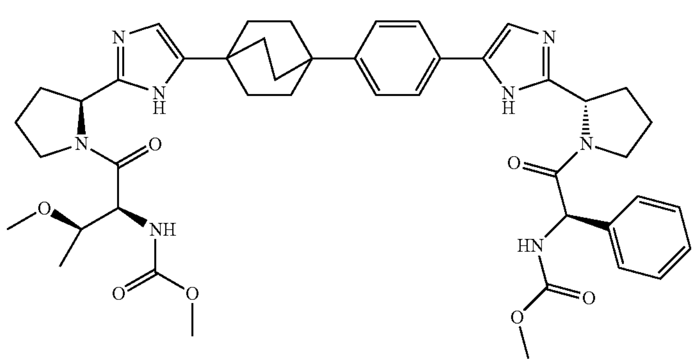 [SMILES: COC(=O)N[C@H](C(=O)N1CCC[C@H]1c1ncc(C23CCC(c4ccc(-c5cnc([C@@H]6CCCN6C(=O)[C@H](NC(=O)OC)c6ccccc6)[nH]5)cc4)(CC2)CC3)[nH]1)[C@@H](C)OC] | **** | 821.4 |

TABLE 5-continued

| Compound # | Structure | Inhibition of HCV genotype 1b | MS (M + H+) |
|---|---|---|---|
| 610 | 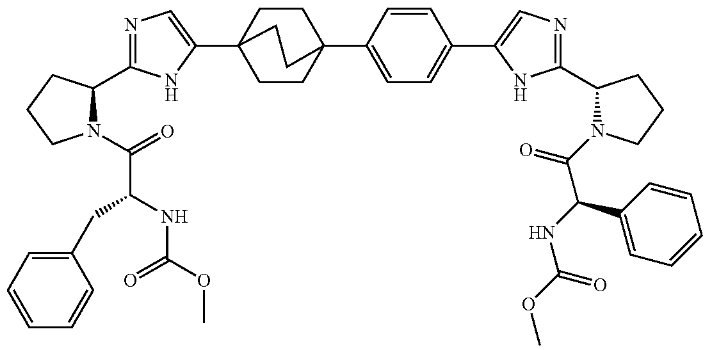 [SMILES: COC(=O)N[C@H](Cc1ccccc1)C(=O)N1CCC[C@H]1c1ncc(C23CCC(c4ccc(-c5cnc([C@@H]6CCCN6C(=O)[C@H](NC(=O)OC)c6ccccc6)[nH]5)cc4)(CC2)CC3)[nH]1] | **** | 853.4 |
| 611 | 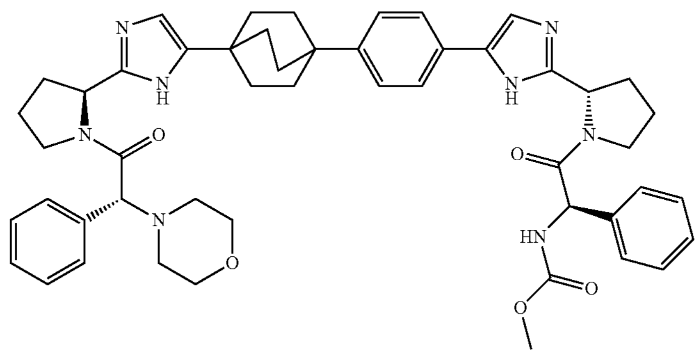 [SMILES: COC(=O)N[C@@H](C(=O)N1CCC[C@H]1c1ncc(-c2ccc(C34CCC(c5cnc([C@@H]6CCCN6C(=O)[C@@H](c6ccccc6)N6CCOCC6)[nH]5)(CC3)CC4)cc2)[nH]1)c1ccccc1] | **** | 851.5 |
| 612 | 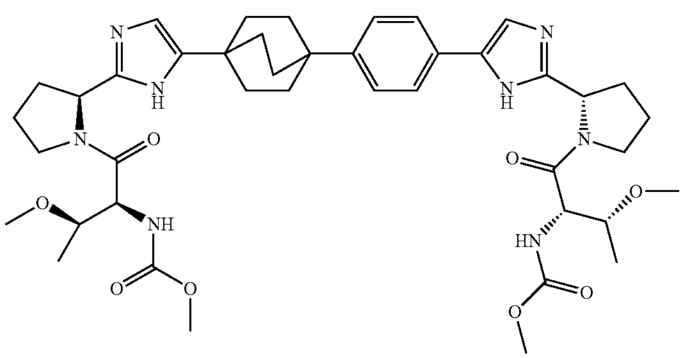 | **** | 803.4 |
| 613 | 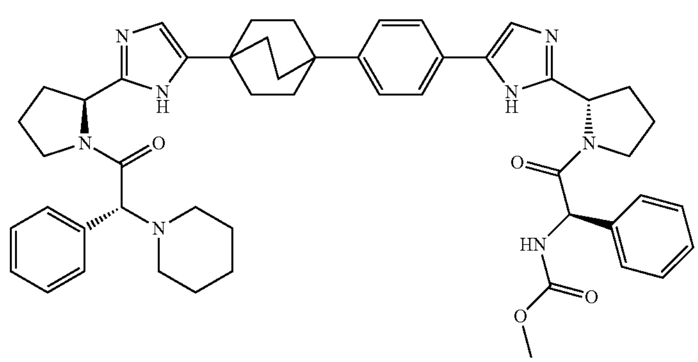 [SMILES: COC(=O)N[C@@H](C(=O)N1CCC[C@H]1c1ncc(-c2ccc(C34CCC(c5cnc([C@@H]6CCCN6C(=O)[C@@H](c6ccccc6)N6CCCCC6)[nH]5)(CC3)CC4)cc2)[nH]1)c1ccccc1] | **** | 933.4 |

TABLE 5-continued

| Compound # | Structure | Inhibition of HCV genotype 1b | MS (M + H⁺) |
|---|---|---|---|
| 614 | 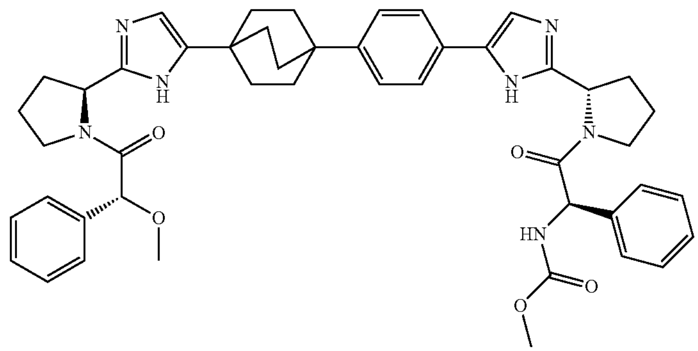 [SMILES: COC(=O)N[C@@H](C(=O)N1CCC[C@H]1c1ncc(-c2ccc(C34CCC(c5cnc([C@@H]6CCCN6C(=O)[C@H](OC)c6ccccc6)[nH]5)(CC3)CC4)cc2)[nH]1)c1ccccc1] | **** | 849.5 |
| 615 | 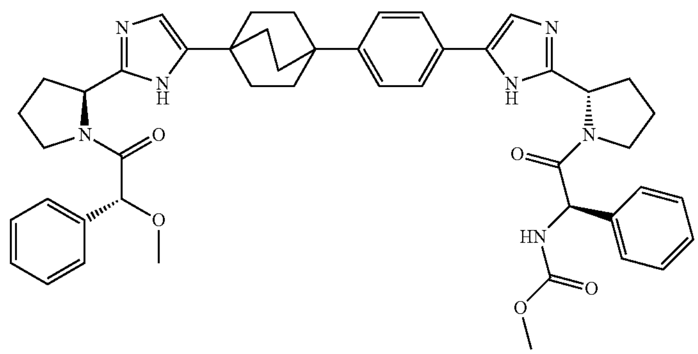 [SMILES: COC(=O)N[C@@H](C(=O)N1CCC[C@H]1c1ncc(-c2ccc(C34CCC(c5cnc([C@@H]6CCCN6C(=O)[C@H](OC)c6ccccc6)[nH]5)(CC3)CC4)cc2)[nH]1)c1ccccc1] | **** | 796.4 |
| 616 | 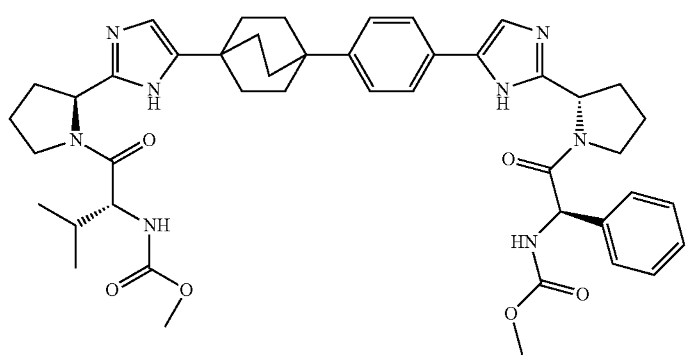 [SMILES: COC(=O)N[C@@H](C(=O)N1CCC[C@H]1c1ncc(-c2ccc(C34CCC(c5cnc([C@@H]6CCCN6C(=O)[C@H](NC(=O)OC)C(C)C)[nH]5)(CC3)CC4)cc2)[nH]1)c1ccccc1] | **** | 805.4 |
| 617 | 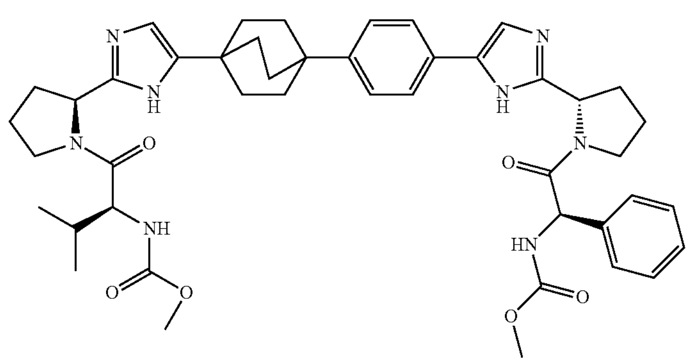 [SMILES: COC(=O)N[C@H](C(=O)N1CCC[C@H]1c1ncc(C23CCC(c4ccc(-c5cnc([C@@H]6CCCN6C(=O)[C@H](NC(=O)OC)c6ccccc6)[nH]5)cc4)(CC2)CC3)[nH]1)C(C)C] | **** | 805.4 |

TABLE 5-continued

| Compound # | Structure | Inhibition of HCV genotype 1b | MS (M + H⁺) |
|---|---|---|---|
| 618 | 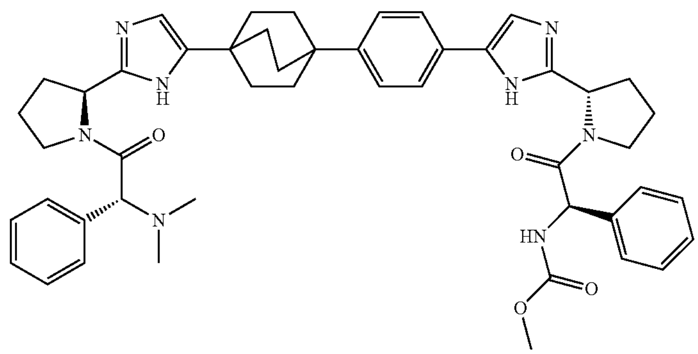 [SMILES: COC(=O)N[C@@H](C(=O)N1CCC[C@H]1c1ncc(-c2ccc(C34CCC(c5cnc([C@@H]6CCCN6C(=O)[C@@H](c6ccccc6)N(C)C)[nH]5)(CC3)CC4)cc2)[nH]1)c1ccccc1] | **** | 809.4 |
| 619 | 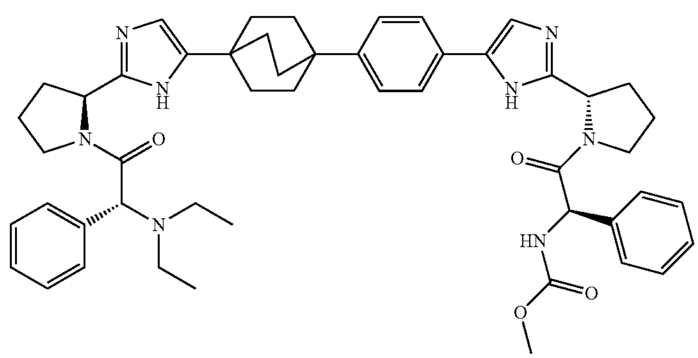 [SMILES: CCN(CC)[C@@H](C(=O)N1CCC[C@H]1c1ncc(C23CCC(c4ccc(-c5cnc([C@@H]6CCCN6C(=O)[C@H](NC(=O)OC)c6ccccc6)[nH]5)cc4)(CC2)CC3)[nH]1)c1ccccc1] | **** | 837.5 |
| 620 | 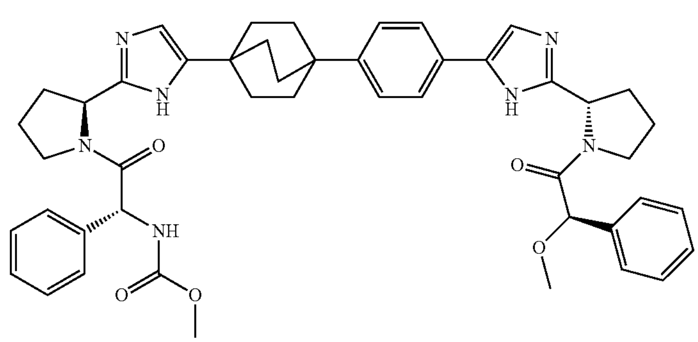 [SMILES: COC(=O)N[C@@H](C(=O)N1CCC[C@H]1c1ncc(C23CCC(c4ccc(-c5cnc([C@@H]6CCCN6C(=O)[C@H](OC)c6ccccc6)[nH]5)cc4)(CC2)CC3)[nH]1)c1ccccc1] | **** | 796.4 |
| 621 | 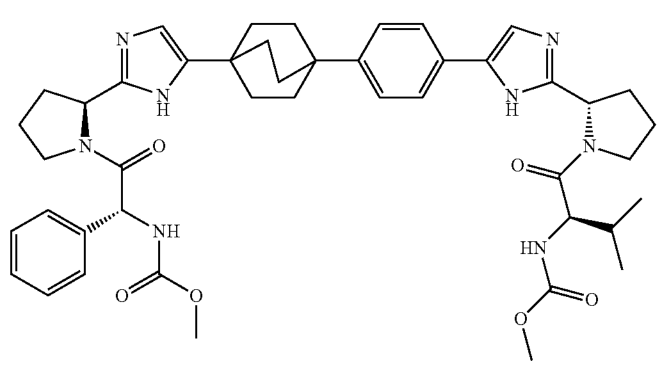 [SMILES: COC(=O)N[C@@H](C(=O)N1CCC[C@H]1c1ncc(C23CCC(c4ccc(-c5cnc([C@@H]6CCCN6C(=O)[C@H](NC(=O)OC)C(C)C)[nH]5)cc4)(CC2)CC3)[nH]1)c1ccccc1] | **** | 805.4 |

TABLE 5-continued

| Compound # | Structure | Inhibition of HCV genotype 1b | MS (M + H⁺) |
|---|---|---|---|
| 622 | 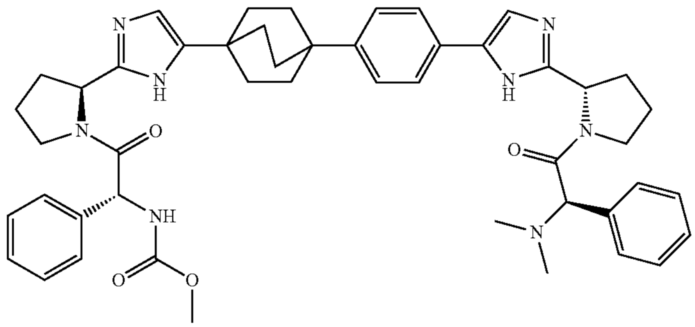 [SMILES: COC(=O)N[C@@H](C(=O)N1CCC[C@H]1c1ncc(C23CCC(c4ccc(-c5cnc([C@@H]6CCCN6C(=O)[C@@H](c6ccccc6)N(C)C)[nH]5)cc4)(CC2)CC3)[nH]1)c1ccccc1] | **** | 809.4 |
| 623 | 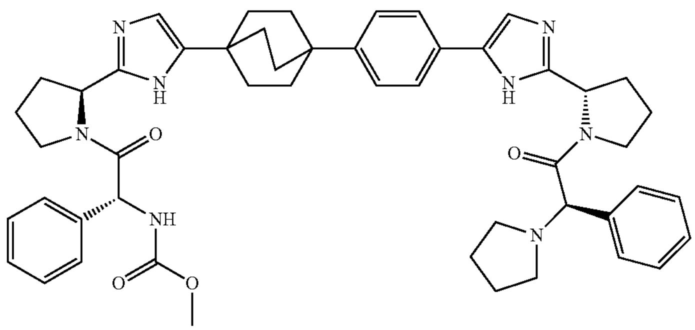 [SMILES: COC(=O)N[C@@H](C(=O)N1CCC[C@H]1c1ncc(C23CCC(c4ccc(-c5cnc([C@@H]6CCCN6C(=O)[C@@H](c6ccccc6)N6CCCC6)[nH]5)cc4)(CC2)CC3)[nH]1)c1ccccc1] | **** | 835.5 |
| 624 | 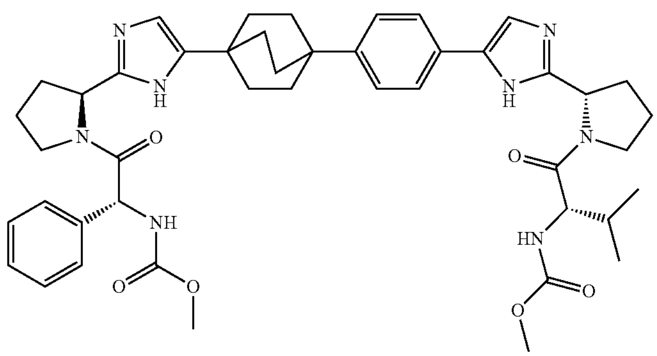 [SMILES: COC(=O)N[C@H](C(=O)N1CCC[C@H]1c1ncc(-c2ccc(C34CCC(c5cnc([C@@H]6CCCN6C(=O)[C@H](NC(=O)OC)c6ccccc6)[nH]5)(CC3)CC4)cc2)[nH]1)C(C)C] | **** | 805.4 |
| 625 | 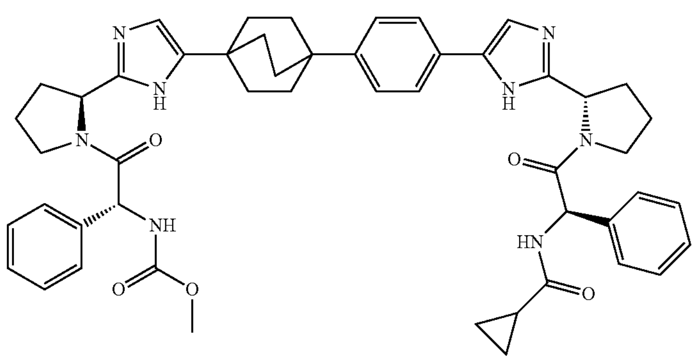 [SMILES: COC(=O)N[C@@H](C(=O)N1CCC[C@H]1c1ncc(C23CCC(c4ccc(-c5cnc([C@@H]6CCCN6C(=O)[C@H](NC(=O)C6CC6)c6ccccc6)[nH]5)cc4)(CC2)CC3)[nH]1)c1ccccc1] | **** | 849.4 |

TABLE 5-continued

| Compound # | Structure | Inhibition of HCV genotype 1b | MS (M + H⁺) |
|---|---|---|---|
| 626 | 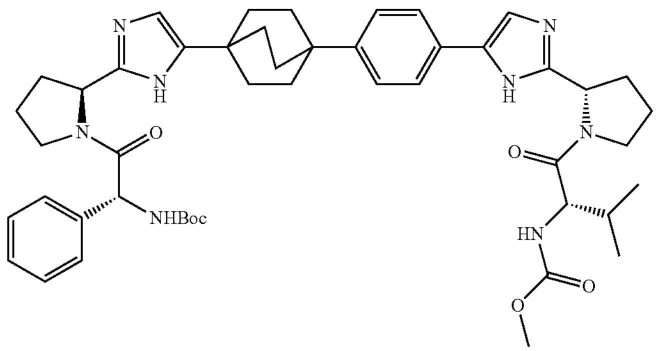 [SMILES: COC(=O)N[C@H](C(=O)N1CCC[C@H]1c1ncc(-c2ccc(C34CCC(c5cnc([C@@H]6CCCN6C(=O)[C@H](NC(=O)OC(C)(C)C)c6ccccc6)[nH]5)(CC3)CC4)cc2)[nH]1)C(C)C] | **** | 847.5 |
| 627 | 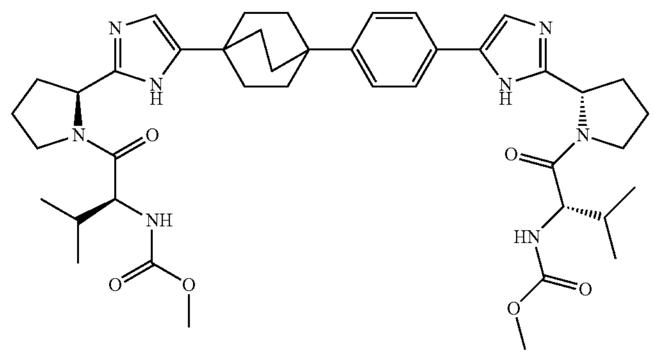 | **** | 771.4 |
| 628 | 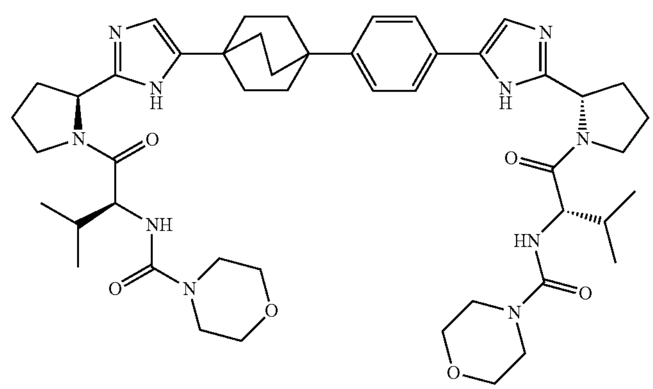 [SMILES: CC(C)[C@H](NC(=O)N1CCOCC1)C(=O)N1CCC[C@H]1c1ncc(-c2ccc(C34CCC(c5cnc([C@@H]6CCCN6C(=O)[C@@H](NC(=O)N6CCOCC6)C(C)C)[nH]5)(CC3)CC4)cc2)[nH]1] | * | 881.5 |
| 629 | 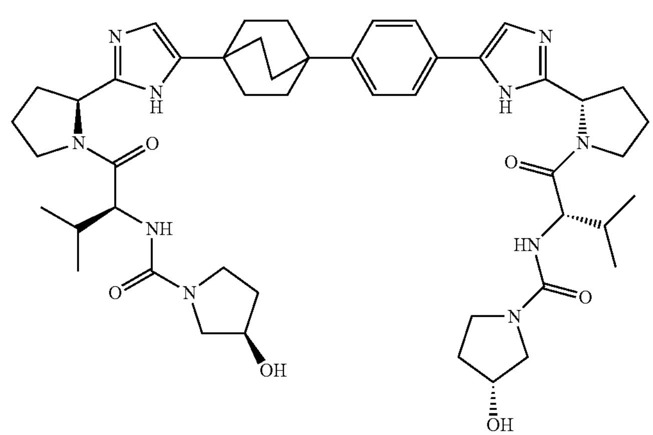 [SMILES: CC(C)[C@H](NC(=O)N1CC[C@@H](O)C1)C(=O)N1CCC[C@H]1c1ncc(-c2ccc(C34CCC(c5cnc([C@@H]6CCCN6C(=O)[C@@H](NC(=O)N6CC[C@@H](O)C6)C(C)C)[nH]5)(CC3)CC4)cc2)[nH]1] | * | 881.5 |

TABLE 5-continued

| Compound # | Structure | Inhibition of HCV genotype 1b | MS (M + H⁺) |
|---|---|---|---|
| 630 | 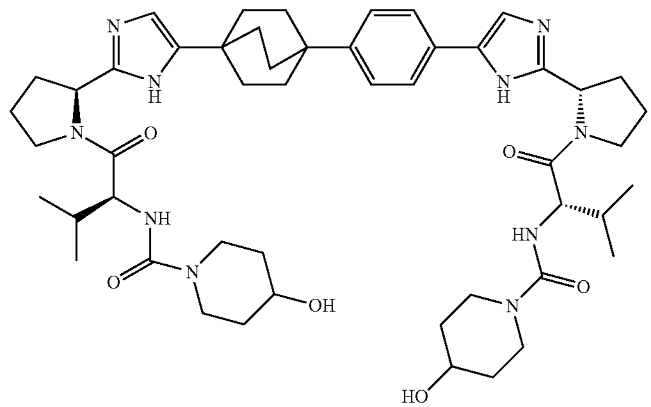 [SMILES: CC(C)[C@H](NC(=O)N1CCC(O)CC1)C(=O)N1CCC[C@H]1c1ncc(-c2ccc(C34CCC(c5cnc([C@@H]6CCCN6C(=O)[C@@H](NC(=O)N6CCC(O)CC6)C(C)C)[nH]5)(CC3)CC4)cc2)[nH]1] | * | 909.6 |
| 631 | 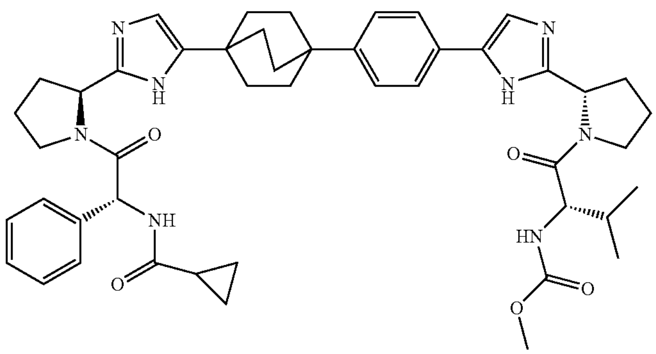 [SMILES: COC(=O)N[C@H](C(=O)N1CCC[C@H]1c1ncc(-c2ccc(C34CCC(c5cnc([C@@H]6CCCN6C(=O)[C@H](NC(=O)C6CC6)c6ccccc6)[nH]5)(CC3)CC4)cc2)[nH]1)C(C)C] | **** | 815.5 |
| 632 | 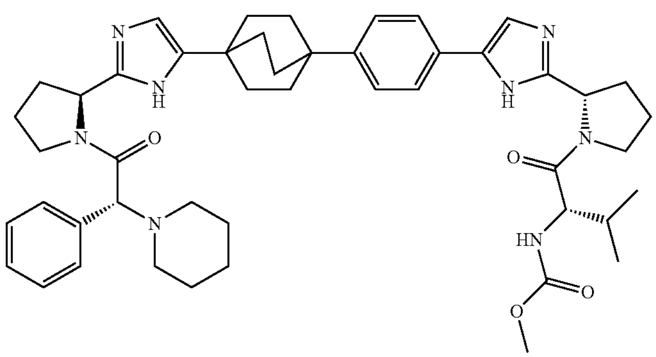 [SMILES: COC(=O)N[C@H](C(=O)N1CCC[C@H]1c1ncc(-c2ccc(C34CCC(c5cnc([C@@H]6CCCN6C(=O)[C@@H](c6ccccc6)N6CCCCC6)[nH]5)(CC3)CC4)cc2)[nH]1)C(C)C] | **** | 815.5 |
| 633 | 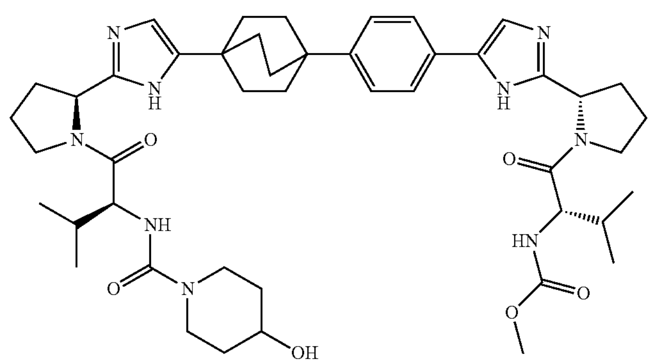 [SMILES: COC(=O)N[C@H](C(=O)N1CCC[C@H]1c1ncc(-c2ccc(C34CCC(c5cnc([C@@H]6CCCN6C(=O)[C@@H](NC(=O)N6CCC(O)CC6)C(C)C)[nH]5)(CC3)CC4)cc2)[nH]1)C(C)C] | **** | 840.5 |

TABLE 5-continued

| Compound # | Structure | Inhibition of HCV genotype 1b | MS (M + H⁺) |
|---|---|---|---|
| 634 | 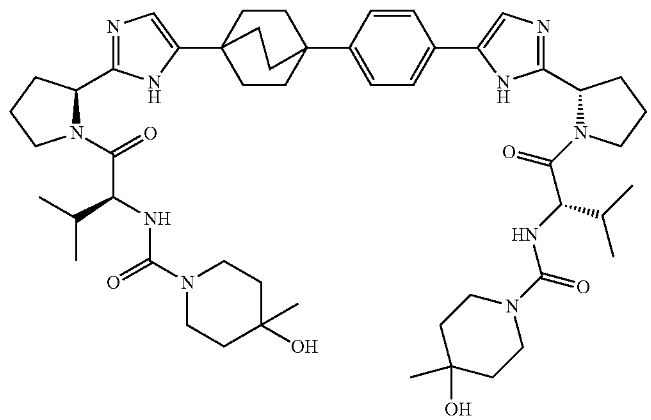 [SMILES: CC(C)[C@H](NC(=O)N1CCC(C)(O)CC1)C(=O)N1CCC[C@H]1c1ncc(-c2ccc(C34CCC(c5cnc([C@@H]6CCCN6C(=O)[C@@H](NC(=O)N6CCC(C)(O)CC6)C(C)C)[nH]5)(CC3)CC4)cc2)[nH]1] | **** | 937.6 |
| 635 | 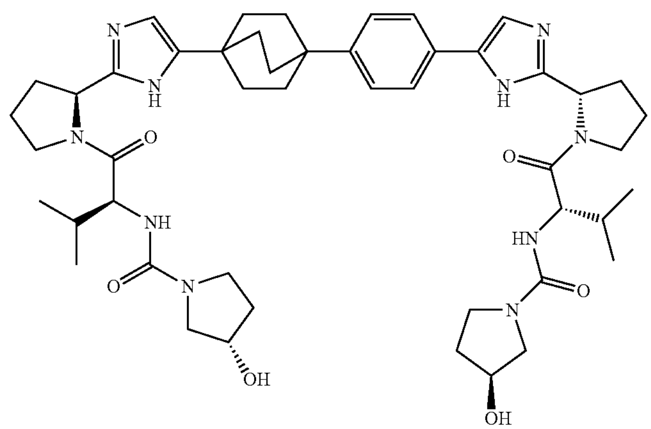 [SMILES: CC(C)[C@H](NC(=O)N1CC[C@H](O)C1)C(=O)N1CCC[C@H]1c1ncc(-c2ccc(C34CCC(c5cnc([C@@H]6CCCN6C(=O)[C@@H](NC(=O)N6CC[C@H](O)C6)C(C)C)[nH]5)(CC3)CC4)cc2)[nH]1] | **** | 881.5 |
| 636 | 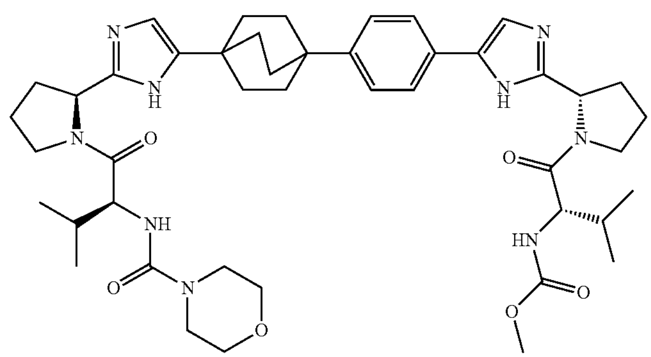 [SMILES: COC(=O)N[C@H](C(=O)N1CCC[C@H]1c1ncc(-c2ccc(C34CCC(c5cnc([C@@H]6CCCN6C(=O)[C@@H](NC(=O)N6CCOCC6)C(C)C)[nH]5)(CC3)CC4)cc2)[nH]1)C(C)C] | **** | 826.5 |
| 637 | 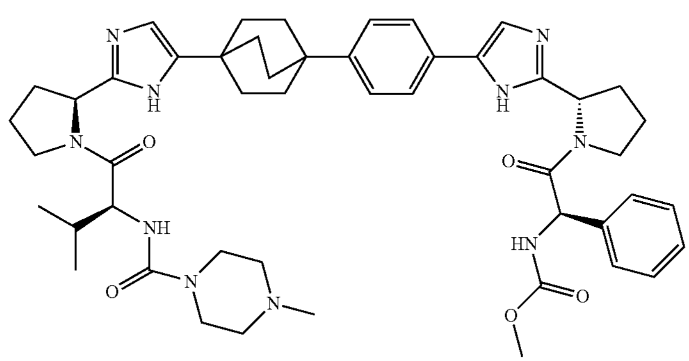 [SMILES: COC(=O)N[C@@H](C(=O)N1CCC[C@H]1c1ncc(-c2ccc(C34CCC(c5cnc([C@@H]6CCCN6C(=O)[C@@H](NC(=O)N6CCN(C)CC6)C(C)C)[nH]5)(CC3)CC4)cc2)[nH]1)c1ccccc1] | *** | 873.5 |

TABLE 5-continued

| Compound # | Structure | Inhibition of HCV genotype 1b | MS (M + H+) |
|---|---|---|---|
| 638 | 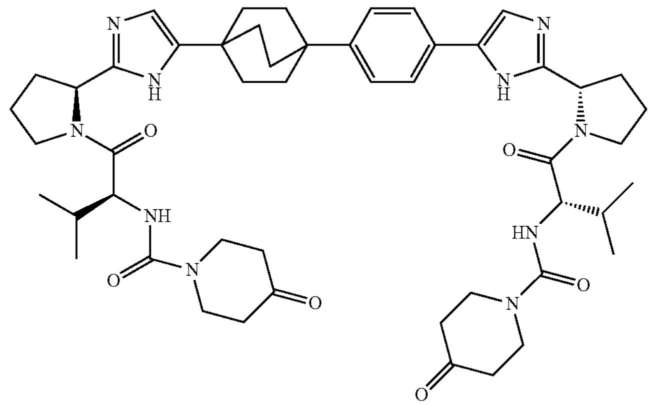 [SMILES: CC(C)[C@H](NC(=O)N1CCC(=O)CC1)C(=O)N1CCC[C@H]1c1ncc(-c2ccc(C34CCC(c5cnc([C@@H]6CCCN6C(=O)[C@@H](NC(=O)N6CCC(=O)CC6)C(C)C)[nH]5)(CC3)CC4)cc2)[nH]1] | * | 905.5 |
| 639 | 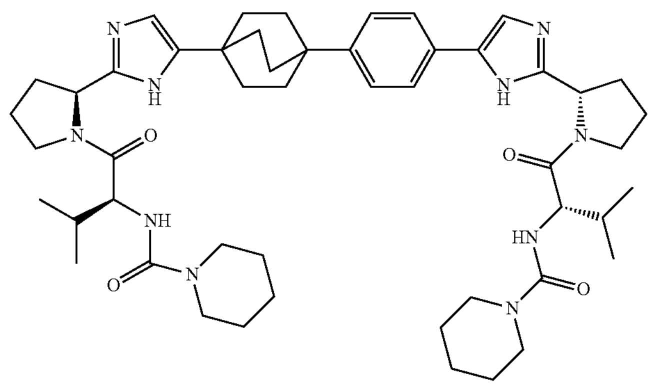 [SMILES: CC(C)[C@H](NC(=O)N1CCCCC1)C(=O)N1CCC[C@H]1c1ncc(-c2ccc(C34CCC(c5cnc([C@@H]6CCCN6C(=O)[C@@H](NC(=O)N6CCCCC6)C(C)C)[nH]5)(CC3)CC4)cc2)[nH]1] | * | 877.6 |
| 640 | 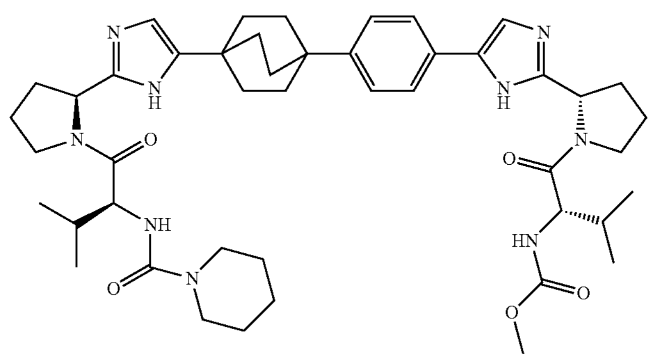 [SMILES: COC(=O)N[C@H](C(=O)N1CCC[C@H]1c1ncc(-c2ccc(C34CCC(c5cnc([C@@H]6CCCN6C(=O)[C@@H](NC(=O)N6CCCCC6)C(C)C)[nH]5)(CC3)CC4)cc2)[nH]1)C(C)C] | * | 824.5 |
| 641 | 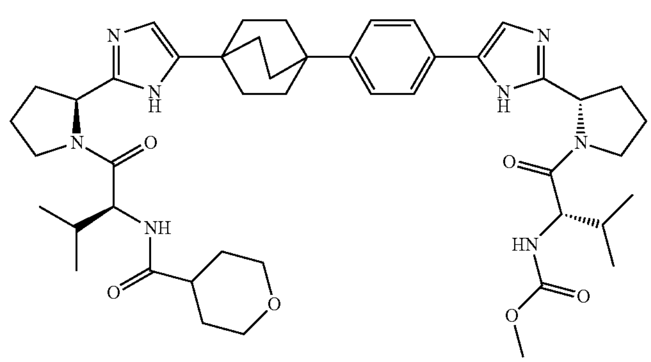 [SMILES: COC(=O)N[C@H](C(=O)N1CCC[C@H]1c1ncc(-c2ccc(C34CCC(c5cnc([C@@H]6CCCN6C(=O)[C@@H](NC(=O)C6CCOCC6)C(C)C)[nH]5)(CC3)CC4)cc2)[nH]1)C(C)C] | * | 825.5 |

TABLE 5-continued

| Compound # | Structure | Inhibition of HCV genotype 1b | MS (M + H+) |
|---|---|---|---|
| 642 | 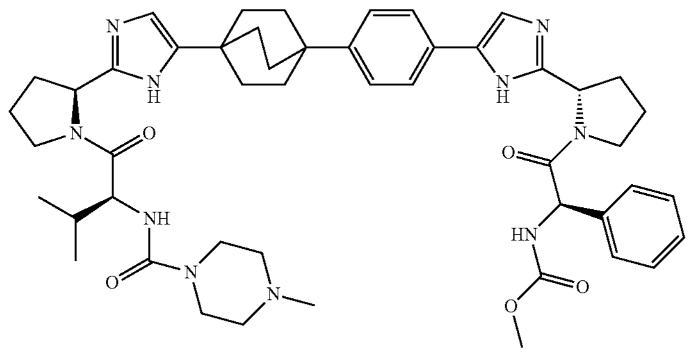 [SMILES: COC(=O)N[C@@H](C(=O)N1CCC[C@H]1c1ncc(-c2ccc(C34CCC(c5cnc([C@@H]6CCCN6C(=O)[C@@H](NC(=O)N6CCN(C)CC6)C(C)C)[nH]5)(CC3)CC4)cc2)[nH]1)c1ccccc1] | *** | 873.5 |
| 643 | 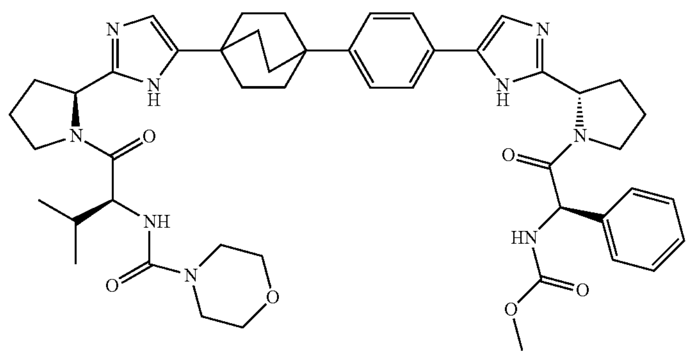 [SMILES: COC(=O)N[C@@H](C(=O)N1CCC[C@H]1c1ncc(-c2ccc(C34CCC(c5cnc([C@@H]6CCCN6C(=O)[C@@H](NC(=O)N6CCOCC6)C(C)C)[nH]5)(CC3)CC4)cc2)[nH]1)c1ccccc1] | *** | 860.5 |
| 644 | 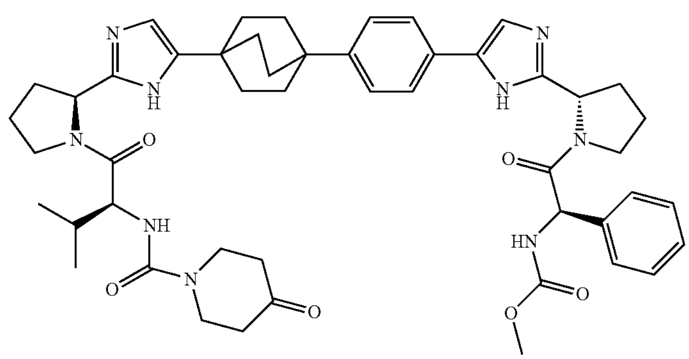 [SMILES: COC(=O)N[C@@H](C(=O)N1CCC[C@H]1c1ncc(-c2ccc(C34CCC(c5cnc([C@@H]6CCCN6C(=O)[C@@H](NC(=O)N6CCC(=O)CC6)C(C)C)[nH]5)(CC3)CC4)cc2)[nH]1)c1ccccc1] | *** | 872.5 |
| 645 | 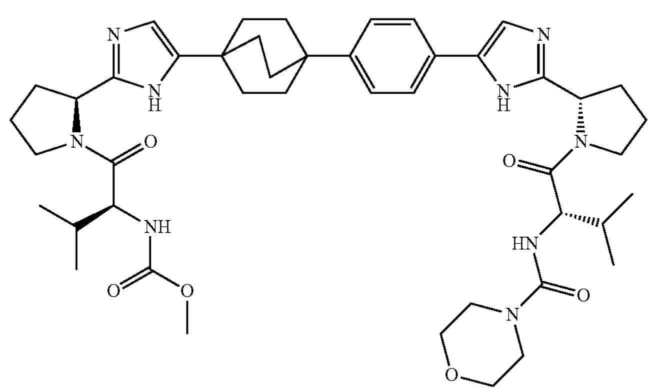 | **** | 826.5 |

TABLE 5-continued

| Compound # | Structure | Inhibition of HCV genotype 1b | MS (M + H+) |
|---|---|---|---|
| 646 | 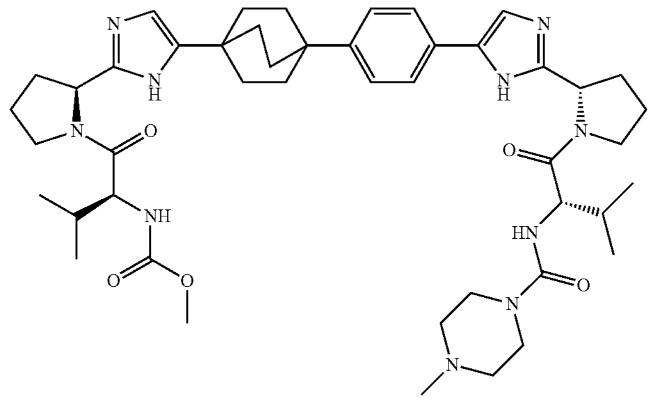 [SMILES: COC(=O)N[C@H](C(=O)N1CCC[C@H]1c1ncc(C23CCC(c4ccc(-c5cnc([C@@H]6CCCN6C(=O)[C@@H](NC(=O)N6CCN(C)CC6)C(C)C)[nH]5)cc4)(CC2)CC3)[nH]1)C(C)C] | ** | 839.5 |
| 647 | 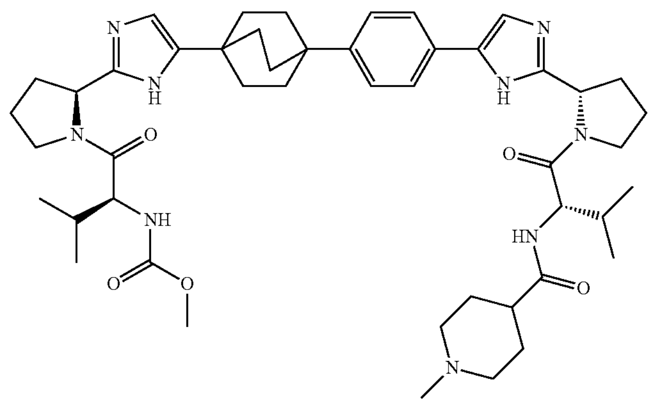 [SMILES: COC(=O)N[C@H](C(=O)N1CCC[C@H]1c1ncc(C23CCC(c4ccc(-c5cnc([C@@H]6CCCN6C(=O)[C@@H](NC(=O)C6CCN(C)CC6)C(C)C)[nH]5)cc4)(CC2)CC3)[nH]1)C(C)C] | ** | 838.5 |
| 648 | 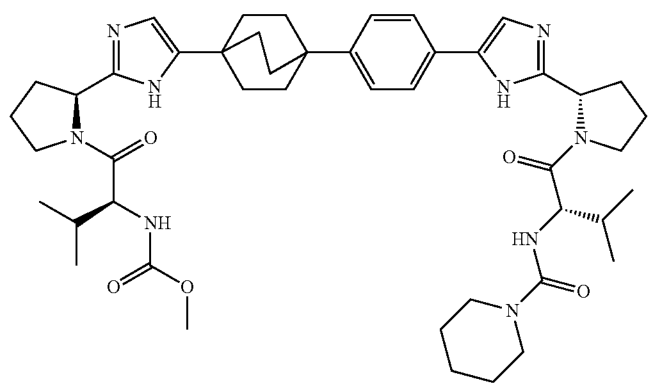 [SMILES: COC(=O)N[C@H](C(=O)N1CCC[C@H]1c1ncc(C23CCC(c4ccc(-c5cnc([C@@H]6CCCN6C(=O)[C@@H](NC(=O)N6CCCCC6)C(C)C)[nH]5)cc4)(CC2)CC3)[nH]1)C(C)C] | ** | 824.5 |
| 649 | 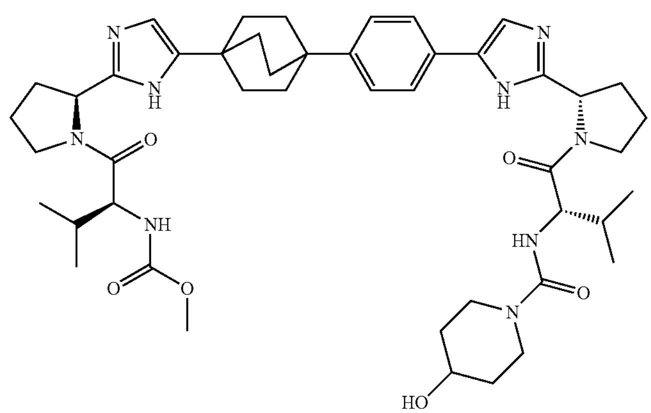 [SMILES: COC(=O)N[C@H](C(=O)N1CCC[C@H]1c1ncc(C23CCC(c4ccc(-c5cnc([C@@H]6CCCN6C(=O)[C@@H](NC(=O)N6CCC(O)CC6)C(C)C)[nH]5)cc4)(CC2)CC3)[nH]1)C(C)C] | **** | 840.5 |

TABLE 5-continued
| Compound # | Structure | Inhibition of HCV genotype 1b | MS (M + H⁺) |
|---|---|---|---|
| 650 | 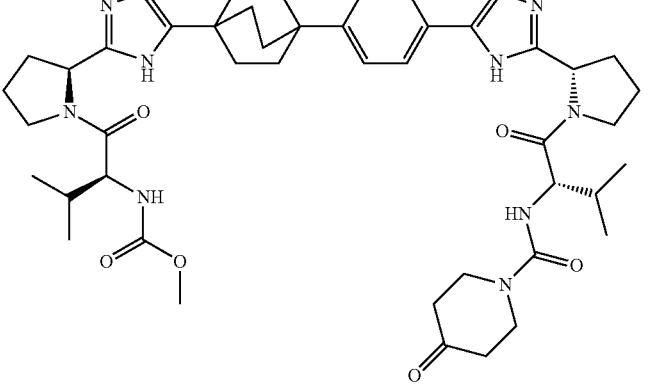 | *** | 838.5 |
| 651 | 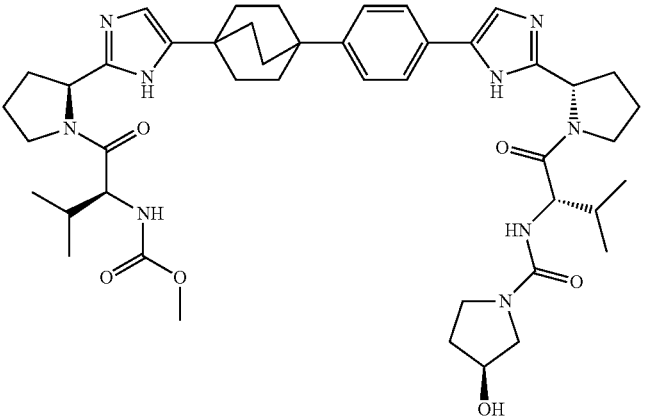 [SMILES: COC(=O)N[C@H](C(=O)N1CCC[C@H]1c1ncc(C23CCC(c4ccc(-c5cnc([C@@H]6CCCN6C(=O)[C@@H](NC(=O)N6CC[C@H](O)C6)C(C)C)[nH]5)cc4)(CC2)CC3)[nH]1)C(C)C] | *** | 826.5 |
| 652 | 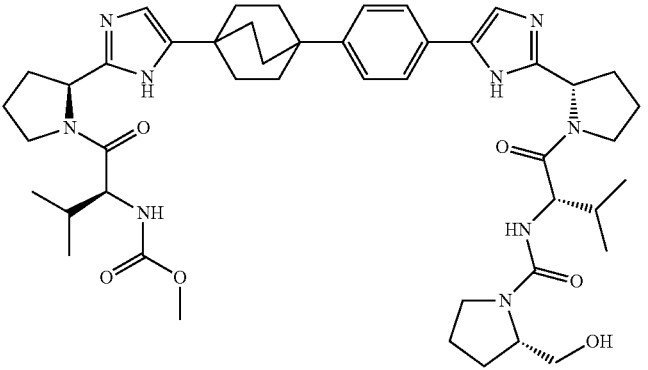 [SMILES: COC(=O)N[C@H](C(=O)N1CCC[C@H]1c1ncc(C23CCC(c4ccc(-c5cnc([C@@H]6CCCN6C(=O)[C@@H](NC(=O)N6CCC[C@H]6CO)C(C)C)[nH]5)cc4)(CC2)CC3)[nH]1)C(C)C] | **** | 840.5 |
| 2051 | 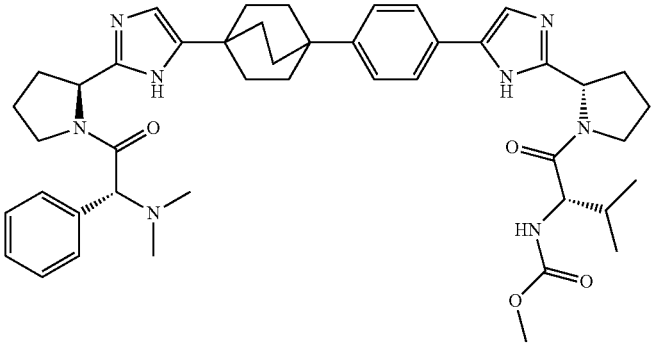 [SMILES: COC(=O)N[C@H](C(=O)N1CCC[C@H]1c1ncc(-c2ccc(C34CCC(c5cnc([C@@H]6CCCN6C(=O)[C@@H](c6ccccc6)N(C)C)[nH]5)(CC3)CC4)cc2)[nH]1)C(C)C] | **** | 775.5 |

TABLE 5-continued

| Compound # | Structure | Inhibition of HCV genotype 1b | MS (M + H⁺) |
|---|---|---|---|
| 2052 | 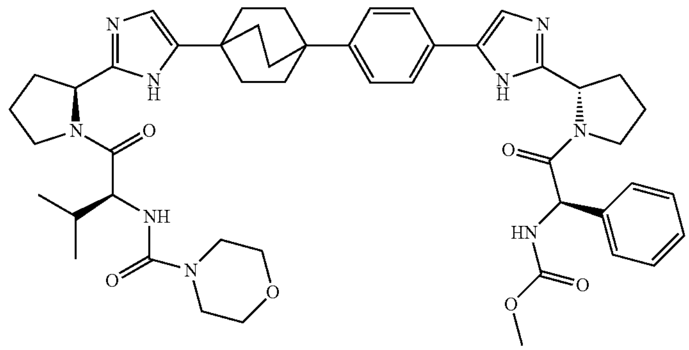 [SMILES: COC(=O)N[C@@H](C(=O)N1CCC[C@H]1c1ncc(-c2ccc(C34CCC(c5cnc([C@@H]6CCCN6C(=O)[C@@H](NC(=O)N6CCOCC6)C(C)C)[nH]5)(CC3)CC4)cc2)[nH]1)c1ccccc1] | **** | 860.5 |
| 2053 | 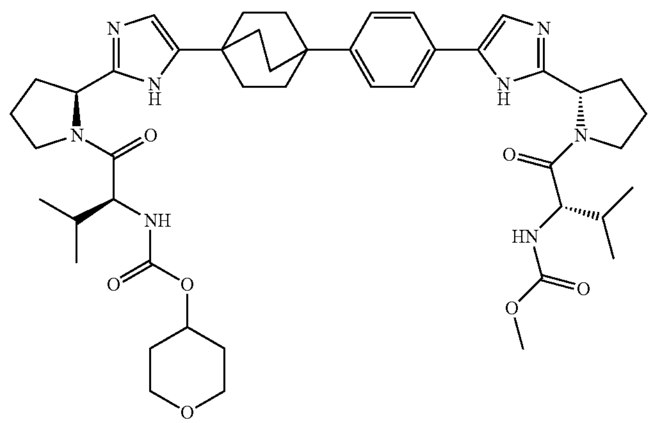 [SMILES: COC(=O)N[C@H](C(=O)N1CCC[C@H]1c1ncc(-c2ccc(C34CCC(c5cnc([C@@H]6CCCN6C(=O)[C@@H](NC(=O)OC6CCOCC6)C(C)C)[nH]5)(CC3)CC4)cc2)[nH]1)C(C)C] | *** | 841.5 |
| 2054 | 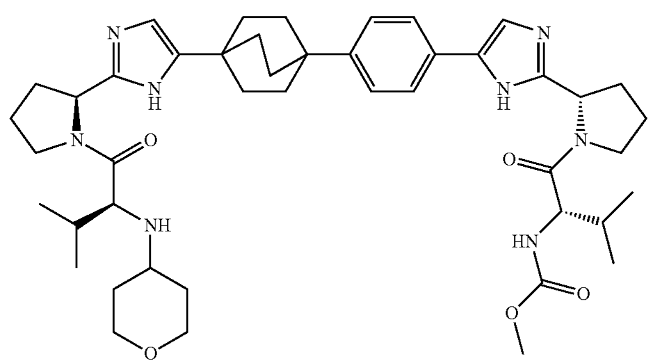 [SMILES: COC(=O)N[C@H](C(=O)N1CCC[C@H]1c1ncc(-c2ccc(C34CCC(c5cnc([C@@H]6CCCN6C(=O)[C@@H](NC6CCOCC6)C(C)C)[nH]5)(CC3)CC4)cc2)[nH]1)C(C)C] | *** | 797.5 |
| 2055 | 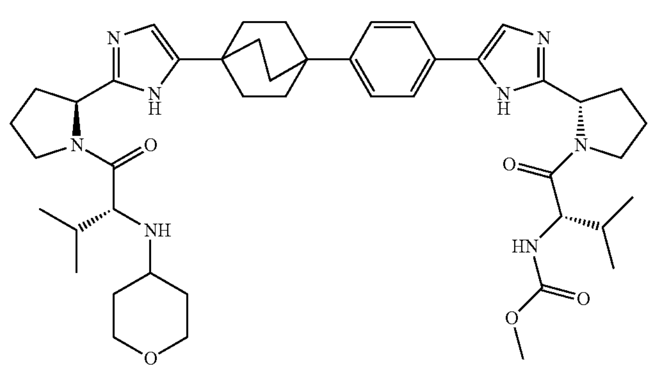 [SMILES: COC(=O)N[C@H](C(=O)N1CCC[C@H]1c1ncc(-c2ccc(C34CCC(c5cnc([C@@H]6CCCN6C(=O)[C@H](NC6CCOCC6)C(C)C)[nH]5)(CC3)CC4)cc2)[nH]1)C(C)C] | **** | 797.5 |

TABLE 5-continued

| Compound # | Structure | Inhibition of HCV genotype 1b | MS (M + H+) |
|---|---|---|---|
| 2056 | 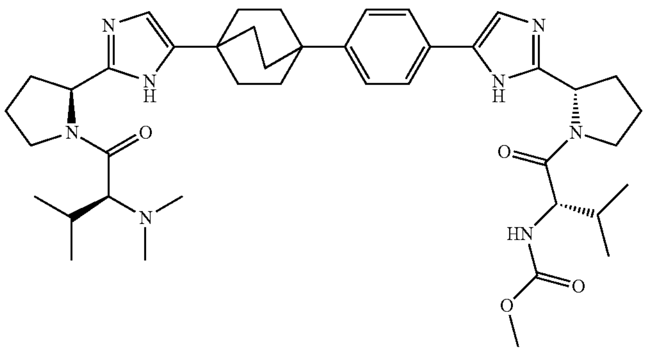 [SMILES: COC(=O)N[C@H](C(=O)N1CCC[C@H]1c1ncc(-c2ccc(C34CCC(c5cnc([C@@H]6CCCN6C(=O)[C@H](C(C)C)N(C)C)[nH]5)(CC3)CC4)cc2)[nH]1)C(C)C] | **** | 741.5 |
| 2057 | 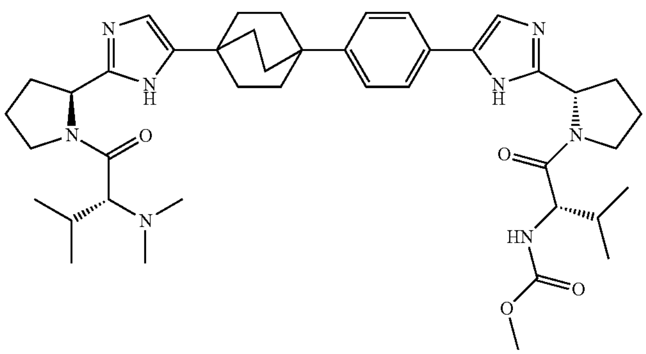 [SMILES: COC(=O)N[C@H](C(=O)N1CCC[C@H]1c1ncc(-c2ccc(C34CCC(c5cnc([C@@H]6CCCN6C(=O)[C@@H](C(C)C)N(C)C)[nH]5)(CC3)CC4)cc2)[nH]1)C(C)C] | **** | 741.5 |
| 2058 | 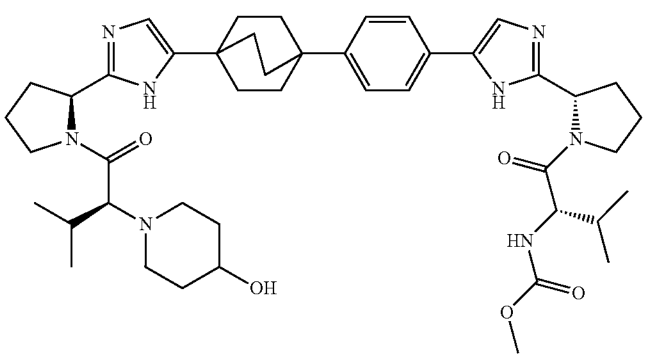 [SMILES: COC(=O)N[C@H](C(=O)N1CCC[C@H]1c1ncc(-c2ccc(C34CCC(c5cnc([C@@H]6CCCN6C(=O)[C@H](C(C)C)N6CCC(O)CC6)[nH]5)(CC3)CC4)cc2)[nH]1)C(C)C] | **** | 797.5 |
| 2059 | 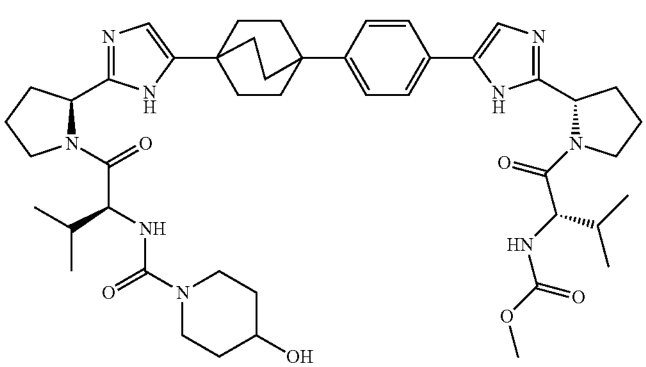 [SMILES: COC(=O)N[C@H](C(=O)N1CCC[C@H]1c1ncc(-c2ccc(C34CCC(c5cnc([C@@H]6CCCN6C(=O)[C@@H](NC(=O)N6CCC(O)CC6)C(C)C)[nH]5)(CC3)CC4)cc2)[nH]1)C(C)C] | **** | 840.5 |

TABLE 5-continued
| Compound # | Structure | Inhibition of HCV genotype 1b | MS (M + H⁺) |
|---|---|---|---|
| 2060 | 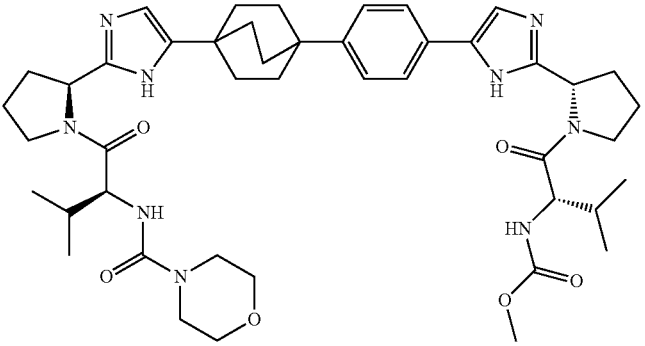 [SMILES: COC(=O)N[C@H](C(=O)N1CCC[C@H]1c1ncc(-c2ccc(C34CCC(c5cnc([C@@H]6CCCN6C(=O)[C@@H](NC(=O)N6CCOCC6)C(C)C)[nH]5)(CC3)CC4)cc2)[nH]1)C(C)C] | **** | 826.5 |
| 2061 | 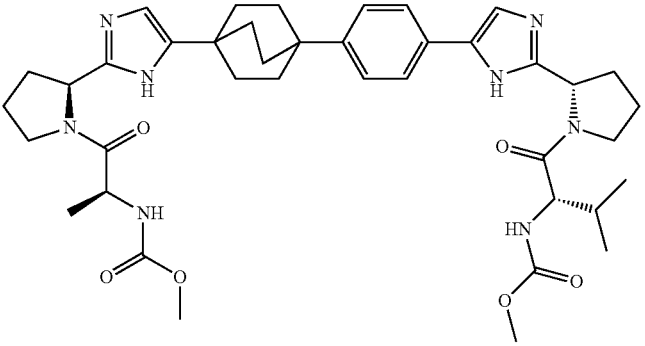 [SMILES: COC(=O)N[C@@H](C)C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1] | **** | 743.4 |
| 2062 | 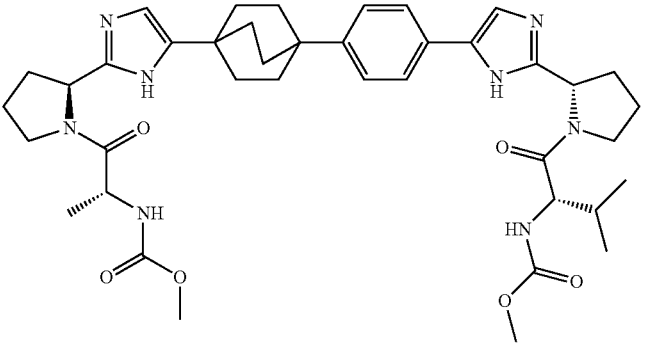 [SMILES: COC(=O)N[C@H](C(=O)N1CCC[C@H]1c1ncc(-c2ccc(C34CCC(c5cnc([C@@H]6CCCN6C(=O)[C@@H](C)NC(=O)OC)[nH]5)(CC3)CC4)cc2)[nH]1)C(C)C] | **** | 743.4 |
| 2063 | 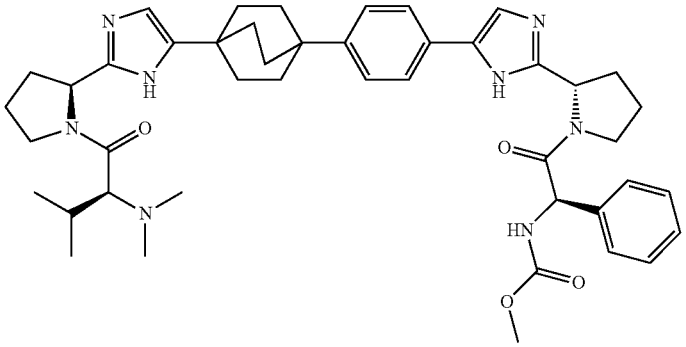 [SMILES: COC(=O)N[C@@H](C(=O)N1CCC[C@H]1c1ncc(-c2ccc(C34CCC(c5cnc([C@@H]6CCCN6C(=O)[C@H](C(C)C)N(C)C)[nH]5)(CC3)CC4)cc2)[nH]1)c1ccccc1] | **** | 775.5 |

TABLE 5-continued

| Compound # | Structure | Inhibition of HCV genotype 1b | MS (M + H⁺) |
|---|---|---|---|
| 2064 | 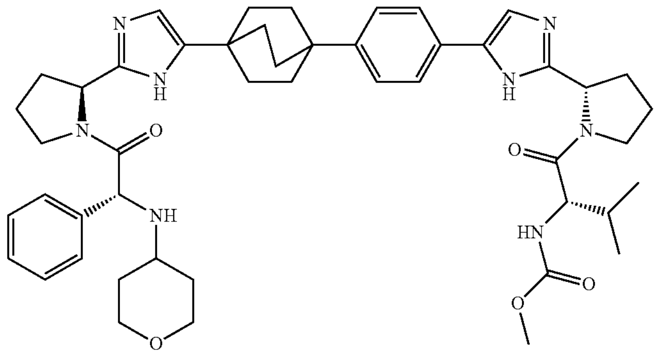 [SMILES: COC(=O)N[C@H](C(=O)N1CCC[C@H]1c1ncc(-c2ccc(C34CCC(c5cnc([C@@H]6CCCN6C(=O)[C@H](NC6CCOCC6)c6ccccc6)[nH]5)(CC3)CC4)cc2)[nH]1)C(C)C] | **** | 831.5 |
| 2065 | 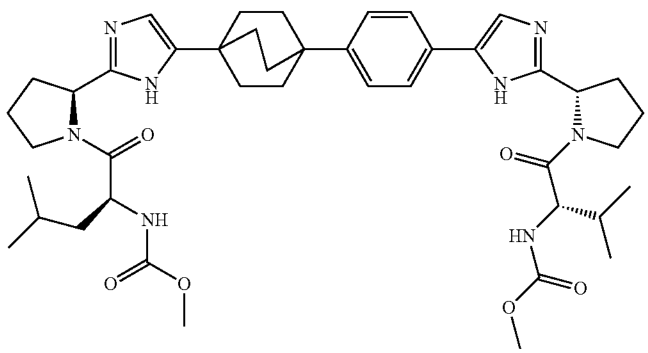 [SMILES: COC(=O)N[C@@H](CC(C)C)C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1] | **** | 785.5 |
| 2066 | 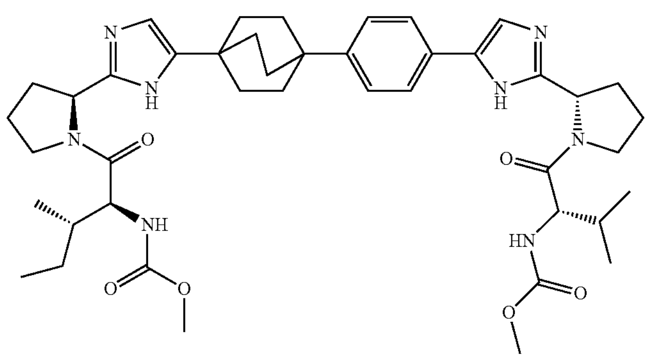 [SMILES: CC[C@H](C)[C@H](NC(=O)OC)C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1] | **** | 785.5 |
| 2067 | 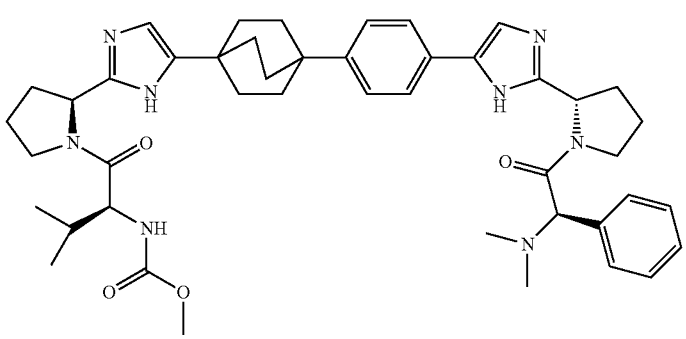 [SMILES: COC(=O)N[C@H](C(=O)N1CCC[C@H]1c1ncc(C23CCC(c4ccc(-c5cnc([C@@H]6CCCN6C(=O)[C@@H](c6ccccc6)N(C)C)[nH]5)cc4)(CC2)CC3)[nH]1)C(C)C] | **** | 775.5 |

TABLE 5-continued
| Compound # | Structure | Inhibition of HCV genotype 1b | MS (M + H+) |
|---|---|---|---|
| 2068 | 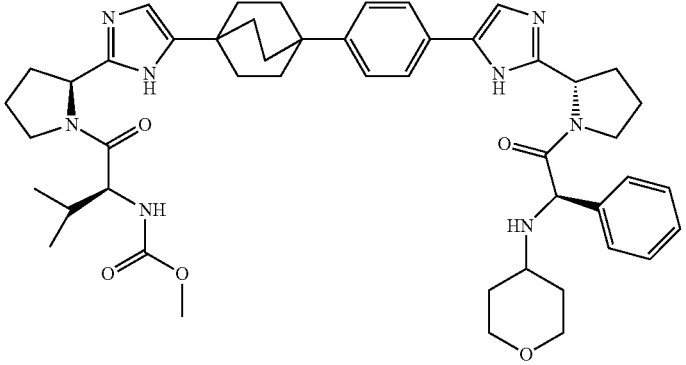 [SMILES: COC(=O)N[C@H](C(=O)N1CCC[C@H]1c1ncc(C23CCC(c4ccc(-c5cnc([C@@H]6CCCN6C(=O)[C@H](NC6CCOCC6)c6ccccc6)[nH]5)cc4)(CC2)CC3)[nH]1)C(C)C] | **** | 831.5 |
| 2069 | 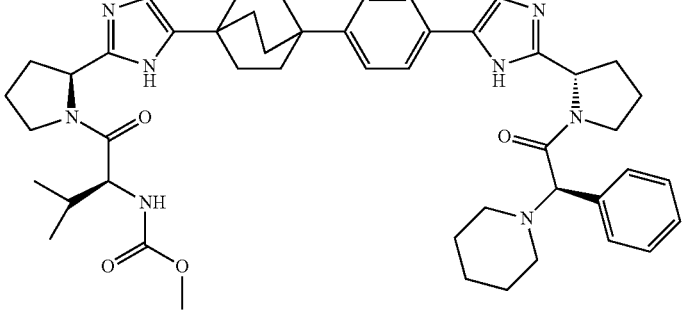 | **** | 815.5 |
| 2070 | 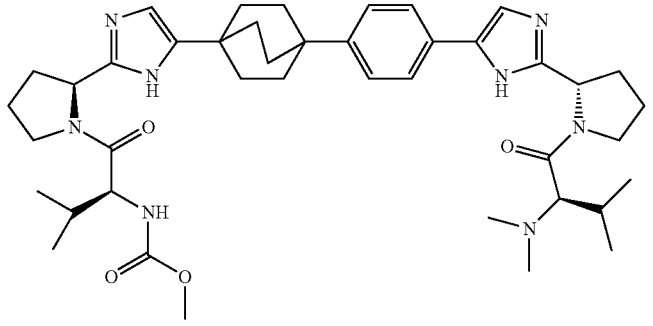 [SMILES: COC(=O)N[C@H](C(=O)N1CCC[C@H]1c1ncc(C23CCC(c4ccc(-c5cnc([C@@H]6CCCN6C(=O)[C@@H](C(C)C)N(C)C)[nH]5)cc4)(CC2)CC3)[nH]1)C(C)C] | **** | 741.5 |
| 2071 | 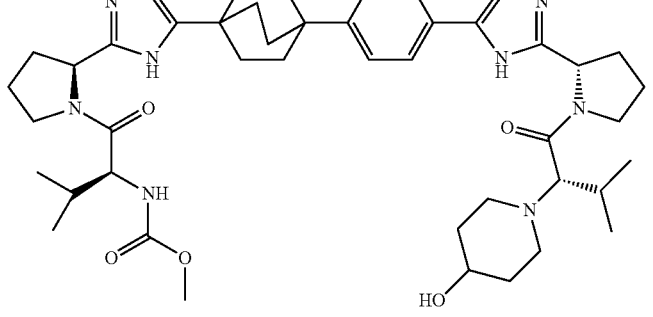 | **** | 797.5 |

TABLE 5-continued

| Compound # | Structure | Inhibition of HCV genotype 1b | MS (M + H⁺) |
|---|---|---|---|
| 2072 | 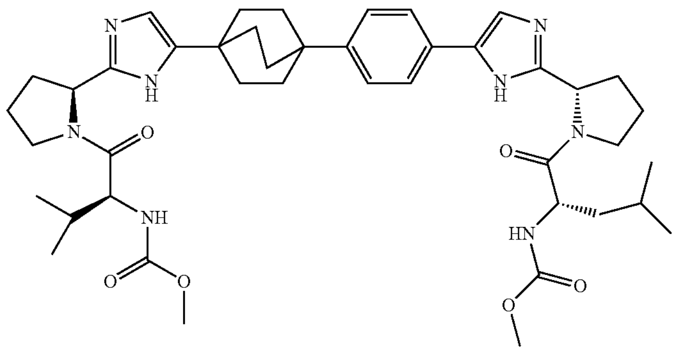 [SMILES: COC(=O)N[C@@H](CC(C)C)C(=O)N1CCC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1] | **** | 785.5 |
| 2073 | 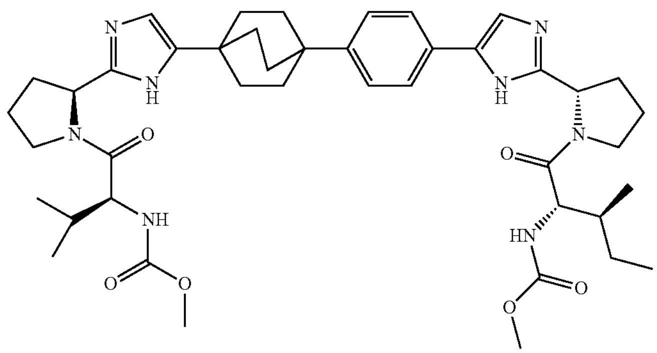 [SMILES: CC[C@H](C)[C@H](NC(=O)OC)C(=O)N1CCC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1] | **** | 785.5 |
| 2074 | 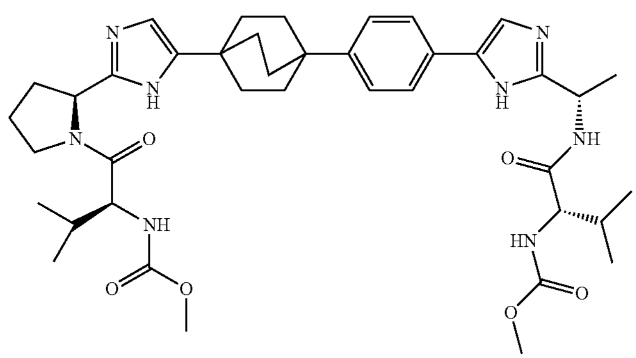 [SMILES: COC(=O)N[C@H](C(=O)N[C@@H](C)c1ncc(-c2ccc(C34CCC(c5cnc([C@@H]6CCCN6C(=O)[C@@H](NC(=O)OC)C(C)C)[nH]5)(CC3)CC4)cc2)[nH]1)C(C)C] | **** | 745.4 |
| 2075 | 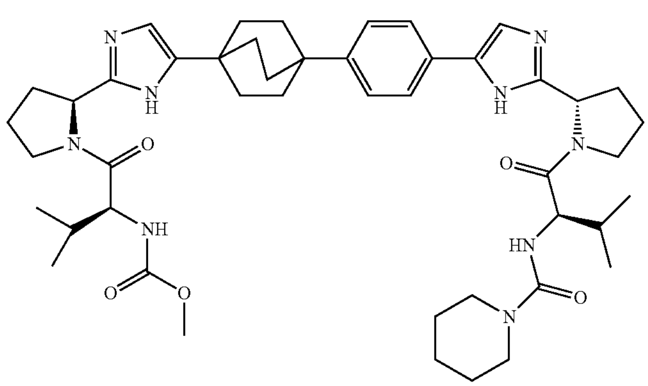 [SMILES: COC(=O)N[C@H](C(=O)N1CCC[C@H]1c1ncc(C23CCC(c4ccc(-c5cnc([C@@H]6CCCN6C(=O)[C@H](NC(=O)N6CCCCC6)C(C)C)[nH]5)cc4)(CC2)CC3)[nH]1)C(C)C] | **** | 824.5 |

TABLE 5-continued

| Compound # | Structure | Inhibition of HCV genotype 1b | MS (M + H⁺) |
|---|---|---|---|
| 2076 | 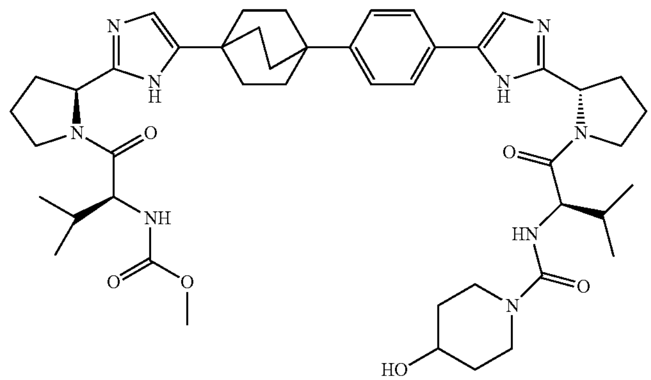 [SMILES: COC(=O)N[C@H](C(=O)N1CCC[C@H]1c1ncc(C23CCC(c4ccc(-c5cnc([C@@H]6CCCN6C(=O)[C@H](NC(=O)N6CCC(O)CC6)C(C)C)[nH]5)cc4)(CC2)CC3)[nH]1)C(C)C] | **** | 840.5 |
| 2077 | 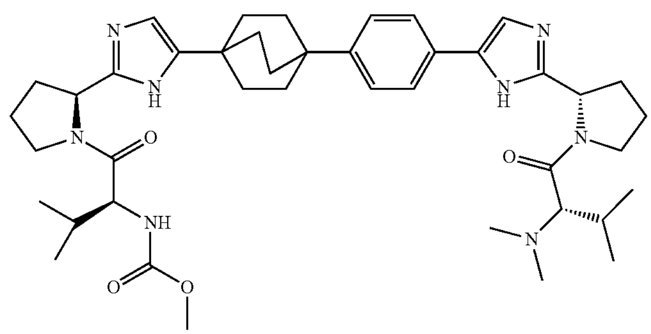 [SMILES: COC(=O)N[C@H](C(=O)N1CCC[C@H]1c1ncc(C23CCC(c4ccc(-c5cnc([C@@H]6CCCN6C(=O)[C@H](C(C)C)N(C)C)[nH]5)cc4)(CC2)CC3)[nH]1)C(C)C] | **** | 741.5 |
| 2078 | 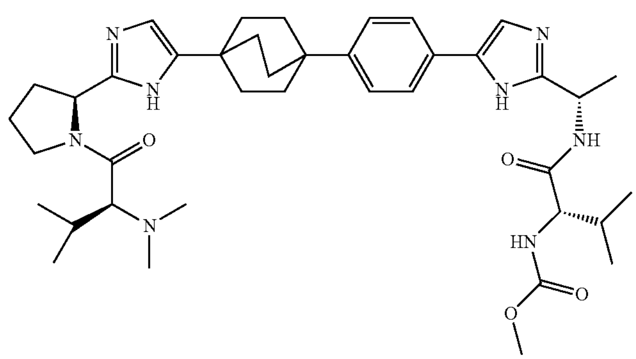 [SMILES: COC(=O)N[C@H](C(=O)N[C@@H](C)c1ncc(-c2ccc(C34CCC(c5cnc([C@@H]6CCCN6C(=O)[C@H](C(C)C)N(C)C)[nH]5)(CC3)CC4)cc2)[nH]1)C(C)C] | **** | 715.5 |
| 2079 | 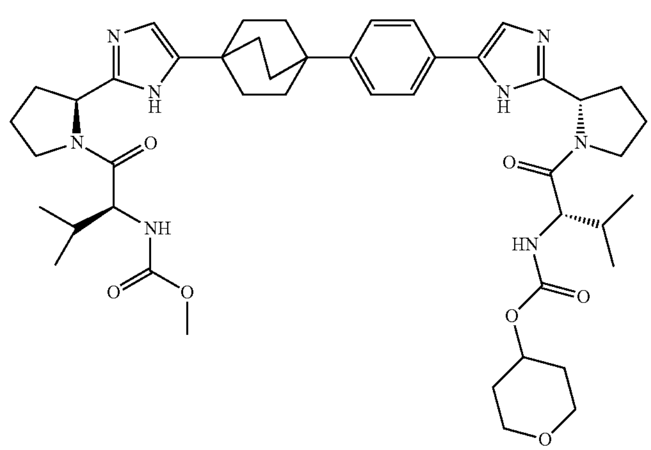 [SMILES: COC(=O)N[C@H](C(=O)N1CCC[C@H]1c1ncc(C23CCC(c4ccc(-c5cnc([C@@H]6CCCN6C(=O)[C@@H](NC(=O)OC6CCOCC6)C(C)C)[nH]5)cc4)(CC2)CC3)[nH]1)C(C)C] | *** | 841.5 |

TABLE 5-continued

| Compound # | Structure | Inhibition of HCV genotype 1b | MS (M + H⁺) |
|---|---|---|---|
| 2080 | 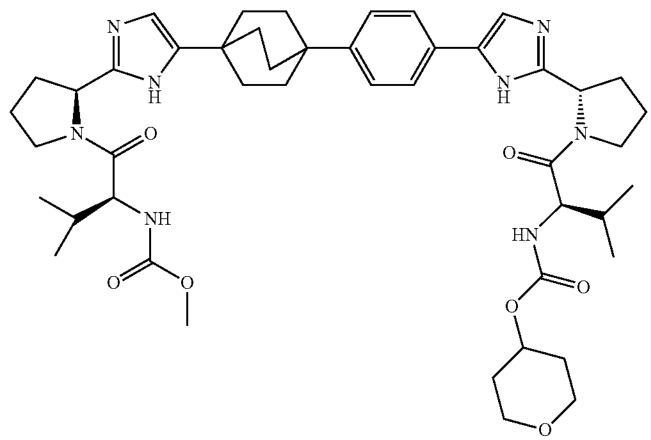 [SMILES: COC(=O)N[C@H](C(=O)N1CCC[C@H]1c1ncc(C23CCC(c4ccc(-c5cnc([C@@H]6CCCN6C(=O)[C@H](NC(=O)OC6CCOCC6)C(C)C)[nH]5)cc4)(CC2)CC3)[nH]1)C(C)C] | **** | 841.5 |
| 2081 | 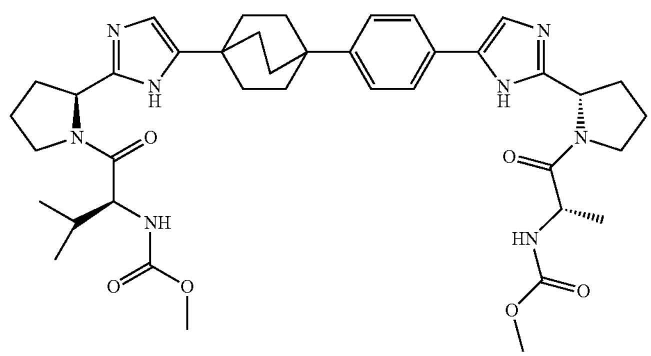 [SMILES: COC(=O)N[C@@H](C)C(=O)N1CCC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1] | **** | 742.4 |
| 2082 | 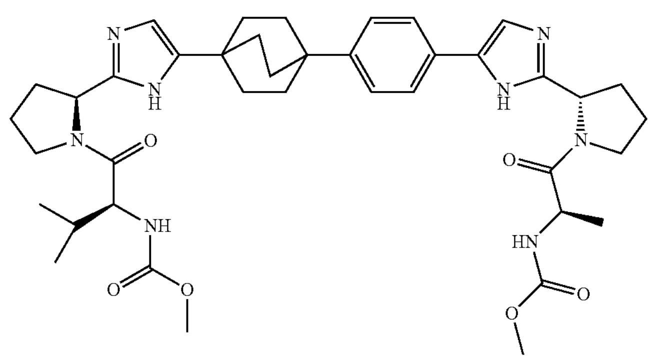 [SMILES: COC(=O)N[C@H](C(=O)N1CCC[C@H]1c1ncc(C23CCC(c4ccc(-c5cnc([C@@H]6CCCN6C(=O)[C@@H](C)NC(=O)OC)[nH]5)cc4)(CC2)CC3)[nH]1)C(C)C] | **** | 742.4 |
| 2083 | 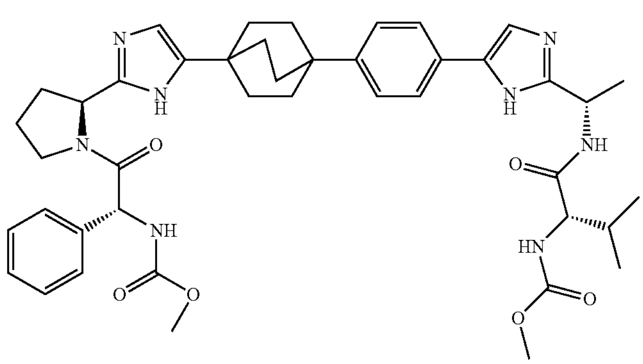 [SMILES: COC(=O)N[C@H](C(=O)N[C@@H](C)c1ncc(-c2ccc(C34CCC(c5cnc([C@@H]6CCCN6C(=O)[C@H](NC(=O)OC)c6ccccc6)[nH]5)(CC3)CC4)cc2)[nH]1)C(C)C] | **** | 779.4 |

TABLE 5-continued

| Compound # | Structure | Inhibition of HCV genotype 1b | MS (M + H⁺) |
|---|---|---|---|
| 2084 | 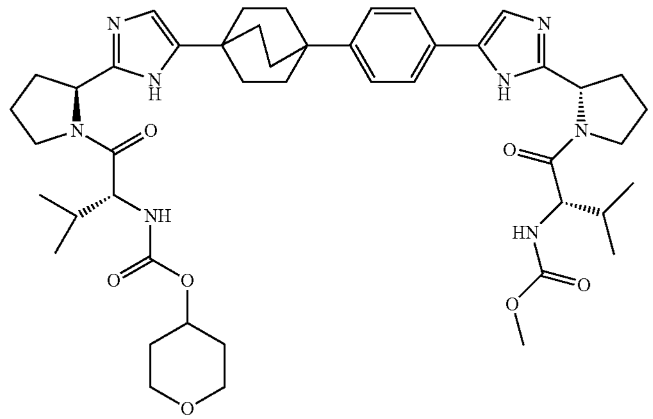 [SMILES: COC(=O)N[C@H](C(=O)N1CCC[C@H]1c1ncc(-c2ccc(C34CCC(c5cnc([C@@H]6CCCN6C(=O)[C@H](NC(=O)OC6CCOCC6)C(C)C)[nH]5)(CC3)CC4)cc2)[nH]1)C(C)C] | **** | 841.5 |
| 2085 | 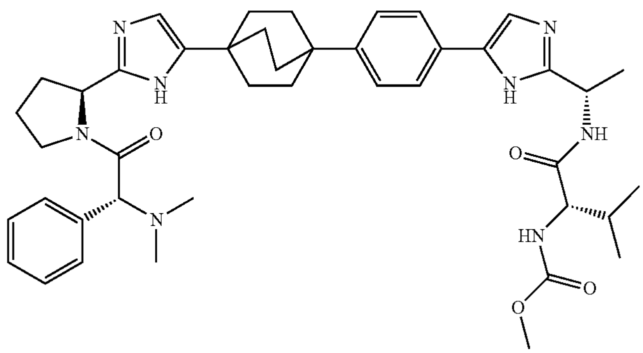 [SMILES: COC(=O)N[C@H](C(=O)N[C@@H](C)c1ncc(-c2ccc(C34CCC(c5cnc([C@@H]6CCCN6C(=O)[C@@H](c6ccccc6)N(C)C)[nH]5)(CC3)CC4)cc2)[nH]1)C(C)C] | **** | 749.4 |
| 908 | 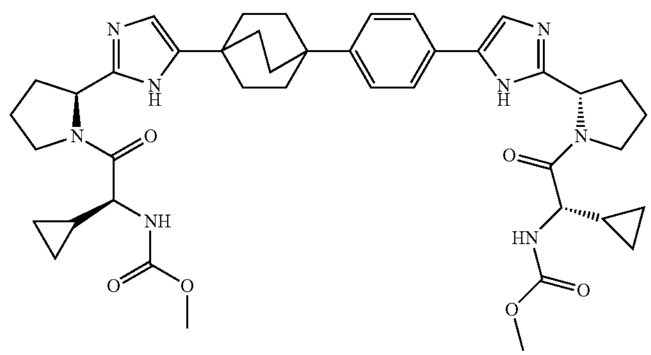 [SMILES: COC(=O)N[C@H](C(=O)N1CCC[C@H]1c1ncc(-c2ccc(C34CCC(c5cnc([C@@H]6CCCN6C(=O)[C@@H](NC(=O)OC)C6CC6)[nH]5)(CC3)CC4)cc2)[nH]1)C1CC1] | **** | 767.4 |
| 909 | 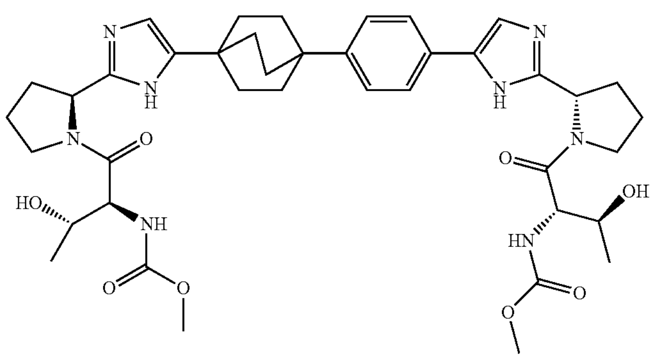 [SMILES: COC(=O)N[C@H](C(=O)N1CCC[C@H]1c1ncc(-c2ccc(C34CCC(c5cnc([C@@H]6CCCN6C(=O)[C@@H](NC(=O)OC)[C@H](C)O)[nH]5)(CC3)CC4)cc2)[nH]1)[C@H](C)O] | *** | 775.4 |

TABLE 5-continued
| Compound # | Structure | Inhibition of HCV genotype 1b | MS (M + H+) |
|---|---|---|---|
| 910 | 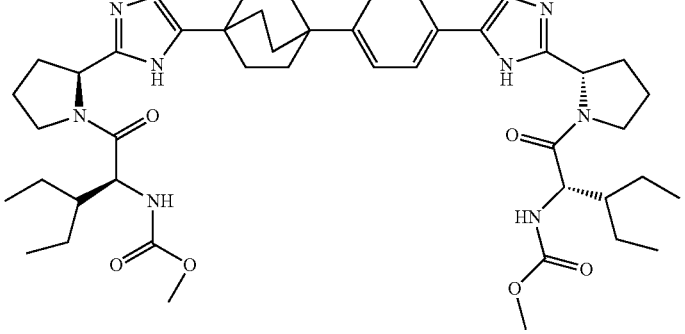 | **** | 827.5 |
| 911 | 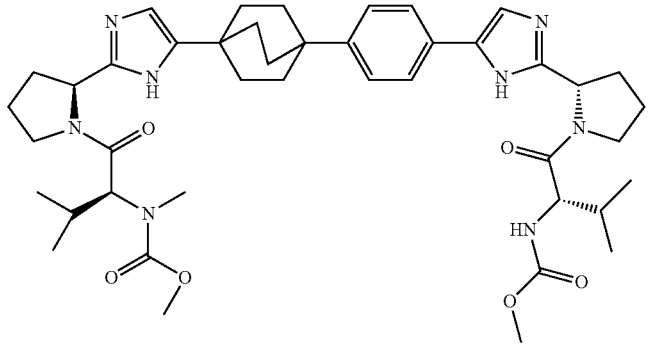 [SMILES: COC(=O)N[C@H](C(=O)N1CCC[C@H]1c1ncc(-c2ccc(C34CCC(c5cnc([C@@H]6CCCN6C(=O)[C@H](C(C)C)N(C)C(=O)OC)[nH]5)(CC3)CC4)cc2)[nH]1)C(C)C] | **** | 785.5 |
| 912 | 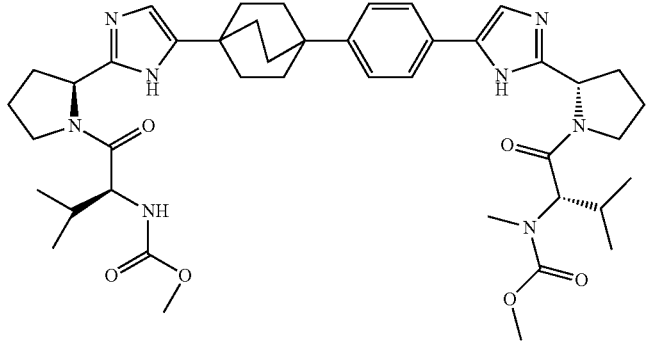 [SMILES: COC(=O)N[C@H](C(=O)N1CCC[C@H]1c1ncc(C23CCC(c4ccc(-c5cnc([C@@H]6CCCN6C(=O)[C@H](C(C)C)N(C)C(=O)OC)[nH]5)cc4)(CC2)CC3)[nH]1)C(C)C] | **** | 785.5 |
| 913 | 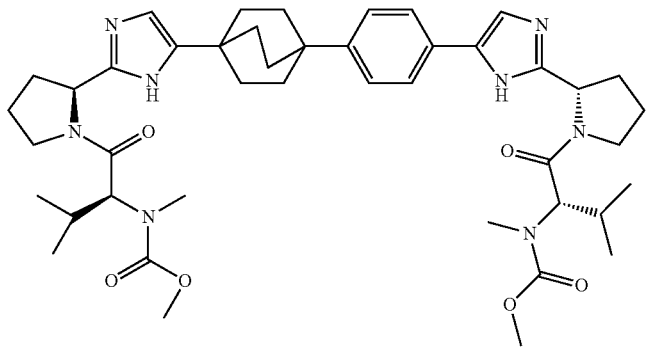 [SMILES: COC(=O)N(C)[C@H](C(=O)N1CCC[C@H]1c1ncc(-c2ccc(C34CCC(c5cnc([C@@H]6CCCN6C(=O)[C@H](C(C)C)N(C)C(=O)OC)[nH]5)(CC3)CC4)cc2)[nH]1)C(C)C] | **** | 799.5 |

TABLE 5-continued

| Compound # | Structure | Inhibition of HCV genotype 1b | MS (M + H⁺) |
|---|---|---|---|
| 914 | 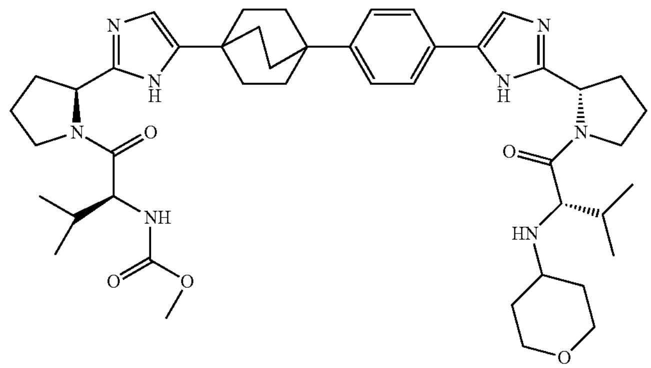 [SMILES: COC(=O)N[C@H](C(=O)N1CCC[C@H]1c1ncc(C23CCC(c4ccc(-c5cnc([C@@H]6CCCN6C(=O)[C@@H](NC6CCOCC6)C(C)C)[nH]5)cc4)(CC2)CC3)[nH]1)C(C)C] | ** | 797.5 |
| 915 | 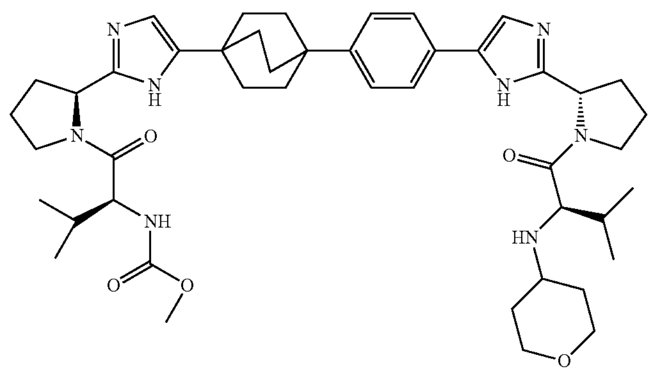 [SMILES: COC(=O)N[C@H](C(=O)N1CCC[C@H]1c1ncc(C23CCC(c4ccc(-c5cnc([C@@H]6CCCN6C(=O)[C@H](NC6CCOCC6)C(C)C)[nH]5)cc4)(CC2)CC3)[nH]1)C(C)C] | **** | 797.5 |
| 916 | 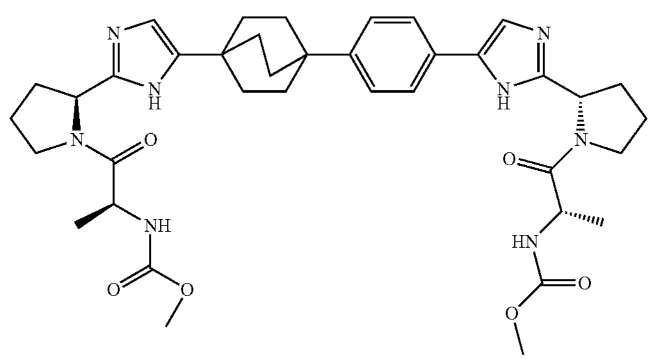 [SMILES: COC(=O)N[C@@H](C)C(=O)N1CCC[C@H]1c1ncc(-c2ccc(C34CCC(c5cnc([C@@H]6CCCN6C(=O)[C@H](C)NC(=O)OC)[nH]5)(CC3)CC4)cc2)[nH]1] | **** | 715.4 |
| 917 | 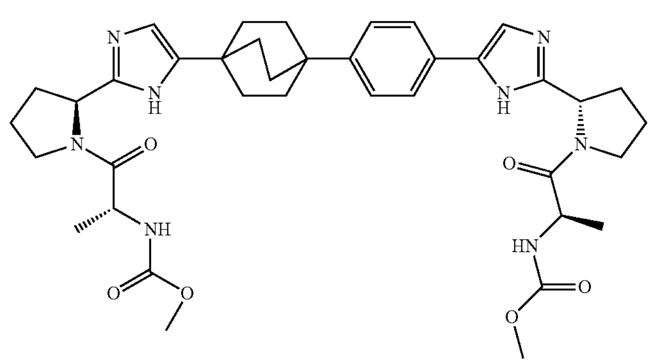 [SMILES: COC(=O)N[C@H](C)C(=O)N1CCC[C@H]1c1ncc(-c2ccc(C34CCC(c5cnc([C@@H]6CCCN6C(=O)[C@@H](C)NC(=O)OC)[nH]5)(CC3)CC4)cc2)[nH]1] | **** | 715.4 |

TABLE 5-continued
| Compound # | Structure | Inhibition of HCV genotype 1b | MS (M + H+) |
|---|---|---|---|
| 918 | 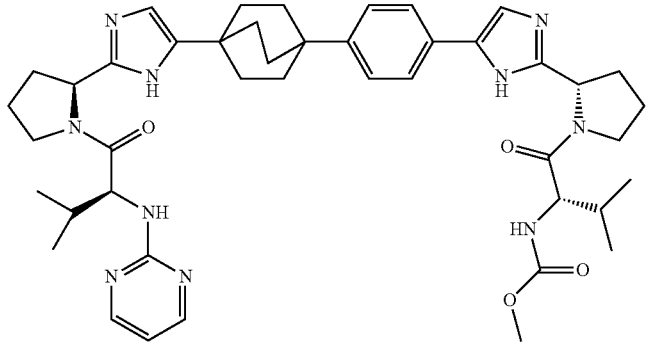 [SMILES: COC(=O)N[C@H](C(=O)N1CCC[C@H]1c1ncc(-c2ccc(C34CCC(c5cnc([C@@H]6CCCN6C(=O)[C@@H](Nc6ncccn6)C(C)C)[nH]5)(CC3)CC4)cc2)[nH]1)C(C)C] | **** | 791.5 |
| 919 | 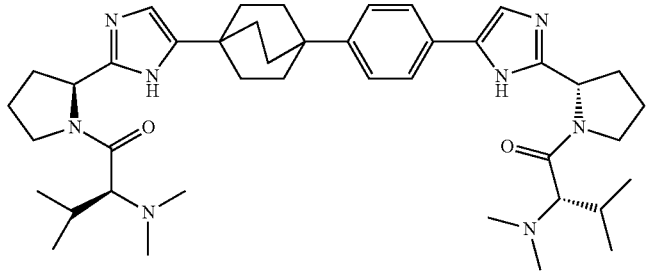 [SMILES: CC(C)[C@@H](C(=O)N1CCC[C@H]1c1ncc(-c2ccc(C34CCC(c5cnc([C@@H]6CCCN6C(=O)[C@H](C(C)C)N(C)C)[nH]5)(CC3)CC4)cc2)[nH]1)N(C)C] | ** | 711.5 |
| 920 | 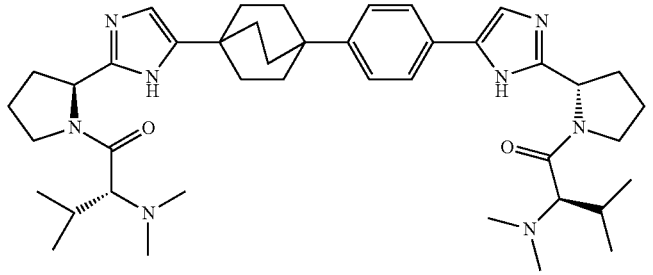 [SMILES: CC(C)[C@H](C(=O)N1CCC[C@H]1c1ncc(-c2ccc(C34CCC(c5cnc([C@@H]6CCCN6C(=O)[C@@H](C(C)C)N(C)C)[nH]5)(CC3)CC4)cc2)[nH]1)N(C)C] | ** | 711.5 |
| 2086 | 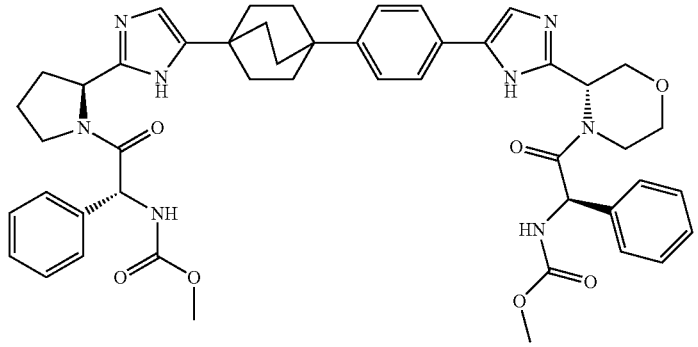 [SMILES: COC(=O)N[C@@H](C(=O)N1CCOC[C@H]1c1ncc(-c2ccc(C34CCC(c5cnc([C@@H]6CCCN6C(=O)[C@H](NC(=O)OC)c6ccccc6)[nH]5)(CC3)CC4)cc2)[nH]1)c1ccccc1] | **** | 855.4 |

TABLE 5-continued

| Compound # | Structure | Inhibition of HCV genotype 1b | MS (M + H⁺) |
|---|---|---|---|
| 2087 | 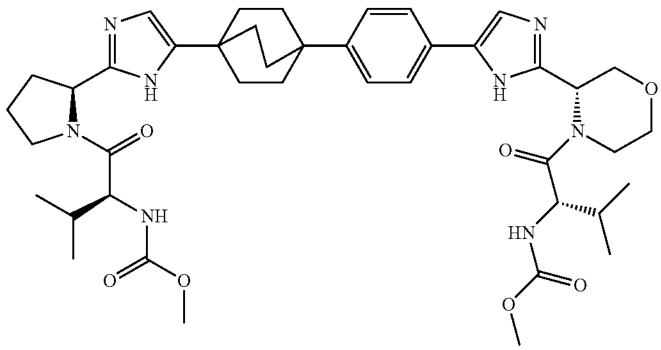 [SMILES: COC(=O)N[C@H](C(=O)N1CCOC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1)C(C)C] | **** | 787.4 |
| 2088 | 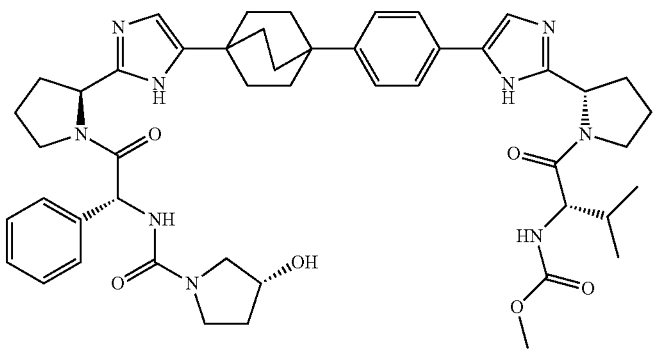 [SMILES: COC(=O)N[C@H](C(=O)N1CCC[C@H]1c1ncc(-c2ccc(C34CCC(c5cnc([C@@H]6CCCN6C(=O)[C@H](NC(=O)N6CC[C@@H](O)C6)c6ccccc6)[nH]5)(CC3)CC4)cc2)[nH]1)C(C)C] | **** | 860.5 |
| 2089 | 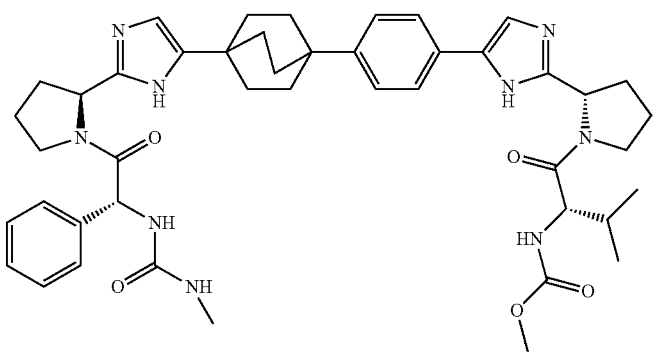 [SMILES: CNC(=O)N[C@@H](C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1)c1ccccc1] | **** | 804.4 |
| 2090 | 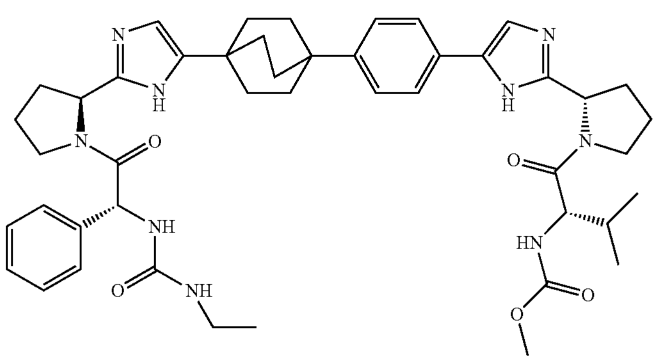 [SMILES: CCNC(=O)N[C@@H](C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1)c1ccccc1] | **** | 818.5 |

TABLE 5-continued
| Compound # | Structure | Inhibition of HCV genotype 1b | MS (M + H⁺) |
|---|---|---|---|
| 2091 | 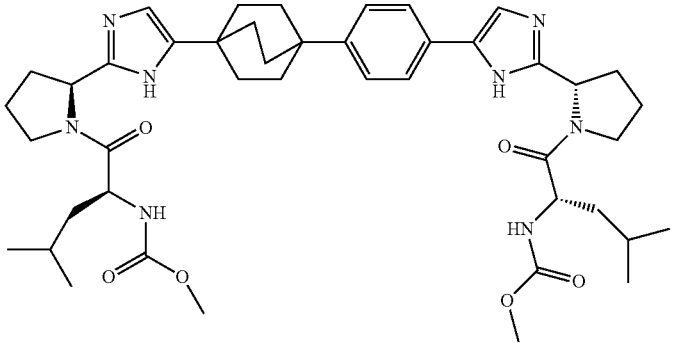 [SMILES: COC(=O)N[C@@H](CC(C)C)C(=O)N1CCC[C@H]1c1ncc(-c2ccc(C34CCC(c5cnc([C@@H]6CCCN6C(=O)[C@H](CC(C)C)NC(=O)OC)[nH]5)(CC3)CC4)cc2)[nH]1] | **** | 799.5 |
| 2092 | 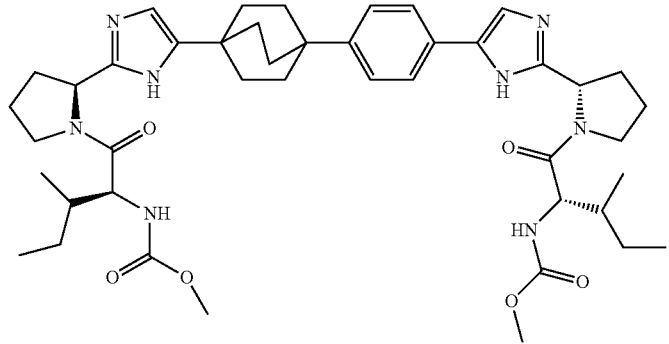 [SMILES: CCC(C)[C@H](NC(=O)OC)C(=O)N1CCC[C@H]1c1ncc(-c2ccc(C34CCC(c5cnc([C@@H]6CCCN6C(=O)[C@@H](NC(=O)OC)C(C)CC)[nH]5)(CC3)CC4)cc2)[nH]1] | **** | 799.5 |
| 2093 | 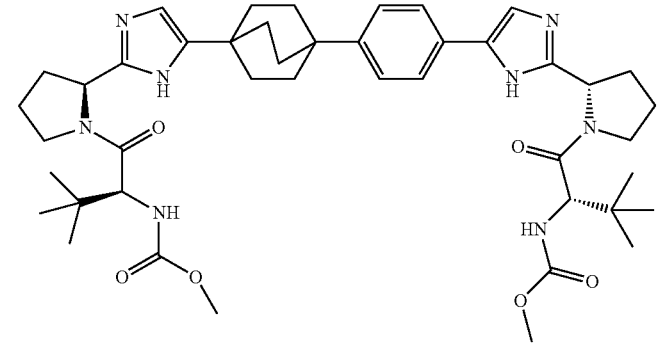 [SMILES: COC(=O)N[C@H](C(=O)N1CCC[C@H]1c1ncc(-c2ccc(C34CCC(c5cnc([C@@H]6CCCN6C(=O)[C@@H](NC(=O)OC)C(C)(C)C)[nH]5)(CC3)CC4)cc2)[nH]1)C(C)(C)C] | **** | 799.5 |
| 2094 | 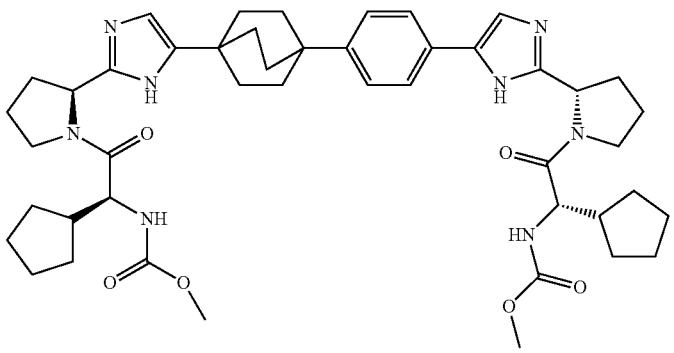 [SMILES: COC(=O)N[C@H](C(=O)N1CCC[C@H]1c1ncc(-c2ccc(C34CCC(c5cnc([C@@H]6CCCN6C(=O)[C@@H](NC(=O)OC)C6CCCC6)[nH]5)(CC3)CC4)cc2)[nH]1)C1CCCC1] | **** | 823.5 |

TABLE 5-continued

| Compound # | Structure | Inhibition of HCV genotype 1b | MS (M + H+) |
|---|---|---|---|
| 2095 | 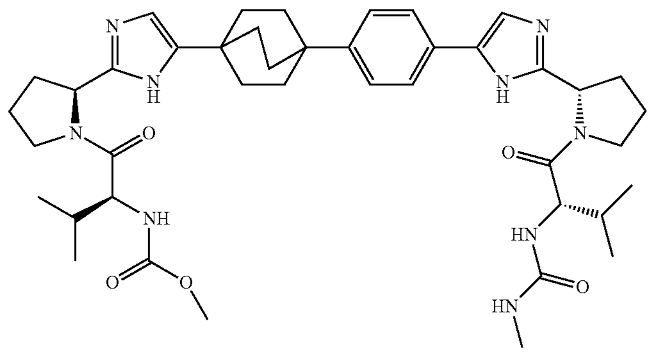 [SMILES: CNC(=O)N[C@H](C(=O)N1CCC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1)C(C)C] | **** | 770.5 |
| 2096 | 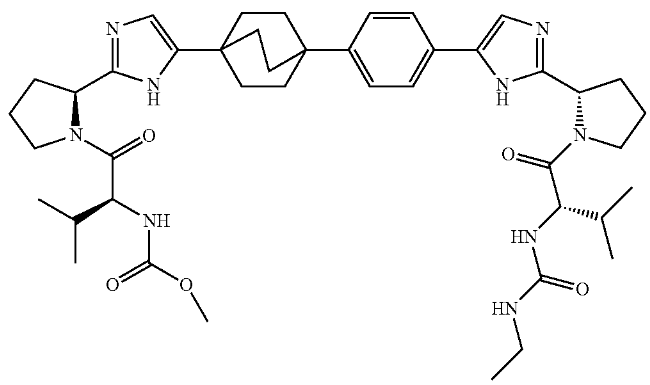 [SMILES: CCNC(=O)N[C@H](C(=O)N1CCC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1)C(C)C] | **** | 784.5 |
| 2097 | 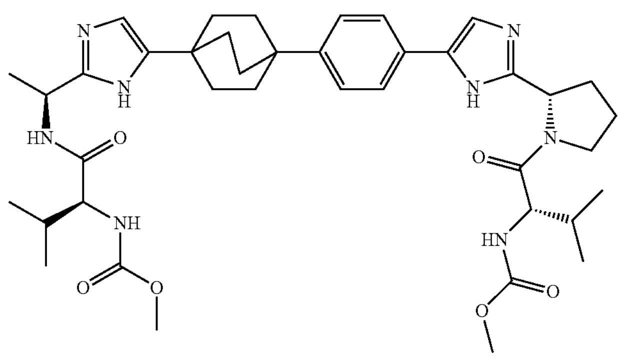 [SMILES: COC(=O)N[C@H](C(=O)N[C@@H](C)c1ncc(C23CCC(c4ccc(-c5cnc([C@@H]6CCCN6C(=O)[C@@H](NC(=O)OC)C(C)C)[nH]5)cc4)(CC2)CC3)[nH]1)C(C)C] | **** | 745.4 |
| 2098 | 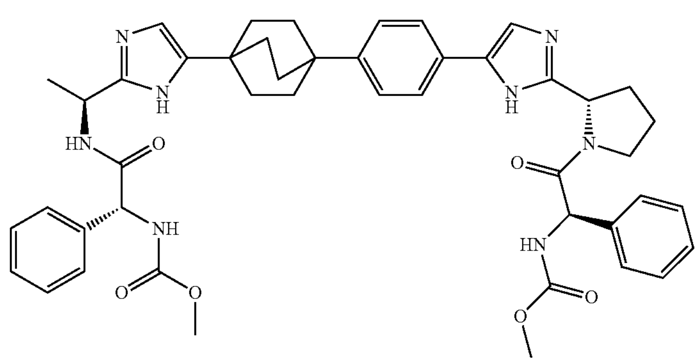 [SMILES: COC(=O)N[C@@H](C(=O)N[C@@H](C)c1ncc(C23CCC(c4ccc(-c5cnc([C@@H]6CCCN6C(=O)[C@H](NC(=O)OC)c6ccccc6)[nH]5)cc4)(CC2)CC3)[nH]1)c1ccccc1] | **** | 813.4 |

TABLE 5-continued

| Compound # | Structure | Inhibition of HCV genotype 1b | MS (M + H+) |
|---|---|---|---|
| 2099 | 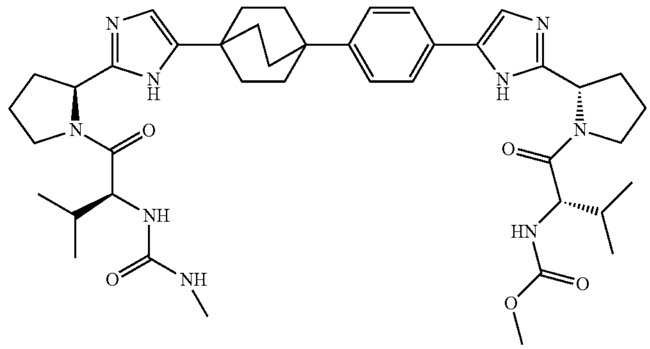 [SMILES: CNC(=O)N[C@H](C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1)C(C)C] | **** | 770.5 |
| 2100 | 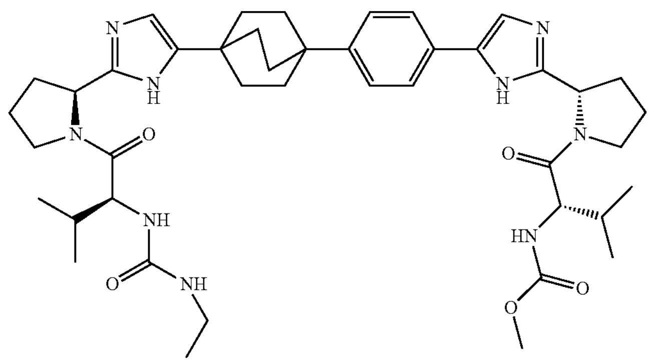 [SMILES: CCNC(=O)N[C@H](C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1)C(C)C] | **** | 784.5 |
| 2101 | 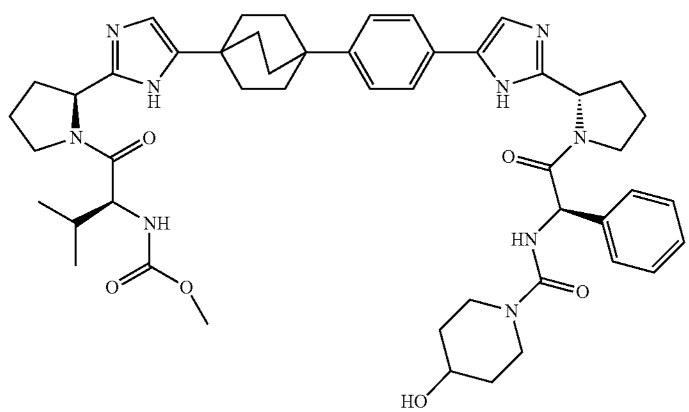 [SMILES: COC(=O)N[C@H](C(=O)N1CCC[C@H]1c1ncc(C23CCC(c4ccc(-c5cnc([C@@H]6CCCN6C(=O)[C@H](NC(=O)N6CCC(O)CC6)c6ccccc6)[nH]5)cc4)(CC2)CC3)[nH]1)C(C)C] | **** | 874.5 |
| 2102 | 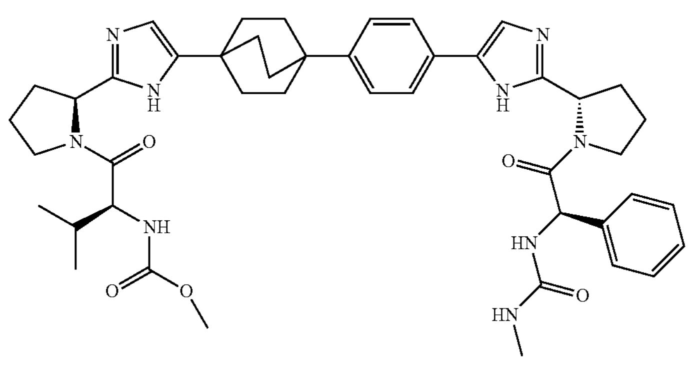 [SMILES: CNC(=O)N[C@@H](C(=O)N1CCC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1)c1ccccc1] | **** | 804.4 |

TABLE 5-continued

| Compound # | Structure | Inhibition of HCV genotype 1b | MS (M + H⁺) |
|---|---|---|---|
| 2103 | 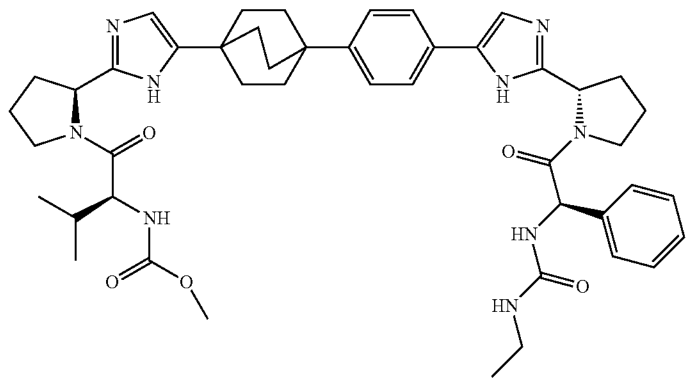 [SMILES: CCNC(=O)N[C@@H](C(=O)N1CCC[C@H]1c1ncc(-c2ccc(C34CCC(c5cnc([C@@H]6CCCN6C(=O)[C@@H](NC(=O)OC)C(C)C)[nH]5)(CC3)CC4)cc2)[nH]1)c1ccccc1] | **** | 818.5 |
| 2104 | 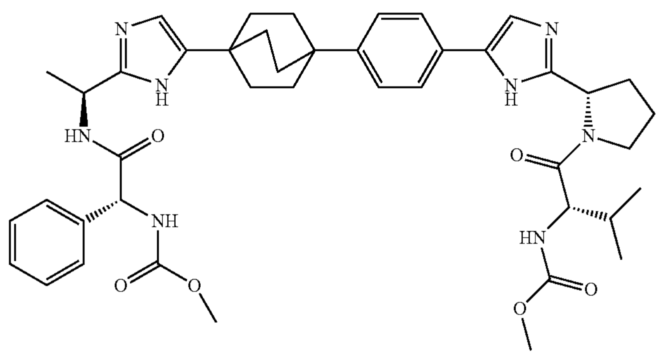 [SMILES: COC(=O)N[C@H](C(=O)N1CCC[C@H]1c1ncc(-c2ccc(C34CCC(c5cnc([C@H](C)NC(=O)[C@H](NC(=O)OC)c6ccccc6)[nH]5)(CC3)CC4)cc2)[nH]1)C(C)C] | **** | 779.4 |
| 2105 | 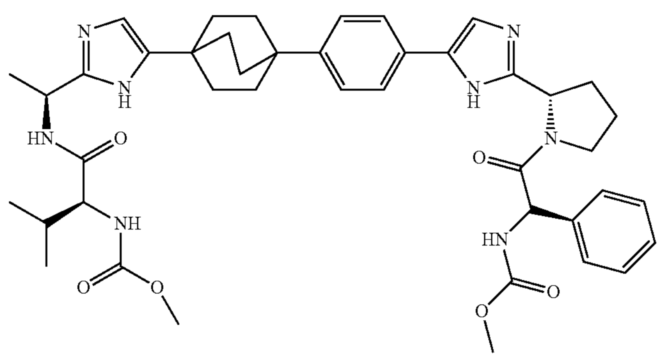 | **** | 779.4 |
| 2106 | 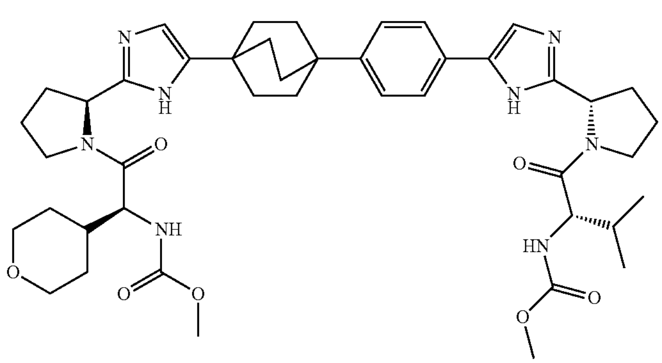 [SMILES: COC(=O)N[C@H](C(=O)N1CCC[C@H]1c1ncc(-c2ccc(C34CCC(c5cnc([C@@H]6CCCN6C(=O)[C@@H](NC(=O)OC)C6CCOCC6)[nH]5)(CC3)CC4)cc2)[nH]1)C(C)C] | **** | 813.5 |

TABLE 5-continued

| Compound # | Structure | Inhibition of HCV genotype 1b | MS (M + H⁺) |
|---|---|---|---|
| 2107 | 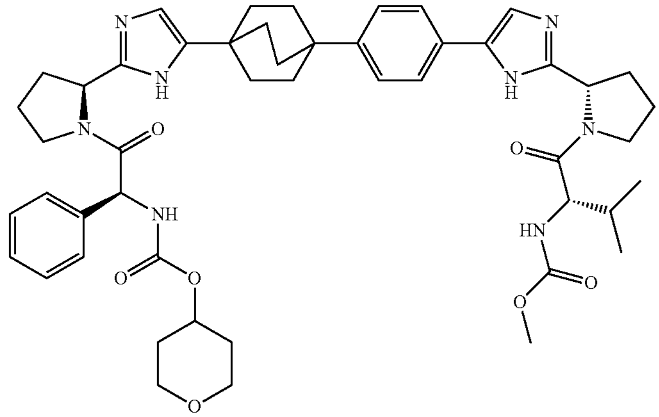 [SMILES: COC(=O)N[C@H](C(=O)N1CCC[C@H]1c1ncc(-c2ccc(C34CCC(c5cnc([C@@H]6CCCN6C(=O)[C@@H](NC(=O)OC6CCOCC6)c6ccccc6)[nH]5)(CC3)CC4)cc2)[nH]1)C(C)C] | **** | 875.5 |
| 2108 | 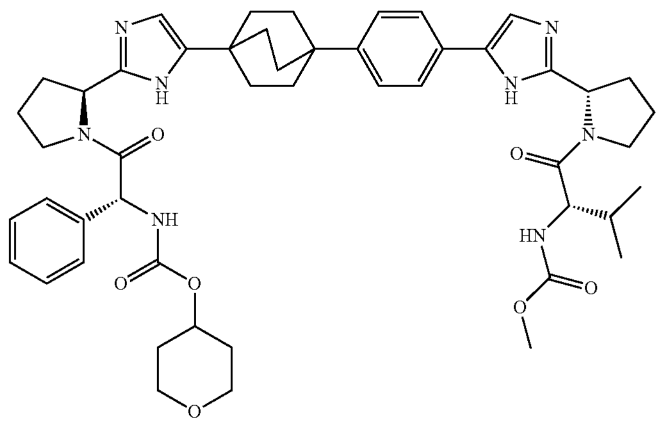 [SMILES: COC(=O)N[C@H](C(=O)N1CCC[C@H]1c1ncc(-c2ccc(C34CCC(c5cnc([C@@H]6CCCN6C(=O)[C@H](NC(=O)OC6CCOCC6)c6ccccc6)[nH]5)(CC3)CC4)cc2)[nH]1)C(C)C] | **** | 875.5 |
| 2109 | 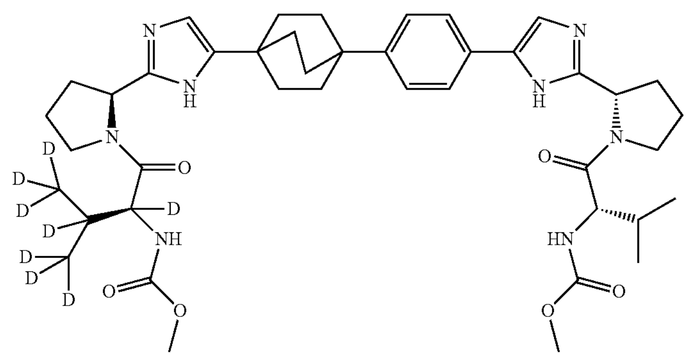 [SMILES: [2H]C([2H])([2H])C([2H])(C([2H])([2H])[2H])[C@@]([2H])(NC(=O)OC)C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1] | | 779.5 |
| 2110 | 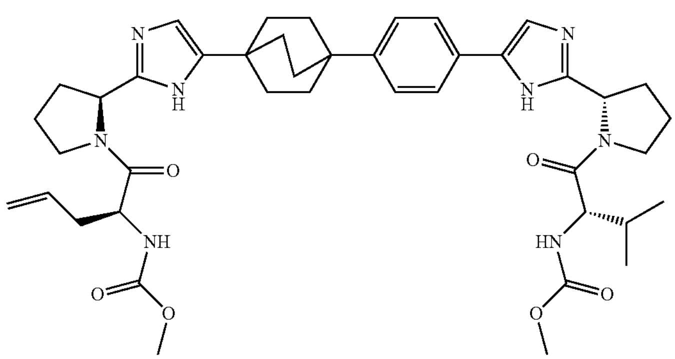 [SMILES: C=CC[C@H](NC(=O)OC)C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1] | | 769.4 |

TABLE 5-continued

| Compound # | Structure | Inhibition of HCV genotype 1b | MS (M + H+) |
|---|---|---|---|
| 2111 | 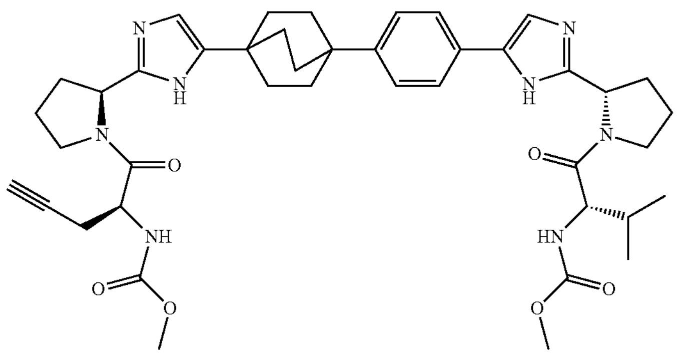 [SMILES: C#CC[C@H](NC(=O)OC)C(=O)N1CCC[C@H]1c1ncc(C23CCC(c4ccc(-c5cnc([C@@H]6CCCN6C(=O)[C@@H](NC(=O)OC)C(C)C)[nH]5)cc4)(CC2)CC3)[nH]1] | | 767.4 |
| 2112 | 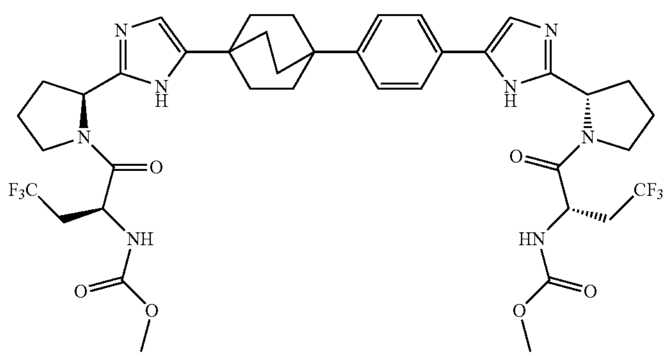 [SMILES: COC(=O)N[C@@H](CC(F)(F)F)C(=O)N1CCC[C@H]1c1ncc(-c2ccc(C34CCC(c5cnc([C@@H]6CCCN6C(=O)[C@H](CC(F)(F)F)NC(=O)OC)[nH]5)(CC3)CC4)cc2)[nH]1] | | |

TABLE 6

| Compound # | Structure | Inhibition of HCV genotype 1b | MS (M + H+) |
|---|---|---|---|
| 850 | 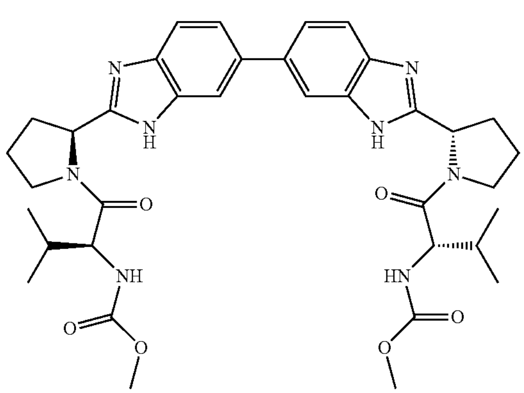 [SMILES: COC(=O)N[C@H](C(=O)N1CCC[C@H]1c1nc2ccc(-c3ccc4nc([C@@H]5CCCN5C(=O)[C@@H](NC(=O)OC)C(C)C)[nH]c4c3)cc2[nH]1)C(C)C] | **** | 687.4 |

TABLE 7

| Compound # | Structure | Inhibition of HCV genotype 1b | MS (M + H+) |
|---|---|---|---|
| 2113 | 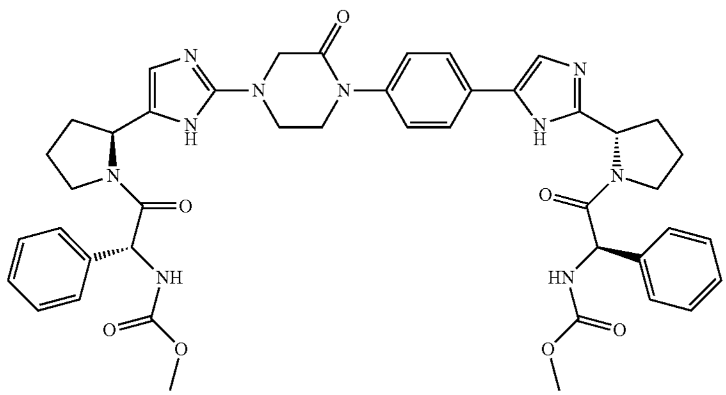 [SMILES: COC(=O)N[C@@H](C(=O)N1CCC[C@H]1c1cnc(N2CCN(c3ccc(-c4cnc([C@@H]5CCCN5C(=O)[C@H](NC(=O)OC)c5ccccc5)[nH]4)cc3)C(=O)C2)[nH]1)c1ccccc1] | **** | 829.4 |
| 2114 | 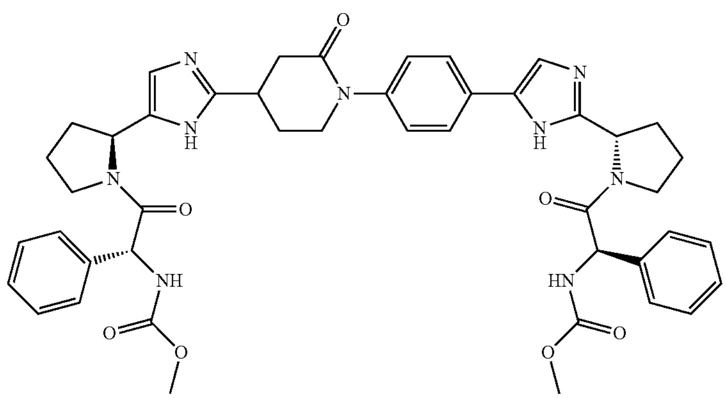 [SMILES: COC(=O)N[C@@H](C(=O)N1CCC[C@H]1c1cnc(C2CCN(c3ccc(-c4cnc([C@@H]5CCCN5C(=O)[C@H](NC(=O)OC)c5ccccc5)[nH]4)cc3)C(=O)C2)[nH]1)c1ccccc1] | | |
| 2115 | 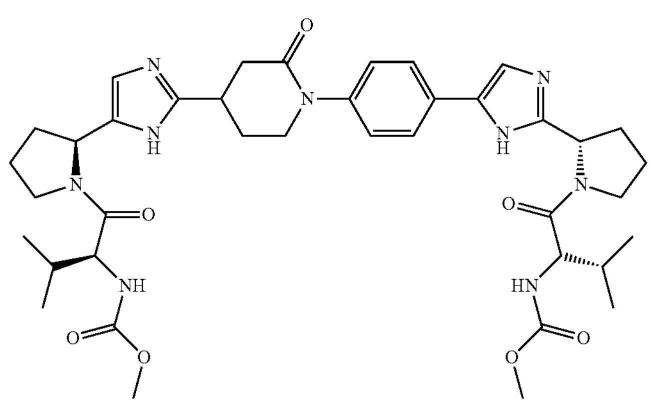 | | |

TABLE 8

| Compound # | Structure | Inhibition of HCV genotype 1b | MS (M + H⁺) |
|---|---|---|---|
| 2116 | 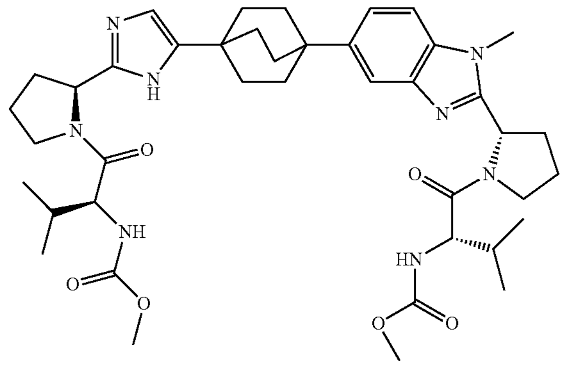 [SMILES: COC(=O)N[C@H](C(=O)N1CCC[C@H]1c1ncc(C23CCC(c4ccc5c(c4)nc([C@@H]4CCCN4C(=O)[C@@H](NC(=O)OC)C(C)C)n5C)(CC2)CC3)[nH]1)C(C)C] | ** | 759.4 |
| 2117 | 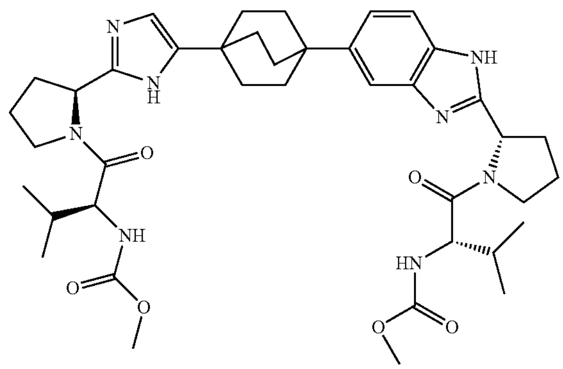 [SMILES: COC(=O)N[C@H](C(=O)N1CCC[C@H]1c1ncc(C23CCC(c4ccc5[nH]c([C@@H]6CCCN6C(=O)[C@@H](NC(=O)OC)C(C)C)nc5c4)(CC2)CC3)[nH]1)C(C)C] | | |
| 2118 | 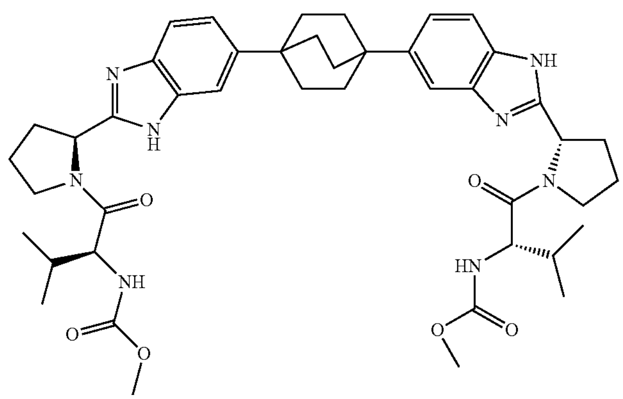 [SMILES: COC(=O)N[C@H](C(=O)N1CCC[C@H]1c1nc2cc(C34CCC(c5ccc6nc([C@@H]7CCCN7C(=O)[C@@H](NC(=O)OC)C(C)C)[nH]c6c5)(CC3)CC4)ccc2[nH]1)C(C)C] | | |
| 2119 | 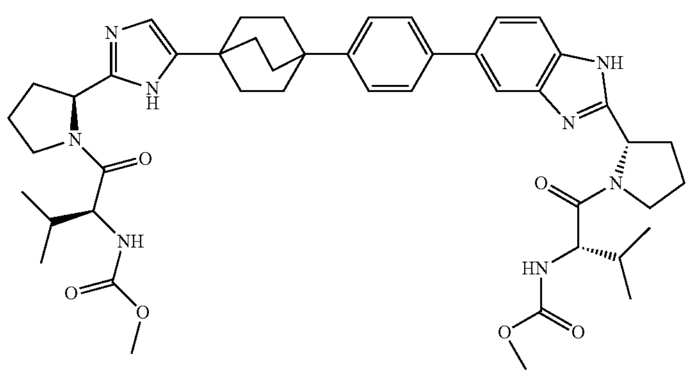 [SMILES: COC(=O)N[C@H](C(=O)N1CCC[C@H]1c1ncc(C23CCC(c4ccc(-c5ccc6[nH]c([C@@H]7CCCN7C(=O)[C@@H](NC(=O)OC)C(C)C)nc6c5)cc4)(CC2)CC3)[nH]1)C(C)C] | | |

TABLE 9

| Compound # | Structure | Inhibition of HCV genotype 1b | MS (M + H⁺) |
|---|---|---|---|
| 2120 | 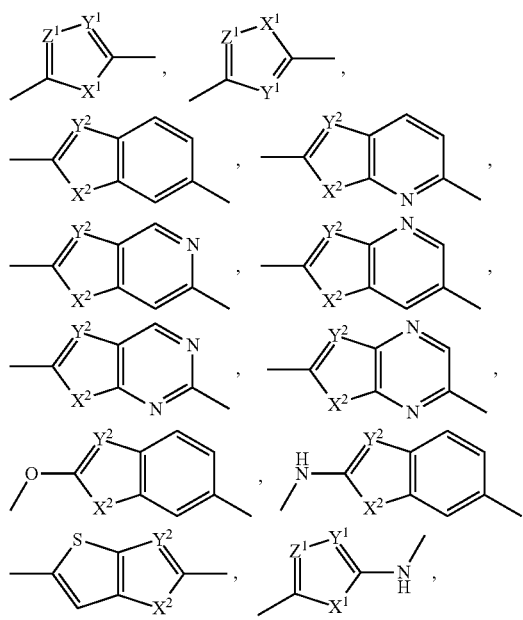 | **** | 833.4 |

The invention claimed is:
1. A compound having formula I:

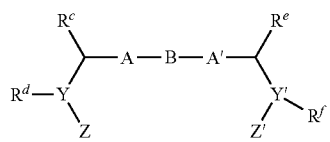

wherein,
A and A' are independently selected from the group consisting of a single bond, —(CR₂)ₙ—O—(CR₂)ₚ—, —(CR₂)ₙ—N(Rᴺ)—(CR₂)ₚ—, —(CR₂)ₙ—S(O)ₖ—N(Rᴺ)—(CR₂)ₚ—, —(CR₂)ₙ—C(O)—N(Rᴺ)—(CR₂)ₚ—, —(CR₂)ₙ—N(Rᴺ)—C(O)—N(Rᴺ)—(CR₂)ₚ—, —(CR₂)ₙ—C(O)—O—(CR₂)ₚ—, —(CR₂)ₙ—N(Rᴺ)—S(O)ₖ—N(Rᴺ)—(CR₂)ₚ— and —(CR₂)ₙ—N(Rᴺ)—C(O)—O—(CR₂)ₚ— and a heteroaryl group selected from the group consisting of

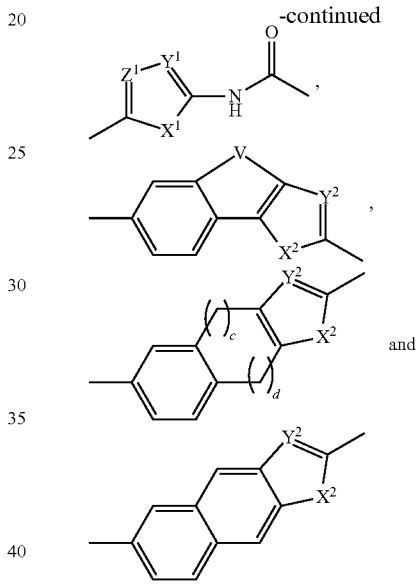

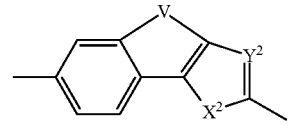

wherein:
X¹ is CH₂, NH, O or S,
Y¹, Y² and Z¹ are each independently CH or N,
X² is NH, O or S,
V is —CH₂—CH₂—, —CH═CH—, —N═CH—, (CH₂)ₐ—N(Rᴺ)—(CH₂)ᵦ— or —(CH₂)ₐ—O—(CH₂)ᵦ—, wherein a and b are independently 0, 1, 2, or 3 with the proviso that a and b are not both 0, optionally includes 1 or 2 nitrogens as heteroatoms on the phenyl residue,
the carbons of the heteroaryl group are each independently optionally substituted with a substituent selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, the nitrogens, if present, of the heteroaryl group are each independently optionally substituted with a substituent selected from the group consisting of —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, a and b are independently 1, 2, or 3, c and d are independently 1 or 2, n and p are independently 0, 1, 2 or 3, k is 0, 1, or 2, each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, each $R^N$ is independently selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and wherein for each A and A', B may be attached to either side of A and A' so that in the example of A or A' being

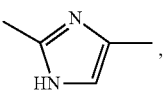

the A-B-A' can be any of:

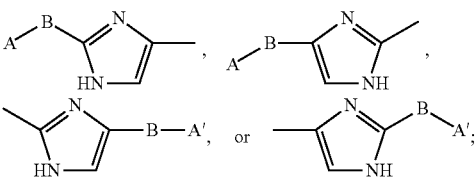

B is Q or Q-Q, wherein each Q is independently selected from the group consisting of a cycloalkyl group, cycloalkenyl group, heterocycle, aryl group or heteroaryl group, with the proviso that only one Q is a six member aromatic ring when B is Q-Q and with the proviso that if B is Q-Q, any Q is that is polycyclic is connected to the remainder of the molecule through only one cycle of the polycycle;

$R^c$, $R^d$, $R^e$ and $R^f$ are each independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 6-membered heterocycle or heteroaryl ring, and $R^e$ and $R^f$ are optionally joined to form a 4- to 8-membered heterocycle which is optionally fused to another 3- to 6-membered heterocycle or heteroaryl ring;

Y and Y' are each independently nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—$(CR^4_2)_t$—$NR^5$—$(CR^4_2)_t]_u$—U—$(CR^4_2)_t$—$NR^7$—$(CR^4_2)_t$—$R^8$, —U—$(CR^4_2)_t$—$R^8$ and —[U—$(CR^4_2)_t$—$NR^5$—$(CR^4_2)_t]_u$—U—$(CR^4_2)_t$—O—$(CR^4_2)_t$—$R^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —S(O)$_2$—$R^{81}$ and —S(O)$_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

2. The compound of claim 1, wherein A and A' are independently selected from the group consisting of a single bond,

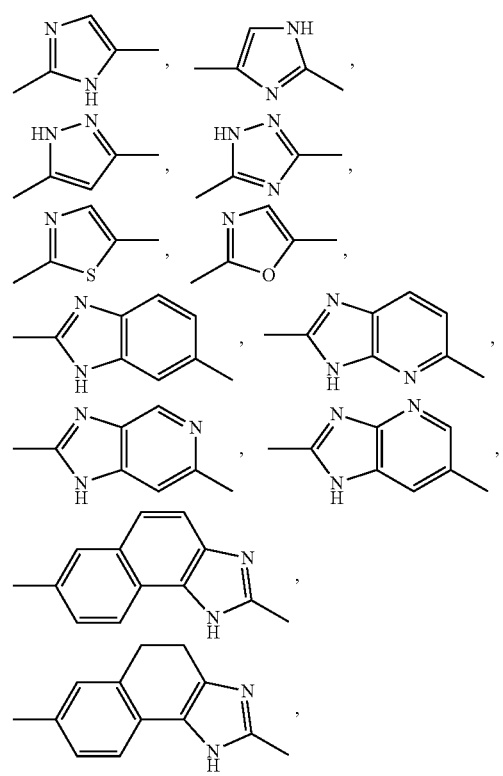

-continued

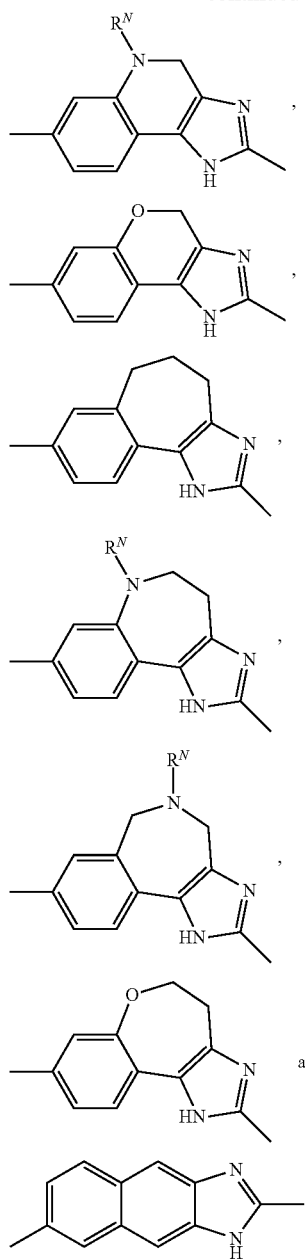

3. The compound of claim 1, wherein:

a) $R^c$ and $R^d$ are joined and form a heterocyclic fused ring system selected from the group consisting of:

-continued

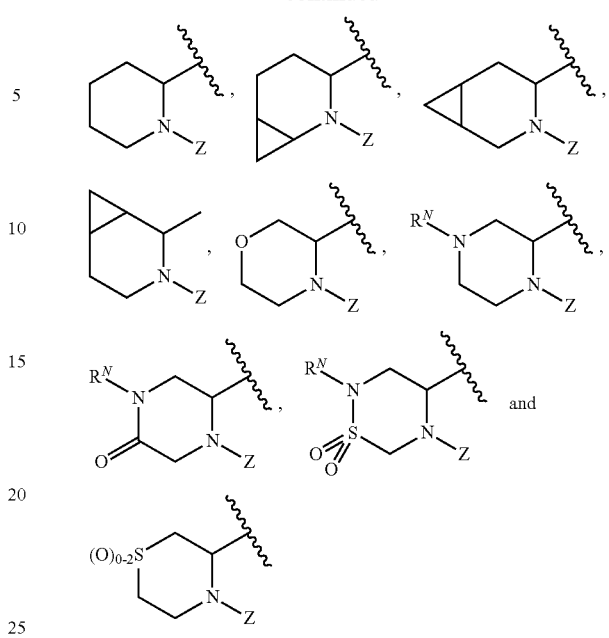

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, or b) $R^e$ and $R^f$ are joined and form a heterocyclic fused ring system selected from the group consisting of:

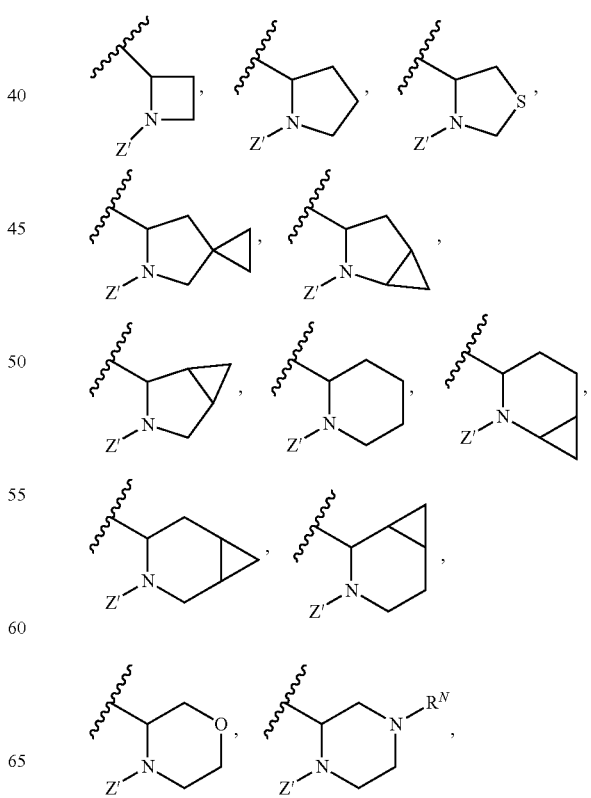

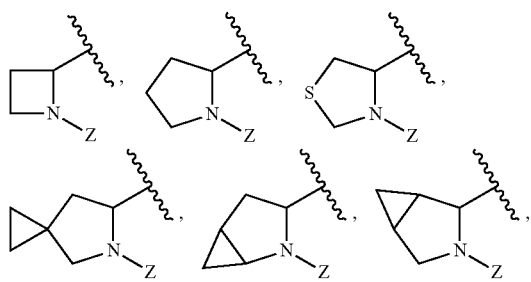

-continued

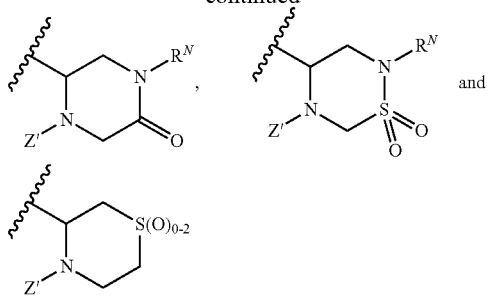

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

4. The compound of claim 1 having formula III:

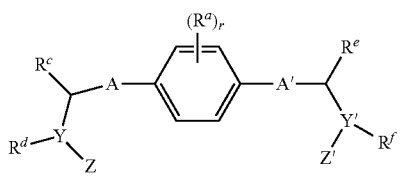

wherein

A is selected from the group consisting of

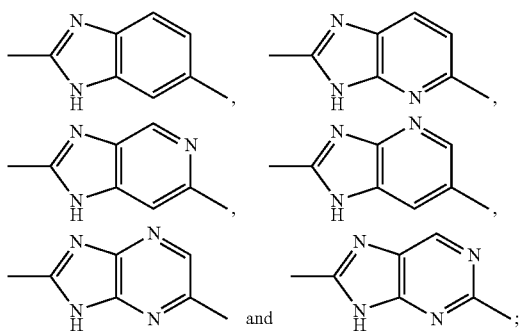

A' is selected from the group consisting of single bond,

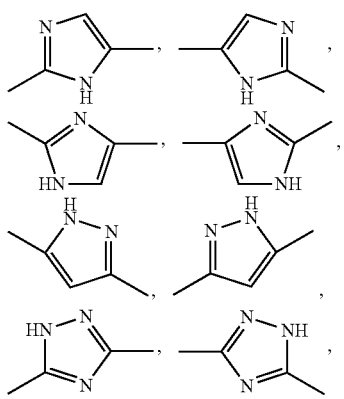

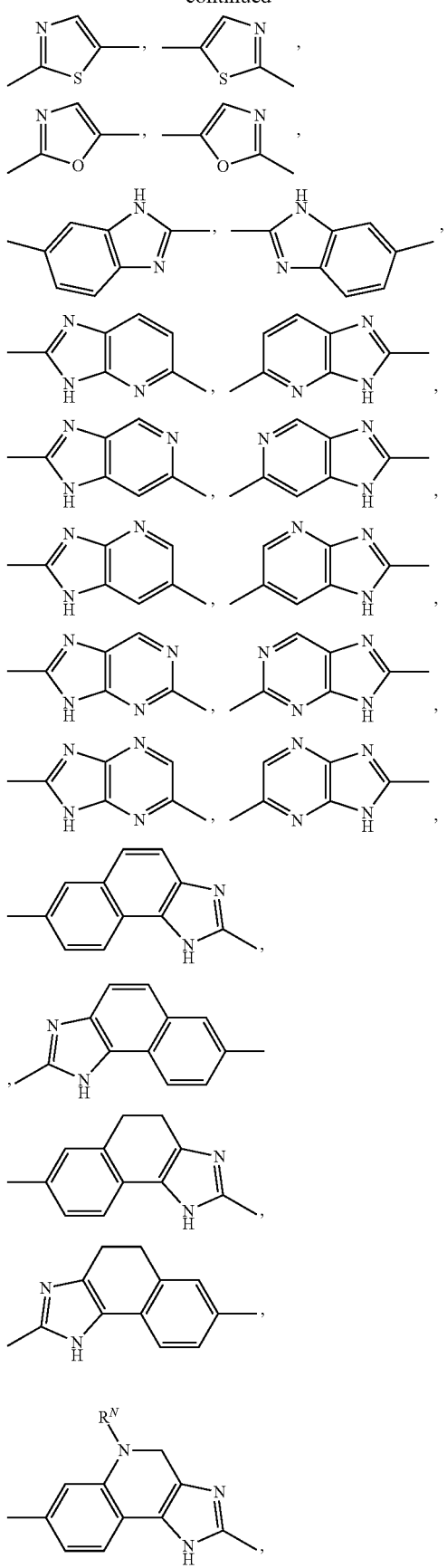

-continued

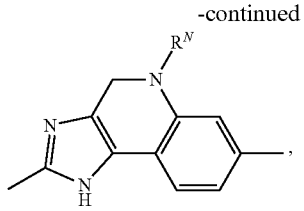

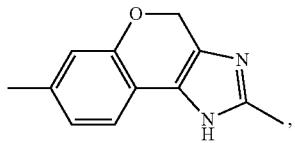

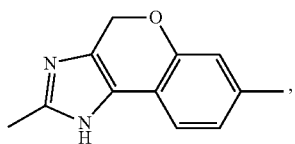

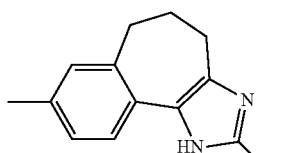

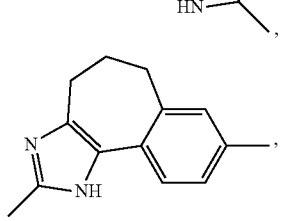

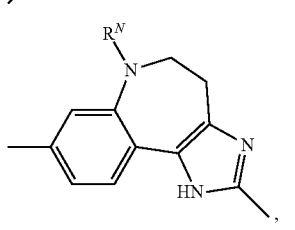

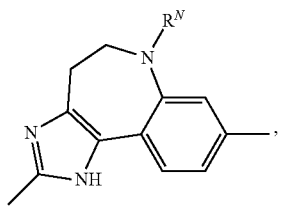

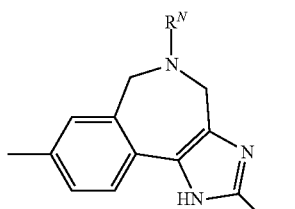

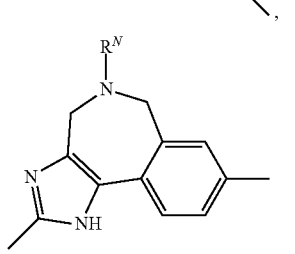

-continued

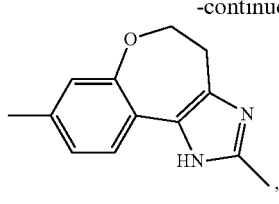

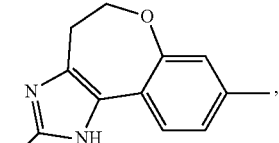

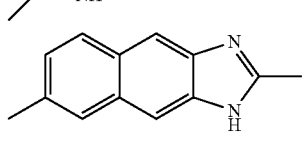

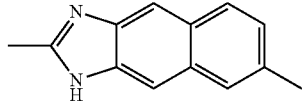

—(CR$_2$)$_n$—O—(CR$_2$)$_p$—, —(CR$_2$)$_n$—C(O)N(R$^N$)—(CR$_2$)$_p$— and —(CR$_2$)$_n$—N(R$^N$)C(O)—(CR$_2$)$_p$— wherein R$^N$ is selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

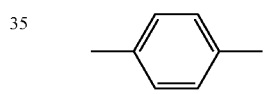

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is selected from the group consisting of 0, 1, 2, 3, or 4.

5. The compound of claim 1, wherein A is selected from the group consisting of

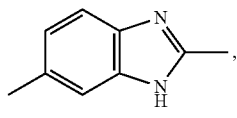 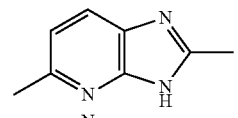

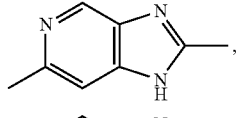 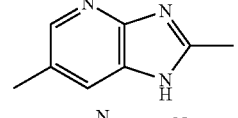

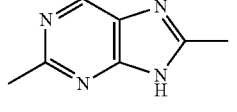 and 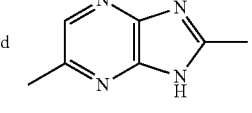.

6. The compound of claim 5 having formula IIIb:

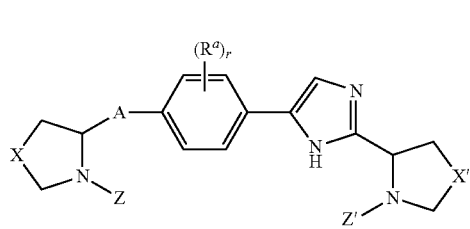

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

7. The compound of claim 1, having formula IVb:

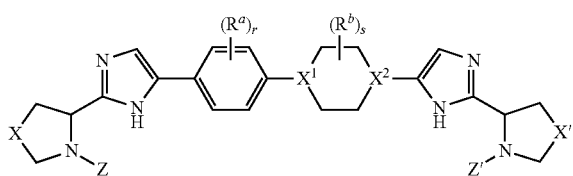

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

8. The compound of claim 1, having formula Vb:

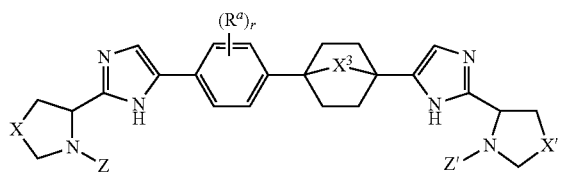

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

9. A compound having formula VI:

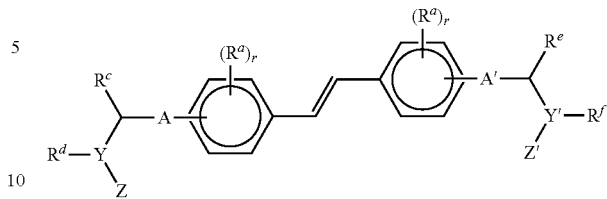

wherein
each

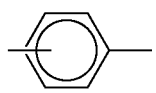

is independently a divalent aryl or heteroaryl group which may be polycyclic with varying connective patterns;
each r is independently 0, 1, 2, 3, or 4;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
A and A' are independently selected from the group consisting of a single bond, —(CR$_2$)$_n$—O—(CR$_2$)$_p$—, —(CR$_2$)$_n$—N(R$^N$)—(CR$_2$)$_p$—, —(CR$_2$)$_n$—S(O)$_k$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$—, —(CR$_2$)$_n$—C(O)—O—(CR$_2$)$_p$—, —(CR$_2$)$_n$—N(R$^N$)—S(O)$_k$—N(R$^N$)—(CR$_2$)$_p$— and —(CR$_2$)$_n$—N(R$^N$)—C(O)—O—(CR$_2$)$_p$— and a heteroaryl group selected from the group consisting of

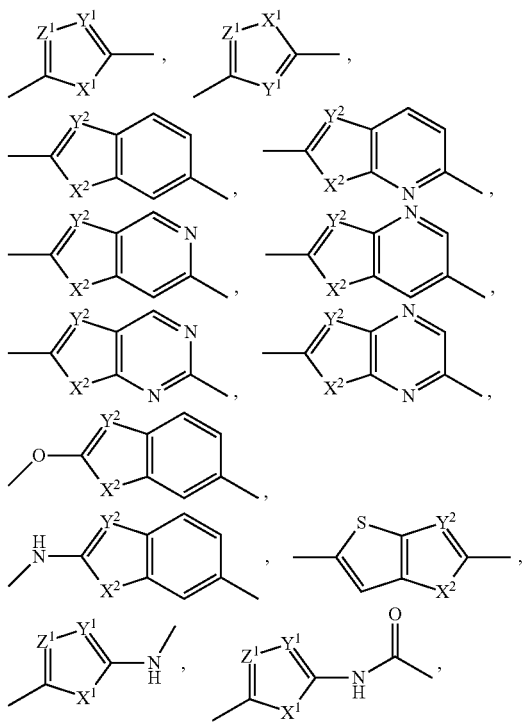

-continued

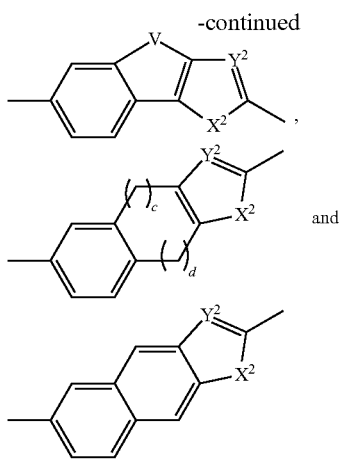

wherein:
X$^1$ is CH$_2$, NH, O or S,
Y$^1$, Y$^2$ and Z$^1$ are each independently CH or N,
X$^2$ is NH, O or S,
V is —CH$_2$—CH$_2$—, —CH=CH—, —N=CH—, (CH$_2$)$_a$—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0,

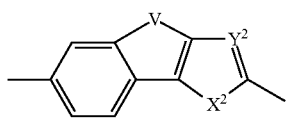

optionally includes 1 or 2 nitrogens as heteroatoms on the phenyl residue,
the carbons of the heteroaryl group are each independently optionally substituted with a substituent selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
a and b are independently 1, 2, or 3,
c and d are independently 1 or 2,
n and p are independently 0, 1, 2 or 3,
k is 0, 1, or 2,
each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and wherein for each A and A', B may be attached to either side of A and A' so that in the example of A or A' being

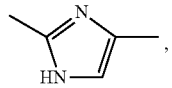

the A-B-A' can be any of:

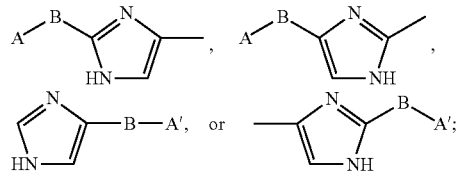

R$^c$, R$^d$, R$^e$ and R$^f$ are each independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein,
each hetero atom, if present, is independently N, O or S,
each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S,
R$^c$ and R$^d$ are optionally joined to form a 4- to 8-membered heterocycle which is optionally fused to another 3- to 6-membered heterocycle or heteroaryl ring, and
R$^e$ and R$^f$ are optionally joined to form a 4- to 8-membered heterocycle which is optionally fused to another 3- to 6-membered heterocycle or heteroaryl ring;
Y and Y' are each independently nitrogen; and
Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4$$_2$)$_t$—NR$^5$—(CR$^4$$_2$)$_t$]$_u$—U—(CR$^4$$_2$)$_t$—NR$^7$—(CR$^4$$_2$)$_t$—R$^8$, —U—(CR$^4$$_2$)$_t$—R$^8$ and —[U—(CR$^4$$_2$)$_t$—NR$^5$—(CR$^4$$_2$)$_t$]$_u$—U—(CR$^4$$_2$)$_t$—O—(CR$^4$$_2$)$_t$—R$^8$, wherein,
U is selected from the group consisting of —C(O)—, —C(S)— and —S(O)$_2$—,
each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl,
R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}$$_2$, —S(O)$_2$—R$^{81}$ and —S(O)2-N—R$^{81}$$_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl,
optionally, R$^7$ and R$^8$ together form a 4-7 membered ring,
each t is independently 0, 1, 2, 3, or 4, and
u is 0, 1, or 2.

10. The compound of claim 9 wherein each

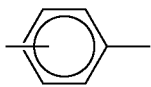

is independently selected from the group consisting of

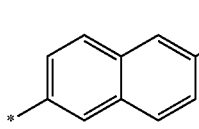 and 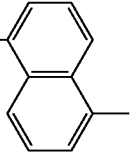

wherein * indicates attachment points to the remainder of the compound and each phenyl residue optionally includes 1 or 2 nitrogens as heteroatoms.

11. The compound of claim 1, wherein A and A' are independently selected from the group consisting of a single bond,

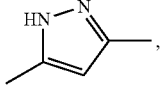 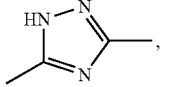

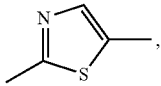 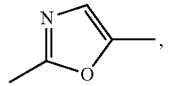

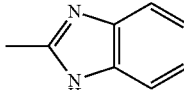 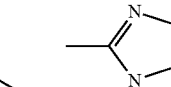

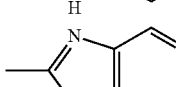 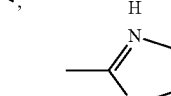

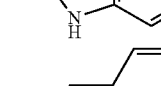

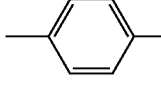

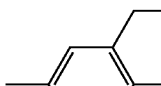

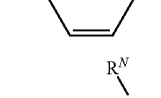

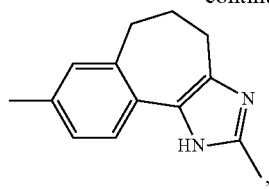

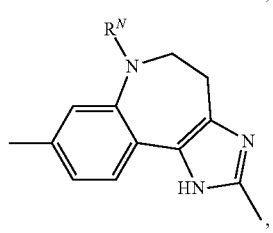

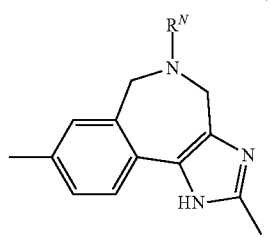

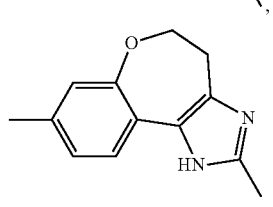 and

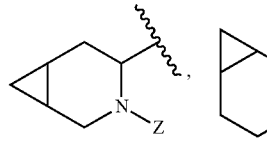

12. The compound of claim 1, wherein:

a) $R^c$ and $R^d$ are joined and form a heterocyclic fused ring system selected from the group consisting of:

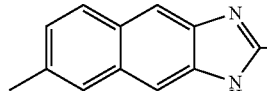

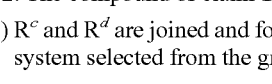

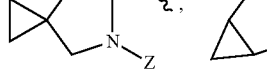

-continued

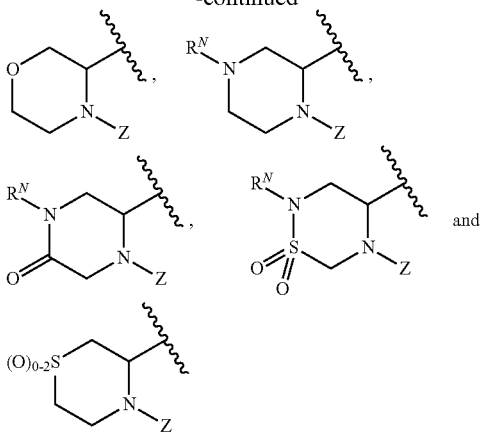

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, or b) $R^e$ and $R^f$ are joined and form a heterocyclic fused ring system selected from the group consisting of:

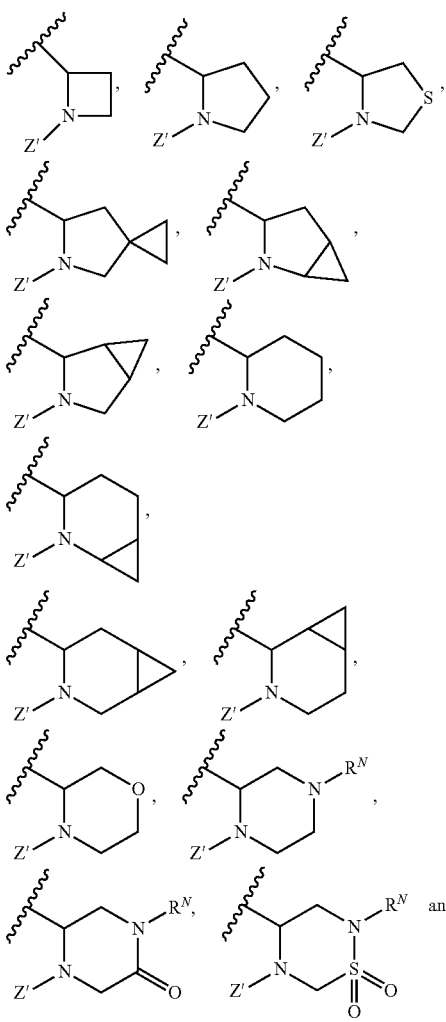

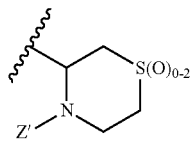

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

13. The compound of claim 1, wherein the amino acids are in the D configuration.

14. The compound of claim 1, wherein Z and Z' are each independently selected from the group consisting of —[U—$(CR^4_2)_t$—$NR^5$—$(CR^4_2)_t]_u$—U—$(CR^4_2)_t$—$NR^7$—$(CR^4_2)_t$—$R^8$, —U—$(CR^4_2)_t$—$R^8$ and —[U—$(CR^4_2)_t$—$NR^5$—$(CR^4_2)_t]_u$—U—$(CR^4_2)_t$—O—$(CR^4_2)_t$—$R^8$.

15. The compound of claim 1, wherein one or both of Z and Z' are selected from the group consisting of:

—C(O)—$(CR^4_2)_t$—$NR^5$—$(CR^4_2)_t$—C(O)—$(CR^4_2)_t$—$NR^7$—$(CR^4_2)_t$—$R^8$;

—C(O)—$(CR^4_2)_t$—$NR^7$—$(CR^4_2)_t$—$R^8$;

—C(O)—$(CR^4_2)_n$—$NR^7$—C(O)—$R^{81}$;

—C(O)—$(CR^4_2)_n$—$NR^7$—C(O)—O—$R^{81}$;

—U—$(CR^4_2)_t$—$NR^5$—$(CR^4_2)_t$—U—$(CR^4_2)_t$—O—$(CR^4_2)_t$—$R^8$;

—C(O)—$(CR^4_2)_t$—$NR^5$—$(CR^4_2)_t$—C(O)—$(CR^4_2)_t$—O—$(CR^4_2)_t$—$R^8$;

—U—$(CR^4_2)_t$—O—$(CR^4_2)_t$—$R^8$;

—C(O)—$(CR^4_2)_t$—O—$(CR^4_2)_t$—$R^8$; and

—C(O)—$(CR^4_2)_n$—$NR^7$—$R^8$ wherein $R^7$ and $R^8$ together form a 4-7 membered ring.

16. The compound of claim 1, wherein the compound is selected from the group consisting of

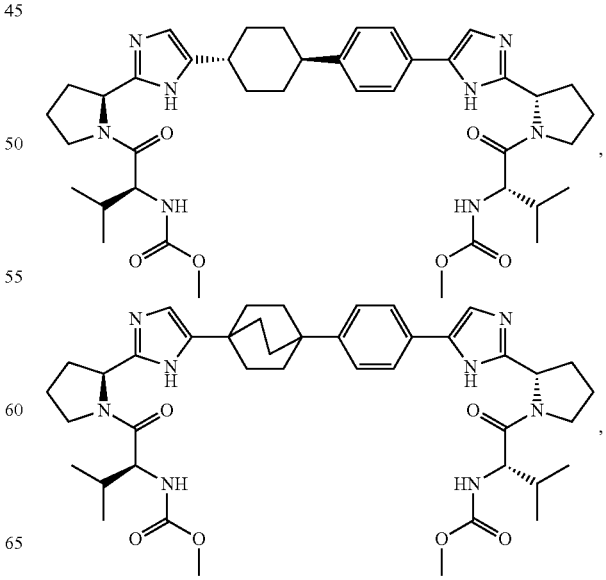

359
-continued
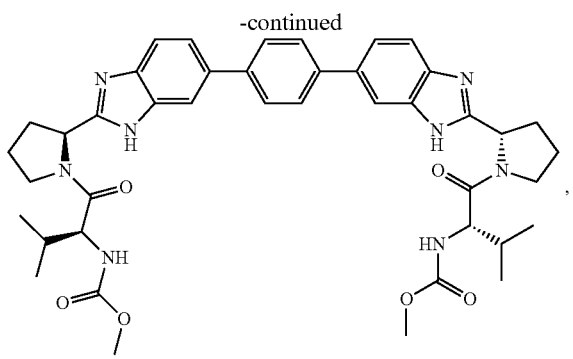
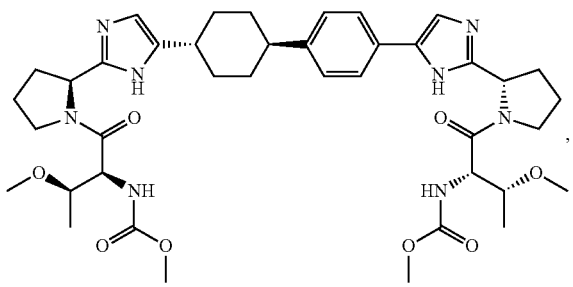
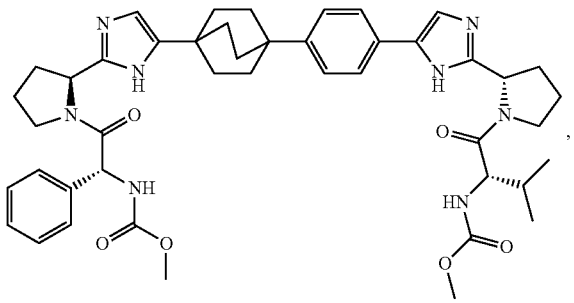
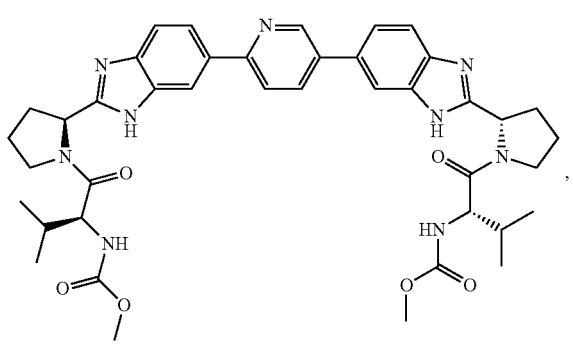
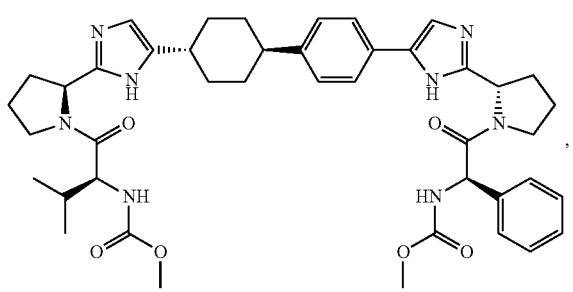
360
-continued
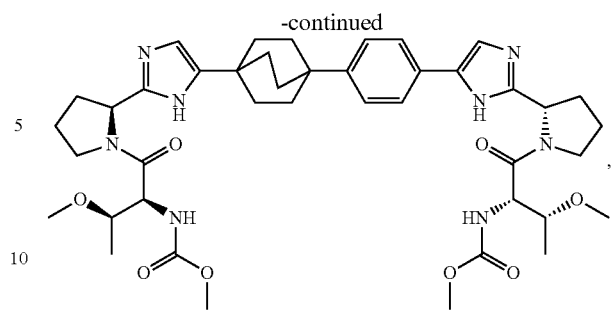
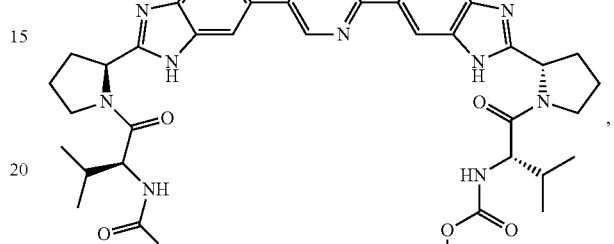
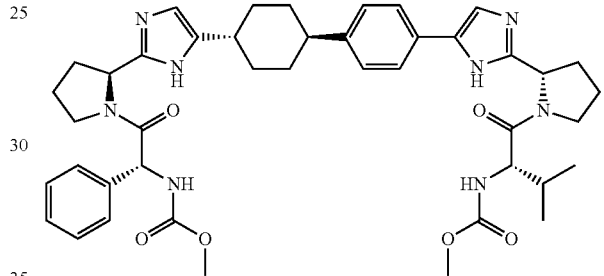
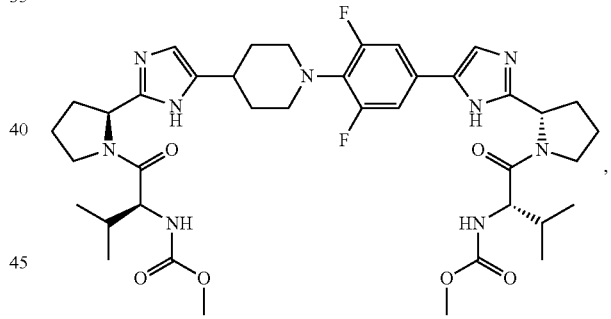
and
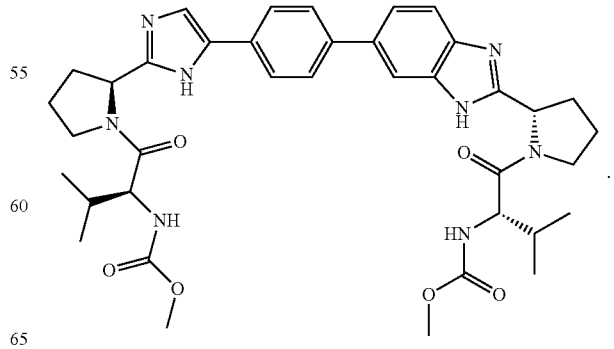

17. A pharmaceutical composition comprising a compound of claim 1.

18. A method of treating hepatitis C comprising administering to a subject in need thereof, a therapeutically effective amount of a compound of claim 1.

* * * * *